United States Patent
Cho et al.

(10) Patent No.: US 8,877,733 B2
(45) Date of Patent: Nov. 4, 2014

(54) 1'-SUBSTITUTED PYRIMIDINE N-NUCLEOSIDE ANALOGS FOR ANTIVIRAL TREATMENT

(75) Inventors: Aesop Cho, Mountain View, CA (US); Choung U. Kim, San Carlos, CA (US); Thorsten A. Kirschberg, Redwood City, CA (US); Michael R. Mish, Foster City, CA (US); Neil Squires, San Francisco, CA (US)

(73) Assignee: Gilead Sciences, Inc., Foster City, CA (US)

( * ) Notice: Subject to any disclaimer, the term of this patent is extended or adjusted under 35 U.S.C. 154(b) by 6 days.

(21) Appl. No.: 13/447,017

(22) Filed: Apr. 13, 2012

(65) Prior Publication Data

US 2012/0263678 A1 Oct. 18, 2012

Related U.S. Application Data

(60) Provisional application No. 61/474,848, filed on Apr. 13, 2011.

(51) Int. Cl.
| | |
|---|---|
| A61K 31/70 | (2006.01) |
| C07H 19/06 | (2006.01) |
| A61K 31/196 | (2006.01) |
| C07H 19/073 | (2006.01) |
| A61K 31/7068 | (2006.01) |
| C07H 19/067 | (2006.01) |
| A61K 31/7072 | (2006.01) |
| C07H 19/09 | (2006.01) |
| C07H 19/10 | (2006.01) |
| A61K 45/06 | (2006.01) |
| A61K 31/351 | (2006.01) |
| A61K 31/245 | (2006.01) |
| C07H 19/11 | (2006.01) |
| A61K 38/21 | (2006.01) |
| A61K 31/13 | (2006.01) |

(52) U.S. Cl.
CPC .............. *C07H 19/06* (2013.01); *A61K 31/196* (2013.01); *C07H 19/073* (2013.01); *A61K 31/7068* (2013.01); *C07H 19/067* (2013.01); *A61K 31/7072* (2013.01); *C07H 19/09* (2013.01); *C07H 19/10* (2013.01); *A61K 45/06* (2013.01); *A61K 31/351* (2013.01); *A61K 31/245* (2013.01); *C07H 19/11* (2013.01); *A61K 38/21* (2013.01); *A61K 31/13* (2013.01)
USPC .......................................... 514/49; 536/28.4

(58) Field of Classification Search
None
See application file for complete search history.

(56) References Cited

U.S. PATENT DOCUMENTS

| | | | |
|---|---|---|---|
| 6,914,054 B2 * | 7/2005 | Sommadossi et al. .......... | 514/49 |
| 7,321,033 B2 * | 1/2008 | Averett et al. ................ | 536/27.2 |
| 2003/0050229 A1 | 3/2003 | Sommadossi et al. | |
| 2004/0097461 A1 | 5/2004 | Sommadossi et al. | |
| 2004/0101535 A1 | 5/2004 | Sommadossi et al. | |
| 2005/0124532 A1 | 6/2005 | Sommadossi et al. | |
| 2005/0137161 A1 | 6/2005 | Sommadossi et al. | |
| 2006/0166315 A1 * | 7/2006 | Murai .......................... | 435/69.1 |
| 2009/0280086 A1 | 11/2009 | Sommadossi et al. | |
| 2013/0017171 A1 | 1/2013 | Sommadossi et al. | |

FOREIGN PATENT DOCUMENTS

WO 01/90121 A2 11/2001

OTHER PUBLICATIONS

Grouiller et al, Synlett, 1993, vol. 3, pp. 221-222.*
Kodama et al., Chemistry—A European Journal, 2001, vol. 7(11), pp. 2332-2340.*
Yoshimura et al., Nucleosides & Nucleotides, 15(1-3), 1996, pp. 305-324.*
Huang, H., et al., "Competitive Inhibition of Uracil DNA Glycosylase by a Modified Nucleotide Whose Triphosphate is a Substrate for DNA Polymerase," J. Am. Chem. Soc., vol. 131, No. 4, pp. 1344-1345 (2009).
Grunefeld, P., et al., "Synthesis of a 1'-Aminomethylthymidine and Oligodeoxyribonucleotides with 1'-Acylamidomethylthymidine Residues," J. Org. Chem., vol. 69, No. 22, pp. 7543-7551 (2004).
Kodama, T., et al., "An Efficient Method for the Preparation of 1'-a-Branched-Chain Sugar Pyrimidine Ribonucleosides from Uridine: The First Conversion of a Natural Nucleoside into 1'-Substituted Ribonucleosides," Chem. Eur. J., vol. 7, No. 11, pp. 2332-2340 (2001).
Uteza, V., et al., "Synthesis and Structure Determination of the First 1'-C-Cyano-B-D-Nucleosides," Tetrahedron, vol. 49, No. 38, pp. 8579-8588 (1993).
International Search Report issued in International Application No. PCT/US2012/033675, mailed Mar. 7, 2013 (4 pages).
Written Opinion of the International Searching Authority issued in International Application No. PCT/US2012/033675, mailed Mar. 7, 2013 (8 pages).
Written Opinion of the International Searching Authority issued in PCT/US2012/033675, dated Oct. 13, 2013 (6 pages).
International Preliminary Report on Patentability issued in PCT/US2012/033675, dated Oct. 15, 2013 (1 page).

* cited by examiner

*Primary Examiner* — Traviss C McIntosh, III

(57) ABSTRACT

Provided are compounds of Formula I:

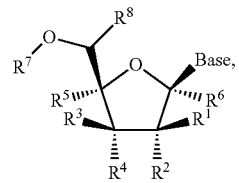

Formula I nucleosides, nucleoside phosphates and prodrugs thereof, wherein $R^6$ is CN, ethenyl, 2-haloethen-1-yl, or $(C_2-C_8)$-alkyn-1-yl. The compounds, compositions, and methods provided are useful for the treatment of Flaviviridae virus infections.

30 Claims, No Drawings

1'-SUBSTITUTED PYRIMIDINE N-NUCLEOSIDE ANALOGS FOR ANTIVIRAL TREATMENT

This application claims the benefit of U.S. provisional application No. 61/474,848, filed Apr. 13, 2011, under 35 U.S.C. 111 (b).

FIELD OF THE INVENTION

The invention relates generally to compounds with antiviral activity, more particularly nucleosides active against Flaviviridae, Paramyxoviridae, Orthomyxoviridae, and Picornaviridae virus infections.

BACKGROUND OF THE INVENTION

Viruses comprising the Flaviviridae family comprise at least three distinguishable genera including *pestiviruses, flaviviruses*, and *hepaciviruses* (Calisher, at al., J. Gen. Virol., 1993, 70, 37-43). While *pestiviruses* cause many economically important animal diseases such as bovine viral diarrhea virus (BVDV), classical swine fever virus (CSFV, hog cholera) and border disease of sheep (BDV), their importance in human disease is less well characterized (Moennig, V., et al., Adv. Vir. Res. 1992, 48, 53-98). *Flaviviruses* are responsible for important human diseases such as dengue fever and yellow fever, while hepaciviruses cause hepatitis C virus infections in humans. Other important viral infections caused by the Flaviviridae family include West Nile virus (WNV) Japanese encephalitis virus (JEV), tick-borne encephalitis virus, Junjin virus, Murray Valley encephalitis, St. Louis encephalitis, Omsk hemorrhagic fever virus and Zika virus. Combined, infections from the Flaviviridae virus family cause significant mortality, morbidity and economic losses throughout the world. Therefore, there is a need to develop effective treatments for Flaviviridae virus infections.

One common member of the Flaviviridae family is hepatitis C virus (HCV). HCV is the leading cause of chronic liver disease worldwide (Boyer, N. et al. J Hepatol. 32:98-112, 2000) so a significant focus of current antiviral research is directed toward the development of improved methods of treatment of chronic HCV infections in humans (Di Besceglie, A. M. and Bacon, B. R., Scientific American, October: 80-85, (1999); Gordon, C. P., et al., *J. Med. Chem.* 2005, 48, 1-20; Maradpour, D.; et al., *Nat. Rev. Micro.* 2007, 5(6), 453-463). A number of HCV treatments are reviewed by Bymock et al. in Antiviral Chemistry & Chemotherapy, 11:2; 79-95 (2000).

RNA-dependent RNA polymerase (RdRp) is one of the best-studied targets for the development of novel HCV therapeutic agents. The NS5B polymerase is a target for inhibitors in early human clinical trials (Sommadossi, J., WO 01/90121 A2, US 2004/0006002 A1). These enzymes have been extensively characterized at the biochemical and structural level, with screening assays for identifying selective inhibitors (De Clercq, E. (2001) J. Pharmacol. Exp. Ther. 297:1-10; De Clercq, E. (2001) J. Clin. Virol. 22:73-89). Biochemical targets such as NS5B are important in developing HCV therapies since HCV does not replicate in the laboratory and there are difficulties in developing cell-based assays and preclinical animal systems.

Currently, there are primarily two antiviral compounds, ribavirin, a nucleoside analog, and interferon-alpha ($\alpha$) (IFN), that are used for the treatment of chronic HCV infections in humans. Ribavirin alone is not effective in reducing viral RNA levels, has significant toxicity, and is known to induce anemia. The combination of IFN and ribavirin has been reported to be effective in the management of chronic hepatitis C (Scott, L. J., et al. *Drugs* 2002, 62, 507-556), but less than half the patients given this treatment show a persistent benefit. Other patent applications disclosing the use of nucleoside analogs to treat hepatitis C virus include WO 01/32153, WO 01/60315, WO 02/057425, WO 02/057287, WO 02/032920, WO 02/18404, WO 04/046331, WO2008/089105 and WO2008/141079, but additional treatments for HCV infections have not yet become available for patients.

Virologic cures of patients with chronic HCV infection are difficult to achieve because of the prodigious amount of daily virus production in chronically infected patients and the high spontaneous mutability of HCV virus (Neumann, et al., *Science* 1998, 282, 103-7; Fukimoto, et al., *Hepatology*, 1996, 24, 1351-4; Domingo, et al., *Gene*, 1985, 40, 1-8; Martell, et al., *J. Virol.* 1992, 66, 3225-9. Experimental anti-viral nucleoside analogs have been shown to induce viable mutations in the HCV virus both in vivo and in vitro (Migliaccio, et al., *J. Biol. Chem.* 2003, 926; Carroll, et al., *Antimicrobial Agents Chemotherapy* 2009, 926; Brown, A. B., *Expert Opin. Investig. Drugs* 2009, 18, 709-725). Therefore, drugs having improved antiviral properties, particularly enhanced activity against resistant strains of virus, improved oral bioavailability, fewer undesirable side effects and extended effective half-life in vivo (De Francesco, R. et al. (2003) Antiviral Research 58:1-16) are urgently needed.

Anti HCV 2'-deoxy-2'-fluoro-nucleosides and nucleotides have been disclosed by Sofia (WO/2008/121634), Attenni (WO/2008/142055), Narjes (WO/2008/085508), Wang (WO/2006/012440), Clark (WO/2005/003147) and Sommadossi (WO/2004/002999) but none of these compounds have become available for patients.

Influenza viruses of the Orthomyxoviridae family that belong to the genera A and B are responsible for seasonal flu epidemics each year, which cause acute contagious respiratory infections. Children, the old, and people with chronic diseases are at high risk to develop severe complications that lead to high morbidity and mortality rates (Memoli et al., *Drug Discovery Today* 2008, 13, 590-595). Among the three influenza genera, type A viruses are the most virulent human pathogens that cause the most severe disease, can be transmitted to other species, and give rise to human influenza pandemics. The recent human influenza outbreak of the aggressive porcine A/H1N1 strain in 2009 has emphasized the need for novel antiviral therapeutics. While yearly vaccination programs are currently used to protect populations from influenza infection, these programs must anticipate the virus strains that will be prevalent during seasonal outbreaks to be effective and they do not address the problem of sudden, unanticipated influenza pandemics. The recent human influenza outbreak of the aggressive porcine A/H1N1 strain in 2009 is an example of this problem. Therefore there is a continuing need for novel anti-influenza therapeutics.

SUMMARY OF THE INVENTION

Provided are compounds that inhibit viruses of the Flaviviridae family. The invention also comprises compounds of Formula I that inhibit viral nucleic acid polymerases, particularly HCV RNA-dependent RNA polymerase (RdRp), rather than cellular nucleic acid polymerases. Without wishing to be bound by theory, the compounds of the invention may inhibit viral RNA-dependent RNA polymerase and thus inhibit the replication of the virus. Compounds of the invention are useful for treating Flaviviridae infections, including hepatitis C, in humans and other animals. It has been surprisingly found that when $R^6$ is other than hydrogen, such as, for example, cyano, alkenyl, or alkynyl, compounds have improved cellular selectivity. This is further explained in the examples below.

In one embodiment, provided are compounds of Formula I:

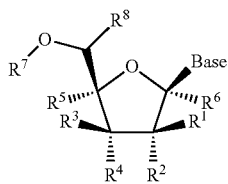

Formula I or a pharmaceutically acceptable salt thereof;
wherein:
Base is a naturally occurring or modified pyrimidine base;
$R^1$ is H, CN, $OR^a$, $(C_1-C_4)$alkyl, $(C_1-C_4)$ substituted alkyl, $(C_2-C_4)$alkenyl, $(C_2-C_4)$ substituted alkenyl, $(C_2-C_4)$alkynyl, $(C_2-C_4)$substituted alkynyl or $S(O)_n R^a$;
$R^2$ is H, $OR^a$, $N(R^a)_2$, $N_3$, CN, $NO_2$, $S(O)_n R^a$, $(C_1-C_4)$ alkyl, $(C_4-C_6)$cycloalkylalkyl, $(C_1-C_4)$substituted alkyl, $(C_2-C_4)$alkenyl, $(C_2-C_4)$substituted alkenyl, $(C_2-C_4)$alkynyl, or $(C_2-C_4)$substituted alkynyl;
or $R^1$ and $R^2$ taken together with the carbon to which they are attached form a 3- to 6-membered cycloalkyl ring wherein 1 to 3 carbon atoms of said cycloalkyl ring is optionally replaced by O or $S(O)_n$;
$R^3$, $R^4$, and $R^5$ are each independently H, $OR^a$, $N(R^a)_2$, $N_3$, CN, $NO_2$, $S(O)_n R^a$, halogen, $(C_1-C_4)$alkyl, $(C_4-C_8)$cycloalkylalkyl, $(C_1-C_4)$substituted alkyl, $(C_2-C_4)$alkenyl, $(C_2-C_4)$substituted alkenyl, $(C_2-C_4)$alkynyl, or $(C_2-C_4)$substituted alkynyl;
or any two of $R^3$, $R^4$ or $R^5$ on adjacent carbon atoms when taken together are —O(CO)O— or when taken together with the ring carbon atoms to which they are attached to form a double bond;
$R^6$ is CN, ethenyl, 2-haloethen-1-yl, or $(C_2-C_8)$alkyn-1-yl,
each n is independently 0, 1, or 2;
each $R^a$ is independently H, $(C_1-C_8)$alkyl, $(C_2-C_8)$alkenyl, $(C_2-C_8)$alkynyl, aryl$(C_1-C_8)$alkyl, $(C_4-C_8)$cycloalkylalkyl, —C(=O)$R^{11}$, —C(=O)$OR^{11}$, —C(=O)$NR^{11}R^{12}$, —C(=O)$SR^{11}$, —S(O)$R^{11}$, —S(O)$_2R^{11}$, —S(O)($OR^{11}$), —S(O)$_2$($OR^{11}$), or —SO$_2NR^{11}R^{12}$;
$R^7$ is H, —C(=O)$R^{11}$, —C(=O)$OR^{11}$, —C(=O)$NR^{11}R^{12}$, —C(=O)$SR^{11}$, —S(O)$R^{11}$, —S(O)$_2R^{11}$, —S(O)($OR^{11}$), —S(O)$_2$($OR^{11}$), —SO$_2NR^{11}R^{12}$, or the group of Formula Ia

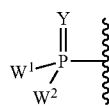

Formula Ia wherein
Y is O, S, NR, $^+N(O)(R)$, N(OR), $^+N(O)(OR)$, or N—NR$_2$;
$W^1$ and $W^2$, when taken together, are —$Y^3$(C(R$^y$)$_2$)$_3Y^3$—;
or one of $W^1$ or $W^2$ together with either $R^3$ or $R^4$ is —$Y^3$— and the other of $W^1$ or $W^2$ is Formula Ib;
or $W^1$ and $W^2$ are each, independently, a group of Formula Ib:

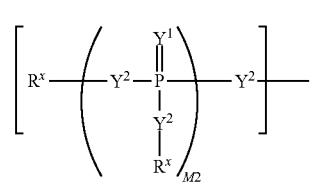

Formula Ib wherein:
each $Y^1$ is independently O, S, NR, $^+N(O)(R)$, N(OR), $^+N(O)(OR)$, or N—NR$_2$;
each $Y^2$ is independently a bond, O, CR$_2$, NR, $^+N(O)(R)$, N(OR), $^+N(O)(OR)$, N—NR$_2$, S, S—S, S(O), or S(O)$_2$;
each $Y^3$ is independently O, S, or NR;
M2 is 0, 1, or 2;
each $R^x$ is a group of Formula Ic

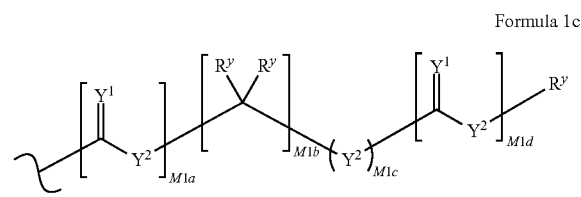

Formula Ic wherein:
each M1a, M1c, and M1d is independently 0 or 1;
M1b is 0, 1, 2, 3, 4, 5, 6, 7, 8, 9, 10, 11 or 12;
each $R^y$ is independently H, F, Cl, Br, I, —CN, —N$_3$, —NO$_2$, —OR, —C(R)$_2$—O—C(R)$_3$, —C(=Y$^1$)R, —C(=Y$^1$)R$^{13}$, —C(=Y$^1$)OR, —C(=Y$^1$)N(R)$_2$, —N(R)$_2$, —$^+$N(R)$_3$, —SR, —S(O)R, —S(O)$_2$R, —S(O)$_2R^{13}$, —S(O)(OR), —S(O)$_2$(OR), —OC(=Y$^1$)R, —OC(=Y$^1$)OR, —OC(=Y$^1$)(N(R)$_2$), —SC(=Y$^1$)R, —SC(=Y$^1$)OR, —SC(=Y$^1$)(N(R)$_2$), —N(R)C(=Y$^1$)R, —N(R)C(=Y$^1$)OR, —N(R)C(=Y$^1$)N(R)$_2$, —SO$_2NR_2$, $(C_1-C_8)$ alkyl, $(C_2-C_8)$ alkenyl, $(C_2-C_8)$ alkynyl, $(C_6-C_{20})$ aryl, $(C_3-C_{20})$ cycloalkyl, $(C_2-C_{20})$ heterocyclyl, arylalkyl, or heteroarylalkyl,
wherein each $(C_1-C_8)$ alkyl, $(C_2-C_8)$alkenyl, $(C_2-C_8)$ alkynyl, $(C_6-C_{20})$ aryl, $(C_3-C_{20})$ cycloalkyl, $(C_2-C_{20})$ heterocyclyl, arylalkyl, or heteroarylalkyl is optionally substituted with 1-3 $R^{20}$ groups;
or when taken together, two $R^y$ on the same carbon atom form a cycloalkyl ring of 3 to 7 carbon atoms;
each R is independently H, $(C_1-C_8)$ alkyl, $(C_2-C_8)$alkenyl, $(C_2-C_8)$ alkynyl, $(C_6-C_{20})$ aryl, $(C_3-C_{20})$ cycloalkyl, $(C_2-C_{20})$ heterocyclyl, or arylalkyl;
$R^8$ is H, $(C_1-C_4)$ alkyl, or $(C_1-C_4)$ substituted alkyl;
each $R^{11}$ or $R^{12}$ is independently H, $(C_1-C_8)$alkyl, $(C_2-C_6)$alkenyl, $(C_2-C_8)$alkynyl, $(C_4-C_8)$cycloalkylalkyl, $(C_3-C_{20})$ cycloalkyl, $(C_2-C_{20})$heterocyclyl, optionally substituted aryl, optionally substituted heteroaryl, —C(=O)$(C_1-C_8)$alkyl, —S(O)$_n(C_1-C_8)$alkyl or aryl$(C_1-C_8)$alkyl; or $R^{11}$ and $R^{12}$ taken together with a nitrogen to which they are both attached form a 3- to 7-membered heterocyclic ring wherein any one carbon atom of said heterocyclic ring can optionally be replaced with —O—, —S— or —$NR^a$—;
each $R^{13}$ is independently a cycloalkyl or heterocycle optionally substituted with 1-3 R or $R^{20}$ groups;
each $R^{20}$ is independently, halogen, CN, $N_3$, N(R)$_2$, OR, —SR, —S(O)R, —S(O)$_2$R, —S(O)(OR), —S(O)$_2$(OR), —C(=Y$^1$)R, —C(=Y$^1$)OR, or C(=Y$^1$)N(R)$_2$;
wherein each alkyl, alkenyl, alkynyl, aryl or heteroaryl of each $R^1$, $R^2$, $R^3$, $R^4$, $R^5$, $R^8$, $R^{11}$ or $R^{12}$ is, independently, optionally substituted with 1 to 3 halo, hydroxy, CN, $N_3$, $N(R^a)_2$ or $OR^a$; and wherein 1 to 3 of the non-terminal carbon atoms of each said $(C_r$-$C_8)$alkyl may be optionally replaced with —O—, —S— or —$NR^a$—;

with the following provisos:

a) when $R^1$, $R^3$, and $R^5$ are hydrogen, $R^2$ and $R^4$ are hydroxy, $R^6$ is cyano and $R^7$ and $R^8$ are hydrogen, then Base is not uracil or thymine;

b) when $R^1$ and $R^4$ are hydroxy, $R^2$, $R^3$, and $R^5$ are hydrogen, $R^6$ is cyano and $R^7$ and $R^8$ are hydrogen, then. Base is not uracil or cytosine;

c) when $R^1$, $R^2$, $R^3$, and $R^5$ are hydrogen, $R^4$ is hydroxy, $R^6$ is cyano and $R^7$ and $R^8$ are hydrogen, then Base is not uracil, cytosine, thymine or 5-iodo-uracil;

d) when $R^1$, $R^3$, and $R^5$ are hydrogen, $R^2$ and $R^4$ are hydroxy, $R^6$ is ethenyl and $R^7$ and $R^8$ are hydrogen, then Base is not uracil or cytosine;

e) when $R^5$ is other than H, then $R^8$ is H;

f) when $R^1$ is hydroxy, $R^2$, $R^3$, $R^5$, and $R^8$ are hydrogen, $R^6$ is cyano, $R^4$ is hydrogen or benzoyl, and $R^7$ is hydrogen or benzoyl, then Base is not cytosine;

g) when $R^1$ is acetyl or hydroxy, $R^2$, $R^3$, $R^5$, $R^7$, and $R^8$ are hydrogen, $R^4$ is hydroxy or —OC(O)phenyl, then Base is not 2-oxo-4-hydroxypyrimidinyl;

h) when $R^1$ is acetoxy, $R^4$ is benzoyloxy, $R^6$ is cyano, $R^7$ is benzoyl, and $R^2$, $R^3$, $R^5$, and $R^8$ are hydrogen, then base is not uracil; and i) at least one of $R^1$, $R^2$, $R^3$, $R^4$ and $R^5$ is not hydrogen.

In another embodiment, provided are compounds of Formula I and pharmaceutically acceptable salts or esters thereof and all racemates, enantiomers, diastereomers, tautomers, polymorphs, pseudopolymorphs and amorphous forms thereof.

In another embodiment, provided are pharmaceutical compositions comprising an effective amount of a Formula I compound as described above, or a pharmaceutically acceptable salt thereof, and a pharmaceutically acceptable diluent or carrier.

In another embodiment, provided are pharmaceutical compositions comprising a pharmaceutically acceptable diluent or carrier and an effective amount of a compound of Formula I:

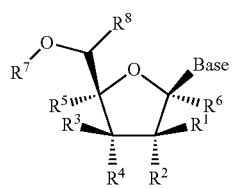

Formula I or a pharmaceutically acceptable salt thereof;
wherein:

Base is a naturally occurring or modified pyrimidine base;

$R^1$ is H, CN, $OR^a$, $(C_1$-$C_4)$alkyl, $(C_1$-$C_4)$substituted alkyl, $(C_2$-$C_4)$alkenyl, $(C_2$-$C_4)$substituted alkenyl, $(C_2$-$C_4)$alkynyl, $(C_2$-$C_4)$substituted alkynyl or $S(O)_nR^a$;

$R^2$ is. H, $OR^a$, $N(R^a)_2$, $N_3$, CN, $NO_2$, $S(O)_nR^a$, $(C_1$-$C_4)$alkyl, $(C_4$-$C_6)$cycloalkylalkyl, $(C_1$-$C_4)$substituted alkyl, $(C_2$-$C_4)$alkenyl, $(C_2$-$C_4)$substituted alkenyl, $(C_2$-$C_4)$alkynyl, or $(C_2$-$C_4)$substituted alkynyl;

or $R^1$ and $R^2$ taken together with the carbon to which they are attached form a 3- to 6-membered cycloalkyl ring wherein 1 to 3 carbon atoms of said cycloalkyl ring is optionally replaced by O or $S(O)_n$;

$R^3$, $R^4$, and $R^5$ are each independently H, $OR^a$, $N(R^a)_2$, $N_3$, CN, $NO_2$, $S(O)_nR^a$, halogen, $(C_1$-$C_4)$alkyl, $(C_4$-$C_8)$cycloalkylalkyl, $(C_1$-$C_4)$substituted alkyl, $(C_2$-$C_4)$alkenyl, $(C_2$-$C_4)$substituted alkenyl, $(C_2$-$C_4)$alkynyl, or $(C_2$-$C_4)$substituted alkynyl;

or any two of $R^3$, $R^4$ or $R^5$ on adjacent carbon atoms when taken together are —O(CO)O— or when taken together with the ring carbon atoms to which they are attached to form a double bond;

$R^6$ is CN, ethenyl, 2-haloethen-1-yl, or $(C_2$-$C_8)$alkyn-1-yl,
each n is independently 0, 1, or 2;
each $R^a$ is independently H, $(C_1$-$C_8)$alkyl, $(C_2$-$C_8)$alkenyl, $(C_2$-$C_8)$alkynyl, aryl$(C_1$-$C_8)$alkyl, $(C_4$-$C_8)$cycloalkylalkyl, —C(=O)$R^{11}$, —C(=O)$OR^{11}$, —C(=O)$NR^{11}R^{12}$, —C(=O)$SR^{11}$, —S(O)$R^{11}$—S(O)$_2R^{11}$, —S(O)(O$R^{11}$), —S(O)$_2$(O$R^{11}$), —SO$_2NR^{11}R^{12}$;

$R^7$ is H, —C(=O)$R^{11}$, —C(=O)$OR^{11}$, —C(=O)$NR^{11}R^{12}$, —C(=O)$SR^{11}$, —S(O)$R^{11}$, —S(O)$_2R^{11}$, —S(O)(O$R^{11}$), —S(O)$_2$(O$R^{11}$), —SO$_2NR^{11}R^{12}$, or the group of Formula Ia

Formula Ia wherein
Y is O, S, NR, $^+$N(O)(R), N(OR), $^+$N(O)(OR), or N—$NR_2$;
$W^1$ and $W^2$, when taken together, are —$Y^3(C(R^y)_2)_3Y^3$—;
or one of $W^1$ or $W^2$ together with either $R^3$ or $R^4$ is —$Y^3$— and the other of $W^1$ or $W^2$ is Formula Ib;
or $W^1$ and $W^2$ are each, independently, a group of Formula Ib:

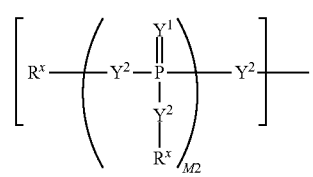

Formula Ib wherein:
each $Y^1$ is independently O, S, NR, $^+$N(O)(R), N(OR), $^+$N(O)(OR), or N—$NR_2$;
each $Y^2$ is independently a bond, O, $CR_2$, NR, $^+$N(O)(R), N(OR), $^+$N(O)(OR), N—$NR_2$, S, S—S, S(O), or S(O)$_2$;
each $Y^3$ is independently O, S, or NR;
M2 is 0, 1, or 2;
each $R^x$ is a group of Formula Ic

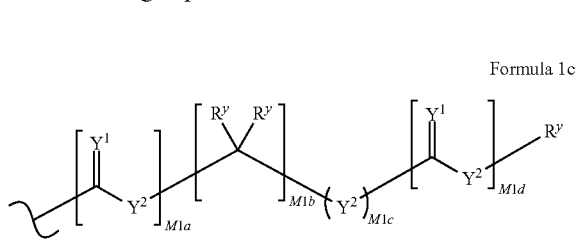

Formula Ic wherein:
each M1a, M1c, and M1d is independently 0 or 1;
M1b is 0, 1, 2, 3, 4, 5, 6, 7, 8, 9, 10, 11 or 12;

each $R^y$ is independently H, F, Cl, Br, I, —CN, —$N_3$, —$NO_2$, —OR, —C(R)$_2$—O—C(R)$_3$, —C($=Y^1$)R, —C($=Y^1$)$R^{13}$, —C($=Y^1$)OR, —C($=Y^1$)N(R)$_2$, —N(R)$_2$, —$^+$N(R)$_3$, —SR, —S(O)R, —S(O)$_2$R, —S(O)$_2R^{13}$, —S(O)(OR), —S(O)$_2$(OR), —OC($=Y^1$)R, —OC($=Y^1$)OR, —OC($=Y^1$)(N(R)$_2$), —SC($=Y^1$)R, —SC($=Y^1$)OR, —SC($=Y^1$)(N(R)$_2$), —N(R)C($=Y^1$)R, —N(R)C($=Y^1$)OR, —N(R)C($=Y^1$)N(R)$_2$, —$SO_2NR_2$, ($C_1$-$C_8$) alkyl, ($C_2$-$C_8$) alkenyl, ($C_2$-$C_8$) alkynyl, ($C_6$-$C_{20}$) aryl, ($C_3$-$C_{20}$) cycloalkyl, ($C_2$-$C_{20}$) heterocyclyl, arylalkyl, or heteroarylalkyl, wherein each ($C_1$-$C_8$) alkyl, ($C_2$-$C_8$)alkenyl, ($C_2$-$C_8$) alkynyl, ($C_6$-$C_{20}$) aryl, ($C_3$-$C_{20}$) cycloalkyl, ($C_2$-$C_{20}$) heterocyclyl, arylalkyl, or heteroarylalkyl is optionally substituted with 1-3 $R^{20}$ groups;

or when taken together, two $R^y$ on the same carbon atom form a cycloalkyl ring of 3 to 7 carbon atoms;

each R is independently H, ($C_1$-$C_8$) alkyl, ($C_2$-$C_8$)alkenyl, ($C_2$-$C_8$) alkynyl, ($C_6$-$C_{20}$) aryl, ($C_3$-$C_{20}$) cycloalkyl, ($C_2$-$C_{20}$) heterocyclyl, or arylalkyl;

$R^8$ is H, ($C_1$-$C_4$) alkyl, or ($C_1$-$C_4$) substituted alkyl;

each $R^{11}$ or $R^{12}$ is independently H, ($C_1$-$C_8$)alkyl, ($C_2$-$C_8$) alkenyl, ($C_2$-$C_8$)alkynyl, ($C_4$-$C_8$)cycloalkylalkyl, ($C_3$-$C_{20}$) cycloalkyl, ($C_2$-$C_{20}$)heterocyclyl, optionally substituted aryl, optionally substituted heteroaryl, —C($=$O)($C_1$-$C_8$)alkyl, —S(O)$_n$($C_1$-$C_8$)alkyl or aryl($C_1$-$C_8$)alkyl; or $R^{11}$ and $R^{12}$ taken together with a nitrogen to which they are both attached form a 3- to 7-membered heterocyclic ring wherein any one carbon atom of said heterocyclic ring can optionally be replaced with —O—, —S— or —$NR^a$—;

each $R^{13}$ is independently a cycloalkyl or heterocycle optionally substituted with 1-3 R or $R^{20}$ groups;

each $R^{20}$ is independently, halogen, CN, $N_3$, N(R)$_2$, OR, —SR, —S(O)R, —S(O)$_2$R, —S(O)(OR), —S(O)$_2$(OR), —C($=Y^1$)R, —C($=Y^1$)OR, or C($=Y^1$)N(R)$_2$;

wherein each alkyl, alkenyl, alkynyl, aryl or heteroaryl of each $R^1$, $R^2$, $R^3$, $R^4$, $R^5$, $R^8$, $R^{11}$ or $R^{12}$ is, independently, optionally substituted with 1 to 3 halo, hydroxy, CN, $N_3$, N($R^a$)$_2$ or $OR^a$; and wherein 1 to 3 of the non-terminal carbon atoms of each said ($C_1$-$C_8$)alkyl may be optionally replaced with —O—, —S— or —$NR^a$— with the proviso that at least one of $R^1$, $R^2$, $R^3$, $R^4$ and $R^5$ is not hydrogen.

In another embodiment of the invention, is provided a method of inhibiting HCV polymerase comprising administering to a mammal in need thereof a compound of the invention as described throughout.

In another embodiment, the present invention is directed to a method of inhibiting HCV polymerase comprising administering to a mammal in need thereof a therapeutically effective amount of a compound of Formula I:

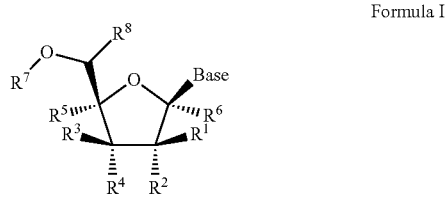

Formula I or a pharmaceutically acceptable salt thereof;
wherein:
Base is a naturally occurring or modified pyrimidine base;
$R^1$ is H, CN, $OR^a$, ($C_1$-$C_4$)alkyl, ($C_1$-$C_4$)substituted alkyl, ($C_2$-$C_4$)alkenyl, ($C_2$-$C_4$)substituted alkenyl, ($C_2$-$C_4$)alkynyl, ($C_2$-$C_4$)substituted alkynyl or S(O)$_nR^a$;

$R^2$ is H, $OR^a$, N($R^a$)$_2$, $N_3$, CN, $NO_2$, S(O)$_nR^a$, ($C_1$-$C_4$) alkyl, ($C_4$-$C_6$)cycloalkylalkyl, ($C_1$-$C_4$)substituted alkyl, ($C_2$-$C_4$)alkenyl, ($C_2$-$C_4$)substituted alkenyl, ($C_2$-$C_4$)alkynyl, or ($C_2$-$C_4$)substituted alkynyl;

or $R^1$ and $R^2$ taken together with the carbon to which they are attached form a 3- to 6-membered cycloalkyl ring wherein 1 to 3 carbon atoms of said cycloalkyl ring is optionally replaced by O or S(O)$_n$;

$R^3$, $R^4$, and $R^5$ are each independently H, $OR^a$, N($R^a$)$_2$, $N_3$, CN, $NO_2$, S(O)$_nR^a$, halogen, ($C_1$-$C_4$)alkyl, ($C_4$-$C_8$)cycloalkylalkyl, ($C_1$-$C_4$)substituted alkyl, ($C_2$-$C_4$)alkenyl, ($C_2$-$C_4$)substituted alkenyl, ($C_2$-$C_4$)alkynyl, or ($C_2$-$C_4$)substituted alkynyl;

or any two of $R^3$, $R^4$ or $R^5$ on adjacent carbon atoms when taken together are —O(CO)O— or when taken together with the ring carbon atoms to which they are attached to form a double bond;

$R^6$ is CN, ethenyl, 2-haloethen-1-yl, or ($C_2$-$C_8$)alkyn-1-yl, each n is independently 0, 1, or 2;

each $R^a$ is independently H, ($C_1$-$C_8$)alkyl, ($C_2$-$C_8$)alkenyl, ($C_2$-$C_8$)alkynyl, aryl($C_1$-$C_8$)alkyl, ($C_4$-$C_8$)cycloalkylalkyl, —C($=$O)$R^{11}$, —C($=$O)$OR^{11}$, —C($=$O)$NR^{11}R^{12}$, —C($=$O)$SR^{11}$, —S(O)$R^{11}$, —S(O)$_2R^{11}$, —S(O)(O$R^{11}$), —S(O)$_2$(O$R^{11}$), or —SO$_2NR^{11}R^{12}$;

$R^7$ is H, —C($=$O)$R^{11}$, —C($=$O)$OR^{11}$, —C($=$O)$NR^{11}R^{12}$, —C($=$O)$SR^{11}$, —S(O)$R^{11}$, —S(O)$_2R^{11}$, —S(O)(O$R^{11}$), —S(O)$_2$(O$R^{11}$), —SO$_2NR^{11}R^{12}$, or the group of Formula Ia

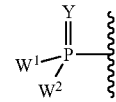

Formula Ia wherein
Y is O, S, NR, $^+$N(O)(R), N(OR), $^+$N(O)(OR), or N—$NR_2$, $W^1$ and $W^2$, when taken together, are —$Y^3$(C($R^y$)$_2$)$_3Y^3$—;

or one of $W^1$ or $W^2$ together with either $R^3$ or $R^4$ is —$Y^3$— and the other of $W^1$ or $W^2$ is Formula Ib;

or $W^1$ and $W^2$ are each, independently, a group of Formula Ib:

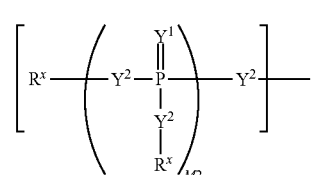

Formula Ib wherein:
each $Y^1$ is independently O, S, NR, $^+$N(O)(R), N(OR), $^+$N(O)(OR), or N—$NR_2$;

each $Y^2$ is independently a bond, O, CR$_2$, NR, $^+$N(O)(R), N(OR), $^+$N(O)(OR), N—$NR_2$, S, S—S, S(O), or S(O)$_2$;

each $Y^3$ is independently O, S, or NR;

M2 is 0, 1, or 2;

each $R^x$ is a group of Formula Ic

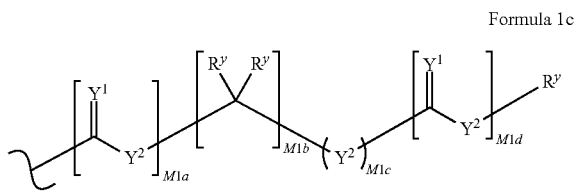

Formula Ic wherein:
each M1a, M1c, and M1d is independently 0 or 1;
M1b is 0, 1, 2, 3, 4, 5, 6, 7, 8, 9, 10, 11 or 12;
each $R^y$ is independently H, F, Cl, Br, I, —CN, —$N_3$, —$NO_2$, —OR, —$C(R)_2$—O—$C(R)_3$, —C(=$Y^1$)R, —C(=$Y^1$)$R^{13}$, —C(=$Y^1$)OR, —C(=$Y^1$)$N(R)_2$, —$N(R)_2$, —$^+N(R)_3$, —SR, —S(O)R, —$S(O)_2$R, —$S(O)_2R^{13}$, —S(O)(OR), —$S(O)_2$(OR), —OC(=$Y^1$)R, —OC(=$Y^1$)OR, —OC(=$Y^1$)($N(R)_2$), —SC(=$Y^1$)R, —SC(=$Y^1$)OR, —SC(=$Y^1$)($N(R)_2$), —N(R)C(=$Y^1$)R, —N(R)C(=$Y^1$)OR, —N(R)C(=$Y^1$)$N(R)_2$, —$SO_2NR_2$, ($C_1$-$C_8$) alkyl, ($C_2$-$C_8$) alkenyl, ($C_2$-$C_8$) alkynyl, ($C_6$-$C_{20}$) aryl, ($C_3$-$C_{20}$) cycloalkyl, ($C_2$-$C_{20}$) heterocyclyl, arylalkyl, or heteroarylalkyl,
  wherein each ($C_1$-$C_8$) alkyl, ($C_2$-$C_8$)alkenyl, ($C_2$-$C_8$) alkynyl, ($C_6$-$C_{20}$) ($C_3$-$C_{20}$) cycloalkyl, ($C_2$-$C_{20}$) heterocyclyl, arylalkyl, or heteroarylalkyl is optionally substituted with 1-3 $R^{20}$ groups;
  or when taken together, two $R^y$ on the same carbon atom form a cycloalkyl ring of 3 to 7 carbon atoms;
each R is independently H, ($C_1$-$C_8$) alkyl, ($C_2$-$C_8$)alkenyl, ($C_2$-$C_8$) alkynyl, ($C_8$-$C_{20}$) aryl, ($C_3$-$C_{20}$) cycloalkyl, ($C_2$-$C_{20}$) heterocyclyl, or arylalkyl;
$R^8$ is H, ($C_1$-$C_4$) alkyl, or ($C_1$-$C_4$) substituted alkyl;
each $R^{11}$ or $R^{12}$ is independently H, ($C_1$-$C_8$)alkyl, ($C_2$-$C_8$) alkenyl, ($C_2$-$C_8$)alkynyl, ($C_4$-$C_8$)cycloalkylalkyl, ($C_3$-$C_{20}$) cycloalkyl, ($C_2$-$C_{20}$)heterocyclyl, optionally substituted aryl, optionally substituted heteroaryl, —C(=O)($C_1$-$C_8$)alkyl, —$S(O)_n$($C_1$-$C_8$)alkyl or aryl($C_1$-$C_8$)alkyl; or $R^{11}$ and $R^{12}$ taken together with a nitrogen to which they are both attached form a 3- to 7-membered heterocyclic ring wherein any one carbon atom of said heterocyclic ring can optionally be replaced with —O—, —S— or —$NR^a$—;
each $R^{13}$ is independently a cycloalkyl or heterocycle optionally substituted with 1-3 R or $R^{20}$ groups;
each $R^{20}$ is independently, halogen, CN, $N_3$, $N(R)_2$, OR, —SR, —S(O)R, —$S(O)_2$R, —S(O)(OR), —$S(O)_2$(OR), —C(=$Y^1$)R, —C(=$Y^1$)OR, or C(=$Y^1$)$N(R)_2$;
wherein each alkyl, alkenyl, alkynyl, aryl or heteroaryl of each of $R^1$, $R^2$, $R^3$, $R^4$, $R^5$, $R^8$, $R^{11}$ or $R^{12}$ is, independently, optionally substituted with 1 to 3 halo, hydroxy, CN, $N_3$, $N(R^a)_2$ or $OR^a$; and wherein 1 to 3 of the non-terminal carbon atoms of each said ($C_1$-$C_8$)alkyl may be optionally replaced with —O—, —S— or —$NR^a$—;
with the proviso that at least one of $R^1$, $R^2$, $R^3$, $R^4$ and $R^5$ is not hydrogen.

In one embodiment, the invention is directed to a method of treating a viral infection caused by a Flaviviridae virus comprising administering to a mammal in need thereof a therapeutically effective amount of a compound or pharmaceutical composition as described above. In one embodiment, the viral infection is caused by Hepatitis C virus.

In another embodiment, the invention is directed to a method of treating a viral infection caused by a Paramyxoviridae virus comprising administering to a mammal in need thereof a therapeutically effective amount of a compound or pharmaceutical composition as described above.

In another embodiment, the invention is directed to a method of treating a viral infection caused by an Orthomyxoviridae virus comprising administering to a mammal in need thereof a therapeutically effective amount of a compound or pharmaceutical composition as described above.

In still other embodiments, the invention is directed to a method of treating a viral infection caused by a Picornaviridae virus comprising administering to a mammal in need thereof a therapeutically effective amount of a compound or pharmaceutical composition as described above.

DETAILED DESCRIPTION OF EXEMPLARY EMBODIMENTS

Reference will now be made in detail to certain embodiments of the invention, examples of which are illustrated in the accompanying description, structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention.

Compounds

In one aspect, the invention provides compounds of Formula I:

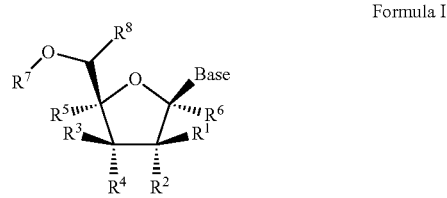

Formula I or a pharmaceutically acceptable salt thereof;
wherein:
Base is a naturally occurring or modified pyrimidine base;
$R^1$ is H, CN, $OR^a$, ($C_1$-$C_4$)alkyl, ($C_1$-$C_4$)substituted alkyl, ($C_2$-$C_4$)alkenyl, ($C_2$-$C_4$)substituted alkenyl, ($C_2$-$C_4$)alkynyl, ($C_2$-$C_4$)substituted alkynyl or $S(O)_n$—$R^a$;
$R^2$ is H, $OR^a$, $N(R^a)_2$, $N_3$, CN, $NO_2$, $S(O)_nR^a$, ($C_1$-$C_4$) alkyl, ($C_4$-$C_6$)cycloalkylalkyl, ($C_1$-$C_4$)substituted alkyl, ($C_2$-$C_4$)alkenyl, ($C_2$-$C_4$)substituted alkenyl, ($C_2$-$C_4$)alkynyl, or ($C_2$-$C_4$)substituted alkynyl;
or $R^1$ and $R^2$ taken together with the carbon to which they are attached form a 3- to 6-membered cycloalkyl ring wherein 1 to 3 carbon atoms of said cycloalkyl ring is optionally replaced by O or $S(O)_n$;
$R^3$, $R^4$, and $R^5$ are each independently H, $OR^a$, $N(R^a)_2$, $N_3$, CN, $NO_2$, $S(O)_nR^a$, halogen, ($C_1$-$C_4$)alkyl, ($C_4$-$C_8$)cycloalkylalkyl, ($C_1$-$C_4$)substituted alkyl, ($C_2$-$C_4$)alkenyl, ($C_2$-$C_4$)substituted alkenyl, ($C_2$-$C_4$)alkynyl, or ($C_2$-$C_4$)substituted alkynyl;
or any two of $R^3$, $R^4$ or $R^5$ on adjacent carbon atoms when taken together are —O(CO)O— or when taken together with the ring carbon atoms to which they are attached to form a double bond;
$R^6$ is CN, ethenyl, 2-haloethen-1-yl, or ($C_2$-$C_8$)alkyn-1-yl,
each n is independently 0, 1, or 2;

each $R^a$ is independently H, $(C_1\text{-}C_8)$alkyl, $(C_2\text{-}C_8)$alkenyl, $(C_2\text{-}C_8)$alkynyl, aryl$(C_1\text{-}C_8)$alkyl, $(C_4\text{-}C_8)$cycloalkylalkyl, —C(=O)NR$^{11}$, —C(=O)OR$^{11}$, —C(=O)NR$^{11}$R$^{12}$, —C(=O)SR$^{11}$, —S(O)R$^{11}$, —S(O)$_2$R$^{11}$, —S(O)(OR$^{11}$), —S(O)$_2$(OR$^{11}$), or —SO$_2$NR$^{11}$R$^{12}$;

$R^7$ is H, —C(=O)R$^{11}$, —C(=O)OR$^{11}$, —C(=O)NR$^{11}$R$^{12}$, —C(=O)SR$^{11}$, —S(O)R$^{11}$, —S(O)$_2$R$^{11}$, —S(O)(OR$^{11}$), —S(O)$_2$(OR$^{11}$), —SO$_2$NR$^{11}$R$^{12}$, or the group of Formula Ia

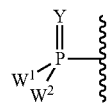

Formula Ia wherein

Y is O, S, NR, $^+$N(O)(R), N(OR), $^+$N(O)(OR), or N—NR$_2$;

$W^1$ and $W^2$, when taken together, are —Y$^3$(C(R$^y$)$_2$)$_3$Y$^3$—; or one of $W^1$ or $W^2$ together with either $R^3$ or $R^4$ is —Y$^3$— and the other of $W^1$ or $W^2$ is Formula Ib;

or $W^1$ and $W^2$ are each, independently, a group of Formula Ib:

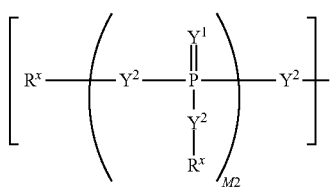

Formula Ib wherein:

each $Y^1$ is independently O, S, NR, $^+$N(O)(R), N(OR), $^+$N(O)(OR), or N—NR$_2$;

each $Y^2$ is independently a bond, O, CR$_2$, NR, $^+$N(O)(R), N(OR), $^+$N(O)(OR), N—NR$_2$, S, S—S, S(O), or S(O)$_2$;

each $Y^3$ is independently O, S, or NR;

M2 is 0, 1, or 2;

each $R^x$ is a group of Formula Ic

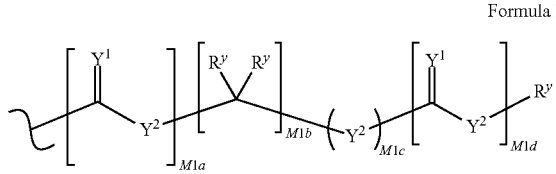

Formula Ic wherein:

each M1a, M1c, and M1d is independently 0 or 1;

M1b is 0, 1, 2, 3, 4, 5, 6, 7, 8, 9, 10, 11 or 12;

each $R^y$ is independently H, F, Cl, Br, I, —CN, —N$_3$, —NO$_2$, —OR, —C(R)$_2$—O—C(R)$_3$, —C(=Y$^1$)R, —C(=Y$^1$)R$^{13}$, —C(=Y$^1$)OR, —C(=Y$^1$)N(R)$_2$, —N(R)$_2$, —$^+$N(R)$_3$, —SR, —S(O)R, —S(O)$_2$R, —S(O)$_2$R$^{13}$, —S(O)(OR), —S(O)$_2$(OR), —OC(=Y$^1$)R, —OC(=Y$^1$)OR, —OC(=Y$^1$)(N(R)$_2$), —SC(=Y$^1$)R, —SC(=Y$^1$)OR, —SC(=Y$^1$)(N(R)$_2$), —N(R)C(=Y$^1$)R, —N(R)C(=Y$^1$)OR, —N(R)C(=Y$^1$)N(R)$_2$, —SO$_2$NR$_2$, $(C_1\text{-}C_8)$ alkyl, $(C_2\text{-}C_8)$ alkenyl, $(C_2\text{-}C_8)$ alkynyl, $(C_6\text{-}C_{20})$ aryl, $(C_3\text{-}C_{20})$ cycloalkyl, $(C_2\text{-}C_{20})$ heterocyclyl, arylalkyl, or heteroarylalkyl, wherein each $(C_1\text{-}C_8)$ alkyl, $(C_2\text{-}C_8)$alkenyl, $(C_2\text{-}C_8)$ alkynyl, $(C_6\text{-}C_{20})$ aryl, $(C_3\text{-}C_{20})$ cycloalkyl, $(C_2\text{-}C_{20})$ heterocyclyl, arylalkyl, or heteroarylalkyl is optionally substituted with 1-3 R$^{20}$ groups;

or when taken together, two $R^y$ on the same carbon atom form a cycloalkyl ring of 3 to 7 carbon atoms;

each R is independently H, $(C_1\text{-}C_8)$ alkyl, $(C_2\text{-}C_8)$alkenyl, $(C_2\text{-}C_8)$ alkynyl, $(C_8\text{-}C_{20})$ aryl, $(C_3\text{-}C_{20})$ cycloalkyl, $(C_2\text{-}C_{20})$ heterocyclyl, or arylalkyl;

$R^8$ is H, $(C_1\text{-}C_4)$ alkyl, or $(C_1\text{-}C_4)$ substituted alkyl;

each R$^{11}$ or R$^{12}$ is independently H, $(C_1\text{-}C_8)$alkyl, $(C_2\text{-}C_8)$alkenyl, $(C_2\text{-}C_8)$alkynyl, $(C_4\text{-}C_8)$cycloalkylalkyl, $(C_3\text{-}C_{20})$cycloalkyl, $(C_2\text{-}C_{20})$heterocyclyl, optionally substituted aryl, optionally substituted heteroaryl, —C(=O)$(C_1\text{-}C_8)$alkyl, —S(O)$_n$$(C_1\text{-}C_8)$alkyl or aryl$(C_1\text{-}C_8)$alkyl; or R$^{11}$ and R$^{12}$ taken together with a nitrogen to which they are both attached form a 3- to 7-membered heterocyclic ring wherein any one carbon atom of said heterocyclic ring can optionally be replaced with —O—, —S— or —NR$^a$—;

each R$^{13}$ is independently a cycloalkyl or heterocycle optionally substituted with 1-3 R or R$^{20}$ groups;

each R$^{20}$ is independently, halogen, CN, N$_3$, N(R)$_2$, OR, —SR, —S(O)R, —S(O)$_2$R, —S(O)(OR), —S(O)$_2$(OR), —C(=Y$^1$)R, —C(=Y$^1$)OR, or C(=Y$^1$)N(R)$_2$;

wherein each alkyl, alkenyl, alkynyl, aryl or heteroaryl of each of R$^1$, R$^2$, R$^3$, R$^4$, R$^5$, R$^8$, R$^{11}$ or R$^{12}$ is, independently, optionally substituted with 1 to 3 halo, hydroxy, CN, N$_3$, N(R$^a$)$_2$ or OR$^a$; and wherein 1 to 3 of the non-terminal carbon atoms of each said $(C_1\text{-}C_8)$alkyl may be optionally replaced with —O—, —S— or —NR$^a$—;

with the following provisos:

a) when R$^1$, R$^3$, and R$^5$ are hydrogen, R$^2$ and R$^4$ are hydroxy, R$^6$ is cyano and R$^7$ and R$^8$ are hydrogen, then Base is not uracil or thymine;

b) when R$^1$ and R$^4$ are hydroxy, R$^2$, R$^3$, and R$^5$ are hydrogen, R$^6$ is cyano and R$^7$ and R$^8$ are hydrogen, then Base is not uracil or cytosine;

c) when R$^1$, R$^2$, R$^3$, and R$^5$ are hydrogen, R$^4$ is hydroxy, R$^6$ is cyano and R$^7$ and R$^8$ are hydrogen, then Base is not uracil, cytosine, thymine or 5-iodo-uracil;

d) when R$^1$, R$^3$, and R$^5$ are hydrogen, R$^2$ and R$^4$ are hydroxy, R$^6$ is ethenyl and R$^7$ and R$^8$ are hydrogen, then Base is not uracil or cytosine;

e) when R$^5$ is other than H, then R$^8$ is H;

f) when R$^1$ is hydroxy, R$^2$, R$^3$, R$^5$, and R$^8$ are hydrogen, R$^6$ is cyano, R$^4$ is hydrogen or benzoyl, and R$^7$ is hydrogen or benzoyl, then Base is not cytosine;

g) when R$^1$ is acetyl or hydroxy, R$^2$, R$^3$, R$^5$, R$^7$, and W are hydrogen, R$^4$ is hydroxy or —OC(O)phenyl, then Base is not 2-oxo-4-hydroxypyrimidinyl;

h) when R$^1$ is acetoxy, R$^4$ is benzoyloxy, R$^6$ is cyano, R$^7$ is benzoyl, and R$^2$, R$^3$, R$^5$, and R$^8$ are hydrogen, then base is not uracil; and i) at least one of R$^1$, R$^2$, R$^3$, R$^4$ and R$^5$ is not hydrogen.

It should be noted that in the provisos discussed throughout when referring to the Base without specifically stating that it is substituted, such as uracil or thymine, the proviso only refers to the unsubstituted Base.

In some embodiments, R$^1$ is H, CN, OR$^a$, $(C_1\text{-}C_4)$alkyl, $(C_2\text{-}C_4)$alkenyl, or $(C_2\text{-}C_4)$alkynyl. In some embodiments, R$^1$ is hydrogen, methyl, or hydroxy.

In some embodiments, R$^2$ is H or OR$^a$. In some embodiments, R$^2$ is hydrogen, methoxy, or hydroxy.

In some embodiments, R$^1$ and R$^2$ taken together with the carbon to which they are attached form a 4-membered cycloalkyl ring wherein 1 to 3 carbon atoms of said cycloalkyl ring is optionally replaced by O.

In some embodiments, $R^3$, $R^4$, and $R^5$ are each independently H, ORE, $N_3$, CN, $(C_1-C_4)$ alkyl, or $(C_2-C_4)$ alkynyl. In some embodiments, $R^3$, $R^4$, and $R^5$ are each independently H, hydroxy, $N_3$, or —OC(O)-isopropyl.

In some embodiments, Base is uracil optionally substituted with halogen, such as, by way of example only, fluoro. In other embodiments, Base is cytosine optionally substituted with halogen, such as, by way of example only, fluoro.

In some embodiments, Base is a pyrimidine represented by Formula VI or VII:

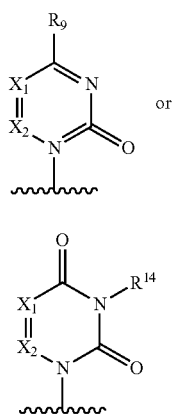

Formula VI

Formula VII or tautomer thereof,
wherein:

each $X^1$ or $X^2$ is independently C—$R^{10}$ or N provided that at least one of $X^1$ or $X^2$ is C—$R^{10}$;

each $R^9$ is H, halogen, $NR^{11}R^{12}$, $N(R^{11})OR^{11}$, $NR^{11}NR^{11}R^{12}$, $N_3$, NO, $NO_2$, $OR^{11}$ or $SR^{11}$; and each $R^{10}$ is independently H, halogen, $NR^{11}R^{12}$, $N(R^{11})OR^{11}$, $NR^{11}NR^{11}R^{12}$, $N_3$, NO, $NO_2$, CHO, CN, —CH(=NR$^{11}$), —CH=NHNR$^{11}$, —CH=N(OR$^{11}$), —CH(OR$^{11}$)$_2$, —C(=O)NR$^{11}$R$^{12}$, —C(=S)NR$^{11}$R$^{12}$, —C(=O)OR$^{11}$, $R^{11}$, $OR^{11}$ or $SR^{11}$;

each $R^{11}$ or $R^{12}$ is independently H, $(C_1-C_8)$alkyl, $(C_2-C_8)$alkenyl, $(C_2-C_8)$alkynyl, $(C_4-C_8)$cycloalkylalkyl, $(C_3-C_{20})$cycloalkyl, $(C_2-C_{20})$heterocyclyl, optionally substituted aryl, optionally substituted heteroaryl, —C(=O)(C$_1$-C$_8$)alkyl, —S(O)$_n$(C$_1$-C$_8$)alkyl or aryl(C$_1$-C$_8$)alkyl; or $R^{11}$ and $R^{12}$ taken together with a nitrogen to which they are both attached form a 3- to 7-membered heterocyclic ring wherein any one carbon atom of said heterocyclic ring can optionally be replaced with —O—, —S— or —NR$^a$—; and $R^{14}$ is H, $(C_1-C_8)$alkyl, or $(C_4-C_8)$cycloalkylalkyl.

In some embodiments, $R^6$ is CN, ethenyl, or ethynyl.

In some embodiments, $R^7$ is H or

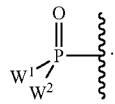

In some embodiments, $R^7$ is H or

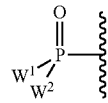

wherein $W^1$ and $W^2$ are each, independently, a group of the Formula Ib.

Additional embodiments of $R^7$ are described below.

In some embodiments,
$R^1$ is H, OH, CN, $(C_1-C_4)$alkyl, $(C_2-C_4)$alkenyl, or $(C_2-C_4)$alkynyl;
$R^2$ is H, OH or O$(C_1-C_4)$alkyl;
or $R^1$ and $R^2$ taken together with the carbon to which they are attached form a 3- to 6-membered cycloalkyl ring wherein 1 to 3 carbon atoms of said cycloalkyl ring is optionally replaced by O;
$R^3$ is H or $(C_1-C_4)$alkyl;
$R^4$ is H, OH, O$(C_1-C_4)$alkyl, or OC(O)—$(C_1-C_4)$alkyl;
$R^5$ is H, CN, $N_3$, $(C_1-C_4)$alkyl, $(C_2-C_4)$alkenyl, or $(C_2-C_4)$alkynyl;
$R^6$ is CN, ethenyl, 2-haloethen-1-yl, or $(C_2-C_8)$alkyn-1-yl; and
$R^8$ is H or $(C_1-C_4)$alkyl.

In some embodiments,
$R^1$ is H, OH, or $(C_1-C_4)$alkyl;
$R^2$ is H, OH or O$(C_1-C_4)$alkyl;
or $R^1$ and $R^2$ taken together with the carbon to which they are attached form a 4-membered cycloalkyl ring wherein one carbon atom of said cycloalkyl ring is optionally replaced by O;
$R^3$ is H or $(C_1-C_4)$alkyl;
$R^4$ is H, OH, O$(C_1-C_4)$alkyl, or —OC(O)—$(C_1-C_4)$alkyl;
$R^5$ is H, $N_3$, or $(C_1-C_4)$alkyl;
$R^6$ is CN, ethenyl, or ethynyl; and
$R^8$ is H or $(C_1-C_4)$ alkyl.

In some embodiments,
Base is a naturally occurring or modified pyrimidine base;
$R^1$ is H, OH, CN, $(C_1-C_4)$alkyl, $(C_2-C_4)$alkenyl, or $(C_2-C_4)$alkynyl;
$R^2$ is H, OH or O$(C_1-C_4)$alkyl;
or $R^1$ and $R^2$ taken together with the carbon to which they are attached form a 3- to 6-membered cycloalkyl ring wherein 1 to 3 carbon atoms of said cycloalkyl ring is optionally replaced by O;
$R^3$ is H or $(C_1-C_4)$alkyl;
$R^4$ is H, OH, O$(C_1-C_4)$alkyl, or —OC(O)—$(C_1-C_4)$alkyl;
$R^5$ is H, CN, $N_3$, $(C_1-C_4)$alkyl, $(C_2-C_4)$alkenyl, or $(C_2-C_4)$alkynyl;
$R^6$ is CN, ethenyl, 2-haloethen-1-yl, or $(C_2-C_8)$alkyn-1-yl;
$R^7$ is H, —C(=O)R$^{11}$, —C(=O)OR$^{11}$, —C(=O)NR$^{11}$R$^{12}$, —C(=O)SR$^{11}$, —S(O)R$^{11}$, S(O)$_2$R$^{11}$, —S(O)(OR$^{11}$), —S(O)$_2$(OR$^{11}$), —SO$_2$NR$^{11}$R$^{12}$, or Formula Ia

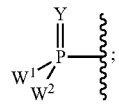

Y is O, S, NR, $^+$N(O)(R), N(OR), $^+$N(O)(OR), or N—NR$^2$;
$W^1$ and $W^2$, when taken together, are —Y$^3$(C(R$^y$)$_2$)$_3$Y$^3$—;
or one of $W^1$ or $W^2$ together with either $R^3$ or $R^4$ is —Y$^3$— and the other of $W^1$ or $W^2$ is Formula Ib;
or $W^1$ and $W^2$ are each, independently, a group of the Formula Ib:

Formula Ib $$\left[ R^x - \left( Y^2 - \underset{\underset{R^x}{\overset{Y^1}{\|}}}{\overset{Y^1}{P}} \right) - Y^2 - \right]_{M2}$$

wherein:
each $Y^1$ is independently O, S, NR, $^+N(O)(R)$, N(OR), $^+N(O)(OR)$, or N—NR$_2$;
each $Y^2$ is independently a bond, O, CR$_2$, NR, $^+N(O)(R)$, N(OR), $^+N(O)(OR)$, N—NR$_2$, S, S—S, S(O), or S(O)$_2$;
each $Y^3$ is independently O, S, or NR;
M2 is 0, 1, or 2;
each $R^8$ is independently $R^y$ or the formula:

[structure shown]

wherein:
each M1a, M1c, and M1d is independently 0 or 1;
M1b is 0, 1, 2, 3, 4, 5, 6, 7, 8, 9, 10, 11 or 12;
each $R^y$ is independently H, F, Cl, Br, I, OH, R, —C(R)$_2$—O—C(R)$_3$, —C(=Y$^1$)R, —C(=Y$^1$)R$^{13}$, —C(=Y$^1$)OR, —C(=Y$^1$)N(R)$_2$, —N(R)$_2$, —$^+$N(R)$_3$, —SR, —S(O)R, —S(O)$_2$R, —S(O)$_2$R$^{13}$, —S(O)(OR), —S(O)$_2$(OR), —OC(=Y$^1$)R, —OC(=Y$^1$)OR, —OC(=Y$^1$)(N(R)$_2$), —SC(=Y$^1$)R, —SC(=Y$^1$)OR, —SC(=Y$^1$)(N(R)$_2$), —N(R)C(=Y$^1$)R, —N(R)C(=Y$^1$)OR, —N(R)C(=Y$^1$)N(R)$_2$, —SO$_2$NR$_2$, —CN, —N$_3$, —NO$_2$, —OR, (C$_1$-C$_8$) alkyl, (C$_2$-C$_8$)alkenyl, (C$_6$-C$_{20}$) aryl, (C$_3$-C$_{20}$) cycloalkyl, (C$_2$-C$_{20}$) heterocycloalkyl, arylalkyl, or heteroarylalkyl,
wherein each (C$_1$-C$_8$) alkyl, (C$_2$-C$_8$)alkenyl, (C$_2$-C$_8$) alkynyl, (C$_6$-C$_{20}$) aryl, (C$_3$-C$_{20}$) cycloalkyl, (C$_2$-C$_{20}$) heterocyclyl, arylalkyl, or heteroarylalkyl is optionally substituted with 1-3 $R^{20}$ groups;
or when taken together, two $R^y$ on the same carbon atom form a cycloalkyl ring of 3 to 7 carbon atoms;
each R is independently H, (C$_1$-C$_8$) alkyl, (C$_2$-C$_8$)alkenyl, (C$_2$-C$_8$) alkynyl, (C$_6$-C$_{20}$) aryl, (C$_3$-C$_{20}$) cycloalkyl, (C$_2$-C$_{20}$) heterocyclyl, or arylalkyl;
$R^8$ is H, (C$_1$-C$_4$) alkyl, or (C$_1$-C$_4$) substituted alkyl;
each $R^{11}$ or $R^{12}$ is independently H, (C$_1$-C$_8$)alkyl, (C$_2$-C$_8$) alkenyl, (C$_2$-C$_8$)alkynyl, (C$_4$-C$_8$)cycloalkylalkyl, optionally substituted aryl, optionally substituted heteroaryl, —C(=O)(C$_1$-C$_8$)alkyl, —S(O)$_n$(C$_1$-C$_8$)alkyl or aryl(C$_1$-C$_8$)alkyl; or $R^{11}$ and $R^{12}$ taken together with a nitrogen to which they are both attached form a 3- to 7-membered heterocyclic ring wherein any one carbon atom of said heterocyclic ring can optionally be replaced with —O—, —S— or —NR$^a$—;
wherein each alkyl, alkenyl, alkynyl, aryl or heteroaryl of each $R^1$, $R^2$, $R^3$, $R^4$, $R^5$, $R^8$, $R^{11}$ or $R^{12}$ is, independently, optionally substituted with 1 to 3 halo, hydroxy, CN, N$_3$, N(R$^a$)$_2$ or OR$^a$; and wherein 1 to 3 of the non-terminal carbon atoms of each said (C$_1$-C$_8$)alkyl may be optionally replaced with —O—, —S— or —NR$^a$—;
provided that least one of $R^1$, $R^2$, $R^3$, and $R^4$ are hydroxy.
In some embodiments, $R^7$ is H or

[structures shown]

In some embodiments, the group —R$^7$—O—C(R$^8$)—C(R$^5$)—C(R$^3$)(R$^4$)— is of the following formula:

[structure shown]

In some embodiments, the group —R$^7$—O—C(R$^8$)—C(R$^5$)—C(R$^3$)(R$^4$)— is of the following formula:

[structure shown]

In some embodiments, the compound is of the following formula:

[structure shown]

In some embodiments, the compound is of the following formula:

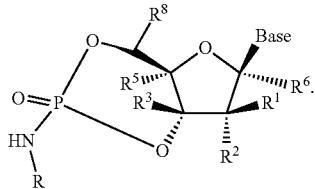

In some embodiments, at least one of $R^1$, $R^2$, $R^3$, and $R^4$ are hydroxy. In some embodiments, at least two of $R^1$, $R^2$, $R^3$, and $R^4$ are hydroxy.

In some embodiments, the compound is represented by Formula II:

Formula II

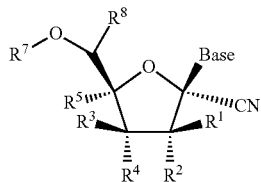

wherein each Y and $Y^1$ is O and each of Base, $R^1$, $R^2$, $R^3$, $R^4$, $R^5$, $R^7$, and $R^8$ is as described above.

In some embodiments, the compound is represented by Formula III:

Formula III

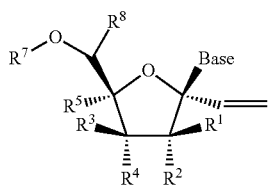

wherein each Y and $Y^1$ is O and each of Base, $R^1$, $R^2$, $R^3$, $R^4$, $R^5$, $R^7$, and $R^8$ is as described above.

In some embodiments, the compound is represented by Formula IV:

Formula IV

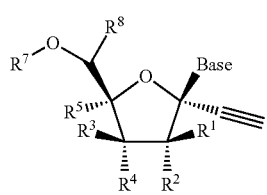

wherein each Y and $Y^1$ is O and each of Base, $R^1$, $R^2$, $R^3$, $R^4$, $R^5$, $R^7$, and $R^8$ is as described above.

In some embodiments, the compound is represented by Formula V:

Formula V

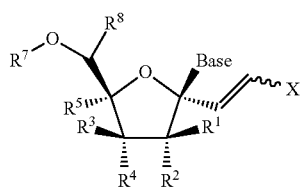

wherein each Y and $Y^1$ is O and X is halogen and each of Base, $R^1$, $R^2$, $R^3$, $R^4$, $R^5$, $R^7$, and $R^8$ is as described above. In some embodiments, halogen is fluoro, chloro, or iodo. In some embodiments, bromovinyl groups are not included in the $R^6$ position.

In another embodiment, the compound of Formula I-V is a compound selected from the group consisting of:

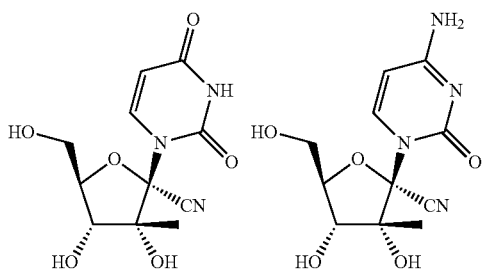

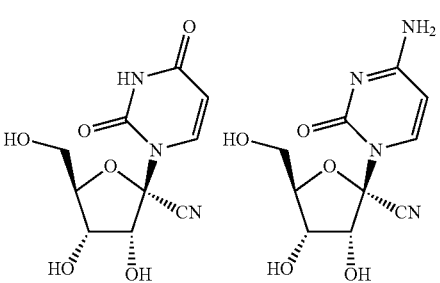

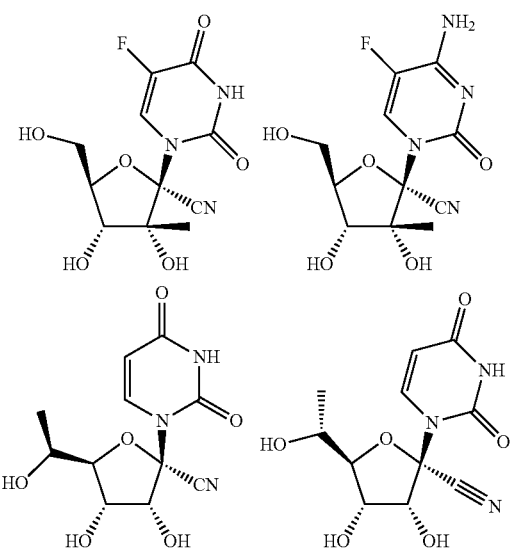

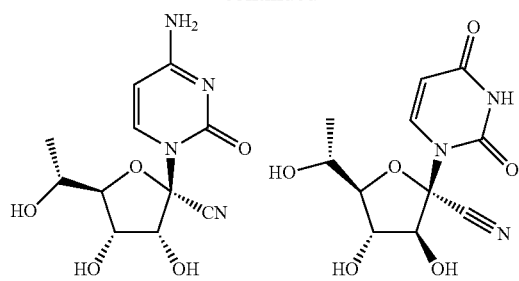
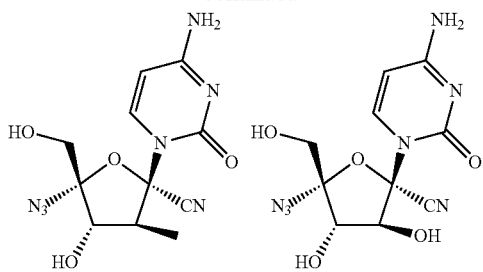
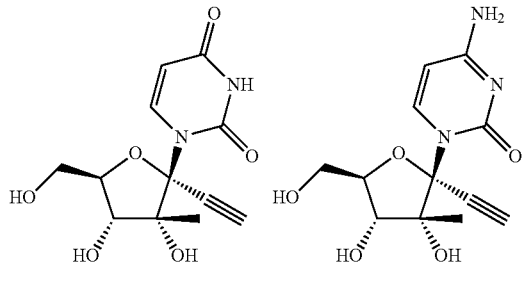
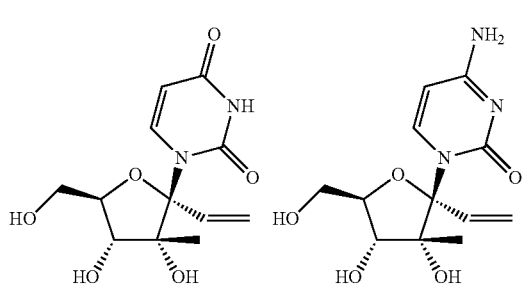
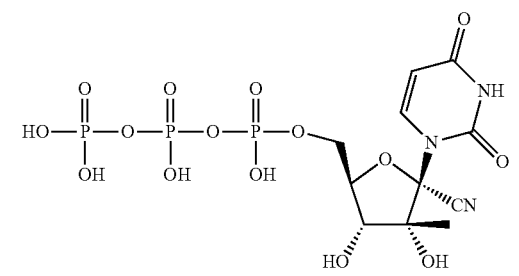
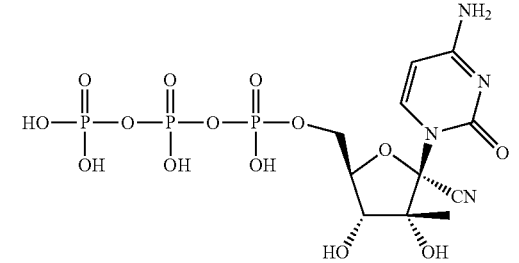
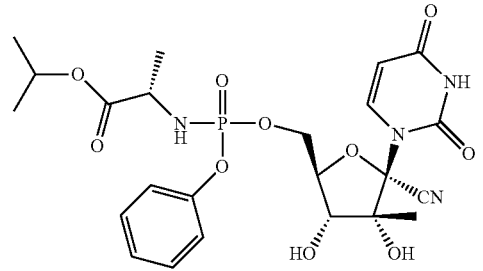

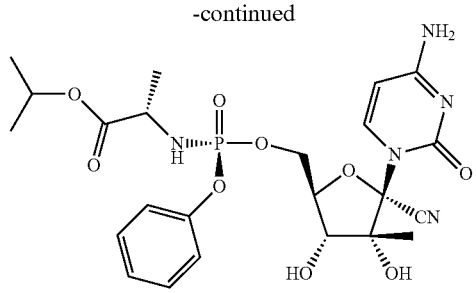
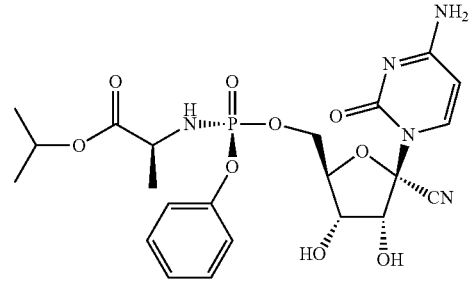
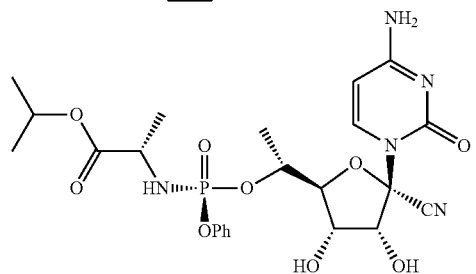
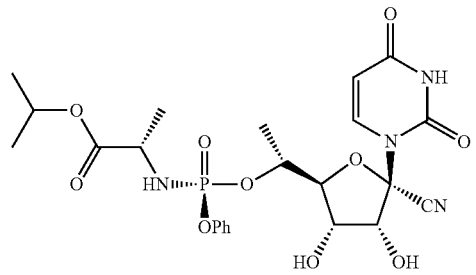
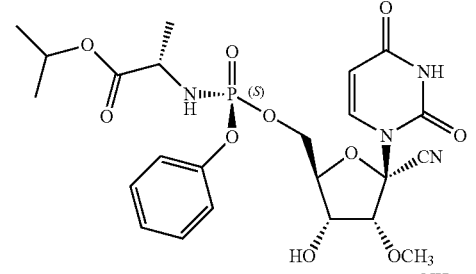
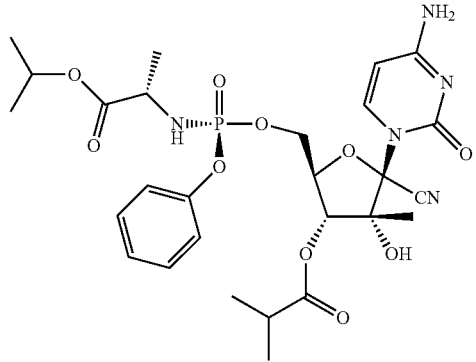
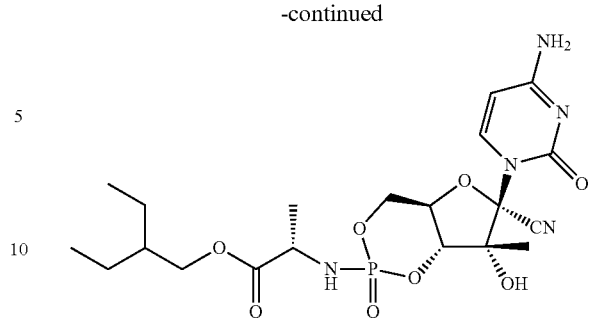
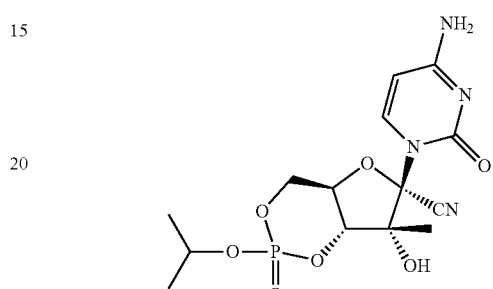
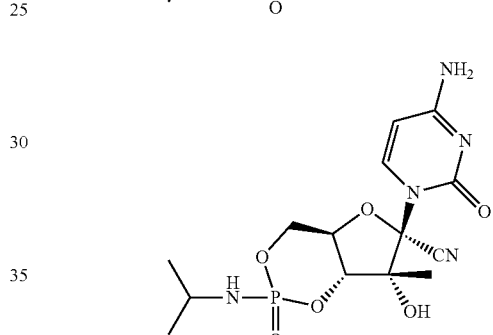
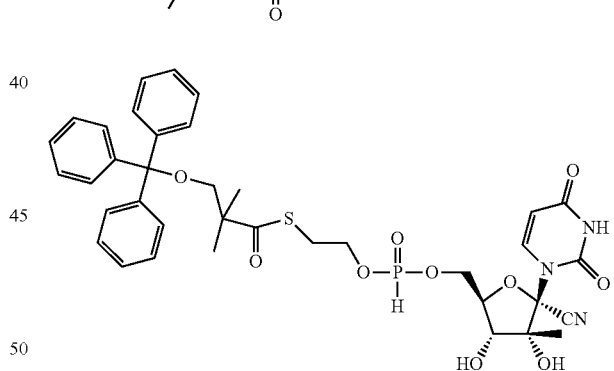
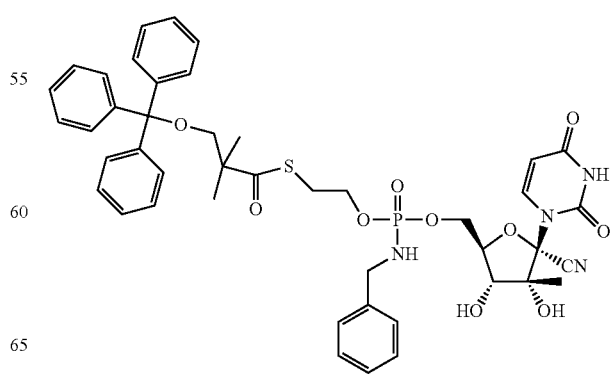

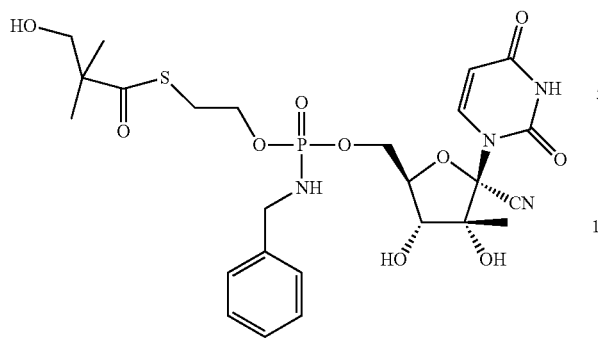
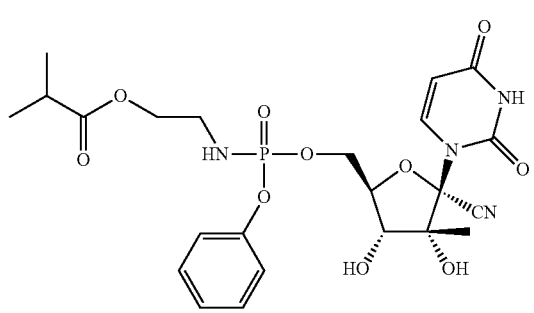 [SMILES: CC(C)C(=O)OCCNP(=O)(OC[C@H]1O[C@@](C#N)(n2ccc(=O)[nH]c2=O)[C@](C)(O)[C@@H]1O)Oc1ccccc1]
or a pharmaceutically acceptable salt thereof.
In another embodiment, the compound of Formula I-V is a compound selected from the group consisting of:
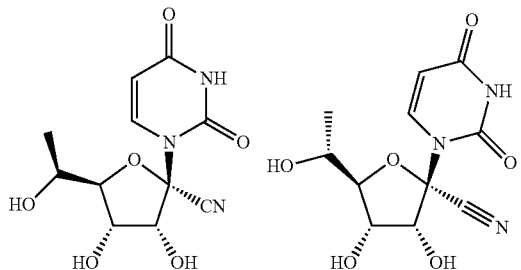
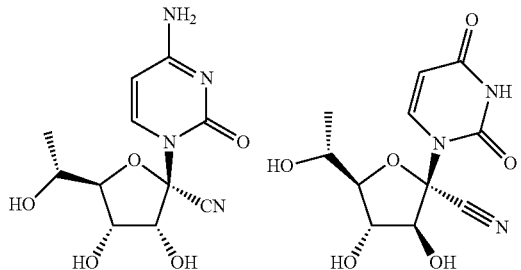
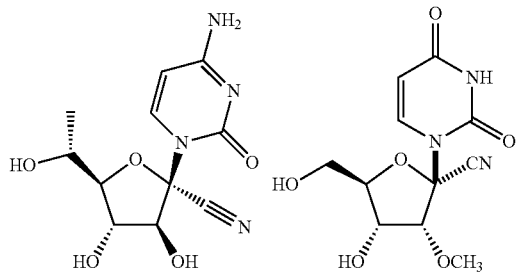
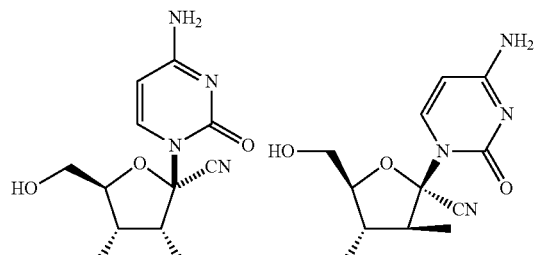
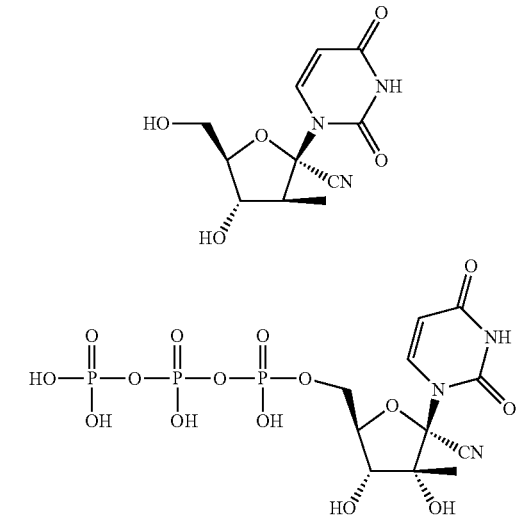

-continued

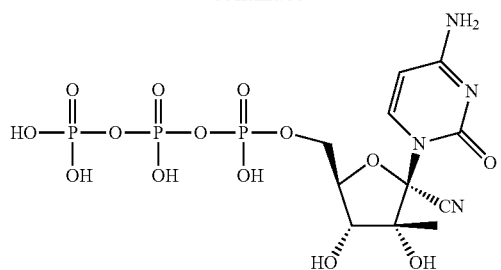

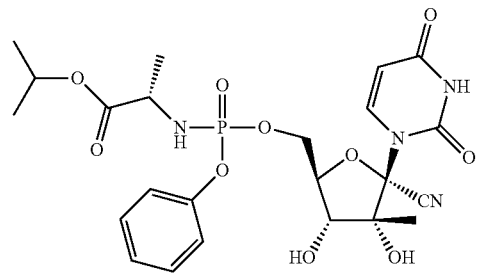

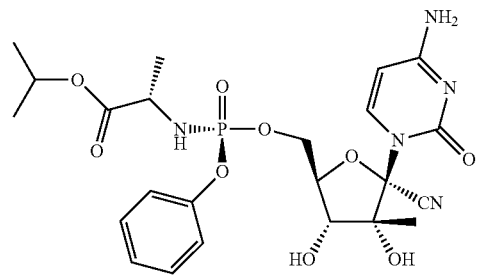

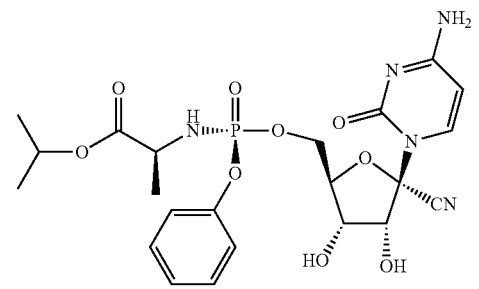

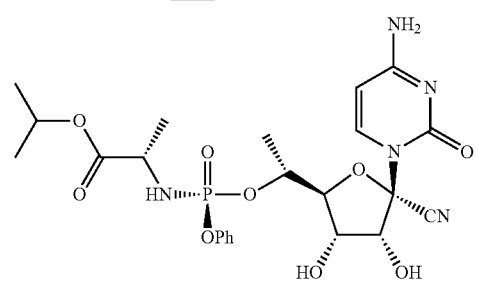

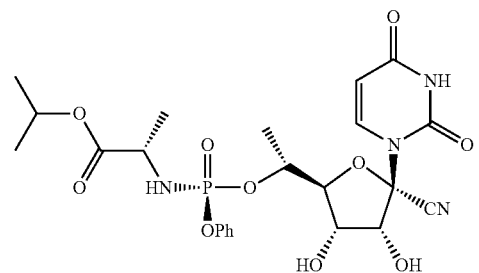

-continued

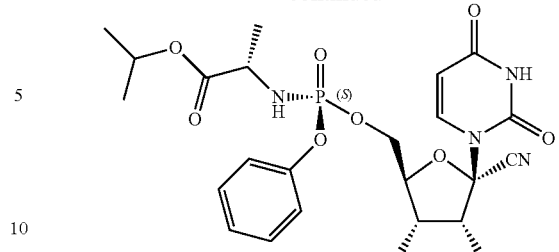

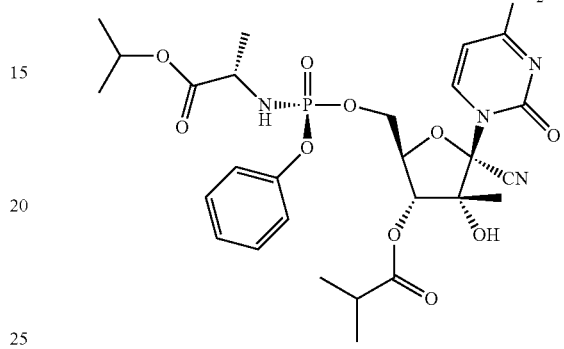

or a pharmaceutically acceptable salt thereof.

In some embodiments, the following compound is not included in the compounds but may be useful in the methods of the invention:

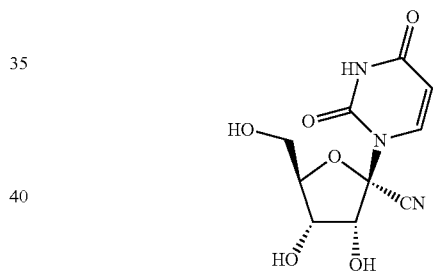

Pharmaceutical Compositions

In another embodiment, provided are pharmaceutical compositions comprising an effective amount of a Formula I-V compound, or a compound as described herein, or a pharmaceutically acceptable salt thereof, in combination with a pharmaceutically acceptable diluent or carrier.

In another embodiment, provided are pharmaceutical compositions comprising a pharmaceutically acceptable diluent or carrier in combination with an effective amount of a compound of Formula I:

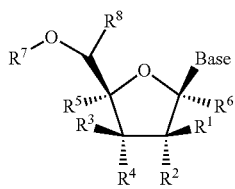

Formula I or a pharmaceutically acceptable salt thereof;

wherein:
Base is a naturally occurring or modified pyrimidine base;
$R^1$ is H, CN, $OR^a$, $(C_1-C_4)$alkyl, $(C_1-C_4)$substituted alkyl, $(C_2-C_4)$alkenyl, $(C_2-C_4)$substituted alkenyl, $(C_2-C_4)$alkynyl, $(C_2-C_4)$substituted alkynyl or $S(O)_nR^a$;
$R^2$ is H, $OR^a$, $N(R^a)_2$, $N_3$, CN, $NO_2$, $S(O)_nR^a$, $(C_1-C_4)$alkyl, $(C_4-C_6)$cycloalkylalkyl, $(C_1-C_4)$substituted alkyl, $(C_2-C_4)$alkenyl, $(C_2-C_4)$substituted alkenyl, $(C_2-C_4)$alkynyl, or $(C_2-C_4)$substituted alkynyl;
or $R^1$ and $R^2$ taken together with the carbon to which they are attached form a 3- to 6-membered cycloalkyl ring wherein 1 to 3 carbon atoms of said cycloalkyl ring is optionally replaced by O or $S(O)_n$;
$R^3$, $R^4$, and $R^5$ are each independently H, $OR^a$, $N(R^a)_2$, $N_3$, CN, $NO_2$, $S(O)_nR^a$, halogen, $(C_1-C_4)$alkyl, $(C_4-C_8)$cycloalkylalkyl, $(C_1-C_4)$substituted alkyl, $(C_2-C_4)$alkenyl, $(C_2-C_4)$substituted alkenyl, $(C_2-C_4)$alkynyl, or $(C_2-C_4)$substituted alkynyl;
or any two of $R^3$, $R^4$ or $R^5$ on adjacent carbon atoms when taken together are —O(CO)O— or when taken together with the ring carbon atoms to which they are attached to form a double bond;
$R^6$ is CN, ethenyl, 2-haloethen-1-yl, or $(C_2-C_8)$alkyn-1-yl, each n is independently 0, 1, or 2;
each $R^a$ is independently H, $(C_1-C_8)$alkyl, $(C_2-C_8)$alkenyl, $(C_2-C_8)$alkynyl, aryl$(C_1-C_8)$alkyl, $(C_4-C_8)$cycloalkylalkyl, —C(=O)$R^{11}$, —C(=O)O$R^{11}$, —C(=O)N$R^{11}R^{12}$, —C(=O)S$R^{11}$, —S(O)$R^{11}$, —S(O)$_2R^{11}$, —S(O)(O$R^{11}$), —S(O)$_2$(O$R^{11}$), or —SO$_2$N$R^{11}R^{12}$;
$R^7$ is H, —C(=O)$R^{11}$, —C(=O)O$R^{11}$, —C(=O)N$R^{11}R^{12}$, —C(=O)S$R^{11}$, —S(O)$R^{11}$, —S(O)$_2R^{11}$, —S(O)(O$R^{11}$), —S(O)$_2$(O$R^{11}$), —SO$_2$N$R^{11}R^{12}$, or the group of Formula Ia

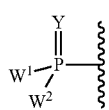

Formula Ia wherein
Y is O, S, NR, $^+$N(O)(R), N(OR), $^+$N(O)(OR), or N—NR$_2$;
$W^1$ and $W^2$, when taken together, are —$Y^3$(C(R$^y$)$_2$)$_3Y^3$—;
or one of $W^1$ or $W^2$ together with either $R^3$ or $R^4$ is —$Y^3$— and the other of $W^1$ or $W^2$ is Formula Ib;
or $W^1$ and $W^2$ are each, independently, a group of Formula Ib:

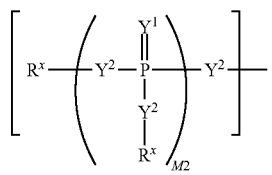

Formula Ib wherein:
each $Y^1$ is independently O, S, NR, $^+$N(O)(R), N(OR), $^+$N(O)(OR), or N—NR$_2$;
each $Y^2$ is independently a bond, O, CR$_2$, NR, $^+$N(O)(R), N(OR), $^+$N(O)(OR), N—NR$_2$, S, S—S, S(O), or S(O)$_2$;
each $Y^3$ is independently O, S, or NR;
M2 is 0, 1, or 2;

each $R^x$ is a group of Formula Ic

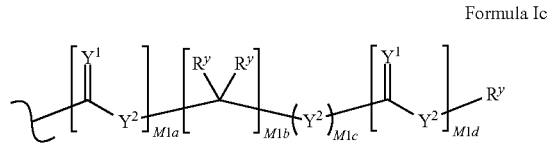

Formula Ic wherein:
each M1a, M1c, and M1d is independently 0 or 1;
M1b is 0, 1, 2, 3, 4, 5, 6, 7, 8, 9, 10, 11 or 12;
each $R^y$ is independently H, F, Cl, Br, I, —CN, —N$_3$, —NO$_2$, —OR, —C(R)$_2$—O—C(R)$_3$, —C(=$Y^1$)R, —C(=$Y^1$)R$^{13}$, —C(=$Y^1$)OR, —C(=$Y^1$)N(R)$_2$, —N(R)$_2$, —$^+$N(R)$_3$, —SR, —S(O)R, —S(O)$_2$R, —S(O)$_2R^{13}$, —S(O)(OR), —S(O)$_2$(OR), —OC(=$Y^1$)R, —OC(=$Y^1$)OR, —OC(=$Y^1$)(N(R)$_2$), —SC(=$Y^1$)R, —SC(=$Y^1$)OR, —SC(=$Y^1$)(N(R)$_2$), —N(R)C(=$Y^1$)R, —N(R)C(=$Y^1$)OR, —N(R)C(=$Y^1$)N(R)$_2$, —SO$_2$NR$_2$, $(C_1-C_8)$ alkyl, $(C_2-C_8)$ alkenyl, $(C_2-C_8)$ alkynyl, $(C_6-C_{20})$ aryl, $(C_3-C_{20})$ cycloalkyl, $(C_2-C_{20})$ heterocyclyl, arylalkyl, or heteroarylalkyl,
wherein each $(C_1-C_8)$ alkyl, $(C_2-C_8)$alkenyl, $(C_2-C_8)$ alkynyl, $(C_6-C_{20})$ aryl, $(C_3-C_{20})$ cycloalkyl, $(C_2-C_{20})$ heterocyclyl, arylalkyl, or heteroarylalkyl is optionally substituted with 1-3 $R^{20}$ groups;
or when taken together, two $R^y$ on the same carbon atom form a cycloalkyl ring of 3 to 7 carbon atoms;
each R is independently H, $(C_1-C_8)$ alkyl, $(C_2-C_8)$alkenyl, $(C_2-C_8)$ alkynyl, $(C_6-C_{20})$ aryl, $(C_3-C_{20})$ cycloalkyl, $(C_2-C_{20})$ heterocyclyl, or arylalkyl;
$R^8$ is H, $(C_1-C_4)$ alkyl, or $(C_1-C_4)$ substituted alkyl;
each $R^{11}$ or $R^{12}$ is independently H, $(C_1-C_8)$alkyl, $(C_2-C_8)$ alkenyl, $(C_2-C_8)$alkynyl, $(C_4-C_8)$cycloalkylalkyl, $(C_3-C_{20})$ cycloalkyl, $(C_2-C_{20})$heterocyclyl, optionally substituted aryl, optionally substituted heteroaryl, —C(=O)$(C_1-C_8)$alkyl, —S(O)$_n(C_1-C_8)$alkyl or aryl$(C_1-C_8)$alkyl; or $R^{11}$ and $R^{12}$ taken together with a nitrogen to which they are both attached form a 3- to 7-membered heterocyclic ring wherein any one carbon atom of said heterocyclic ring can optionally be replaced with —O—, —S— or —NR$^a$—;
each $R^{13}$ is independently a cycloalkyl or heterocycle optionally substituted with 1-3 R or $R^{20}$ groups;
each $R^{20}$ is independently, halogen, CN, N$_3$, N(R)$_2$, OR, —SR, —S(O)R, —S(O)$_2$R, —S(O)(OR), —S(O)$_2$(OR), —C(=$Y^1$)R, —C(=$Y^1$)OR, or C(=$Y^1$)N(R)$_2$;
wherein each alkyl, alkenyl, alkynyl, aryl or heteroaryl of each of $R^1$, $R^2$, $R^3$, $R^4$, $R^5$, $R^8$, $R^{11}$ or $R^{12}$ is, independently, optionally substituted with 1 to 3 halo, hydroxy, CN, N$_3$, N(R$^a$)$_2$ or OR$^a$; and wherein 1 to 3 of the non-terminal carbon atoms of each said $(C_1-C_8)$alkyl may be optionally replaced with —O—, —S— or —NR$^a$—
with the proviso that at least one of $R^1$, $R^2$, $R^3$, $R^4$ and $R^5$ is not hydrogen.

In another embodiment, the pharmaceutical compositions further comprise at least one additional therapeutic agent selected from the group consisting of interferons, ribavirin analogs, NS3 protease inhibitors, NS5a inhibitors, NS5b polymerase inhibitors, alpha-glucosidase 1 inhibitors, cyclophilin inhibitors, hepatoprotectants, other nucleoside inhibitors of HCV, non-nucleoside inhibitors of HCV, and other drugs for treating HCV.

In still other embodiments, the pharmaceutical compositions further comprise at least one viral neuramidase inhibitor or viral M2 channel inhibitor, such as, by way of example only oseltamivir, zanamivir, laninamivir, peramivir, amantadine and rimantadine.

Additional combination therapies are provided below.

Methods

In another embodiment, is provided a method of inhibiting HCV polymerase comprising administering to a mammal in need thereof a compound of the invention.

In another embodiment, the present invention is directed to a method of inhibiting HCV polymerase comprising administering to a mammal in need thereof a therapeutically effective amount of a compound of Formula I:

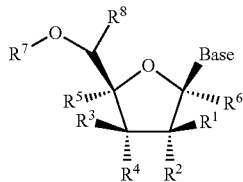

Formula I or a pharmaceutically acceptable salt thereof;
wherein:
Base is a naturally occurring or modified pyrimidine base;
$R^1$ is H, CN, $OR^a$, $(C_1\text{-}C_4)$alkyl, $(C_1\text{-}C_4)$substituted alkyl, $(C_2\text{-}C_4)$alkenyl, $(C_2\text{-}C_4)$substituted alkenyl, $(C_2\text{-}C_4)$alkynyl, $(C_2\text{-}C_4)$substituted alkynyl or $S(O)_nR^a$;
$R^2$ is H, $OR^a$, $N(R^a)_2$, $N_3$, CN, $NO_2$, $S(O)_nR^a$, $(C_1\text{-}C_4)$ alkyl, $(C_4\text{-}C_6)$cycloalkylalkyl, $(C_1\text{-}C_4)$substituted alkyl, $(C_2\text{-}C_4)$alkenyl, $(C_2\text{-}C_4)$substituted alkenyl, $(C_2\text{-}C_4)$alkynyl, or $(C_2\text{-}C_4)$substituted alkynyl;
or $R^1$ and $R^2$ taken together with the carbon to which they are attached form a 3- to 6-membered cycloalkyl ring wherein 1 to 3 carbon atoms of said cycloalkyl ring is optionally replaced by O or $S(O)_n$;
$R^3$, $R^4$, and $R^5$ are each independently H, $OR^a$, $N(R^a)_2$, $N_3$, CN, $NO_2$, $S(O)_nR^a$, halogen, $(C_1\text{-}C_4)$alkyl, $(C_4\text{-}C_8)$cycloalkylalkyl, $(C_1\text{-}C_4)$substituted alkyl, $(C_2\text{-}C_4)$alkenyl, $(C_2\text{-}C_4)$substituted alkenyl, $(C_2\text{-}C_4)$alkynyl, or $(C_2\text{-}C_4)$substituted alkynyl;
or any two of $R^3$, $R^4$ or $R^5$ on adjacent carbon atoms when taken together are —O(CO)O— or when taken together with the ring carbon atoms to which they are attached to form a double bond;
$R^6$ is CN, ethenyl, 2-haloethen-1-yl, or $(C_2\text{-}C_8)$alkyn-1-yl,
each n is independently 0, 1, or 2;
each $R^a$ is independently H, $(C_1\text{-}C_8)$alkyl, $(C_2\text{-}C_8)$alkenyl, $(C_2\text{-}C_8)$alkynyl, aryl$(C_1\text{-}C_8)$alkyl, $(C_4\text{-}C_8)$cycloalkylalkyl, —C(=O)$R^{11}$, —C(=O)$OR^{11}$, —C(=O)$NR^{11}R^{12}$, —C(=O)$SR^{11}$, —S(O)$R^{11}$, —S(O)$_2R^{11}$, —S(O)(OR$^{11}$), —S(O)$_2$(OR$^{11}$), or —SO$_2NR^{11}R^{12}$;
$R^7$ is H, —C(=O)$R^{11}$, —C(=O)$OR^{11}$, —C(=O)$NR^{11}R^{12}$, —C(=O)$SR^{11}$, —S(O)$R^{11}$, —S(O)$_2R^{11}$, —S(O)(OR$^{11}$), —S(O)$_2$(OR$^{11}$), —SO$_2NR^{11}R^{12}$, or the group of Formula Ia

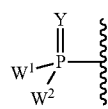

Formula Ia wherein
Y is O, S, NR, $^+$N(O)(R), N(OR), $^+$N(O)(OR), or N—NR$_2$;
$W^1$ and $W^2$, when taken together, are —Y$^3$(C(R$^y$)$_2$)$_3$Y$^3$—;

or one of $W^1$ or $W^2$ together with either $R^3$ or $R^4$ is —Y$^3$— and the other of $W^1$ or $W^2$ is Formula Ib;
or $W^1$ and $W^2$ are each, independently, a group of Formula Ib:

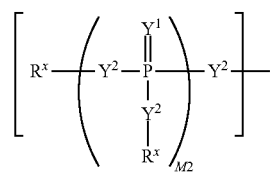

Formula Ib wherein:
each $Y^1$ is independently O, S, NR, $^+$N(O)(R), N(OR), $^+$N(O)(OR), or N—NR$_2$;
each $Y^2$ is independently a bond, O, CR$_2$, NR, $^+$N(O)(R), N(OR), $^+$N(O)(OR), N—NR$_2$, S, S—S, S(O), or S(O)$_2$;
each $Y^3$ is independently O, S, or NR;
M2 is 0, 1, or 2;
each $R^x$ is a group of Formula Ic

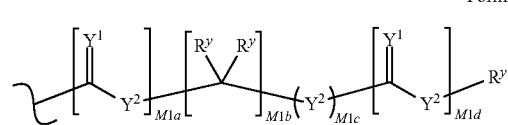

Formula Ic wherein:
each M1a, M1c, and M1d is independently 0 or 1;
M1b is 0, 1, 2, 3, 4, 5, 6, 7, 8, 9, 10, 11 or 12;
each $R^y$ is independently H, F, Cl, Br, I, —CN, —N$_3$, —NO$_2$, —OR, —C(R)$_2$—O—C(R)$_3$, —C(=Y$^1$)R, —C(=Y$^1$)R$^{13}$, —C(=Y$^1$)OR, —C(=Y$^1$)N(R)$_2$, —N(R)$_2$, —$^+$N(R)$_3$, —SR, —S(O)R, —S(O)$_2$R, —S(O)$_2$R$^{13}$, —S(O)(OR), —S(O)$_2$(OR), —OC(=Y$^1$)R, —OC(=Y$^1$)OR, —OC(=Y$^1$)(N(R)$_2$), —SC(=Y$^1$)R, —SC(=Y$^1$)OR, —SC(=Y$^1$)(N(R)$_2$), —N(R)C(=Y$^1$)R, —N(R)C(=Y$^1$)OR, —N(R)C(=Y$^1$)N(R)$_2$, —SO$_2NR_2$, $(C_1\text{-}C_8)$ alkyl, $(C_2\text{-}C_8)$ alkenyl, $(C_2\text{-}C_8)$ alkynyl, $C_6\text{-}C_{20}$ aryl, $C_3\text{-}C_{20}$ cycloalkyl, $C_2\text{-}C_{20}$ heterocyclyl, arylalkyl, or heteroarylalkyl,
wherein each $(C_1\text{-}C_8)$ alkyl, $(C_2\text{-}C_8)$alkenyl, $(C_2\text{-}C_8)$ alkynyl, $(C_6\text{-}C_{20})$ aryl, $(C_3\text{-}C_{20})$ cycloalkyl, $(C_2\text{-}C_{20})$ heterocyclyl, arylalkyl, or heteroarylalkyl is optionally substituted with 1-3 $R^{20}$ groups;
or when taken together, two $R^y$ on the same carbon atom form a cycloalkyl ring of 3 to 7 carbon atoms;
each R is independently H, $(C_1\text{-}C_8)$ alkyl, $(C_2\text{-}C_8)$alkenyl, $(C_2\text{-}C_8)$ alkynyl, $C_6\text{-}C_{20}$ aryl, $C_3\text{-}C_{20}$ cycloalkyl, $C_2\text{-}C_{20}$ heterocyclyl, or arylalkyl;
$R^8$ is H, $(C_1\text{-}C_4)$ alkyl, or $(C_1\text{-}C_4)$ substituted alkyl;
each $R^{11}$ or $R^{12}$ is independently H, $(C_1\text{-}C_8)$alkyl, $(C_2\text{-}C_8)$alkenyl, $(C_2\text{-}C_8)$alkynyl, $(C_4\text{-}C_8)$cycloalkylalkyl, $(C_3\text{-}C_{20})$ cycloalkyl, $(C_2\text{-}C_{20})$heterocyclyl, optionally substituted aryl, optionally substituted heteroaryl, —C(=O)(C$_1$-C$_8$)alkyl, —S(O)$_o$(C$_1$-C$_8$)alkyl or aryl(C$_1$-C$_8$)alkyl; or $R^{11}$ and $R^{12}$ taken together with a nitrogen to which they are both attached form a 3- to 7-membered heterocyclic ring wherein any one carbon atom of said heterocyclic ring can optionally be replaced with —O—, —S— or —NR$^a$—;
each $R^{13}$ is independently a cycloalkyl or heterocycle optionally substituted with 1-3 R or $R^{20}$ groups;

each $R^{20}$ is independently, halogen, CN, $N_3$, $N(R)_2$, OR, —SR, —S(O)R, —S(O)$_2$R, —S(O)(OR), —S(O)$_2$(OR), —C(=Y$^1$)R, —C(=Y$^1$)OR, or C(=Y$^1$)N(R)$_2$;

wherein each alkyl, alkenyl, alkynyl, aryl or heteroaryl of each of $R^1$, $R^2$, $R^3$, $R^4$, $R^5$, $R^8$, $R^{11}$ or $R^{12}$ is, independently, optionally substituted with 1 to 3 halo, hydroxy, CN, $N_3$, $N(R^a)_2$ or OR$^a$; and wherein 1 to 3 of the non-terminal carbon atoms of each said ($C_1$-$C_8$)alkyl may be optionally replaced with —O—, —S— or —NR$^a$—;

with the proviso that at least one of $R^1$, $R^2$, $R^3$, $R^4$ and $R^5$ is not hydrogen.

In one embodiment, the invention is directed to a method of treating a viral infection caused by a Flaviviridae virus comprising administering to a mammal in need thereof a therapeutically effective amount of a compound or pharmaceutical composition as described above. In some embodiments, the virus is selected from the group consisting of dengue virus, yellow fever virus, West Nile virus, Japanese encephalitis virus, tick-borne encephalitis virus, Kunjin virus, Murray Valley encephalitis virus, St. Louis encephalitis virus, Omsk hemorrhagic fever virus, bovine viral diarrhea virus, Zika virus and Hepatitis C virus. In one embodiment, the viral infection is caused by Hepatitis C virus.

In methods of the invention, the method further comprises administering at least one additional therapeutic agent selected from the group consisting of interferons, ribavirin analogs, NS3 protease inhibitors, NS5b polymerase inhibitors, NS5a inhibitors, alpha-glucosidase 1 inhibitors, cyclophilin inhibitors, hepatoprotectants, other nucleoside inhibitors of HCV, non-nucleoside inhibitors of HCV, and other drugs for treating HCV.

In another embodiment, the invention is directed to a method of treating a viral infection caused by a Paramyxoviridae virus comprising administering to a mammal in need thereof a therapeutically effective amount of a compound or pharmaceutical composition as described above. In one embodiment, the virus is a respiratory syncytial virus.

In another embodiment, the invention is directed to a method of treating a viral infection caused by an Orthomyxoviridae virus comprising administering to a mammal in need thereof a therapeutically effective amount of a compound or pharmaceutical composition as described above. In some embodiments, the virus is an Influenzavirus A, Influenzavirus B or Influenzavirus C. In some embodiments, the method further comprises administering at least one additional therapeutic agent selected from the group consisting of oseltamivir, zanamivir, laninamivir, peramivir, amantadine and rimantadine.

In still other embodiments, the invention is directed to a method of treating a viral infection caused by a Picornaviridae virus comprising administering to a mammal in need thereof a therapeutically effective amount of a compound or pharmaceutical composition as described above. In some methods, the virus is an Enterovirus. In some methods, an additional agent, such as pleconaril and/or BTA-798 are administered.

DEFINITIONS

Unless stated otherwise, the following terms and phrases as used herein are intended to have the following meanings:

When trade names are used herein, applicants intend to independently include the trade name product and the active pharmaceutical ingredient(s) of the trade name product.

As used herein, "a compound," "a compound of the invention," or "a compound of Formula I" means a compound of Formula I or a pharmaceutically acceptable salt, thereof.

Similarly, with respect to isolatable intermediates, the phrase "a compound of Formula (number)" means a compound of that formula and pharmaceutically acceptable salts, thereof.

"Alkyl" is hydrocarbon containing normal, secondary, tertiary or cyclic carbon atoms. For example, an alkyl group can have 1 to 20 carbon atoms (i.e., $C_1$-$C_{20}$ alkyl), 1 to 8 carbon atoms (i.e., $C_1$-$C_8$ alkyl), 1 to 6 carbon atoms (i.e., $C_1$-$C_6$ alkyl) or 1 to 4 carbon atoms (i.e., $C_1$-$C_4$ alkyl). Examples of suitable alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (1-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), and octyl (—(CH$_2$)$_7$CH$_3$).

"Alkoxy" means a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), or 1 to 6 carbon atoms (i.e., $C_1$-$C_6$ alkoxy). Examples of suitable alkoxy groups include, but are not limited to, methoxy (—O—CH$_3$ or —OMe), ethoxy (—OCH$_2$CH$_3$ or —OEt), t-butoxy (—O—C(CH$_3$)$_3$ or —OtBu) and the like.

"Haloalkyl" is an alkyl group, as defined above, in which one or more hydrogen atoms of the alkyl group is replaced with a halogen atom. The alkyl portion of a haloalkyl group can have 1 to 20 carbon atoms (i.e., $C_1$-$C_{20}$ haloalkyl), 1 to 12 carbon atoms (i.e., $C_1$-$C_{12}$ haloalkyl), or 1 to 6 carbon atoms (i.e., $C_1$-$C_6$ alkyl). Examples of suitable haloalkyl groups include, but are not limited to, —CF$_3$, —CHF$_2$, —CFH$_2$, —CH$_2$CF$_3$, and the like.

"Alkenyl" is a hydrocarbon containing normal, secondary, tertiary or cyclic carbon atoms with at least one site of unsaturation, i.e., a carbon-carbon, sp$^2$ double bond. For example, an alkenyl group can have 2 to 20 carbon atoms (i.e., $C_2$-$C_{20}$ alkenyl), 2 to 8 carbon atoms (i.e., $C_2$-$C_8$ alkenyl), 2 to 6 carbon atoms (i.e., $C_2$-$C_6$ alkenyl) or 2 to 4 carbon atoms (i.e., $C_2$-$C_4$ alkenyl). Examples of suitable alkenyl groups include, but are not limited to, ethenyl or vinyl (both having a structure —CH=CH$_2$), allyl (—CH$_2$CH=CH$_2$), cyclopentenyl (—C$_5$H$_7$), and 5-hexenyl (—CH$_2$CH$_2$CH$_2$CH$_2$CH=CH$_2$).

"Alkynyl" is a hydrocarbon containing normal, secondary, tertiary or cyclic carbon atoms with at least one site of unsaturation, i.e., a carbon-carbon, sp triple bond. For example, an alkynyl group can have 2 to 20 carbon atoms (i.e., $C_2$-$C_{20}$ alkynyl), 2 to 8 carbon atoms (i.e., $C_2$-$C_8$ alkyne,), 2 to 6 carbon atoms (i.e., $C_2$-$C_6$ alkynyl), or 2 to 4 carbon atoms (i.e., $C_2$-$C_4$ alkynyl). Examples of suitable alkynyl groups include, but are not limited to, ethynyl or acetylenic (—C≡CH), propargyl (—CH$_2$C≡CH), and the like.

"Alkylene" refers to a saturated, branched or straight chain or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Typical alkylene radicals include, but are not limited to, methylene (—$CH_2$—), 1,1-ethyl (—CH($CH_3$)—), 1,2-ethyl (—$CH_2CH_2$—), 1,1-propyl (—CH($CH_2CH_3$)—), 1,2-propyl (—$CH_2$CH($CH_3$)—), 1,3-propyl (—$CH_2CH_2CH_2$—), 1,4-butyl (—$CH_2CH_2CH_2CH_2$—), and the like.

"Alkenylene" refers to an unsaturated, branched or straight chain or cyclic hydrocarbon radical having two monovalent radical centers derived by the removal of two hydrogen atoms from the same or two different carbon atoms of a parent alkene. For example, and alkenylene group can have 1 to 20 carbon atoms, 1 to 10 carbon atoms, or 1 to 6 carbon atoms. Typical alkenylene radicals include, but are not limited to, 1,2-ethylene (—CH=CH—).

"Alkynylene" refers to an unsaturated, branched or straight chain or cyclic hydrocarbon radical having two monovalent radical centers derived by the removal of two hydrogen atoms from the same or two different carbon atoms of a parent alkyne. For example, an alkynylene group can have 1 to 20 carbon atoms, 1 to 10 carbon atoms, or 1 to 6 carbon atoms. Typical alkynylene radicals include, but are not limited to, acetylene (—C≡C—), propargyl (—$CH_2$C≡C—), and 4-pentynyl (—$CH_2CH_2CH_2$C≡C—).

"Amino" refers generally to a nitrogen radical which can be considered a derivative of ammonia, having the formula —N(X)$_2$, where each "X" is independently H, substituted or unsubstituted alkyl, substituted or unsubstituted carbocyclyl, substituted or unsubstituted heterocyclyl, etc. The hybridization of the nitrogen is approximately $sp^3$. Nonlimiting types of amino include —$NH_2$, —N(alkyl)$_2$, —NH(alkyl), —N(carbocyclyl)$_2$, —NH(carbocyclyl), —N(heterocyclyl)$_2$, —NH(heterocyclyl), —N(aryl)$_2$, —NH(aryl), —N(alkyl)(aryl), —N(alkyl)(heterocyclyl), —N(carbocyclyl)(heterocyclyl), —N(aryl)(heteroaryl), —N(alkyl)(heteroaryl), etc. The term "alkylamino" refers to an amino group substituted with at least one alkyl group. Nonlimiting examples of amino groups include —$NH_2$, —NH($CH_3$), —N($CH_3$)$_2$, —NH($CH_2CH_3$), —N($CH_2CH_3$)$_2$, —NH(phenyl), —N(phenyl)$_2$, —NH(benzyl), —N(benzyl)$_2$, etc. Substituted alkylamino refers generally to alkylamino groups, as defined above, in which at least one substituted alkyl, as defined herein, is attached to the amino nitrogen atom. Non-limiting examples of substituted alkylamino includes —NH(alkylene-C(O)—OH), —NH(alkylene-C(O)—O-alkyl), —N(alkylene-C(O)—OH)$_2$, —N(alkylene-C(O)—O-alkyl)$_2$, etc.

"Carbocycle" or "carbocyclyl" refers to a saturated (i.e., "cycloalkyl"), partially unsaturated (e.g.; "cycloalkenyl," cycloalkadienyl, etc.) or aromatic ring (i.e., "aryl") having 3 to 7 carbon atoms as a monocycle, 7 to 12 carbon atoms as a bicycle, and up to about 20 carbon atoms as a polycycle. Monocyclic carbocycles have 3 to 7 ring atoms, still more typically 5 or 6 ring atoms. In certain embodiments, cycloalkyl groups can have 3 to 6 carbon atoms, or 5 or 6 carbon atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system, or spiro-fused rings. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and phenyl. Non-limiting examples of bicyclo carbocycles includes naphthyl, tetrahydronapthalene, and decaline.

"Cycloalkylalkyl" or "carbocyclylalkyl" or "cycloalkylalkylene" refers to an acyclic alkyl radical in which one of the hydrogen atoms bonded to a carbon atom is replaced with a cycloalkyl or carbocyclyl radical as described herein. Typical, but non-limiting, examples of cycloalkylalkyl groups include cyclopropylmethyl, cyclopropylethyl, cyclobutylmethyl, cyclopentylmethyl and cyclohexylmethyl. In cycloalkyl-alkylene groups, typically comprises 4 to 20 (i.e., $C_4$ to $C_{20}$) carbon atoms, e.g., the alkyl portion of the group is 1 to 6 (i.e., $C_1$ to $C_6$) carbon atoms and the cycloalkyl moiety is 3 to 14 carbon atoms.

"Aryl" means an aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 10 carbon atoms. Typical aryl groups include, but are not limited to, radicals derived from benzene (e.g., phenyl), substituted benzene, naphthalene, anthracene, biphenyl, and the like.

"Arylalkyl" refers to an acyclic alkyl radical in which one of the hydrogen atoms bonded to a carbon atom, typically a terminal or $sp^3$ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group can comprise 7 to 20 carbon atoms, e.g., the alkyl moiety is 1 to 6 carbon atoms and the aryl moiety is 6 to 14 carbon atoms.

The term "substituted" in reference to alkyl, alkylene, aryl, arylalkyl, alkoxy, heterocyclyl, heteroaryl, carbocyclyl, etc., for example, "substituted alkyl", "substituted alkylene", "substituted aryl", "substituted arylalkyl", "substituted heterocyclyl", and "substituted carbocyclyl" means alkyl, alkylene, aryl, arylalkyl, heterocyclyl, carbocyclyl respectively, in which one or more hydrogen atoms are each independently replaced with a non-hydrogen substituent. Typical substituents include, but are not limited to, —$X^1$, —$R^b$, —$O^-$, =O, —$OR^b$, —$SR^b$, —$S^-$, —$NR^b_2$, —$N^+R^b_3$, =$NR^b$, —$CX_3$, —CN, —OCN, —SCN, —N=C=O, —NCS, —NO, —$NO_2$, =$N_2$, —$N_3$, —NHC(=O)$R^b$, —OC(=O)$R^b$, —NHC(=O)$NR^b_2$, —S(=O)$_2$—, —S(=O)$_2$OH, —S(=O)$_2$ $R^b$, —OS(=O)$_2$$OR^b$, —S(=O)$_2$$NR^b_2$, —S(=O)$R^b$, —OP(=O)($OR^b$)$_2$, —P(=O)($OR^b$)$_2$, —P(=O)($O^-$)$_2$, —P(=O)(OH)$_2$, —P(O)($OR^b$)($O^-$), —C(=O)$R^b$, —C(=O)X, —C(S)$R^b$, —C(O)$OR^b$, —C(O) $O^-$, —C(S)$OR^b$, —C(O)$SR^b$, —C(S)$SR^b$, —C(O)$NR^b_2$, —C(S)$NR^b_2$, —C(=$NR^b$)$NR^b_2$, where each $X^1$ is independently a halogen: F, Cl, Br, or I; and each $R^b$ is independently H, alkyl, aryl, arylalkyl, a heterocycle, or a protecting group or prodrug moiety. Alkylene, alkenylene, and alkynylene groups may also be similarly substituted. Unless otherwise indicated, when the term "substituted" is used in conjunction with groups such as arylalkyl, which have two or more moieties capable of substitution, the substituents can be attached to the aryl moiety, the alkyl moiety, or both.

The term "prodrug" as used herein refers to any compound that when administered to a biological system generates the drug substance, i.e., active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound.

"Heterocycle" or "heterocyclyl" as used herein includes by way of example and not limitation those heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g., 1, 2, 3, or 4) carbon atoms have been replaced with a heteroatom (e.g., O, N, or S). The terms "heterocycle" or "heterocyclyl" includes saturated rings, partially unsaturated rings, and aromatic rings (i.e., heteroaromatic rings). Substituted heterocyclyls include, for example, heterocyclic rings substituted with any of the substituents disclosed herein including carbonyl groups. A non-limiting example of a carbonyl substituted heterocyclyl is:

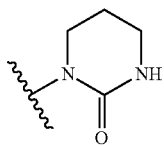

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl:

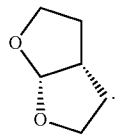

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or 13-carboline. Still more typically, nitrogen bonded heterocycles include 1-aziridyl, 1-azetedyl, 1-pyrrolyl, 1-imidazolyl, 1-pyrazolyl, and 1-piperidinyl.

"Heterocyclylalkyl" or "heterocyclylalkylene" refers to an acyclic alkyl radical in which one of the hydrogen atoms bonded to a carbon atom, typically a terminal or $sp^a$ carbon atom, is replaced with a heterocyclyl radical (i.e., a heterocyclyl-alkylene-moiety). Typical heterocyclyl alkyl groups include, but are not limited to heterocyclyl-$CH_2$—, 2-(heterocyclyl)ethan-1-yl, and the like, wherein the "heterocyclyl" portion includes any of the heterocyclyl groups described above, including those described in *Principles of Modern Heterocyclic Chemistry*. One skilled in the art will also understand that the heterocyclyl group can be attached to the alkyl portion of the heterocyclyl alkyl by means of a carbon-carbon bond or a carbon-heteroatom bond, with the proviso that the resulting group is chemically stable. The heterocyclyl alkyl group comprises 3 to 20 (i.e., $C_3$ to $C_{20}$) carbon atoms, e.g., the alkyl portion of the group is 1 to 6 (i.e., $C_1$ to $C_6$) carbon atoms and the heterocyclyl moiety is 2 to 14 carbon atoms. Examples of heterocyclylalkyls include by way of example and not limitation 5-membered sulfur, oxygen, and/or nitrogen containing heterocycles such as thiazolylmethyl, 2-thiazolylethan-1-yl, imidazolylmethyl, oxazolylmethyl, thiadiazolylmethyl, etc., 6-membered sulfur, oxygen, and/or nitrogen containing heterocycles such as piperidinylmethyl, piperazinylmethyl, morpholinylmethyl, pyridinylmethyl, pyridizylmethyl, pyrimidylmethyl, pyrazinylmethyl, etc.

"Heteroaryl" refers to an aromatic heterocyclyl having at least one heteroatom in the ring. Non-limiting examples of suitable heteroatoms which can be included in the aromatic ring include oxygen, sulfur, and nitrogen. Non-limiting examples of heteroaryl rings include all of those aromatic rings listed in the definition of "heterocyclyl", including pyridinyl, pyrrolyl, oxazolyl, indolyl, isoindolyl, purinyl, furanyl, thienyl, benzofuranyl, benzothiophenyl, carbazolyl, imidazolyl, thiazolyl, isoxazolyl, pyrazolyl, isothiazolyl, quinolyl, isoquinolyl, pyridazyl, pyrimidyl, pyrazyl, etc.

"Heteroarylalkyl" refers to an alkyl group, as defined herein, in which a hydrogen atom has been replaced with a heteroaryl group as defined herein. Non-limiting examples of heteroaryl alkyl include —$CH_2$-pyridinyl, —$CH_2$-pyrrolyl, —$CH_2$-oxazolyl, —$CH_2$-indolyl, —$CH_2$-isoindolyl, —$CH_2$-purinyl, —$CH_2$-furanyl, —$CH_2$-thienyl, —$CH_2$-benzofuranyl, —$CH_2$-benzothiophenyl, —$CH_2$-carbazolyl, —$CH_2$-imidazolyl, —$CH_2$-thiazolyl, —$CH_2$-isoxazolyl, —$CH_2$-pyrazolyl, —$CH_2$-isothiazolyl, —$CH_2$-quinolyl, —$CH_2$-isoquinolyl, —$CH_2$-pyridazyl, —$CH_2$-pyrimidyl, —$CH_2$-pyrazyl, —$CH(CH_3)$-pyridinyl, —$CH(CH_3)$-pyrrolyl, —$CH(CH_3)$-oxazolyl, —$CH(CH_3)$-indolyl, —$CH(CH_3)$-isoindolyl, —$CH(CH_3)$-purinyl, —$CH(CH_3)$-furanyl, —$CH(CH_3)$-thienyl, —$CH(CH_3)$-benzofuranyl, —$CH(CH_3)$-benzothiophenyl, —$CH(CH_3)$-carbazolyl, —$CH(CH_3)$-imidazolyl, —$CH(CH_3)$-thiazolyl, —$CH(CH_3)$-isoxazolyl, —$CH(CH_3)$-pyrazolyl, —$CH(CH_3)$-isothiazolyl, —$CH(CH_3)$-quinolyl, —$CH(CH_3)$-isoquinolyl, —$CH(CH_3)$-pyridazyl, —$CH(CH_3)$-pyrimidyl, —$CH(CH_3)$-pyrazyl, etc.

The term "optionally substituted" in reference to a particular moiety of the compound of Formula I-V (e.g., an optionally substituted aryl group) refers to a moiety wherein all substituents are hydrogen or wherein one or more of the hydrogens of the moiety may be replaced by substituents such as those listed under the definition of "substituted".

The term "optionally replaced" in reference to a particular moiety of the compound of Formula I-V (e.g., the carbon atoms of said $(C_1-C_8)$alkyl may be optionally replaced by —O—, —S—, or —NR$^a$—) means that one or more of the methylene groups of the $(C_1-C_8)$alkyl may be replaced by 0, 1, 2, or more of the groups specified (e.g., —O—, —S—, or —NR$^a$—).

The term "non-terminal carbon atom(s)" in reference to an alkyl, alkenyl, alkynyl, alkylene, alkenylene, or alkynylene moiety refers to the carbon atoms in the moiety that intervene between the first carbon atom of the moiety and the last carbon atom in the moiety. Therefore, by way of example and not limitation, in the alkyl moiety —CH$_2$(C*)H$_2$(C*)H$_2$CH$_3$ or alkylene moiety —CH$_2$(C*)H$_2$(C*)H$_2$CH$_2$— the C* atoms would be considered to be the non-terminal carbon atoms.

Certain Y and Y$^1$ alternatives are nitrogen oxides such as $^+$N(O)(R) or $^+$N(O)(OR). These nitrogen oxides, as shown here attached to a carbon atom, can also be

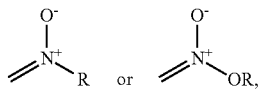

represented by charge separated groups such as respectively, and are intended to be equivalent to the aforementioned representations for the purposes of describing this invention.

The term "pyrimidine" base comprises, but is not limited to naturally occurring or modified pyrimidine bases, such as thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, C$^5$-alkylpyrimidines, C$^5$-benzylpyrimidines, C$^5$-halopyrimidines, C$^5$-vinylpyrimidine, C$^5$-acetylenic pyrimidine, C$^5$-acyl pyrimidine, C$^5$-amidopyrimidine, C$^5$-cyanopyrimidine, C$^5$-5-iodopyrimidine, C$^6$-iodo-pyrimidine, C$^5$—Br-vinyl pyrimidine, C$^6$—Br-vinyl pyrimidine, C$^5$-nitropyrimidine, C$^5$-amino-pyrimidine, 5-azacytidinyl, and 5-azauracilyl. Tautomers of these bases are also included in the scope of the invention. For example, uracil tautomers have the following structures:

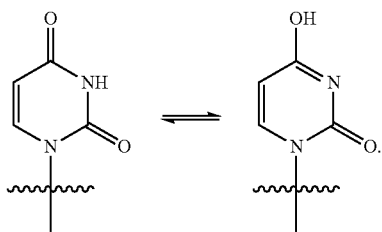 [SMILES: *n1ccc(=O)[nH]c1=O ; *n1ccc(O)nc1=O]

The pyrimidine bases of Formula I-V are linked to the ribose sugar, or analog thereof, through a nitrogen atom of the base. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, and acyl groups such as acetyl and propionyl, methanesulfonyl, and p-toluenesulfonyl.

Unless otherwise specified, the carbon atoms of the compounds of Formula I-V are intended to have a valence of four. In some chemical structure representations where carbon atoms do not have a sufficient number of variables attached to produce a valence of four, the remaining carbon substituents needed to provide a valence of four should be assumed to be hydrogen. For example,

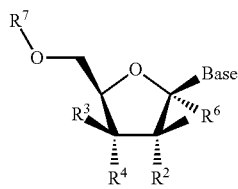

has the same meaning as

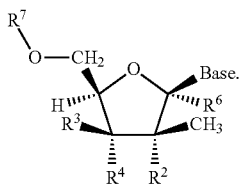

"Protecting group" refers to a moiety of a compound that masks or alters the properties of a functional group or the properties of the compound as a whole. The chemical substructure of a protecting group varies widely. One function of a protecting group is to serve as an intermediate in the synthesis of the parental drug substance. Chemical protecting groups and strategies for protection/deprotection are well known in the art. See: "Protective Groups in Organic Chemistry", Theodora W. Greene (John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g., alcohols, be physiologically acceptable, although in general it is more desirable if the products are pharmacologically innocuous.

"Prodrug moiety" means a labile functional group which separates from the active inhibitory compound during metabolism, systemically, inside a cell, by hydrolysis, enzymatic cleavage, or by some other process (Bundgaard, Hans, "Design and Application of Prodrugs" in (1991), P. Krogsgaard-Larsen and H. Bundgaard, Eds. Harwood Academic Publishers *Textbook of Drug Design and Development*, pp. 113-191). Enzymes which are capable of an enzymatic activation mechanism with the phosphonate prodrug compounds of the invention include, but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy.

A prodrug moiety may include an active metabolite or drug itself.

Exemplary prodrug moieties include the hydrolytically sensitive or labile acyloxymethyl esters —$CH_2OC(=O)R^{30}$ and acyloxymethyl carbonates —$CH_2C(=O)OR^{30}$ where $R^{30}$ is $C_1$-$C_6$ alkyl, $C_1$-$C_6$ substituted alkyl, $C_6$-$C_{20}$ aryl or $C_6$-$C_{20}$ substituted aryl. The acyloxyalkyl ester was used as a prodrug strategy for carboxylic acids and then applied to phosphates and phosphonates by Farquhar et al. (1983) *J. Pharm. Sci.* 72: 324; also U.S. Pat. Nos. 4,816,570, 4,968,788, 5,663,159 and 5792756. In certain compounds of the invention, a prodrug moiety is part of a phosphate group. The acyloxyalkyl ester may be used to deliver phosphoric acids across cell membranes and to enhance oral bioavailability. A close variant of the acyloxyalkyl ester, the alkoxycarbonyloxyalkyl ester (carbonate), may also enhance oral bioavailability as a prodrug moiety in the compounds of the combinations of the invention. An exemplary acyloxymethyl ester is pivaloyloxymethoxy, (POM) —$CH_2C(=O)C(CH_3)_3$. An exemplary acyloxymethyl carbonate prodrug moiety is pivaloyloxymethylcarbonate (POC) —$CH_2C(=O)OC(CH_3)_3$.

The phosphate group may be a phosphate prodrug moiety. The prodrug moiety may be sensitive to hydrolysis, such as, but not limited to those comprising a pivaloyloxymethyl carbonate (POC) or POM group. Alternatively, the prodrug moiety may be sensitive to enzymatic potentiated cleavage, such as a lactate ester or a phosphonamidate-ester group.

Aryl esters of phosphorus groups, especially phenyl esters, are reported to enhance oral bioavailability (DeLambert et al. (1994) *J. Med. Chem.* 37: 498). Phenyl esters containing a carboxylic ester ortho to the phosphate have also been described (Khamnei and Torrence, (1996) *J. Med. Chem.* 39:4109-4115). Benzyl esters are reported to generate the parent phosphonic acid. In some cases, substituents at the ortho- or para-position may accelerate the hydrolysis. Benzyl analogs with an acylated phenol or an alkylated phenol may generate the phenolic compound through the action of enzymes, e.g., esterases, oxidases, etc., which in turn undergoes cleavage at the benzylic C—O bond to generate the phosphoric acid and the quinone methide intermediate. Examples of this class of prodrugs are described by Mitchell et al. (1992) *J. Chem. Soc. Perkin Trans. I* 2345; Brook et al. WO 91/19721. Still other benzylic prodrugs have been described containing a carboxylic ester-containing group attached to the benzylic methylene (Glazier et al. WO 91/19721). Thio-containing prodrugs are reported to be useful for the intracellular delivery of phosphonate drugs. These proesters contain an ethylthio group in which the thiol group is either esterified with an acyl group or combined with another thiol group to form a disulfide. Deesterification or reduction of the disulfide generates the free thio intermediate which subsequently breaks down to the phosphoric acid and episulfide (Puech et al. (1993) *Antiviral Res.*, 22: 155-174; Benzaria et al. (1996) *J. Med. Chem.* 39: 4958). Cyclic phosphonate esters have also been described as prodrugs of phosphorus-containing compounds (Erion et al., U.S. Pat. No. 6,312,662).

It is to be noted that all enantiomers, diastereomers, and racemic mixtures, tautomers, polymorphs, pseudopolymorphs of compounds within the scope of Formula I-V and pharmaceutically acceptable salts thereof are embraced by the present invention. All mixtures of such enantiomers and diastereomers are within the scope of the present invention.

A compound of Formula I-V and its pharmaceutically acceptable salts may exist as different polymorphs or pseudopolymorphs. As used herein, crystalline polymorphism means the ability of a crystalline compound to exist in different crystal structures. The crystalline polymorphism may result from differences in crystal packing (packing polymorphism) or differences in packing between different conformers of the same molecule (conformational polymorphism). As used herein, crystalline pseudopolymorphism means the ability of a hydrate or solvate of a compound to exist in different crystal structures. The pseudopolymorphs of the instant invention may exist due to differences in crystal packing (packing pseudopolymorphism) or due to differences in packing between different conformers of the same molecule (conformational pseudopolymorphism). The instant invention comprises all polymorphs and pseudopolymorphs of the compounds of Formula I-V and their pharmaceutically acceptable salts.

A compound of Formula I-V and its pharmaceutically acceptable salts may also exist as an amorphous solid. As used herein, an amorphous solid is a solid in which there is no long-range order of the positions of the atoms in the solid. This definition applies as well when the crystal size is two nanometers or less. Additives, including solvents, may be used to create the amorphous forms of the instant invention. The instant invention comprises all amorphous forms of the compounds of Formula I-V and their pharmaceutically acceptable salts.

Selected substituents comprising the compounds of Formula I-V are present to a recursive degree. In this context, "recursive substituent" means that a substituent may recite another instance of itself. Because of the recursive nature of such substituents, theoretically, a large number of compounds may be present in any given embodiment. For example, $R^x$ comprises a $R^y$ substituent. $R^y$ can be R. R can be $W^3$. $W^3$ can be $W^4$ and $W^4$ can be R or comprise substituents comprising R. One of ordinary skill in the art of medicinal chemistry understands that the total number of such substituents is reasonably limited by the desired properties of the compound intended. Such properties include, by way of example and not limitation, physical properties such as molecular weight, solubility or log P, application properties such as activity against the intended target, and practical properties such as ease of synthesis.

By way of example and not limitation, $W^3$ and $R^y$ are recursive substituents in certain embodiments. Typically, each recursive substituent can independently occur 20, 19, 18, 17, 16, 15, 14, 13, 12, 11, 10, 9, 8, 7, 6, 5, 4, 3, 2, 1, or 0, times in a given embodiment. More typically, each recursive substituent can independently occur 12 or fewer times in a given embodiment. Even more typically, each recursive substituent can independently occur 3 or fewer times in a given embodiment. For example, $W^3$ will occur 0 to 8 times, $R^y$ will occur 0 to 6 times in a given embodiment. Even more typically, $W^3$ will occur 0 to 6 times and $R^y$ will occur 0 to 4 times in a given embodiment.

Recursive substituents are an intended aspect of the invention. One of ordinary skill in the art of medicinal chemistry understands the versatility of such substituents. To the degree that recursive substituents are present in an embodiment of the invention, the total number will be determined as set forth above.

The modifier "about" used in connection with a quantity is inclusive of the stated value and has the meaning dictated by the context (e.g., includes the degree of error associated with measurement of the particular quantity).

The compounds of the Formula I-V may comprise a phosphate group as $R^7$, which may be a prodrug moiety

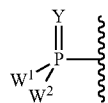

wherein each Y or $Y^1$ is, independently, O, S, NR, $^+$N(O)(R), N(OR), $^+$N(O)(OR), or N—NR$_2$; $W^1$ and $W^2$, when taken together, are —Y$^3$(C(R$^y$)$_2$)$_3$Y$^3$—; or one of $W^1$ or $W^2$ together with either $R^3$ or $R^4$ is —Y$^3$— and the other of $W^1$ or $W^2$ is Formula Ib; or $W^1$ and $W^2$ are each, independently, a group of Formula Ib:

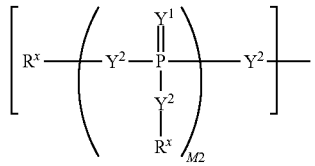

wherein:
each $Y^2$ is independently a bond, O, CR$_2$, NR, $^+$N(O)(R), N(OR), $^+$N(O)(OR), N—NR$_2$, S, S—S, S(O), or S(O)$_2$;
each $Y^3$ is independently O, S, or NR;
M2 is 0, 1 or 2;
each $R^y$ is independently H, F, Cl, Br, I, OH, R, —C(=Y$^1$)R, —C(=Y$^1$)OR, —C(=Y$^1$)N(R)$_2$, —N(R)$_2$, —$^+$N(R)$_3$, —SR, —S(O)R, —S(O)$_2$R, —S(O)(OR), —S(O)$_2$(OR), —OC(=Y$^1$)R, —OC(=Y$^1$)OR, —OC(=Y$^1$)(N(R)$_2$), —SC(=Y$^1$)R, —SC(=Y$^1$)OR, —SC(=Y$^1$)(N(R)$_2$), —N(R)C(=Y$^1$)R, —N(R)C(=Y$^1$)OR, or —N(R)C(=Y$^1$)N(R)$_2$, —SO$_2$NR$_2$, —CN, —N$_3$, —NO$_2$, —OR, a protecting group or $W^3$; or when taken together, two $R^y$ on the same carbon atom form a carbocyclic ring of 3 to 7 carbon atoms;
each $R^8$ is independently $R^y$, a protecting group, or the formula:

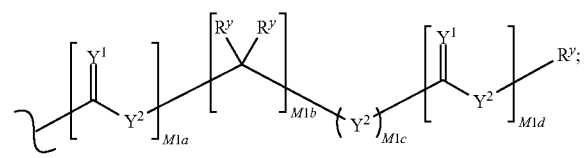

wherein:
M1a, M1c, and M1d are independently 0 or 1;
M1b is 0, 1, 2, 3, 4, 5, 6, 7, 8, 9, 10, 11 or 12;

each R is H, halogen, (C$_1$-C$_8$) alkyl, (C$_1$-C$_8$) substituted alkyl, (C$_2$-C$_8$) alkenyl, (C$_2$-C$_8$) substituted alkenyl, (C$_2$-C$_8$) alkynyl, (C$_2$-C$_8$) substituted alkynyl, C$_6$-C$_{20}$ aryl, C$_6$-C$_{20}$ substituted aryl, (C$_2$-C$_{20}$) heterocycle, (C$_2$-C$_{20}$) substituted heterocyclyl, arylalkyl, substituted arylalkyl or a protecting group;

$W^3$ is $W^4$ or $W^5$; $W^4$ is R, —C(Y$^1$)R$^y$, —C(Y$^1$)W$^5$, —SO$_2$R$^y$, or —SO$_2$W$^5$; and $W^5$ is a carbocycle or a heterocycle wherein $W^5$ is independently substituted with 0 to 3 R$^y$ groups.

$W^5$ carbocycles and $W^5$ heterocycles may be independently substituted with 0 to 3 R$^y$ groups. $W^5$ may be a saturated, unsaturated or aromatic ring comprising a mono- or bicyclic carbocycle or heterocycle. $W^5$ may have 3 to 10 ring atoms, e.g., 3 to 7 ring atoms. The $W^5$ rings are saturated when containing 3 ring atoms, saturated or mono-unsaturated when containing 4 ring atoms, saturated, or mono- or di-unsaturated when containing 5 ring atoms, and saturated, mono- or di-unsaturated, or aromatic when containing 6 ring atoms.

A $W^5$ heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S). $W^5$ heterocyclic monocycles may have 3 to 6 ring atoms (2 to 5 carbon atoms and 1 to 2 heteroatoms selected from N, O, and S); or 5 or 6 ring atoms (3 to 5 carbon atoms and 1 to 2 heteroatoms selected from N and S). $W^5$ heterocyclic bicycles have 7 to 10 ring atoms (6 to 9 carbon atoms and 1 to 2 heteroatoms selected from N, O, and S) arranged as a bicyclo [4,5], [5,5], [5,6], or [6,6] system; or 9 to 10 ring atoms (8 to 9 carbon atoms and 1 to 2 hetero atoms selected from N and S) arranged as a bicyclo [5,6] or [6,6] system. The $W^5$ heterocycle may be bonded to $Y^2$ through a carbon, nitrogen, sulfur or other atom by a stable covalent bond.

$W^5$ heterocycles include for example, pyridyl, dihydropyridyl isomers, piperidine, pyridazinyl, pyrimidinyl, pyrazinyl, s-triazinyl, oxazolyl, imidazolyl, thiazolyl, isoxazolyl, pyrazolyl, isothiazolyl, furanyl, thiofuranyl, thienyl, and pyrrolyl. $W^5$ also includes, but is not limited to, examples such as:

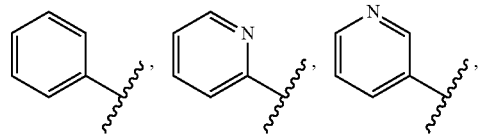

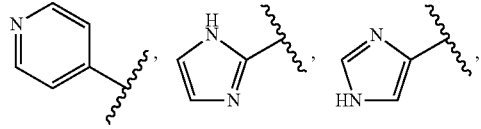

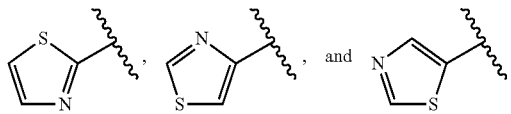

$W^5$ carbocycles and heterocycles may be independently substituted with 0 to 3 R groups, as defined above. For example, substituted $W^5$ carbocycles include:

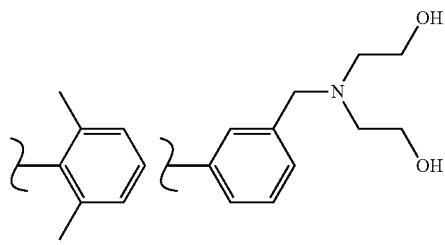

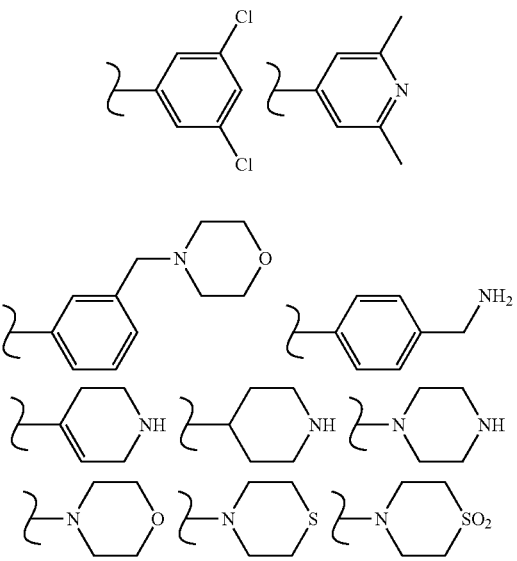

Examples of substituted phenyl carbocycles include:

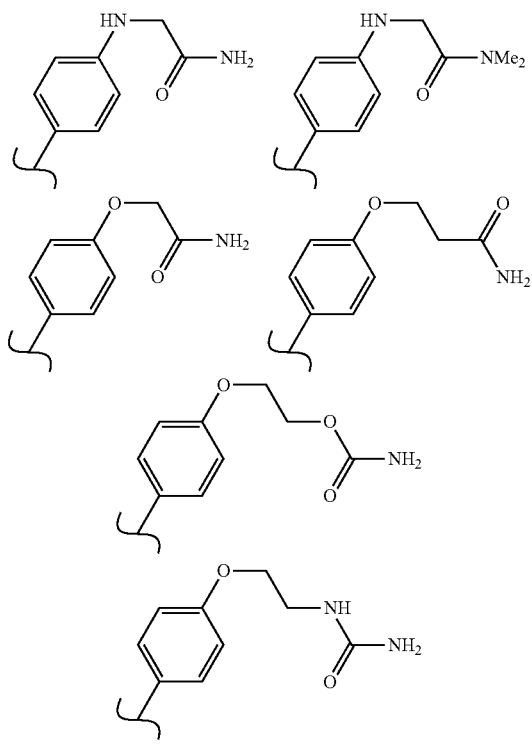

Embodiments of

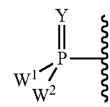

of Formula I-V compounds include substructures such as:

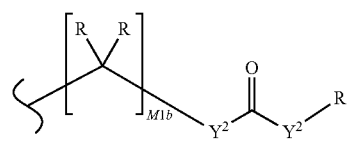

wherein each $Y^{2b}$ is, independently, O or N(R). In another aspect of this embodiment, each $Y^{2b}$ is O and each $R^x$ is independently:

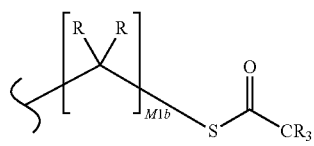

wherein M1b is 1, 2 or 3 and each $Y^2$ is independently a bond, O, $CR_2$, or S. In another aspect of this embodiment, one $Y^{2b}$—$R^x$ is NH(R) and the other $Y^{2b}$—$R^x$ is O—$R^x$ wherein $R^x$ is:

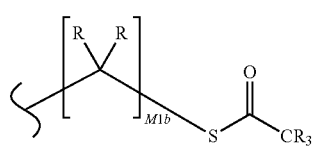

wherein M1b is 2. In another aspect of this embodiment, each $Y^{2b}$ is O and each $R^x$ is independently:

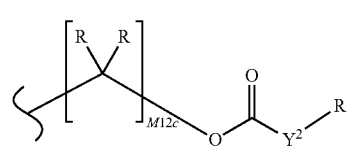

wherein M1b is 2. In another aspect of this embodiment, each $Y^{2b}$ is O and each $R^x$ is independently:

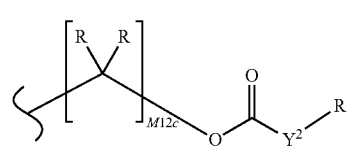

wherein M1b is 1 and $Y^2$ is a bond, O, or $CR_2$.

Other embodiments of

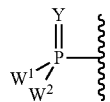

of Formulas I-V compounds include substructures such as:

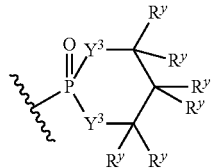

wherein each $Y^3$ is, independently, O or N(R). In another aspect of this embodiment, each $Y^3$ is O. In another aspect of this embodiment, the substructure is:

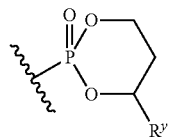

wherein $R^y$ is $W^5$ as defined herein.

Another embodiment of

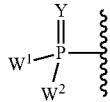

of Formula I-V includes the substructures:

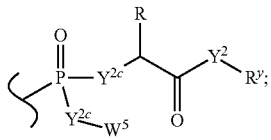

wherein each $Y^{2c}$ is, independently, O, N($R^y$) or S.

Another embodiment of

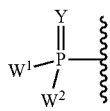

of Formula I-V compounds includes the substructures wherein one of $W^1$ or $W^2$ together with either $R^3$ or $R^4$ is —$Y^3$— and the other of $W^1$ or $W^2$ is Formula Ib. Such an embodiment is represented by a compound of Formula Ic selected from:

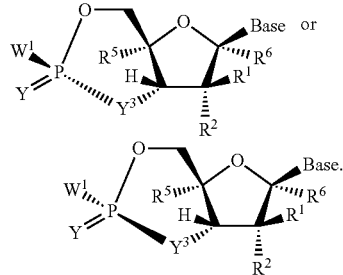

Formula Id

In another aspect of the embodiment of Formula Id, each Y and $Y^3$ is O. In another aspect of the embodiment of Formula Id, $W^1$ or $W^2$ is $Y^{2b}$—$R^x$; each Y, $Y^3$ and $Y^{2b}$ is O and $R^x$ is:

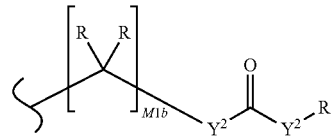

wherein M1b is 1, 2 or 3 and each $Y^2$ is independently a bond, O, $CR_2$, or S. In another aspect of the embodiment of Formula Id, $W^1$ or $W^2$ is $Y^{2b}$—$R^x$; each Y, $Y^3$ and $Y^{2b}$ is O and $R^x$ is:

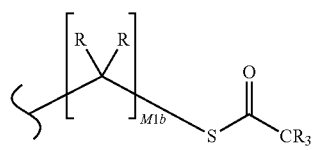

wherein M1b is 2. In another aspect of the embodiment of Formula Id, $W^1$ or $W^2$ is $Y^{2b}$—$R^x$; each Y, $Y^3$ and $Y^{2b}$ is O and $R^x$ is:

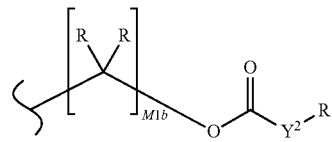

wherein M1b is 1 and $Y^2$ is a bond, O, or $CR_2$.

Another embodiment of

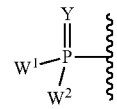

of Formula I-V compounds includes a substructure:

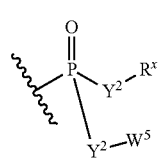

wherein $W^5$ is a carbocycle such as phenyl or substituted phenyl. In another aspect of this embodiment, the substructure is:

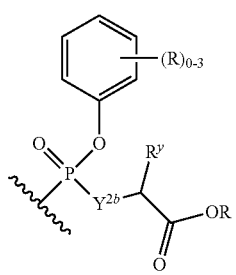

wherein $Y^{2b}$ is O or N(R) and the phenyl carbocycle is substituted with 0 to 3 R groups. In another aspect of this embodiment of the substructure, $R^x$ is:

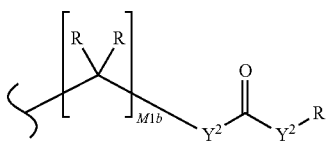

wherein M1b is 1, 2 or 3 and each $Y^2$ is independently a bond, O, $CR_2$, or S.

Another embodiment of

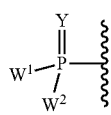

of Formula I-V includes substructures:

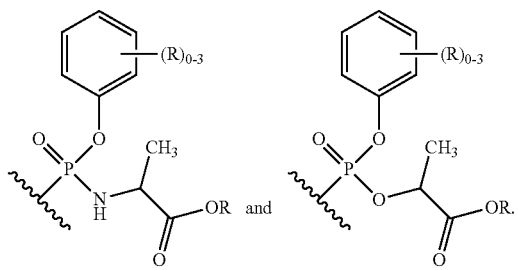

The chiral carbon of the amino acid and lactate moieties may be either the R or S configuration or the racemic mixture.

Another embodiment of

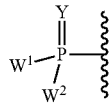

of Formula I-V is substructure

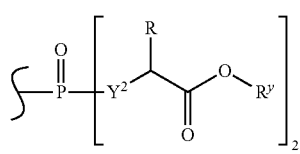

wherein each $Y^2$ is, independently, —O— or —NH—. In another aspect of this embodiment, $R^y$ is ($C_1$-$C_8$) alkyl, ($C_1$-$C_8$) substituted alkyl, ($C_2$-$C_8$) alkenyl, ($C_2$-$C_8$) substituted alkenyl, ($C_2$-$C_8$) alkynyl or ($C_2$-$C_8$) substituted alkynyl. In another aspect of this embodiment, $R^y$ is ($C_1$-$C_8$) alkyl, ($C_1$-$C_8$) substituted alkyl, ($C_2$-$C_8$) alkenyl, ($C_2$-$C_8$) substituted alkenyl, ($C_2$-$C_8$) alkynyl or ($C_2$-$C_8$) substituted alkynyl; and R is $CH_3$. In another aspect of this embodiment, $R^y$ is ($C_1$-$C_8$) alkyl, ($C_1$-$C_8$) substituted alkyl, ($C_2$-$C_8$) alkenyl, ($C_2$-$C_8$) substituted alkenyl, ($C_2$-$C_8$) alkynyl or ($C_2$-$C_8$) substituted alkynyl; R is $CH_3$; and each $Y^2$ is —NH—. In a aspect of this embodiment, $W^1$ and $W^2$ are, independently, nitrogen-linked, naturally occurring amino acids or naturally occurring amino acid esters. In another aspect of this embodiment, $W^1$ and $W^2$ are, independently, naturally-occurring 2-hydroxy carboxylic acids or naturally-occurring 2-hydroxy carboxylic acid esters wherein the acid or ester is linked to P through the 2-hydroxy group.

Another embodiment of

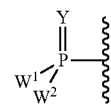

of Formula I to V is substructure:

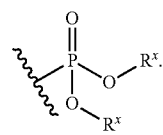

In one aspect of this embodiment, each $R^x$ is, independently, ($C_1$-$C_8$) alkyl. In another aspect of this embodiment, each $R^x$ is, independently, $C_6$-$C_{20}$ aryl or $C_6$-$C_{20}$ substituted aryl.

In one embodiment,

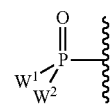

is selected from

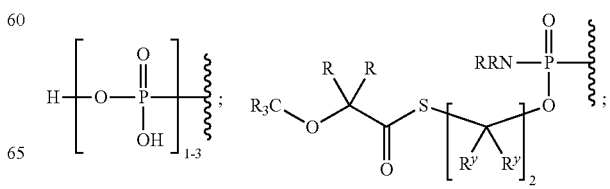

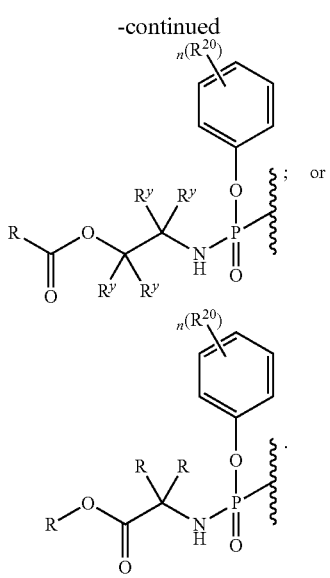

In some embodiments, the group —$R^7$—O—C($R^8$)—C($R^5$)—C($R^3$)($R^4$)— is of the following formula:

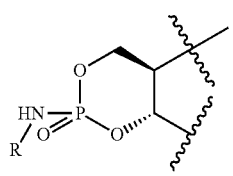

Another embodiment of

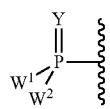

of Formulas I-V is substructure

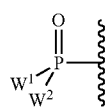

wherein $W^1$ and $W^2$ are independently selected from one of the formulas in Tables 1.1-1.37 and Table 2.1 below. The variables used in Tables 1.1-1.37 (e.g., $W^{23}$, $R^{21}$, etc.) pertain only to Tables 1.1-1.37, unless otherwise indicated.

The variables used in Tables 1.1 to 1.37 have the following definitions:

each $R^{21}$ is independently H or ($C_1$-$C_8$)alkyl;
each $R^{22}$ is independently H, $R^{21}$, $R^{23}$ or $R^{24}$ wherein each $R^{24}$ is independently substituted with 0 to 3 $R^{23}$;
each $R^{23}$ is independently $R^{23a}$, $R^{23b}$, $R^{23c}$ or $R^{23d}$, provided that when $R^{23}$ is bound to a heteroatom, then $R^{23}$ is $R^{23c}$ or $R^{23d}$;
each $R^{23a}$ is independently F, Cl, Br, I, —CN, $N_3$ or —$NO_2$;
each $R^{23b}$ is independently $Y^{21}$;
each $R^{23c}$ is independently —$R^{2x}$, —N($R^{2x}$)($R^{2x}$), —$SR^{2x}$, —S(O)$R^{2x}$, —S(O)$_2R^{2x}$, —S(O)(O$R^{2x}$), —S(O)$_2$(O$R^{2x}$), —OC(=$Y^{21}$)$R^{2x}$, —OC(=$Y^{21}$)O$R^{2x}$, —OC(=$Y^{21}$)(N($R^{2x}$)($R^{2x}$)), —SC(=$Y^{21}$)$R^{2x}$, —SC(=$Y^{21}$)O$R^{2x}$, —SC(=$Y^{21}$)(N($R^{2x}$)($R^{2x}$)), N($R^{2x}$)C(=$Y^{21}$)$R^{2x}$, —N($R^{2x}$)C(=$Y^{21}$)O$R^{2x}$, or —N($R^{2x}$)C(=$Y^{21}$)(N($R^{2x}$)($R^{2x}$));

each $R^{23d}$ is independently —C(=$Y^{21}$)$R^{2x}$, —C(=$Y^{21}$)O$R^{2x}$ or —C(=$Y^{21}$)(N($R^{2x}$)($R^{2x}$));

each $R^{2x}$ is independently H, ($C_1$-$C_8$)alkyl, ($C_2$-$C_8$)alkenyl, ($C_2$-$C_8$)alkynyl, aryl, heteroaryl; or two $R^{2x}$ taken together with a nitrogen to which they are both attached form a 3- to 7-membered heterocyclic ring wherein any one carbon atom of said heterocyclic ring can optionally be replaced with —O—, —S— or —$NR^{21}$—; and wherein one or more of the non-terminal carbon atoms of each said ($C_1$-$C_8$)alkyl may be optionally replaced with —O—, —S— or —$NR^{21}$—;

each $R^{24}$ is independently ($C_1$-$C_8$)alkyl, ($C_2$-$C_8$)alkenyl, or ($C_2$-$C_8$)alkynyl;

each $R^{25}$ is independently $R^{24}$ wherein each $R^{24}$ is substituted with 0 to 3 $R^{23}$ groups;

each $R^{25a}$ is independently ($C_1$-$C_8$)alkylene, ($C_2$-$C_8$)alkenylene, or ($C_2$-$C_8$)alkynylene any one of which said ($C_1$-$C_8$)alkylene, ($C_2$-$C_8$)alkenylene, or ($C_2$-$C_8$)alkynylene is substituted with 0-3 $R^{23}$ groups;

each $W^{23}$ is independently $W^{24}$ or $W^{25}$;
each $W^{24}$ is independently $R^{25}$, —C(=$Y^{21}$)$R^{25}$, —C(=$Y^{21}$)$W^{25}$, —$SO_2R^{25}$, or —$SO_2W^{25}$;
each $W^{25}$ is independently carbocycle or heterocyclyl wherein $W^{25}$ is independently substituted with 0 to 3 $R^{22}$ groups; and
each $Y^{21}$ is independently O or S.

TABLE 1.1

| | |
|---|---|
| 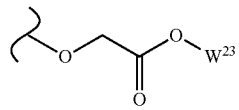 | 1 |
| 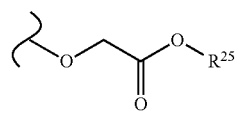 | 2 |
| 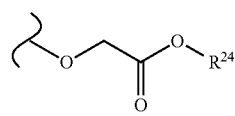 | 3 |
| 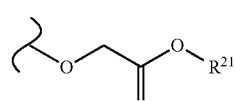 | 4 |
| 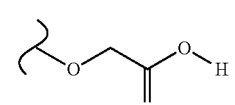 | 5 |
| 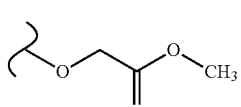 | 6 |
| 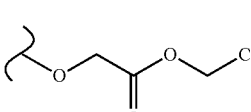 | 7 |

TABLE 1.1-continued
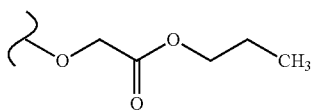
8
TABLE 1.2
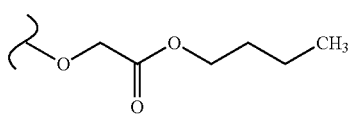
9
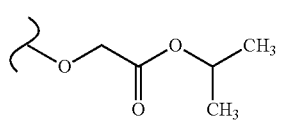
10
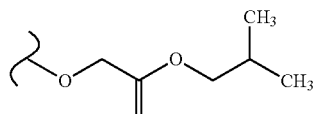
11
TABLE 1.3
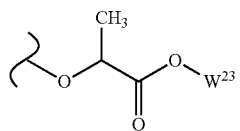
12
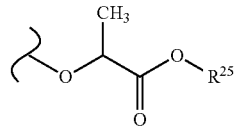
13
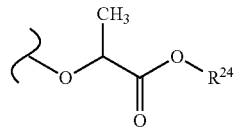
14
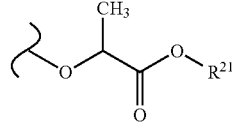
15
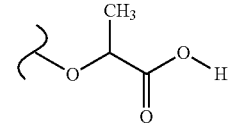
16
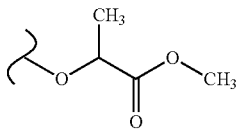
17
TABLE 1.3-continued
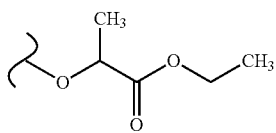
18
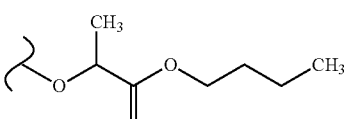
19
TABLE 1.4
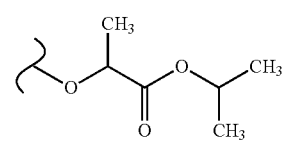
20
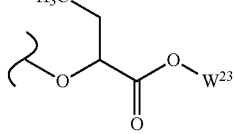
21
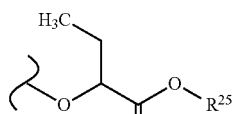
22
TABLE 1.5
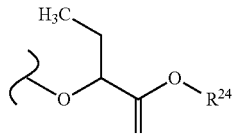
23
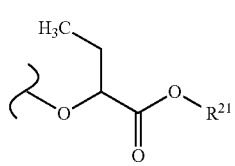
24
25
26

TABLE 1.5-continued
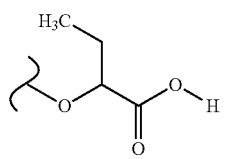
27
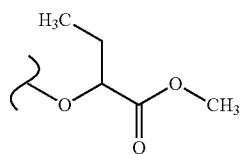
28
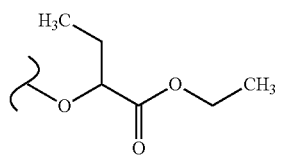
29
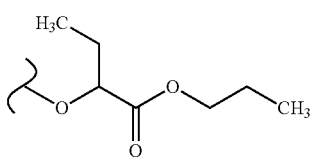
30
TABLE 1.6
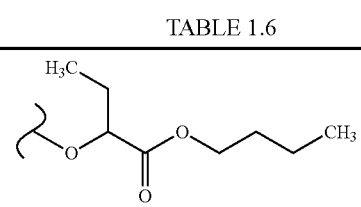
31
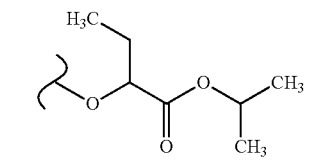
32
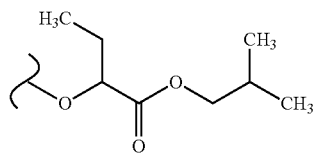
33
TABLE 1.7
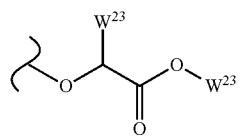
34
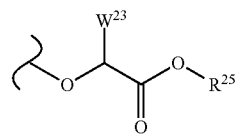
35
TABLE 1.7-continued
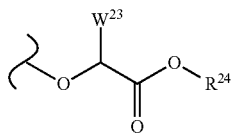
36
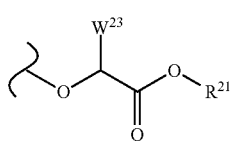
37
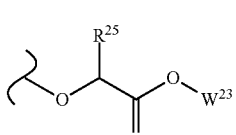
38
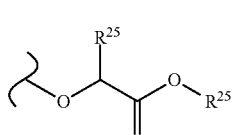
39
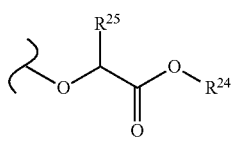
40
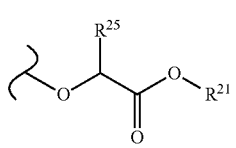
41
TABLE 1.8
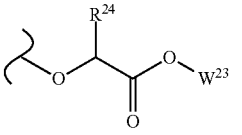
42
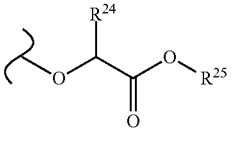
43
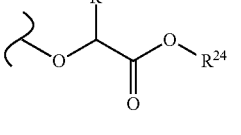
44
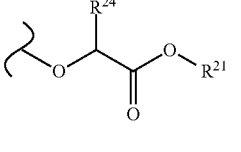
45

TABLE 1.8-continued
| | |
|---|---|
| 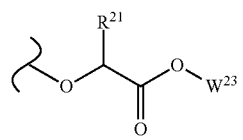 | 46 |
| 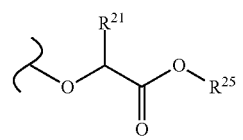 | 47 |
| 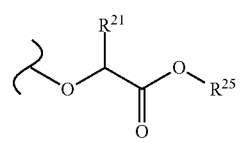 | 48 |
| 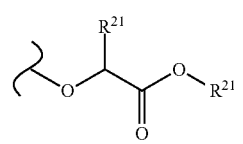 | 49 |
TABLE 1.9
| | |
|---|---|
| 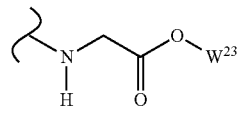 | 50 |
| 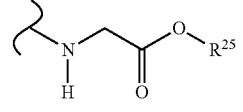 | 51 |
| 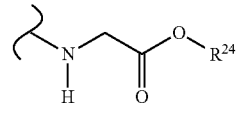 | 52 |
| 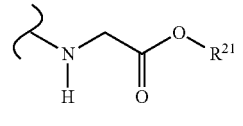 | 53 |
| 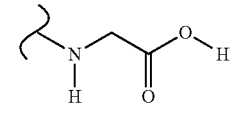 | 54 |
| 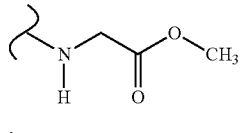 | 55 |
| 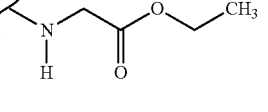 | 56 |
| 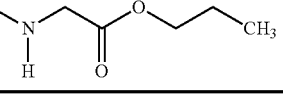 | 57 |
TABLE 1.10
| | |
|---|---|
| 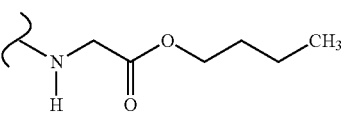 | 58 |
| 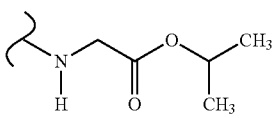 | 59 |
| 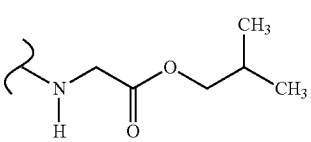 | 60 |
TABLE 1.11
| | |
|---|---|
| 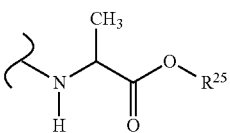 | 61 |
| 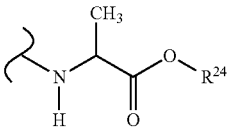 | 62 |
| 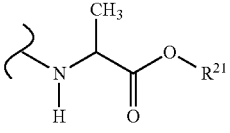 | 63 |
| 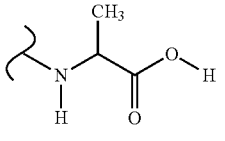 | 64 |
| 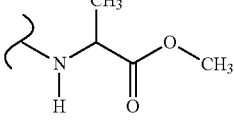 | 65 |
| 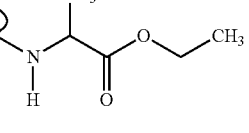 | 66 |
| 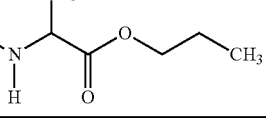 | 67 |
| 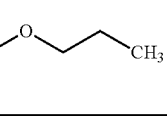 | 68 |

TABLE 1.12
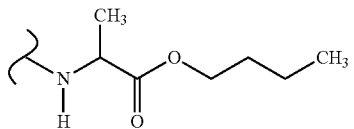 69
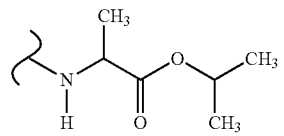 70
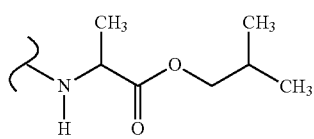 71
TABLE 1.13
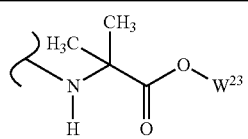 72
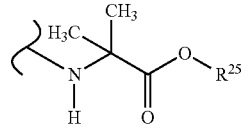 73
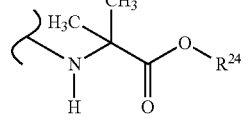 74
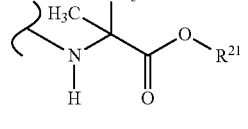 75
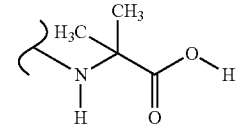 76
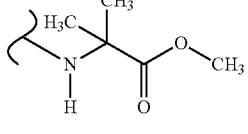 77
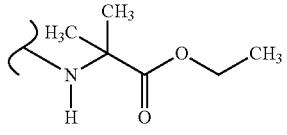 78
TABLE 1.13-continued
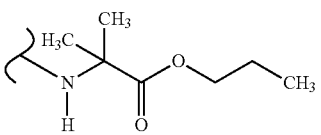 79
TABLE 1.14
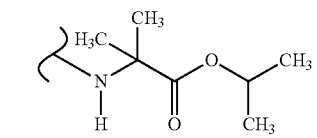 80
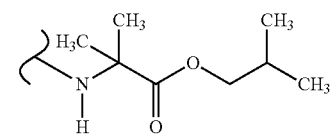 81
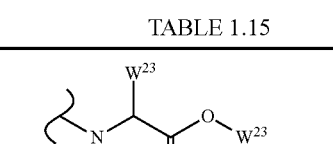 82
TABLE 1.15
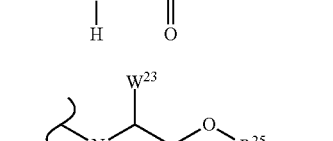 83
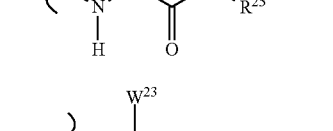 84
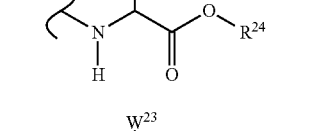 85
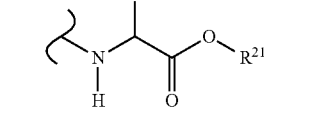 86
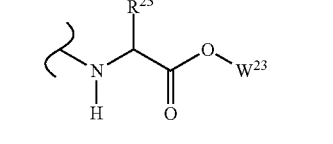 87
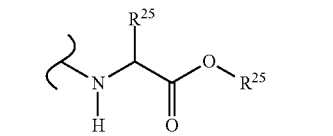 88

TABLE 1.15-continued
| | |
|---|---|
| 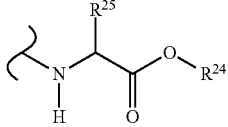 | 89 |
| 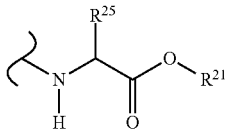 | 90 |
TABLE 1.16
| | |
|---|---|
| 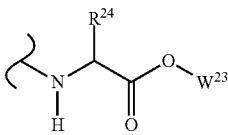 | 91 |
| 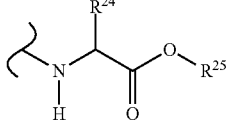 | 92 |
| 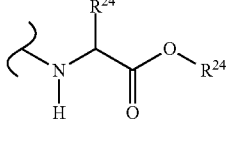 | 93 |
| 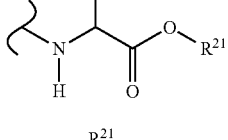 | 94 |
| 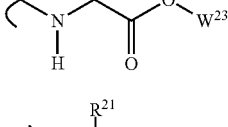 | 95 |
| 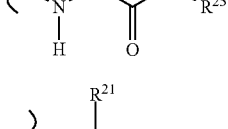 | 96 |
| 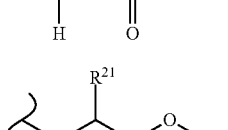 | 97 |
| 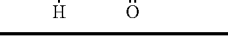 | 98 |
TABLE 1.17
| | |
|---|---|
| 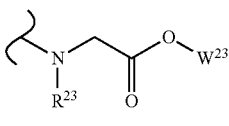 | 99 |
| 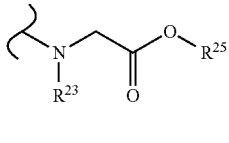 | 100 |
| 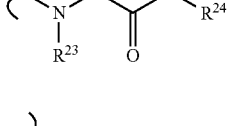 | 101 |
| 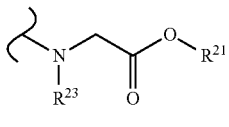 | 102 |
| 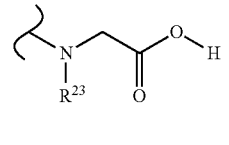 | 103 |
| 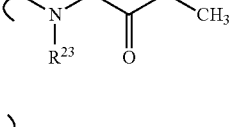 | 104 |
| 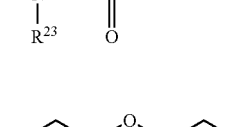 | 105 |
| 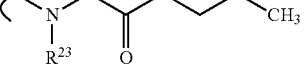 | 106 |
TABLE 1.18
| | |
|---|---|
| 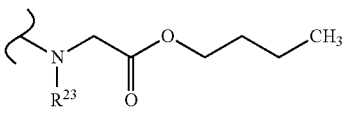 | 107 |
| 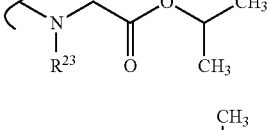 | 108 |
| 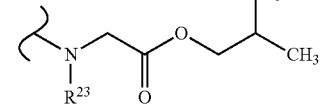 | 109 |

TABLE 1.19
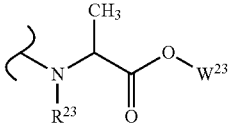 110
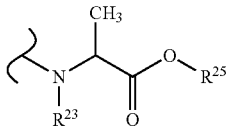 111
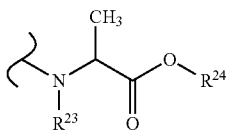 112
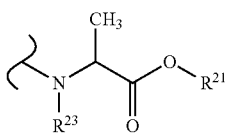 113
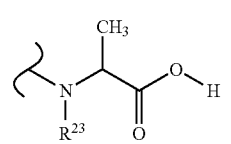 114
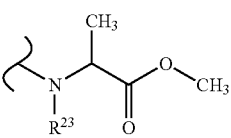 115
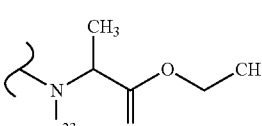 116
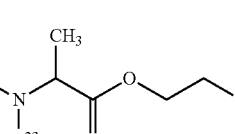 117
TABLE 1.20
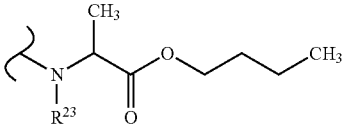 118
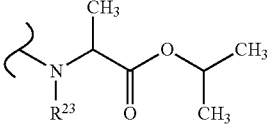 119
TABLE 1.20-continued
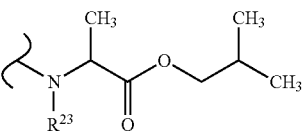 120
TABLE 1.21
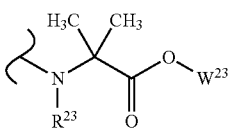 121
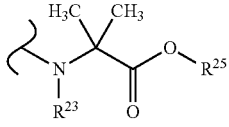 122
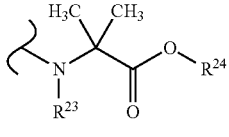 123
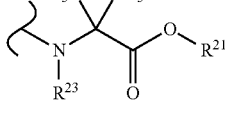 124
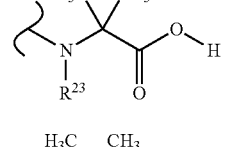 125
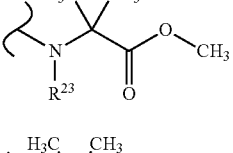 126
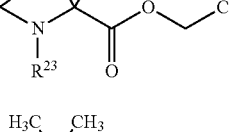 127
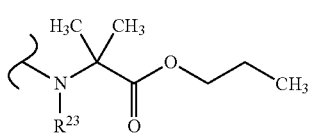 128
TABLE 1.22
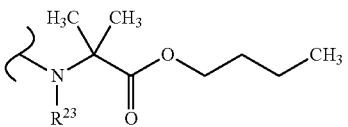 129

TABLE 1.22-continued
| Structure | No. |
|---|---|
| 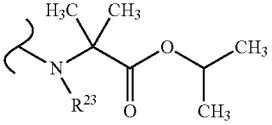 | 130 |
| 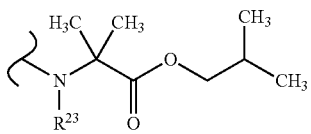 | 131 |
TABLE 1.23
| Structure | No. |
|---|---|
| 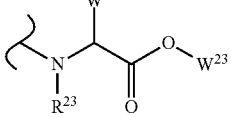 | 132 |
| 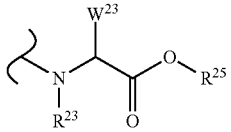 | 133 |
| 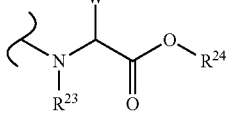 | 134 |
| 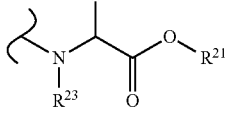 | 135 |
| 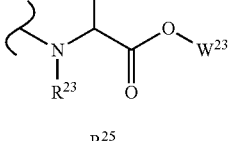 | 136 |
| 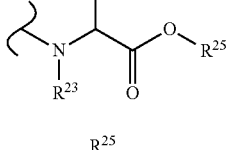 | 137 |
| 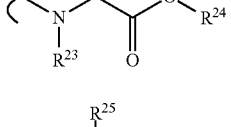 | 138 |
| 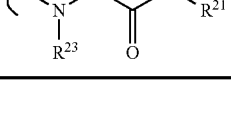 | 139 |
TABLE 1.24
| Structure | No. |
|---|---|
| 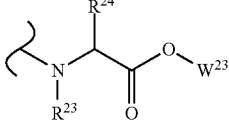 | 140 |
| 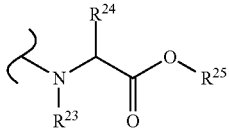 | 141 |
| 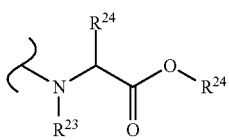 | 142 |
| 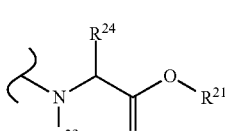 | 143 |
| 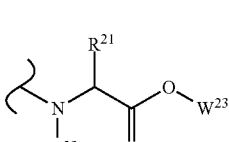 | 144 |
| 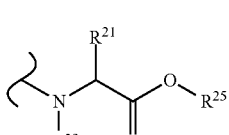 | 145 |
| 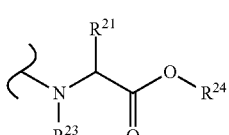 | 146 |
| 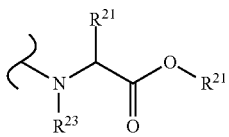 | 147 |
TABLE 1.25
| Structure | No. |
|---|---|
| 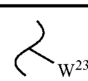 | 148 |
| 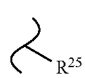 | 149 |
| 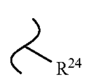 | 150 |
| 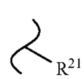 | 151 |

TABLE 1.25-continued

| | |
|---|---|
| {-H | 152 |
| {-R²³ | 153 |
| {-O-W²³ | 154 |
| {-O-R²⁵ | 155 |
| {-O-R²⁴ | 156 |
| {-O-R²¹ | 157 |
| {-O-H | 158 |
| {-O-R²³ | 159 |

TABLE 1.26

| | |
|---|---|
| {-NH-W²³ | 160 |
| {-NH-R²⁵ | 161 |
| {-NH-R²⁴ | 162 |
| {-NH-R²¹ | 163 |
| {-NH-H | 164 |
| {-NH-R²³ | 165 |
| {-N(R²³)-W²³ | 166 |

TABLE 1.26-continued

| | |
|---|---|
| {-N(R²³)-R²⁵ | 167 |
| {-N(R²³)-R²⁴ | 168 |
| {-N(R²³)-R²¹ | 169 |
| {-N(R²³)-H | 170 |
| {-N(R²³)-R²³ | 171 |

TABLE 1.27

| | |
|---|---|
| {-O-R²⁵ᵃ-O-C(=O)-W²³ | 172 |
| {-O-R²⁵ᵃ-O-C(=O)-R²⁵ | 173 |
| {-O-R²⁵ᵃ-O-C(=O)-R²⁴ | 174 |
| {-O-R²⁵ᵃ-O-C(=O)-R²¹ | 175 |
| {-O-R²⁵ᵃ-O-C(=O)-H | 176 |
| {-O-R²⁵ᵃ-O-C(=O)-CH₃ | 177 |
| {-O-R²⁵ᵃ-O-C(=O)-CH₂CH₃ | 178 |
| {-O-R²⁵ᵃ-O-C(=O)-CH₂CH₂CH₃ | 179 |

TABLE 1.28
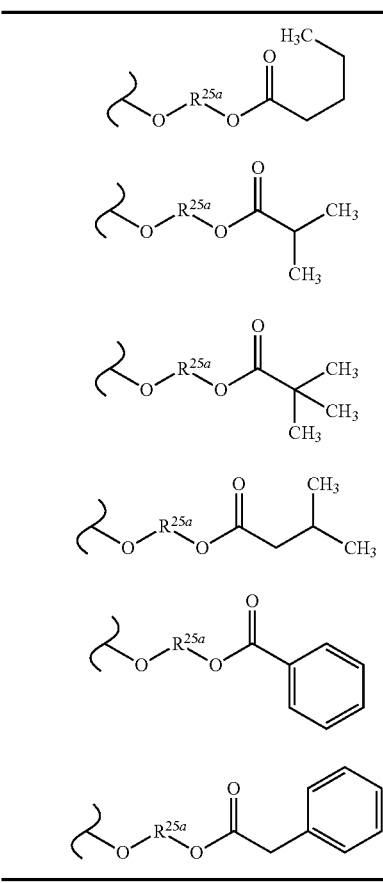
TABLE 1.29
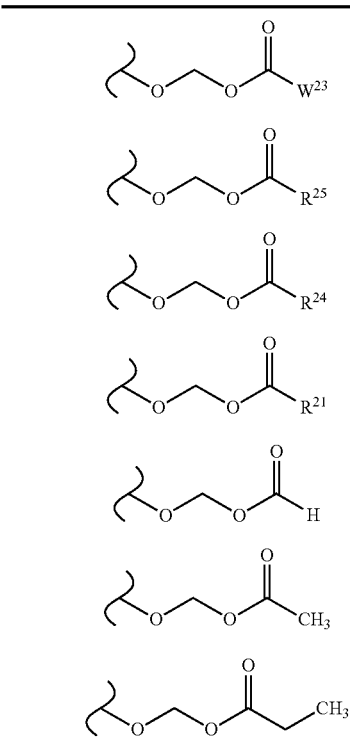
TABLE 1.29-continued
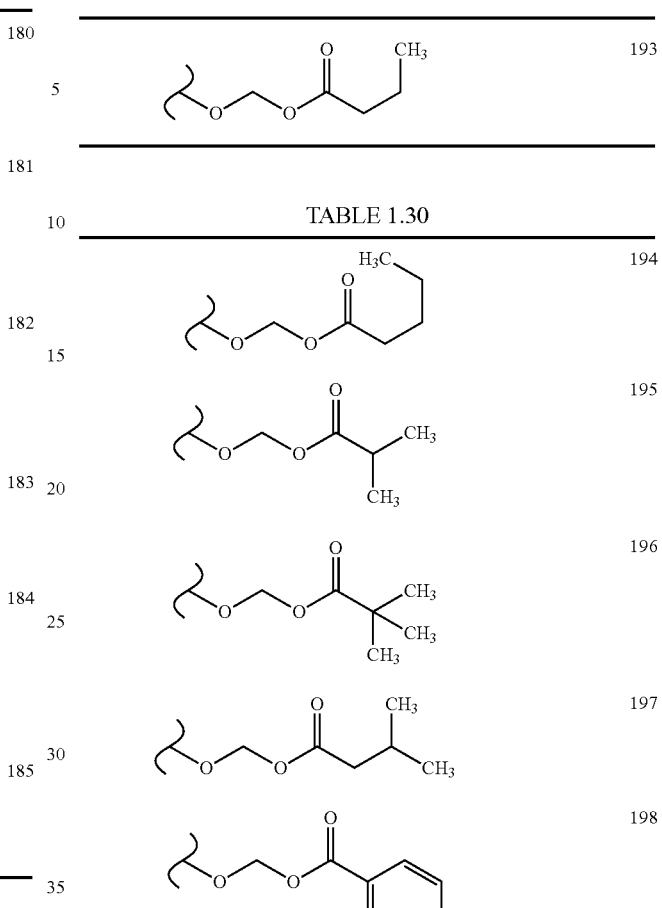
TABLE 1.30
TABLE 1.31
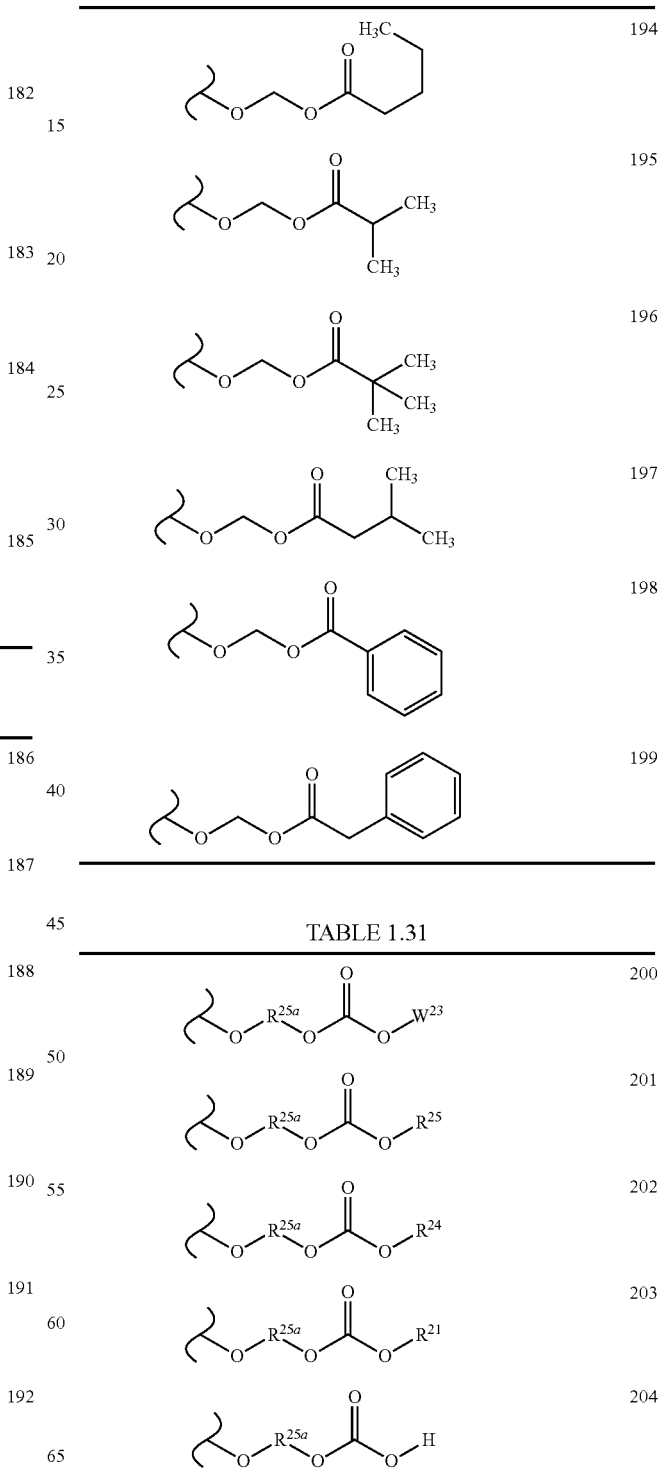

TABLE 1.31-continued

205

206

207

TABLE 1.32

208

209

210

211

212

213

TABLE 1.33

214

215

216

TABLE 1.33-continued

217

218

219

220

221

TABLE 1.34

222

223

224

225

226

227

TABLE 1.35

228

TABLE 1.35-continued
| | |
|---|---|
| 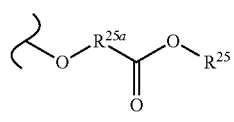 | 229 |
| 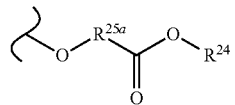 | 230 |
| 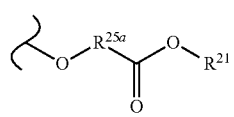 | 231 |
| 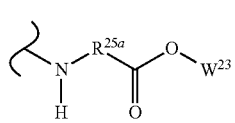 | 232 |
| 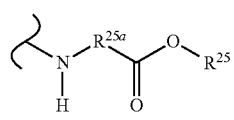 | 233 |
| 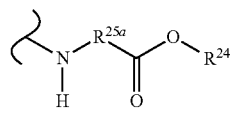 | 234 |
| 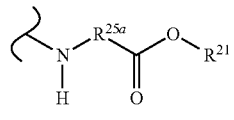 | 235 |
TABLE 1.36
| | |
|---|---|
| 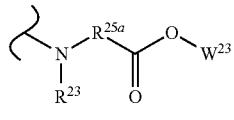 | 236 |
| 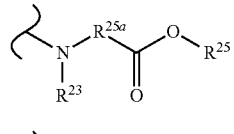 | 237 |
| 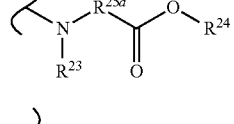 | 238 |
| 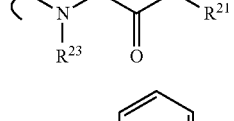 | 239 |
| 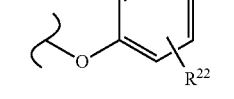 | 240 |
TABLE 1.36-continued
| | |
|---|---|
| 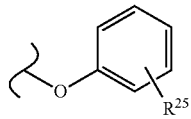 | 241 |
| 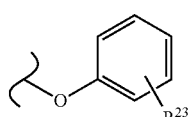 | 242 |
| 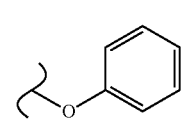 | 243 |
TABLE 1.37
| | |
|---|---|
| 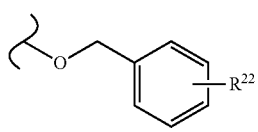 | 244 |
| 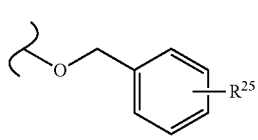 | 245 |
| 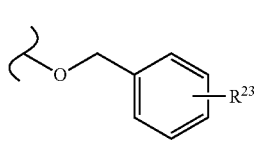 | 246 |
| 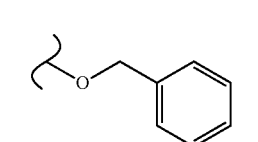 | 247 |
TABLE 2.1
| | |
|---|---|
| 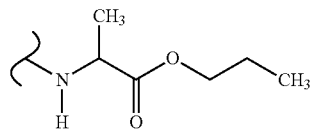 | 67 |
| 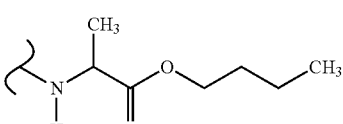 | 68 |
|  | 69 |

TABLE 2.1-continued

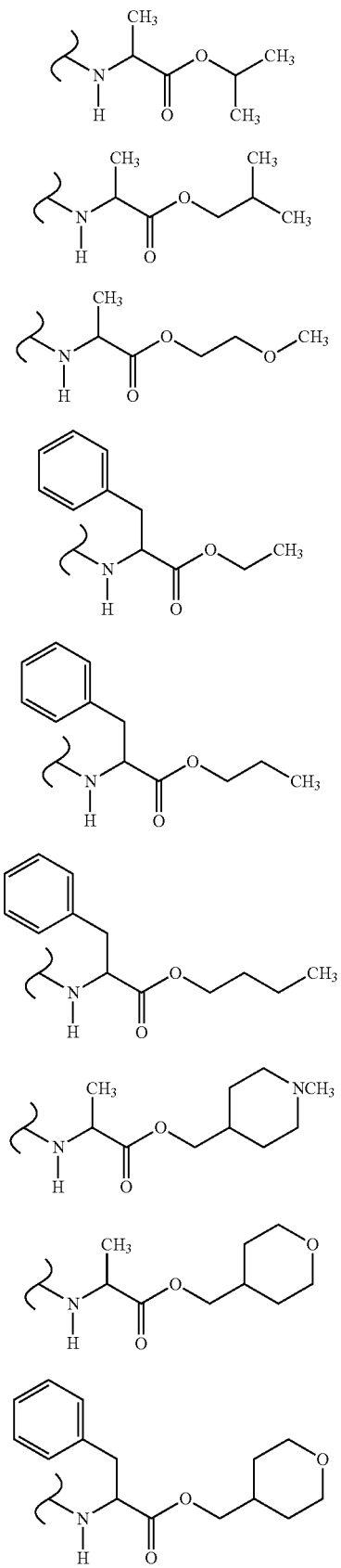

| | |
|---|---|
| | 70 |
| | 71 |
| | 258 |
| | 248 |
| | 249 |
| | 250 |
| | 251 |
| | 252 |
| | 253 |

TABLE 2.1-continued

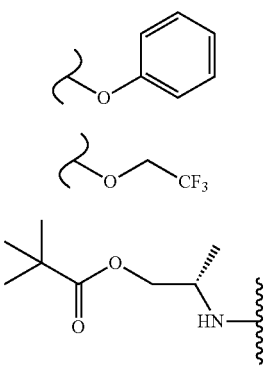

| | |
|---|---|
| | 254 |
| | 255 |
| | 256 |
| | 257 |

Embodiments of $R^x$ include esters, carbamates, carbonates, thioesters, amides, thioamides, and urea groups:

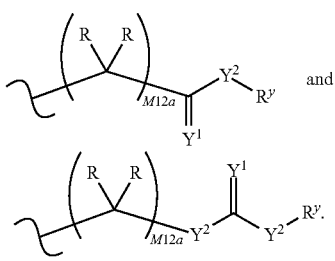

Any reference to the compounds of the invention described herein also includes a reference to a physiologically acceptable salt thereof. Examples of physiologically acceptable salts of the compounds of the invention include salts derived from an appropriate base, such as an alkali metal or an alkaline earth (for example, $Na^+$, $Li^+$, $K^+$, $Ca^{+2}$ and $Mg^{+2}$), ammonium and $NR_4^+$ (wherein R is defined herein). Physiologically acceptable salts of a nitrogen atom or an amino group include (a) acid addition salts formed with inorganic acids, for example, hydrochloric acid, hydrobromic acid, sulfuric acid, sulfamic acids, phosphoric acid, nitric acid and the like; (b) salts formed with organic acids such as, for example, acetic acid, oxalic acid, tartaric acid, succinic acid, maleic acid, fumaric acid, gluconic acid, citric acid, malic acid, ascorbic acid, benzoic acid, isethionic acid, lactobionic acid, tannic acid, palmitic acid, alginic acid, polyglutamic acid, naphthalenesulfonic acid, methanesulfonic acid, p-toluenesulfonic acid, benzenesulfonic acid, naphthalenedisulfonic acid, polygalacturonic acid, malonic acid, sulfosalicylic acid, glycolic acid, 2-hydroxy-3-naphthoate, pamoate, salicylic acid, stearic acid, phthalic acid, mandelic acid, lactic acid, ethanesulfonic acid, lysine, arginine, glutamic acid, glycine, serine, threonine, alanine, isoleucine, leucine and the like; and (c) salts formed from elemental anions for example, chlorine, bromine, and iodine. Physiologically acceptable salts of a compound of a hydroxy group include the anion of said compound in combination with a suitable cation such as $Na^+$ and $NR_4^+$.

For therapeutic use, salts of active ingredients of the compounds of the invention will be physiologically acceptable, i.e., they will be salts derived from a physiologically acceptable acid or base. However, salts of acids or bases which are not physiologically acceptable may also find use, for example, in the preparation or purification of a physiologically acceptable compound. All salts, whether or not derived from a physiologically acceptable acid or base, are within the scope of the present invention.

Finally, it is to be understood that the compositions herein comprise compounds of the invention in their un-ionized, as well as zwitterionic form, and combinations with stoichiometric amounts of water as in hydrates.

The compounds of the invention, exemplified by Formula I-V may have chiral centers, e.g., chiral carbon or phosphorus atoms. The compounds of the invention thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures are separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Mill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and I, D and L, or (+) and (−) are employed to designate the sign of rotation of plane-polarized light by the compound, with S, (−), or l meaning that the compound is levorotatory while a compound prefixed with R, (+), or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Whenever a compound described herein is substituted with more than one of the same designated group, e.g., "R" or "$R^1$", then it will be understood that the groups may be the same or different, i.e., each group is independently selected. Wavy lines, ⌇⌇⌇⌇ , indicate the site of covalent bond attachments to the adjoining substructures, groups, moieties, or atoms.

The compounds of the invention can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Methods of Inhibition of HCV Polymerase

Another aspect of the invention relates to methods of inhibiting the activity of HCV polymerase comprising the step of treating a sample suspected of containing HCV with a composition of the invention.

Compositions of the invention may act as inhibitors of HCV polymerase, as intermediates for such inhibitors or have other utilities as described below. The inhibitors will bind to locations on the surface or in a cavity of HCV polymerase having a geometry unique to HCV polymerase. Compositions binding HCV polymerase may bind with varying degrees of reversibility. Those compounds binding substantially irreversibly are ideal candidates for use in this method of the invention. Once labeled, the substantially irreversibly binding compositions are useful as probes for the detection of HCV polymerase. Accordingly, the invention relates to methods of detecting HCV polymerase in a sample suspected of containing HCV polymerase comprising the steps of: treating a sample suspected of containing HCV polymerase with a composition comprising a compound of the invention bound to a label; and observing the effect of the sample on the activity of the label. Suitable labels are well known in the diagnostics field and include stable free radicals, fluorophores, radioisotopes, enzymes, chemiluminescent groups and chromogens. The compounds herein are labeled in conventional fashion using functional groups such as hydroxyl, carboxyl, sulfhydryl or amino.

Within the context of the invention, samples suspected of containing HCV polymerase include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing an organism which produces HCV polymerase, frequently a pathogenic organism such as HCV. Samples can be contained in any medium including water and organic solvent\water mixtures. Samples include living organisms such as humans, and man made materials such as cell cultures.

The treating step of the invention comprises adding the composition of the invention to the sample or it comprises adding a precursor of the composition to the sample. The addition step comprises any method of administration as described above.

If desired, the activity of HCV polymerase after application of the composition can be observed by any method including direct and indirect methods of detecting HCV polymerase activity. Quantitative, qualitative, and semiquantitative methods of determining HCV polymerase activity are all contemplated. Typically one of the screening methods described above are applied, however, any other method such as observation of the physiological properties of a living organism are also applicable.

Organisms that contain HCV polymerase include the HCV virus. The compounds of this invention are useful in the treatment or prophylaxis of HCV infections in animals or in man.

However, in screening compounds capable of inhibiting human immunodeficiency viruses, it should be kept in mind that the results of enzyme assays may not correlate with cell culture assays. Thus, a cell based assay should be the primary screening tool.

Screens for HCV Polymerase Inhibitors

Compositions of the invention are screened for inhibitory activity against HCV polymerase by any of the conventional techniques for evaluating enzyme activity. Within the context of the invention, typically compositions are first screened for inhibition of HCV polymerase in vitro and compositions showing inhibitory activity are then screened for activity in vivo. Compositions having in vitro Ki (inhibitory constants) of less then about $5\times10^{-6}$ M and preferably less than about $1\times10^{-7}$ M are preferred for in vivo use.

Useful in vitro screens have been described in detail and will not be elaborated here. However, the examples describe suitable in vitro assays.

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the "Handbook of Pharmaceutical Excipients" (1986). Excipients include ascorbic acid and other antioxidants, chelating agents such as EDTA, carbohydrates such as dextran, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone, it may be preferable to present them as pharmaceutical formulations. The formulations, both for veterinary and for human use, of the invention comprise at least one active ingredient, as above defined, together with one or more acceptable carriers and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For infections of the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise a combination according to the invention together with one or more pharmaceutically acceptable carriers or excipients and optionally other therapeutic agents. Pharmaceutical formulations containing the active ingredient may be in any form suitable for the intended method of administration. When used for oral use, for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example, calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally-occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example, sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally-occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose, any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 mg of the active ingredient per milliliter of solution in order that infusion of a suitable volume at a rate of about 30 mL/hr can occur.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10%, and particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example, cocoa butter or a salicylate.

Formulations suitable for intrapulmonary or nasal administration have a particle size, for example, in the range of 0.1 to 500 microns, such as 0.5, 1, 30, 35 etc., which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of HCV infections as described below.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example, sealed ampoules and vials, and may be stored in a freeze-dried (lyophilized) condition requiring only the addition of the sterile liquid carrier, for example, water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example, those suitable for oral administration may include flavoring agents.

The invention further provides veterinary compositions comprising at least one active ingredient as above defined together with a veterinary carrier therefore.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention are used to provide controlled release pharmaceutical formulations containing as active ingredient one or more compounds of the invention ("controlled release formulations") in which the release of the active ingredient are controlled and regulated to allow less frequency dosing or to improve the pharmacokinetic or toxicity profile of a given active ingredient.

Effective dose of active ingredient depends at least on the nature of the condition being treated, toxicity, whether the compound is being used prophylactically (lower doses) or against an active viral infection, the method of delivery, and the pharmaceutical formulation, and will be determined by the clinician using conventional dose escalation studies. It can be expected to be from about 0.0001 to about 100 mg/kg body weight per day; typically, from about 0.01 to about 10 mg/kg body weight per day; more typically, from about 0.01 to about 5 mg/kg body weight per day; most typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with, for example, the condition of the recipient. An advantage of the compounds of this invention is that they are orally bioavailable and can be dosed orally.

Combination Therapy

Compositions of the invention are also used in combination with other active ingredients. For the treatment of HCV infections, preferably, the other active therapeutic ingredients or agents are interferons, ribavirin analogs, NS3 protease inhibitors, NS5a inhibitors, NS5b polymerase inhibitors, alpha-glucosidase 1 inhibitors, cyclophilin inhibitors, hepatoprotectants, other nucleoside inhibitors of HCV, non-nucleoside inhibitors of HCV, and other drugs for treating HCV.

Combinations of the compounds of Formula I-V are typically selected based on the condition to be treated, cross-reactivities of ingredients and pharmaco-properties of the combination. For example, when treating an infection (e.g., HCV), the compositions of the invention are combined with other active therapeutic agents (such as those described herein).

Suitable active therapeutic agents or ingredients which can be combined with the compounds of Formula I-V can include interferons, e.g., pegylated rIFN-alpha 2b, pegylated rIFN-alpha 2a, rIFN-alpha 2b, IFN alpha-2b XL, rIFN-alpha 2a, consensus IFN alpha, infergen, rebif, locteron, AVI-005, PEG-infergen, pegylated IFN-beta, oral interferon alpha, feron, reaferon, intermax alpha, r-IFN-beta, infergen+actimmune, IFN-omega with DUROS, and albuferon; ribavirin analogs, e.g., rebetol, copegus, VX-497, and viramidine (taribavirin); NS5a inhibitors, e.g., A-831, A-689 and BMS-790052; NS5b polymerase inhibitors, e.g., NM-283, valopicitabine, R1626, IDX184, PSI-7851, PSI-6130 (R1656), HCV-796, BILB 1941, MK-0608, NM-107, R7128, VCH-759, PF-868554, GSK625433, and XTL-2125; NS3 protease inhibitors, e.g., SCH-503034 (SCH-7), VX-950 (Telaprevir), ITMN-191, and BILN-2065; alpha-glucosidase 1 inhibitors, e.g., MX-3253 (celgosivir) and UT-231B; hepatoprotectants, e.g., IDN-6556, ME 3738, MitoQ, and LB-84451; non-nucleoside inhibitors of HCV, e.g., benzimidazole derivatives, benzo-1,2,4-thiadiazine derivatives, and phenylalanine derivatives; and other drugs for treating HCV, e.g., zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, GI-5005, ANA-975, XTL-6865, ANA 971, NOV-205, tarvacin, EHC-18, and NIM811.

In yet another embodiment, the present application discloses pharmaceutical compositions comprising a compound of the present invention, or a pharmaceutically acceptable salt, solvate, and/or ester thereof, in combination with at least one additional therapeutic agent, and a pharmaceutically acceptable carrier or excipient.

According to the present invention, the therapeutic agent used in combination with the compound of the present invention can be any agent having a therapeutic effect when used in combination with the compound of the present invention. For example, the therapeutic agent used in combination with the compound of the present invention can be interferons, ribavirin analogs, NS3 protease inhibitors, NS5a inhibitors, NS5b polymerase inhibitors alpha-glucosidase 1 inhibitors, cyclophilin inhibitors, hepatoprotectants, other nucleoside inhibitors of HCV, non-nucleoside inhibitors of HCV, and other drugs for treating HCV.

In another embodiment, the present application provides pharmaceutical compositions comprising a compound of the present invention, or a pharmaceutically acceptable salt, solvate, and/or ester thereof, in combination with at least one additional therapeutic agent selected from the group consisting of pegylated rIFN-alpha 2b, pegylated rIFN-alpha 2a, rIFN-alpha 2b, IFN alpha-2b XL, rIFN-alpha 2a, consensus IFN alpha, infergen, rebif, locteron, AVI-005, PEG-infergen, pegylated IFN-beta, oral interferon alpha, feron, reaferon, intermax alpha, r-IFN-beta, infergen+actimmune, IFN-omega with DUROS, albuferon, rebetol, copegus, VX-497, viramidine (taribavirin), A-831, A-689, NM-283, valopicitabine, R1626, PSI-6130 (R1656), IDX184, PSI-7851, HCV-796, BILB 1941, MK-0608, NM-107, R7128, VCH-759, PF-868554, GSK625433, XTL-2125, SCH-503034 (SCH-7), VX-950 (Telaprevir), ITMN-191, and BILN-2065, MX-3253 (celgosivir), UT-231B, IDN-6556, ME 3738, MitoQ, and LB-84451, benzimidazole derivatives, benzo-1,2,4-thiadiazine derivatives, and phenylalanine derivatives, zadaxin, nitazoxanide (alinea), BIVN-401 (virostat), DEBIO-025, VGX-410C, EMZ-702, AVI 4065; bavituximab, oglufanide, PYN-17, KPE02003002, actilon (CPG-10101), KRN-7000, civacir, GI-5005, ANA-975, XTL-6865, ANA 971, NOV-205, tarvacin, EHC-18, and NIM811 and a pharmaceutically acceptable carrier or excipient.

In yet another embodiment, the present application provides a combination pharmaceutical agent comprising:
 a) a first pharmaceutical composition comprising a compound of the present invention, or a pharmaceutically acceptable salt, solvate, or ester thereof; and
 b) a second pharmaceutical composition comprising at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, interferons, ribavirin analogs, NS3 protease inhibitors, NS5a inhibitors, alpha-glucosidase 1 inhibitors, cyclophilin inhibitors, hepatoprotectants, other nucleoside inhibitors of HCV, non-nucleoside inhibitors of HCV, and other drugs for treating HCV, and combinations thereof.

Combinations of the compounds of Formula I-V and additional active therapeutic agents may be selected to treat patients infected with HCV and other conditions such as HIV infections. Accordingly, the compounds of Formula I-V may be combined with one or more compounds useful in treating HIV, for example, HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, interferons, ribavirin analogs, NS3 protease inhibitors, NS5a inhibitors, alpha-glucosidase 1 inhibitors, cyclophilin inhibitors, hepatoprotectants, other nucleoside inhibitors of HCV, non-nucleoside inhibitors of HCV, and other drugs for treating HCV.

More specifically, one or more compounds of the present invention may be combined with one or more compounds selected from the group consisting of 1) HIV protease inhibitors, e.g., amprenavir, atazanavir, fosamprenavir, indinavir, lopinavir, ritonavir, lopinavir+ritonavir, nelfinavir, saquinavir, tipranavir, brecanavir, darunavir, TMC-126, TMC-114, mozenavir (DMP-450), JE-2147 (AG1776), AG1859, DG35, L-756423, R00334649, KNI-272, DPC-681, DPC-684, and GW640385X, DG17, PPL-100, 2) a HIV non-nucleoside inhibitor of reverse transcriptase, e.g., capravirine, emivirine, delaviridine, efavirenz, nevirapine, (+) calanolide A, etravirine, GW5634, DPC-083, DPC-961, DPC-963, MIV-150, and TMC-120, TMC-278 (rilpivirine), efavirenz, BILR 355 BS, VRX 840773, UK-453,061, RDEA806, 3) a HIV nucleoside inhibitor of reverse transcriptase, e.g., zidovudine, emtricitabine, didanosine, stavudine, zalcitabine, lamivudine, abacavir, amdoxovir, elvucitabine, alovudine, MIV-210, racivir (±-FTC), D-d4FC, emtricitabine, phosphazide, fozivudine tidoxil, fosalvudine tidoxil, apricitibine (AVX754), amdoxovir, KP-1461, abacavir+lamivudine, abacavir+lamivudine+zidovudine, zidovudine+lamivudine, 4) a HIV nucleotide inhibitor of reverse transcriptase, e.g., tenofovir, tenofovir disoproxil fumarate+emtricitabine, tenofovir disoproxil fumarate+emtricitabine+efavirenz, and adefovir, 5) a HIV integrase inhibitor, e.g., curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-870810, MK-0518 (raltegravir), BMS-707035, MK-2048, BA-011, BMS-538158, GSK364735C, 6) a gp41 inhibitor, e.g., enfuvirtide, sifuvirtide, FB006M, TRI-1144, SPC3, DES6, Locus gp41, CovX, and REP 9, 7) a CXCR4 inhibitor, e.g., AMD-070, 8) an entry inhibitor, e.g., SP01A, TNX-355, 9) a gp120 inhibitor, e.g., BMS-488043 and BlockAide/CR, 10) a G6PD and NADH-oxidase inhibitor, e.g., immunitin, 10) a CCR5 inhibitor, e.g., aplaviroc, vicriviroc, INCB9471, PRO-140, INCB15050, PF-232798, CCR5 mAb004, and maraviroc, 11) an interferon, e.g., pegylated rIFN-alpha 2b, pegylated rIFN-alpha 2a, rIFN-alpha 2b, IFN alpha-2b XL, rIFN-alpha 2a, consensus IFN alpha, infergen, rebif, locteron, AVI-005, PEG-infergen, pegylated IFN-beta, oral interferon alpha, feron, reaferon, intermax alpha, r-IFN-beta, infergen+actimmune, IFN-omega with DUROS, and albuferon, 12) ribavirin analogs, e.g., rebetol, copegus, VX-497, and viramidine (taribavirin) 13) NS5a inhibitors, e.g., A-831, A-689 and BMS-790052, 14) NS5b polymerase inhibitors, e.g., NM-283, valopicitabine, R1626, PSI-6130 (R1656), IDX184, PSI-7851, HCV-796, BILB 1941, MK-0608, NM-107, R7128, VCH-759, PF-868554, GSK625433, and XTL-2125, 15) NS3 protease inhibitors, e.g., SCH-503034 (SCH-7), VX-950 (Telaprevir), ITMN-191, and BILN-2065, 16) alpha-glucosidase 1 inhibitors, e.g., MX-3253 (celgosivir) and UT-231B, 17) hepatoprotectants, e.g., IDN-6556, ME 3738, MitoQ, and LB-84451, 18) non-nucleoside inhibitors of HCV, e.g., benzimidazole derivatives, benzo-1,2,4-thiadiazine derivatives, and phenylalanine derivatives, 19) other drugs for treating HCV, e.g., zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, GI-5005, ANA-975, XTL-6865, ANA 971, NOV-205, tarvacin, EHC-18, and NIM811, 19) pharmacokinetic enhancers, e.g., BAS-100 and SPI452, 20)RNAse H inhibitors, e.g., ODN-93 and ODN-112, 21) other anti-HIV agents, e.g., VGV-1, PA-457 (bevirimat), ampligen, HRG214, cytolin, polymun, VGX-410, KD247, AMZ 0026, CYT 99007, A-221 HIV, BAY 50-4798, MDX010 (iplimumab), PBS119, ALG889, and PA-1050040.

For the treatment of Paramyxoviridae virus infections, preferably, the other active therapeutic agent is active against Paramyxoviridae virus infections, particularly respiratory syncytial virus infections and/or parainfluenza virus infections. Non-limiting examples of these other active therapeutic agents are ribavirin and/or palivizumab.

For the treatment of Orthomyxoviridae virus infections, preferably, the other active therapeutic agent is active against Orthomyxoviridae virus infections, particularly Influenzavirus infections. Non-limiting examples of these other active therapeutic agents are viral neuramidase inhibitors and/or viral M2 channel inhibitors. Non-limiting examples of neuramidase inhibitors include oseltamivir, zanamivir, laninamivir and peramivir. Non-limiting examples of viral M2 channel inhibitors include amantadine and rimantadine.

For the treatment of Picornaviridae virus infections, preferably, the other active therapeutic agent is active against Picornaviridae virus infections, particularly Enterovirus infections. Non-limiting examples of these other active therapeutic agents are capsid binding inhibitors such as pleconaril, BTA-798 and other compounds disclosed by Wu, et al. (U.S. Pat. No. 7,078,403) and Watson (U.S. Pat. No. 7,166,604).

Many of the infections of the Paramyxoviridae, Orthomyxoviridae, and Picornaviridae viruses are respiratory infections. Therefore, additional active therapeutics used to treat respiratory symptoms and sequelae of infection may be used in combination with the compounds of Formula I-V. For example, other preferred additional therapeutic agents in combination with the compounds of Formula I-V for the treatment of viral respiratory infections include, but are not limited to, bronchodilators and corticosteroids. Glucocorticoids, which were first introduced as an asthma therapy in 1950 (Carryer, Journal of Allergy, 21, 282-287, 1950), remain the most potent and consistently effective therapy for this disease, although their mechanism of action is not yet fully understood (Morris, J. Allergy Clin. Immunol., 75 (1 Pt) 1-13, 1985). Unfortunately, oral glucocorticoid therapies are associated with profound undesirable side effects such as truncal obesity, hypertension, glaucoma, glucose intolerance, acceleration of cataract formation, bone mineral loss, and psychological effects, all of which limit their use as long-term therapeutic agents (Goodman and Gilman, $10^{th}$ edition, 2001). A solution to systemic side effects is to deliver steroid drugs directly to the site of inflammation. Inhaled corticosteroids (ICS) have been developed to mitigate the severe adverse effects of oral steroids. Non-limiting examples of corticosteroids that may be used in combinations with the compounds of Formula I-V are dexamethasone, dexamethasone sodium phosphate, fluorometholone, fluorometholone acetate, loteprednol, loteprednol etabonate, hydrocortisone, prednisolone, fludrocortisones, triamcinolone, triamcinolone acetonide, betamethasone, beclomethasone diprorionate, methylprednisolone, fluocinolone, fluocinolone acetonide, flunisolide, fluocortin-21-butylate, flumethasone, flumetasone pivalate, budesonide, halobetasol propionate, mometasone furoate, fluticasone propionate, ciclesonide; or a pharmaceutically acceptable salts thereof.

Other anti-inflammatory agents working through anti-inflammatory cascade mechanisms are also useful as additional therapeutic agents in combination with the compounds of Formula I-V for the treatment of viral respiratory infections. Applying "anti-inflammatory signal transduction modulators" (referred to in this text as AISTM), like phosphodiesterase inhibitors (e.g., PDE-4, PDE-5, or PDE-7 specific), transcription factor inhibitors (e.g., blocking NFκB through IKK inhibition), or kinase inhibitors (e.g., blocking P38 MAP, JNK, PI3K, EGFR or Syk) is a logical approach to switching off inflammation as these small molecules target a limited number of common intracellular pathways—those signal transduction pathways that are critical points for the anti-inflammatory therapeutic intervention (see review by P. J. Barnes, 2006). These non-limiting additional therapeutic agents include: 5-(2,4-Difluoro-phenoxy)-1-isobutyl-1H-indazole-6-carboxylic acid (2-dimethylamino-ethyl)-amide (P38 Map kinase inhibitor ARRY-797); 3-Cyclopropylmethoxy-N-(3,5-dichloro-pyridin-4-yl)-4-difluorormethoxy-benzamide (PDE-4 inhibitor Roflumilast); 4-[2-(3-cyclopentyloxy-4-methoxyphenyl)-2-phenyl-ethyl]-pyridine (PDE-4 inhibitor CDP-840); N-(3,5-dichloro-4-pyridinyl)-4-(difluoromethoxy)-8-[(methylsulfonyl)amino]-1-dibenzofurancarboxamide (PDE-4 inhibitor Oglemilast); N-(3,5-Dichloro-pyridin-4-yl)-2-[1-(4-fluorobenzyl)-5-hydroxy-1H-indol-3-yl]-2-oxo-acetamide (PDE-4 inhibitor AWD 12-281); 8-Methoxy-2-trifluoromethyl-quinoline-5-carboxylic acid (3,5-dichloro-1-oxy-pyridin-4-yl)-amide (PDE-4 inhibitor Sch 351591); 4-[5-(4-Fluorophenyl)-2-(4-methanesulfinyl-phenyl)-1H-imidazol-4-yl]-pyridine (P38 inhibitor SB-203850); 4-[4-(4-(4-Fluoro-phenyl)-1-(3-phenyl-propyl)-5-pyridin-4-yl-1H-imidazol-2-yl]-but-3-yn-1-ol (P38 inhibitor RWJ-67657); 4-Cyano-4-(3-cyclopentyloxy-4-methoxy-phenyl)-cyclohexanecarboxylic acid 2-diethylamino-ethyl ester (2-diethyl-ethyl ester prodrug of Cilomilast, PDE-4 inhibitor); (3-Chloro-4-fluorophenyl)-[7-methoxy-6-(3-morpholin-4-yl-propoxy)-quinazolin-4-yl]-amine (Gefitinib, EGFR inhibitor); and 4-(4-Methyl-piperazin-1-ylmethyl)-N-[4-methyl-3-(4-pyridin-3-yl-pyrimidin-2-ylamino)-phenyl]-benzamide (Imatinib, EGFR inhibitor).

Combinations comprising inhaled β2-adrenoreceptor agonist bronchodilators such as formoterol, albuterol or salmeterol with the compounds of Formula I-V are also suitable, but non-limiting, combinations useful for the treatment of respiratory viral infections.

Combinations of inhaled β2-adrenoreceptor agonist bronchodilators such as formoterol or salmeterol with ICS's are also used to treat both the bronchoconstriction and the inflammation (Symbicort® and Advair®, respectively). The combinations comprising these ICS and β2-adrenoreceptor agonist combinations along with the compounds of Formula I-V are also suitable, but non-limiting, combinations useful for the treatment of respiratory viral infections.

For the treatment or prophylaxis of pulmonary bronchoconstriction, anticholinergics are of potential use and, therefore, useful as an additional therapeutic agents in combination with the compounds of Formula I-V for the treatment of viral respiratory infections. These anticholinergics include, but are not limited to, antagonists of the muscarinic receptor (particularly of the M3 subtype) which have shown therapeutic efficacy in man for the control of cholinergic tone in COPD (Witek, 1999); 1-{4-Hydroxy-1-[3,3,3-tris-(4-fluoro-phenyl)-propionyl]-pyrrolidine-2-carbonyl}-pyrrolidine-2-carboxylic acid (1-methyl-piperidin-4-ylmethyl)-amide; 3-[3-(2-Diethylamino-acetoxy)-2-phenyl-propionyloxy]-8-isopropyl-8-methyl-8-azonia-bicyclo[3.2.1]octane (Ipratropium-N,N-diethylglycinate); 1-Cyclohexyl-3,4-dihydro-1H-isoquinoline-2-carboxylic acid 1-aza-bicyclo

[2.2.2]oct-3-yl ester (Solifenacin); 2-Hydroxymethyl-4-methanesulfinyl-2-phenyl-butyric acid 1-aza-bicyclo[2.2.2]oct-3-yl ester (Revatropate); 2-{1-[2-(2,3-Dihydro-benzofuran-5-yl)-ethyl]-pyrrolidin-3-yl}-2,2-diphenyl-acetamide (Darifenacin); 4-Azepan-1-yl-2,2-diphenyl-butyramide (Buzepide); 7-[3-(2-Diethylamino-acetoxy)-2-phenyl-propionyloxy]-9-ethyl-9-methyl-3-oxa-9-azonia-tricyclo[3.3.1.02,4]nonane (Oxitropium-N,N-diethylglycinate); 7-[2-(2-Diethylamino-acetoxy)-2,2-di-thiophen-2-yl-acetoxy]-9,9-dimethyl-3-oxa-9-azonia-tricyclo[3.3.1.02,4]nonane (Tiotropium-N,N-diethylglycinate); Dimethylamino-acetic acid 2-(3-diisopropylamino-1-phenyl-propyl)-4-methyl-phenyl ester (Tolterodine-N,N-dimethylglycinate); 3-[4,4-Bis-(4-fluoro-phenyl)-2-oxo-imidazolidin-1-yl]-1-methyl-1-(2-oxo-2-py-ridin-2-yl-ethyl)-pyrrolidinium; 1-[1-(3-Fluoro-benzyl)-pip-eridin-4-yl]-4,4-bis-(4-fluoro-phenyl)-imidazolidin-2-one; 1-Cyclooctyl-3-(3-methoxy-1-aza-bicyclo[2.2.2]oct-3-yl)-1-phenyl-prop-2-yn-1-ol; 3-[2-(2-Diethylamino-acetoxy)-2,2-di-thiophen-2-yl-acetoxy]-1-(3-phenoxy-propyl)-1-azo-nia-bicyclo[2.2.2]octane (Aclidinium-N,N-diethylglycinate); or (2-Diethylamino-acetoxy)-di-thiophen-2-yl-acetic acid 1-methyl-1-(2-phenoxy-ethyl)-piperidin-4-yl ester.

The compounds of Formula I-V may also be combined with mucolytic agents to treat both the infection and symptoms of respiratory infections. A non-limiting example of a mucolytic agent is ambroxol. Similarly, the compounds of Formula I-V may be combined with expectorants to treat both the infection and symptoms of respiratory infections. A non-limiting example of an expectorant is guaifenesin.

It is also possible to combine any compound of the invention with one or more other active therapeutic agents in a unitary dosage form for simultaneous or sequential administration to a patient. The combination therapy may be administered as a simultaneous or sequential regimen. When administered sequentially, the combination may be administered in two or more administrations.

Co-administration of a compound of the invention with one or more other active therapeutic agents generally refers to simultaneous or sequential administration of a compound of the invention and one or more other active therapeutic agents, such that therapeutically effective amounts of the compound of the invention and one or more other active therapeutic agents are both present in the body of the patient.

Co-administration includes administration of unit dosages of the compounds of the invention before or after administration of unit dosages of one or more other active therapeutic agents, for example, administration of the compounds of the invention within seconds, minutes, or hours of the administration of one or more other active therapeutic agents. For example, a unit dose of a compound of the invention can be administered first, followed within seconds or minutes by administration of a unit dose of one or more other active therapeutic agents. Alternatively, a unit dose of one or more other therapeutic agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active therapeutic agents. In other cases, it may be desirable to administer a unit dose of one or more other active therapeutic agents first, followed, after a period of hours (e.g., 1-12 hours), by administration of a unit dose of a compound of the invention.

The combination therapy may provide "synergy" and "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e., serially, whereas in combination therapy, effective dosages of two or more active ingredients are administered together. A synergistic anti-viral effect denotes an antiviral effect which is greater than the predicted purely additive effects of the individual compounds of the combination.

In still yet another embodiment, the present application provides for methods of inhibiting HCV polymerase in a cell, comprising: contacting a cell infected with HCV with an effective amount of a compound of Formula I-V, or a pharmaceutically acceptable salt, solvate, and/or ester thereof, whereby HCV polymerase is inhibited.

In still yet another embodiment, the present application provides for methods of inhibiting HCV polymerase in a cell, comprising: contacting a cell infected with HCV with an effective amount of a compound of Formula I-V, or a pharmaceutically acceptable salt, solvate, and/or ester thereof, and at least one additional active therapeutic agent, whereby HCV polymerase is inhibited.

In still yet another embodiment, the present application provides for methods of inhibiting HCV polymerase in a cell, comprising: contacting a cell infected with HCV with an effective amount of a compound of Formula I-V, or a pharmaceutically acceptable salt, solvate, and/or ester thereof, and at least one additional active therapeutic agent selected from the group consisting of interferons, ribavirin analogs, NS3 protease inhibitors, NS5a inhibitors, alpha-glucosidase 1 inhibitors, cyclophilin inhibitors, hepatoprotectants, other nucleoside inhibitors of HCV, non-nucleoside inhibitors of HCV, and other drugs for treating HCV.

In still yet another embodiment, the present application provides for methods of treating HCV in a patient, comprising: administering to the patient a therapeutically effective amount of a compound of Formula I-V, or a pharmaceutically acceptable salt, solvate, and/or ester thereof.

In still yet another embodiment, the present application provides for methods of treating HCV in a patient, comprising: administering to the patient a therapeutically effective amount of a compound of Formula I-V, or a pharmaceutically acceptable salt, solvate, and/or ester thereof, and at least one additional active therapeutic agent, whereby HCV polymerase is inhibited.

In still yet another embodiment, the present application provides for methods of treating HCV in a patient, comprising: administering to the patient a therapeutically effective amount of a compound of Formula I-V, or a pharmaceutically acceptable salt, solvate, and/or ester thereof, and at least one additional active therapeutic agent selected from the group consisting of interferons, ribavirin analogs, NS3 protease inhibitors, NS5a inhibitors, alpha-glucosidase 1 inhibitors, cyclophilin inhibitors, hepatoprotectants, other nucleoside inhibitors of HCV, non-nucleoside inhibitors of HCV, and other drugs for treating HCV.

In still yet another embodiment, the present application provides for the use of a compound of the present invention, or a pharmaceutically acceptable salt, solvate, and/or ester thereof, for the preparation of a medicament for treating an HCV infection in a patient.

Metabolites of the Compounds of the Invention

Also falling within the scope of this invention are the in vivo metabolic products of the compounds described herein, to the extent such products are novel and unobvious over the prior art. Such products may result, for example, from the oxidation, reduction, hydrolysis, amidation, esterification and the like of the administered compound, primarily due to enzymatic processes. Accordingly, the invention includes novel and unobvious compounds produced by a process comprising contacting a compound of this invention with a mammal for a period of time sufficient to yield a metabolic product thereof. Such products typically are identified by preparing a radiolabelled (e.g., $^{14}C$ or $^{3}H$) compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no HCV polymerase inhibitory activity of their own.

Recipes and methods for determining stability of compounds in surrogate gastrointestinal secretions are known. Compounds are defined herein as stable in the gastrointestinal tract where less than about 50 mole percent of the protected groups are deprotected in surrogate intestinal or gastric juice upon incubation for 1 hour at 37° C. Simply because the compounds are stable to the gastrointestinal tract does not mean that they cannot be hydrolyzed in vivo. The prodrugs of the invention typically will be stable in the digestive system but may be substantially hydrolyzed to the parental drug in the digestive lumen, liver or other metabolic organ, or within cells in general.

EXAMPLES

Certain abbreviations and acronyms are used in describing the experimental details. Although most of these would be understood by one skilled in the art, Table 3 contains a list of many of these abbreviations and acronyms.

TABLE 3

List of abbreviations and acronyms.

| Abbreviation | Meaning |
|---|---|
| Ac$_2$O | Acetic anhydride |
| ACN | Acetonitrile |
| AcOH or HOAc | Acetic acid |
| AIBN | 2,2'-azobis(2-methylpropionitrile) |
| Ar | Aryl |
| Bn | Benzyl |
| bs or br s | Broad singlet |
| Bu | Butyl |
| Bz | Benzoyl |
| cm | Centimeters |
| conc. | Concentration |
| d | Doublet |
| DABCO | 1,4-diazabicyclo[2.2.2]octane |
| DBN | 1,5-diazabicyclo[4.3.0]non-5-ene |
| DBU | 1,5-diazabicyclo[5.4.0]undec-5-ene |
| DCC | Dicyclohexylcarbodiimide |
| DCE | Dichloroethane |
| DCM | Dichloromethane |
| dd | Doublet of doublets |
| ddd | Doublet of doublets of doublets |
| DMAP | 4-dimethylaminopyridine |
| DMEM | Dulbecco's modified Eagle's medium |
| DMF | Dimethylformamide |
| DMSO | Dimethylsulfoxide |
| dt | Double triplet |
| DTT | Dithiothreitol |
| EDTA | Ethylenediaminetetraacetic acid |
| equiv. | Equivalents |
| Et | Ethyl |
| EtOAc | Ethyl acetate |
| FBS | Fetal bovine serum |
| g | Gram |
| h or hr | Hour |
| Hex | Hexane or Hexanes |
| HPLC | High pressure liquid chromatography |
| IBX | 2-Iodoxybenzoic acid |
| IPA | Isopropyl alcohol |
| kg | Kilogram |
| LC/MS | liquid chromatography/mass spectrometry |
| m | Meter |
| m/z or m/e | Mass to charge ratio |
| MDCK | Madin-Darby Canine Kidney Cells |
| Me | Methyl |
| MeCN | Acetonitrile |
| MeOH | Methanol |
| mg | Milligram |
| MH$^-$ | Mass minus 1 |
| MH$^+$ | Mass plus 1 |
| MHz | Megahertz |
| min | Minute |
| mL | Milliliter |
| mmol | Millimole |
| MS or ms | Mass spectrum |
| Ms-Cl | Methane sulfonyl chloride |
| N | Normal |
| NBS | N-bromosuccinimide |
| NMP | N-methylpyrrolidinone |
| NMR | Nuclear magnetic resonance |
| PBS | Phosphate buffered saline |
| PEG | Polyethylene glycol |
| Ph | Phenyl |
| ppm | Parts per million |
| Pyr or Py | Pyridine |
| q | Quartet |
| RP | Reverse phase |
| RPMI | Roswell Park Memorial Institute |
| rt or r.t. or RT | Room temperature |
| s | Singlet |
| sat. | Saturated |
| t | Triplet |
| TBAF | Tetrabutylammonium fluoride |
| TBDMS | tert-butyldimethylsilyl |
| TEA | Triethylamine |
| TES | Triethylsilane |
| Tf | Trifluoromethanesulfonate |
| TFA | Trifluoroacetic acid |
| THF | Tetrahydrofuran |
| TIPDS-Cl | 1,3-dichloro-1,1,3,3-tetraisopropoxy |
| TLC or tlc | Thin layer chromatography |
| TMS | Trimethylsilane |
| TMSOTf | (trimethylsilyl)trifluoromethylsulfonate |
| Tr | Triphenylmethyl or trityl |

TABLE 3-continued

List of abbreviations and acronyms.

| Abbreviation | Meaning |
| --- | --- |
| XTT | {2,3-bis(2-methoxy-4-nitro-5-sulfophenyl)-5-[(phenylamino)carbonyl]-2H-tetrazolium hydroxide} |
| δ | parts per million down field from tetramethylsilane |

Preparation of Compounds

General method for the preparation of 1'-CN substituted nucleosides

The 1'-CN substituted nucleoside (Compound G-C) can be prepared by following a method similar to that described in *Tetrahedron Letters*, 1993, 8579. Accordingly, an appropriately protected 1'-bromo-1'-cyano hexose (Compound G-B), which is obtained from a reaction of the corresponding 1'-cyano hexose (Compound G-A) with a brominating agent such as NBS, is coupled to a silylated pyrimidine base with or without a Lewis acid such as tine tetrachloride, mercuric cyanide, or silver triflate. The coupled product is then de-protected to obtain a 1'-CN substituted nucleoside (Compound G-C, Scheme 1). References for preparation of each individual Compound G-A are cited in the Examples section below.

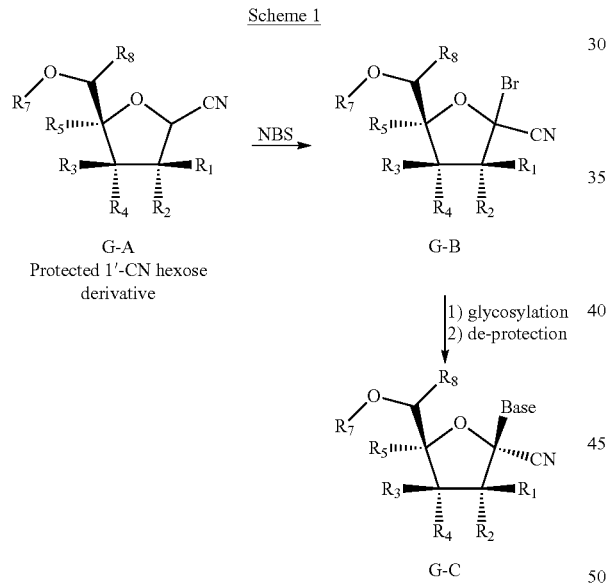

Scheme 1

G-A
Protected 1'-CN hexose derivative

G-B

G-C

General method for the preparation of 1'-alkenyl, 1'-haloethenyl or 1'-alkynyl substituted nucleosides The 1'-alkenyl, 1'-haloethenyl, or 1'-alkynyl substituted nucleoside can be prepared following a method similar to that described in *Journal of Organic Chemistry*, 2004, 1831. Accordingly, an appropriately protected 1',2'-unsaturated uridine nucleoside (Compound G-D) is converted to the 1',2'-epoxide (Compound G-E), which is reacted with an appropriate tri(alkenyl), tri(haloethenyl) or tri(alkynyl)aluminum to afford an 1'-alkenyl, 1'-haloethenyl, or alkynyl substituted uridine nucleoside (Compound G-F) (Scheme 2A). The uridine analog can be converted to the corresponding cytidine analog (Compound G-G) following general methods well-established in the practice of nucleoside chemistry, some of which detailed procedures are described in the Examples section below (Scheme 2B).

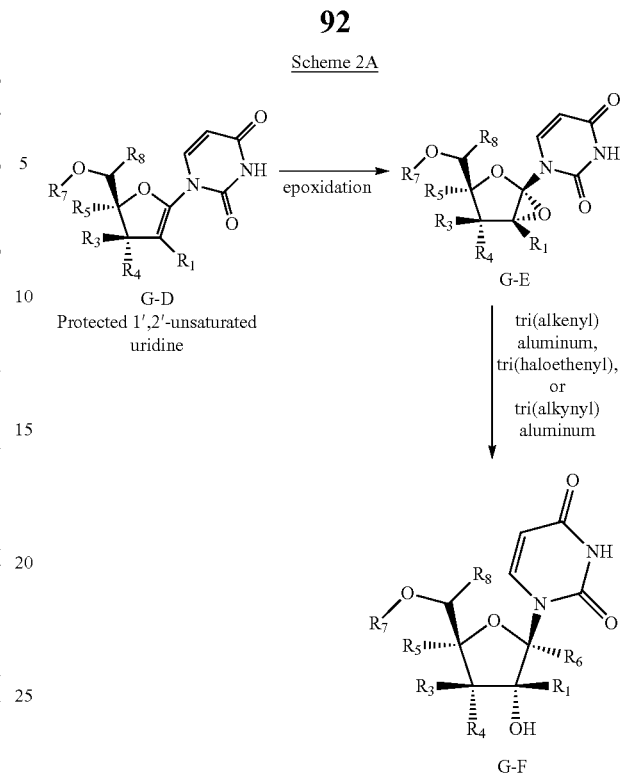

Scheme 2A

G-D
Protected 1',2'-unsaturated uridine

G-E tri(alkenyl) aluminum, tri(haloethenyl), or tri(alkynyl) aluminum

G-F

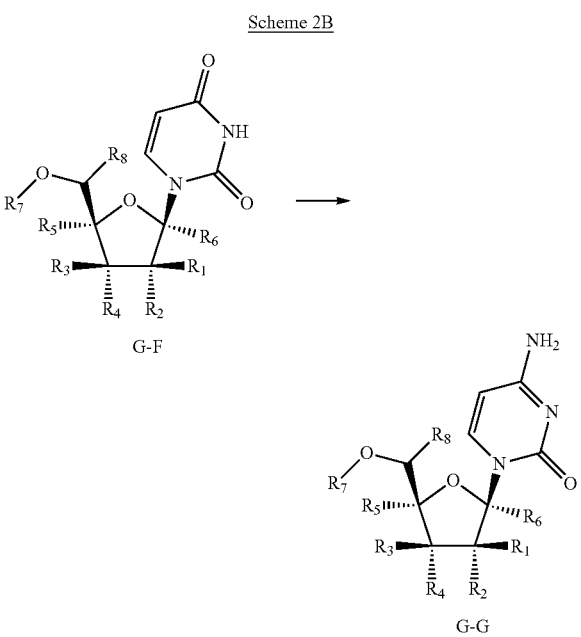

Scheme 2B

G-F

G-G

Preparation of Exemplary Compounds

Compound 1

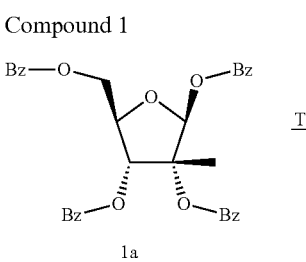

1a

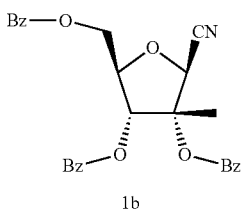

1b

Compound 1a (prepared according to J. Organic Chemistry, 1968, 2490) was subjected to the reaction conditions similar to those described in WO200512308, affording Compound 1b (Yield; 74%). Melting point; 101-103° C.

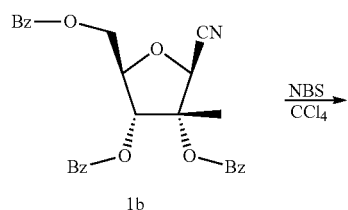

1b

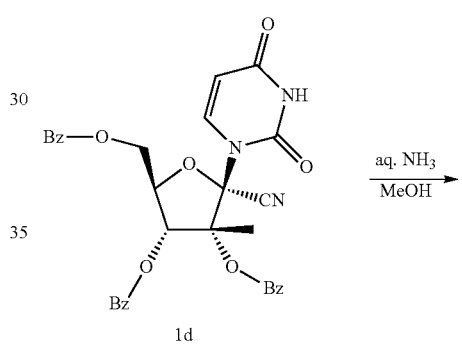

1c

Compound 1b was subjected to the reaction conditions similar to those described in Tetrahedron Letters, 1993, 8579, affording Compound 1c. Melting point; 44-49° C.

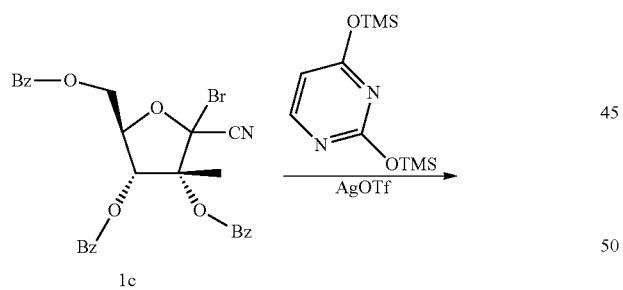

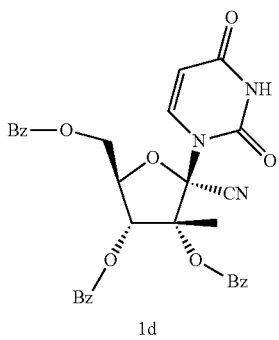

1d

Compound 1c (300 mg, 0.53 mmol) was placed into a microwave vial under argon and dissolved with a 1:1 mixture of anhydrous dichloroethane and acetonitrile (12 mL). 2,6-Lutidine (0.3 mL, 2.6 mmol) was added, followed by 0.3 mL bis-TMS uracil. Then, 300 mg (1.17 mmol) Ag(OTf) was added and the mixture was sealed, and heated to 150° C. for 30 minutes via use of a microwave reactor. After this time, the reaction was judged complete by LC/MS analysis. The reaction was filtered, and the filtrate diluted with 300 mL DCM. The organic layer was washed with 300 mL saturated sodium bicarbonate solution, then 2×300 mL $H_2O$, and then with 300 mL sat. brine solution. The organic phase was dried by passage through a hydrophobic membrane filter and the volatiles removed to give 330 mg crude product. Chromatography using a 40 g silica column and a gradient of 7:3 hexanes/EtOAc to 100% EtOAc gave 90 mg 1d (28% yield) as a single isomer. $^1$H-NMR (400 MHz, $CD_3CN$): δ 9.30 (bs, 1H), 8.15 (m, 1H), 8.08 (m, 2H), 7.78 (d, J=8.4 Hz, 2H), 7.65 (m, 2H), 7.58 (m, 4H), 7.25 (m, 2H), 5.92 (d, J=2.8 Hz, 1H), 5.72 (d, J=8.4 Hz, 1H), 4.98 (m, 1H), 4.87 (m, 2H), 1.68 (s, 3H). MS=596 (M+H$^+$). LC/MS retention time on a 3.5 minute LC/MS method (Polar RP column)=2.48 min.

Compound 1

To a solution of Compound 1d (40 mg, 0.07 mmol) in MeOH (1 mL) at room temperature was added 2 mL conc. aq. ammonia. The reaction mixture was stirred at room temperature for 20 h. LC/MS analysis indicated that the reaction had gone to completion. The reaction was concentrated to a residue and the crude product, 40 mg, was dissolved in water, and purified via revered phase HPLC. Concentration of the product fractions furnished 14 mg (74% yield) of tris-debenzoylated product Compound 1. $^1$H-NMR (400 MHz, $D_2O$): δ 7.91 (d, J=8.4 Hz, 1H), 5.78 (d, J=8.4 Hz, 1H), 4.15 (m, 1H), 3.94 (m, 1H), 3.75 (m, 1H), 3.67 (m, 1H), 1.18 (s, 3H). MS=282 (M−H$_+$). LC/MS retention time on a 3.5 minute LC/MS method (Polar RP column)=0.52 min.

Compound 2

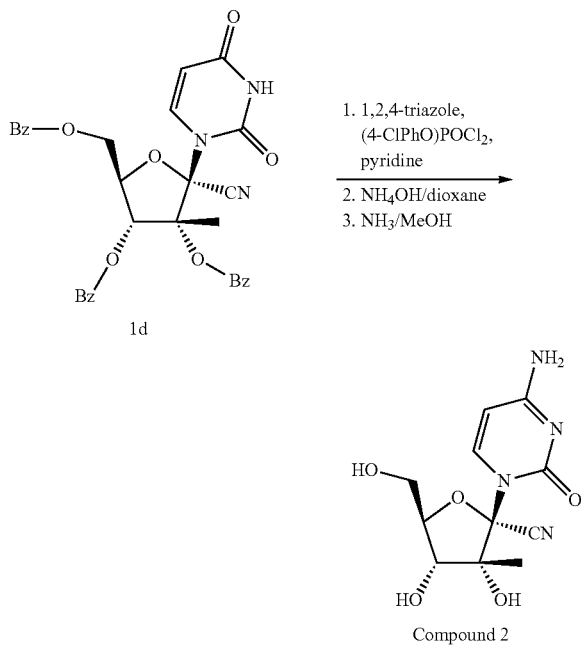

To a solution of Compound 1c (250 mg, 0.4 mmol) in pyridine (8 mL) at 0° C. was added 0.5 g (2 mmol, 5 equiv) 4-Cl-phenyl phosphorodichloridate, followed by 350 mg (5 mmol, 12.5 equiv) 1,2,4-triazole. The reaction was allowed to warm to rt and stir for an additional 3 h. LC/MS analysis indicated that the reaction had gone to completion. The reaction was concentrated to a residue, dissolved in 100 mL DCM, washed with 2×50 mL water, 50 mL 50% saturated NaHCO₃ aq. solution, followed by drying and concentration to give 340 mg of the crude intermediate product.

175 mg of the crude residue was taken up in 10 mL of a 1:3 mixture of conc. aq. NH₄OH and dioxane. The reaction was stirred for 5 h, at which time the solvent was removed and the residue azeotroped with toluene to give 160 mg intermediate product. At this time, 10 mL of 7N NH₃ in methanol was added and the resulting solution stirred for 18 h. LC/MS showed that the reaction had gone to completion, and the resulting material was purified via reversed phase HPLC. Concentration of the product fractions furnished 23 mg (28% overall yield) of tris-debenzoylated product Compound 2. ¹H-NMR (400 MHz, D₂O): δ 7.74 (d, J=8.0 Hz, 1H), 5.84 (d, J=8.0 Hz, 1H), 4.20 (m, 1H), 3.81 (m, 1H), 3.68 (m, 1H), 3.62 (m, 1H), 1.08 (s, 3H). MS=281 (M−H⁺). LC/MS retention time on a 3.5 minute LC/MS method (Polar RP column)=0.37 min.

Compound 3

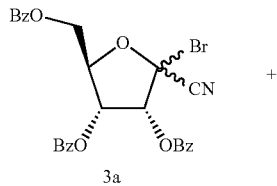

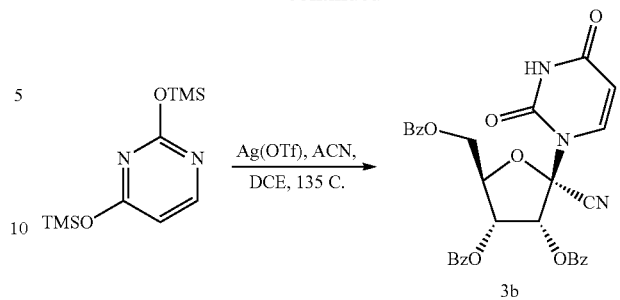

Compound 3a (prepared according to Tetrahedron Letters, 1993, 8579; 16.4 g, 30 mmol) was dissolved in 75 mL of each DCE and ACN in a 400 mL high pressure vessel. To this was added Bis(TMS)uracil (12 g, 47 mmol) as solid and lastly Ag(OTf) (11 g, 43 mmol) was added. The reaction was sealed and heated at 135° C. for 90 minutes. The reaction mixture was then cooled to rt and precipitous AgBr filtered off. Solvents were then removed under vacuum and resulting residue was redissolved in EtOAc and aq. NaHCO₃. Resulting mixture was extracted 3× with EtOAc, then organics were washed with water (1×), aq. sodium bicarbonate (2×), water (2×) and brine (1×) before drying over sodium sulfate. The solution was then filtered and evaporated to dryness. The residue was purified by silica gel chromatography with Hex:EtOAc to afford 3b (12.8 g; yield 74%). MS [M+H⁺]=581.9. ¹H NMR: (400 MHz, CD₃OD) δ 8.15 (1H, d, J=8.4 Hz), 5.68 (1H, d, J=8.4 Hz), 4.52 (1H, d), 4.26 (1H, m), 4.06 (1H, dd), 3.97 (1H, dd, J=12.8, 2.0 Hz), 3.73 (1H, dd, J=12.8, 2.0 Hz). MS [M−H⁺]=268.0.

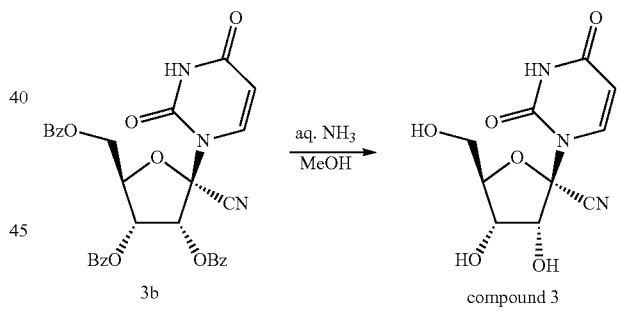

Compound 3b was converted to Compound 3 in a way similar to preparation of Compound 1.

Compound 4

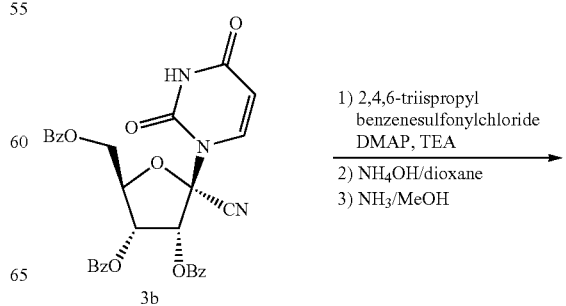

Compound 6

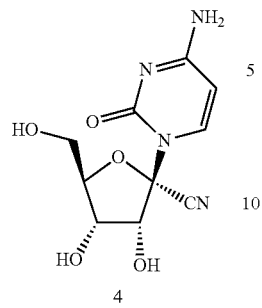

4

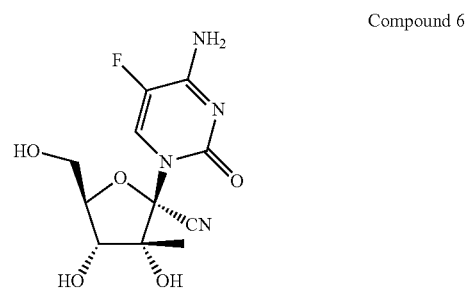 [SMILES: C[C@@]1(O)[C@H](O)[C@@H](CO)O[C@@]1(C#N)n1cc(F)c(N)nc1=O]

Compound 6

To a stirring solution of Compound 3b (2 g, 3.44 mmol) in ACN (100 mL) was added TEA (0.96 mL, 6.88 mmol) and then 2,4,6 triisopropylbenzenesulfonyl chloride (2.08 g, 6.88 mmol). Lastly was added DMAP (840 mg, 6.88 mmol) and the reaction was allowed to stir at room temperature under argon overnight. Next day, the reaction was determined to be complete by LCMS and the solvents were removed under reduced pressure. The crude was then aminated followed by de-benzoylated, following the procedure described in preparation of Compound 2. The resulting crude product was dissolved in water and purified by prep HPLC to give Compound 4 (330 mg, 36% yield). MS [M−H$^+$]=267.0. $^1$H NMR: (400 MHz, D$_2$O) δ 7.84 (1H, d, J=7.6 Hz), 5.91 (1H, d, J=7.6 Hz), 4.44 (1H, d), 4.26 (1H, m), 3.96 (1H, dd), 3.88 (1H, dd, J=12.8, 2.0 Hz), 3.67 (1H, dd, J=12.8, 2.0 Hz). MS [M−H$^+$]=267.0.

Compound 5

Compound 6 was prepared in a similar way to prepare Compound 4. $^1$H NMR (400 MHz, CD$_3$OD) δ 8.47 (d, J=7.5 Hz, 1H), 4.15 (dt, J=8.5, 2.5 Hz, 1H), 4.01 (dd, J=12.8, 2.3 Hz, 1H), 3.80 (dd, J=12.8, 2.6 Hz, 1H), 3.73 (t, J=9.4 Hz, 1H), 1.24 (s, 3H). MS=301 (M+H$^+$). LC/MS retention time on a 3.5 minute LC/MS method (Polar RP column)=0.50 min.

Compound 7

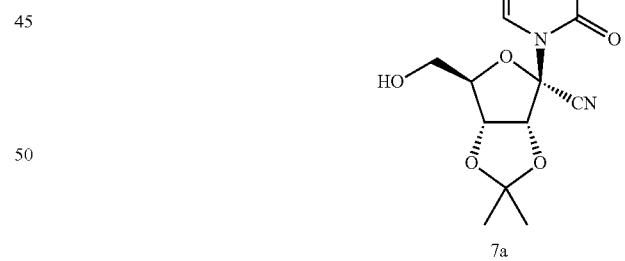

3

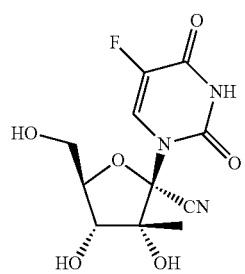

Compound 5

Compound 5 was prepared in a matter similar to that of Compound 3 substituting bis(TMS) 5-F uracil for bis(TMS) 5-unsubstituted uracil.

$^1$H NMR: (400 MHz, D$_2$O) δ 8.16 (1H, d, J=7.2 Hz), 4.15 (1H, m), 3.95 (1H, dd, J=12.8, 2.4 Hz), 3.73 (1H, dd, J=12.8, 2.4 Hz), 3.69 (1H, d, J=8.8 Hz), 1.19 (3H, s). $^{19}$F NMR: (376 MHz, D$_2$O) δ−165.4 ppm.

LC/MS: m/z (M−H)$^-$=300, rt=0.67 min on a 3.5 min C18 HPLC method.

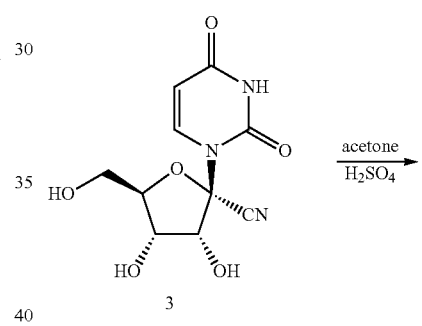

7a

Concentrated sulfuric acid (0.7 mL) was added to a solution (cloudy) of Compound 3 (2.57 g, 9.5 mmol) in acetone (70 mL). The resulting solution (clear) was stirred at room temperature for 3 hours. The reaction was neutralized with triethylamine (3.5 mL) and the solvent was removed under reduced pressure. The resulting yellow oil was subjected to silica gel chromatography with an eluent of (20% methanol in dichloromethane) and dichloromethane at a gradient of 0-100%. The product containing fractions were combined and the solvent was removed under reduced pressure providing Compound 7a (2.13 g, 72%).

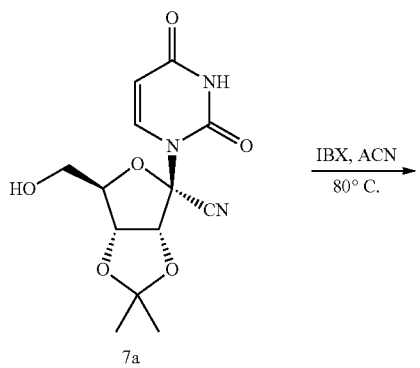

7a

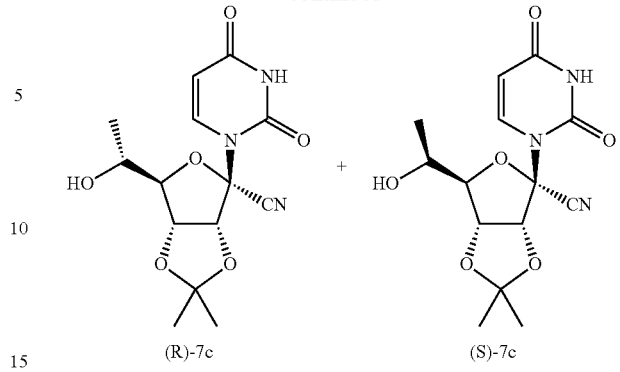

(R)-7c      (S)-7c

A solution of methylmagnesium bromide (2.69 mL, 8.1 mmol, 3M in diethyl ether) was added to a solution of Compound 7b (495 mg, 1.6 mmol) in tetrahydrofuran (20 mL) at −20° C. under an atmosphere of argon. After 5 minutes, the mixture was allowed to warm to room temperature. After 45 minutes, the mixture was cooled to 0° C. and the reaction was quenched with saturated ammonium chloride (10 mL). The tetrahydrofuran was removed under reduced pressure and the aqueous phase was extracted with ethyl acetate (3×25 mL). The combined organic phases were dried over sodium sulfate and filtered. The solvent was removed under reduced pressure. The resulting residue was subjected to reverse phase HPLC with an eluent of water and acetonitrile. The product containing fractions were combined and the solvent was removed by lyophilization providing Compound (R)-7c (35 mg, 7%) and Compound (S)-7c (15 mg, 3%).

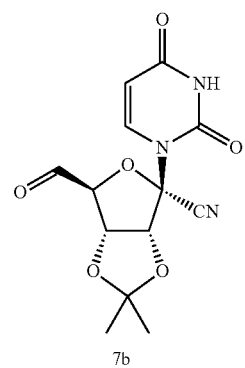

7b

2-Iodoxybenzoic acid (IBX) (3 g, 4.8 mmol, 45% wt) was stirred with ethyl acetate (15 mL) for 15 minutes until a smooth mixture formed. The solid was isolated by suction filtration and then added to a solution of Compound 7a (500 mg, 1.6 mmol) in acetonitrile (20 mL). The mixture was heated at 80° C. for 30 min. The reaction mixture was cooled in an ice bath and the mother liquor was isolated by suction filtration. The solvent was removed under reduced pressure, and the white solid was azeotroped with toluene. The material Compound 7b was used immediately, and the yield was assumed to be 100%.

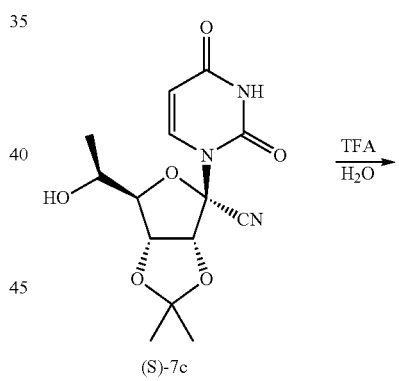

(S)-7c

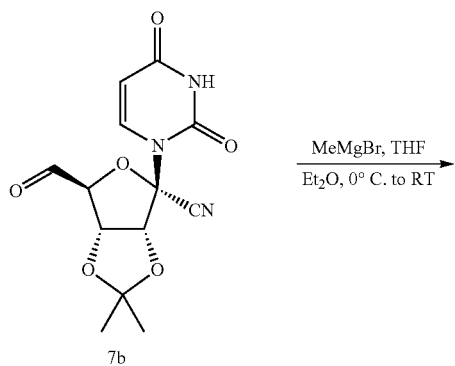

7b

Compound 7

A solution of Compound (S)-7c (15 mg, 0.046 mmol) and trifluoroacetic acid (1 mL) in water (1 mL) was stirred at room temperature for 5.5 hours. The solution was diluted with water (5 mL) and acetonitrile (5 mL), and the solvent was removed by lyophilization. The resulting residue was subjected to reverse phase HPLC with an eluent of water and acetonitrile. The product containing fractions were combined and the solvent was removed by lyophilization, providing Compound 7 (4.2 mg, 32%). ¹H-NMR (400 MHz, D₂O): δ 8.15 (d, J=8.4 Hz, 1H), 5.59 (d, J=8.4 Hz, 1H), 4.42 (d, J=4.4 Hzm 1H), 4.00 (dd, J₁=2.8 Hz, J₂=8.8 Hz, 1H), 3.94 (dd, J₁=4.0 Hz, J₂=8.4 Hz, 1H), 3.85 (dd, J=2.4 Hz, J₂=6.4 Hz, 1H), 1.27 (d, J=6.4 Hz, 3H). MS=281.8 (M LC/MS retention time on a 6.0 minute LC/MS method (Polar RP column)=0.33 min.

Compound 8

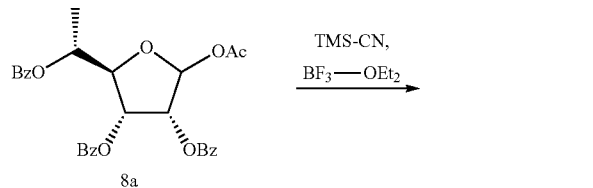

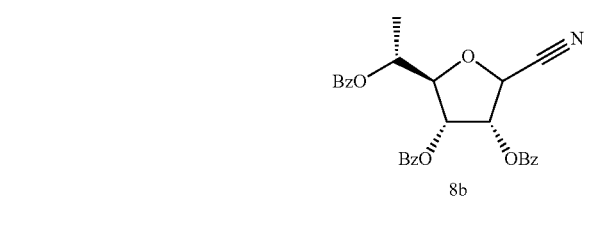

Compound 8a (prepared by a method reported on *Journal of Medicinal Chemistry*, 2000, 43, 2566; 1.0 g, 2.06 mmol) was dissolved in nitromethane (20 mL) at room temperature. TMS-cyanide (296 mg, 2.97 mmol) was added followed by BF₃ etherate (0.246 mL). Stirring at room temperature was continued. After 45 minutes, the volatiles were removed in vacuo. The crude material was taken into DCM and the solution was washed with aqueous saturated sodium bicarbonate solution. The organic layer was dried over sodium sulfate. Filtration and evaporation of solvents yielded the crude material Compound 8b (923 mg), which was used in the next step without further purification. ¹H-NMR (400 MHz, CDCl₃): δ 8.08 (m, 2H), 7.92 (m, 4H), 7.57 (m, 3H), 7.43-7.35 (m, 6H), 6.00-5.93 (m, 2H), 5.51 (m, 1H), 4.94 (d, J=4.4 Hz, 1H), 4.53 (m, 1H), 1.52 (d, J=6.8 Hz, 3H) ppm. LC/MS retention time on a 6.0 minute LC/MS method (Polar RP column)=4.87 min.

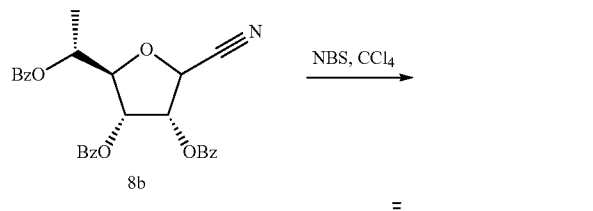

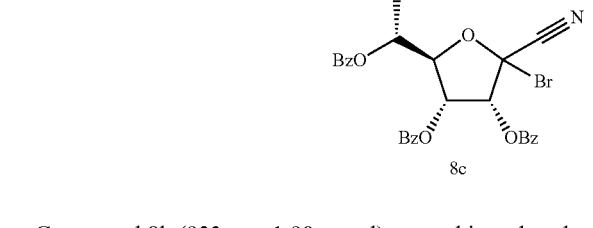

Compound 8b (923 mg, 1.90 mmol) was subjected to the reaction conditions similar to those described in *Tetrahedron Letters*, 1993, 8579, affording Compound 8c (768.0 mg, 1.36 mmol). Compound 8c was obtained as a mixture of two isomers. ¹H-NMR (400 MHz, CDCl₃): δ 8.10-7.88 (m, 6H), 7.62-7.34 (m, 9H), 6.33-6.26 (m, 1H), 6.10 & 5.90 (m, 1H), 5.58 (m, 1H), 4.81-4.75 (m, 1H), 1.56 & 1.52 (d, J=6.8 Hz, 3H) ppm. LC/MS retention time on a 6.0 minute LC/MS method (Polar RP column)=5.14 min.

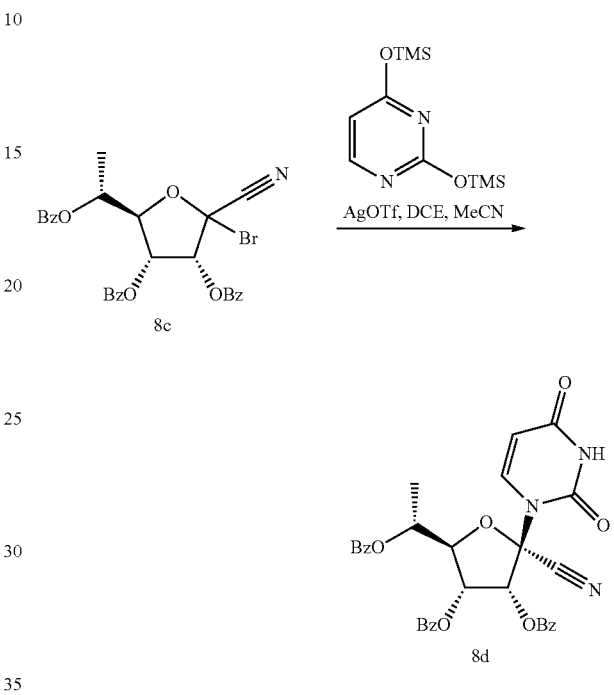

Compound 8c (703 mg, 1.24 mmol), bis-TMS uracil (630 mg, 2.46 mmol), and silver(I)triflate (630 mg, 2.46 mmol) were placed into a microwave vial under argon, and anhydrous dichloroethane (5 mL) and acetonitrile (5 mL) were added. The mixture was heated at 135° C. for 30 minutes via use of a microwave reactor. The reaction mixture was cooled to room temperature, filtered, and the volatiles were removed in vacuo. The crude material was purified via chromatography on silica gel (eluent: hexanes/EtOAc) affording Compound 8d (504 mg, 0.845 mmol) as a single isomer. ¹H-NMR (400 MHz, CDCl₃): δ 8.08 (d, J=7.2 Hz, 2H), 8.03-8.00 (m, 4H), 7.62-7.37 (m, 10H), 6.36 (d, J=5.6 Hz, 1H), 6.11 (m, 1H), 5.66 (dq, J=7.2/2.8 Hz, 1H), 4.50 (dd, J=8.4/2.4 Hz, 1H), 4.90 (m, 1H), 1.57 (d, J=6.8 Hz, 3H) ppm. MS=596 (M+H⁺). LC/MS retention time on a 6 minute LC/MS method (Polar RP column)=4.43 min.

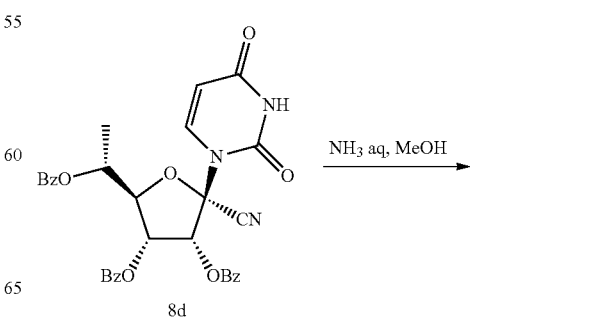

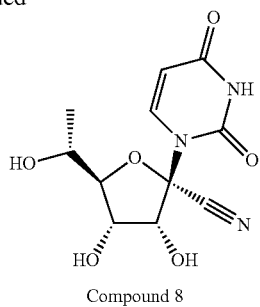

Compound 8

To a solution of Compound 8d (65 mg, 0.109 mmol) in MeOH (1 mL) at room temperature was added 2 mL conc. aq. ammonia. The reaction mixture was stirred at room temperature for 8 h. LC/MS analysis indicated that almost all the starting material was consumed. The reaction was concentrated in vacuo. The crude reaction product was dissolved in water, and purified via reverse phase HPLC (eluent: water/MeCN). The product containing fractions were combined, frozen, and lyophilized to afford Compound 8 (22.0 mg, 0.077 mmol). $^1$H-NMR (400 MHz, D$_2$O): □δ 7.93 (d, J=8.4 Hz, 1H), 5.75 (d, J=8.4 Hz, 1H), 4.50 (m, 1H), 4.15 (m, 3H), 1.16 (d, J=6.8 Hz, 3H) ppm. MS=282 (M−H$^+$). LC/MS retention time on a 6 minute LC/MS method (Polar RP column)=0.97 min.

Compound 9

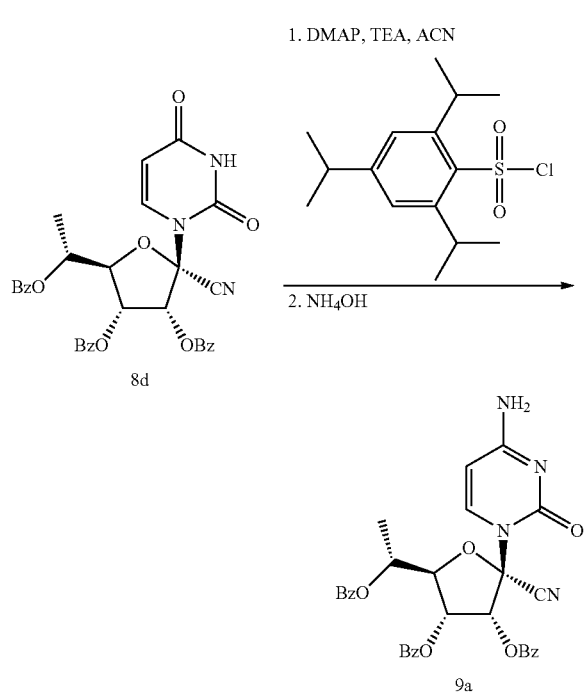

and then brine (20 mL). The organic phase was dried over sodium sulfate and filtered. The solvent was removed under reduced pressure and the residue was subjected to silica gel chromatography with an eluent of methanol and dichloromethane. The product containing fractions were combined and the solvent was removed under pressure to provide Compound 9a (920 mg, 60%).

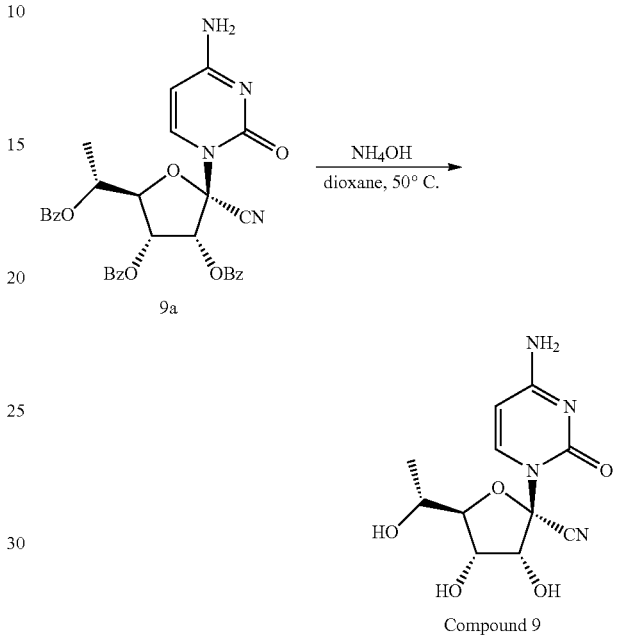

Compound 9

Concentrated ammonium hydroxide (30 mL) was added to a solution of Compound 9a (460 mg, 7.7 mmol) in 1,4-dioxane (15 mL). The solution was stirred at 50° C. in a sealed vessel. After 9 hours, the solution was cooled and the solvent was concentrated to a volume of 10 mL. The mixture was cooled at 0° C. for 5 min and filtered. The filtrate was subjected to reverse phase HPLC with an eluent of water and acetonitrile. The product containing fractions were combined. The solvent was removed by lyophilization to provide Compound 9 (148 mg, 67%). $^1$H-NMR (400 MHz, D$_2$O): □ δ 7.88 (d, J=7.6 Hz, 1H), 5.91 (d, J=8.0 Hz, 1H), 4.42 (d, J=5.2 Hz, 1H), 4.16 (m, 1H), 4.09 (m, 2H), 1.16 (d, J=7.2 Hz, 3H). MS=283.1 (M+H$^+$). LC/MS retention time on a 6.0 minute LC/MS method (Polar RP column)=0.28 min.

Compound 10

2,4,6-Triisopropylbenzene-1-sulfonyl chloride (1.58 g, 5.2 mmol) was added to a solution of Compound 8d (1.56 g, 2.6 mmol), N,N-dimethylaminopyridine (640 mg, 5.2 mmol) and triethylamine (0.73 mL, 5.2 mmol) in acetonitrile (30 ml) and stirred at room temperature for 30 minutes. Concentrated aqueous ammonium hydroxide (6 mL) was added and after 15 minutes the acetonitrile was removed under reduced pressure. The residue was taken up in ethyl acetate (75 mL) and washed with water (20 mL), saturated ammonium chloride (20 mL),

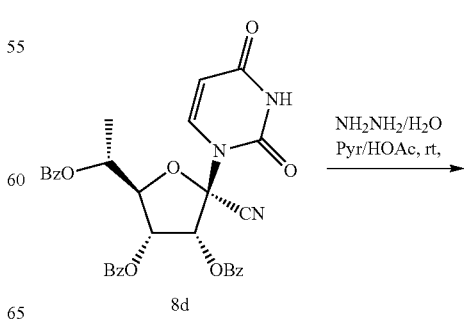

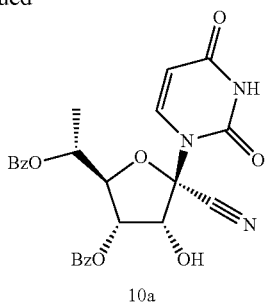

10a

To a solution of Compound 8d (4.32 g, 7.25 mmol) in pyridine/glacial acid (55 mL/13.5 mL) at room temperature was added hydrazine hydrate (598 mg, 10.87 mmol). The reaction mixture was stirred at room temperature for 40 hours. Acetone (4 mL) was added and stirring at room temperature was continued. After 2 additional hours, the solvent volume was reduced in vacuo to ~1/3 of the original volume. The mixture was diluted with EtOAc, washed with aqueous HCl (1N) and aqueous saturated sodium bicarbonate solution/brine (1/1). The organic layer was dried over sodium sulfate. Filtration and evaporation of solvents afforded crude Compound 10a (3.33 g, 6.77 mmol). The material was used in the next step without further purification. $^1$H-NMR (400 MHz, CDCl$_3$): □δ 8.43 (m, 1H), 8.17 (d, J=6.8 Hz, 2H), 7.86 (d, J=7.6 Hz, 2H), 7.61-7.41 (m, 7H), 6.04 (dd, J=5.2/1.2 Hz, 1H), 5.63 (m, 2H), 4.99 (s, 1H), 4.94 (m, 1H), 4.79 (m, 1H), 1.54 (d, J=6.8 Hz, 3H) ppm. MS=489 (M−H$^+$). LC/MS retention time on a 6 minute LC/MS method (Polar RP column)=3.53 min.

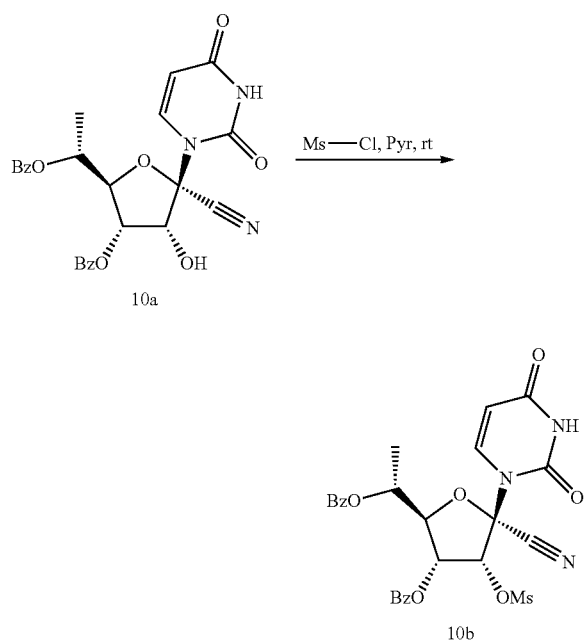

To a solution of Compound 10a (3.25 g, 6.61 mmol) in pyridine (40 mL) at room temperature was added methanesulfonyl chloride (1.51 g, 13.22 mmol). The reaction mixture was stirred at room temperature. After 3 hours, more methylsulfonylchloride (0.75 g, 6.61 mmol) was added and stirring at room temperature was continued. After 5 hours, the volatiles were removed in vacuo. The crude reaction mixture was diluted with EtOAc, washed with aqueous HCl (1N), and aqueous saturated sodium bicarbonate solution/brine (1/1). The organic layer was dried over sodium sulfate. Filtration and evaporation of solvents afforded crude material which was purified by chromatography on silica gel (eluent: EtOAc/hexanes) to afford Compound 10b (2.53 g, 4.27 mmol). $^1$H-NMR (400 MHz, CDCl$_3$): □δ 9.22 (m, 1H), 8.07 (d, J=7.6 Hz, 2H), 7.95 (d, J=7.2 Hz, 2H), 7.61 (m, 2H), 7.47-7.39 (m, 5H), 5.81-5.72 (m, 3H), 5.29 (d,d, J=8.4/1.6 Hz, 1H), 4.87 (dd, J=9.2/3.2 Hz, 1H), 3.36 (s, 3H), 1.45 (d, J=7.2 Hz, 3H) ppm. MS=570 (M+H$^+$). LC/MS retention time on a 6 minute LC/MS method (Polar RP column)=3.84 min.

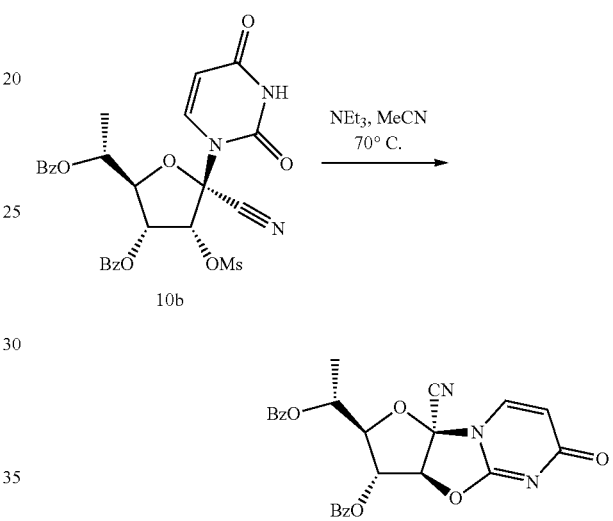

To a solution of Compound 10b (2.45 g, 4.30 mmol) in acetonitrile (40 mL) at room temperature was added triethylamine (2.45 g, 24.20 mmol). The reaction mixture was heated at 65° C. (oil bath). After 2 hours, the reaction was cooled to room temperature and the volatiles were removed in vacuo. The crude reaction mixture was diluted with EtOAc, and washed with aqueous HCl (1N) and aqueous saturated sodium bicarbonate solution/brine (1/1). The organic layer was dried over sodium sulfate. Filtration and evaporation of solvents afforded product Compound 10c (1.78 g, 3.76 mmol). $^1$H-NMR (400 MHz, CDCl$_3$): □δ 8.07 (d, J=7.2 Hz, 2H), 7.92 (d, J=7.2 Hz, 2H), 7.69-7.37 (m, 7H), 6.01 (d, J=7.6 Hz, 1H), 5.91 (m, 1H), 5.78 (d, J=0.8 Hz, 1H), 5.43 (m, 1H), 4.81 (m, 1H), 1.40 (d, J=6.4 Hz, 3H) ppm. MS=472 (M−H$^+$). LC/MS retention time on a 6 minute LC/MS method (Polar RP column)=4.09 min.

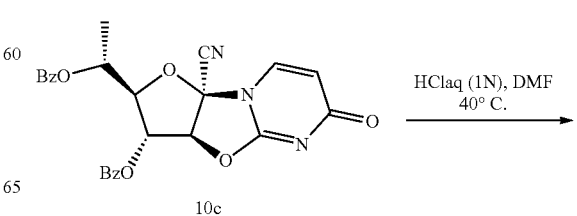

-continued

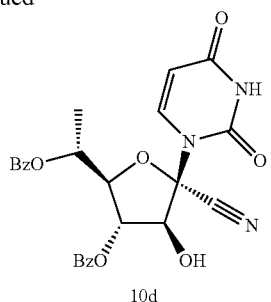

10d

To a solution of Compound 10c (1.70 g, 3.59 mmol) in DMF (10 mL) was added aqueous HCl (1N, 10 mL) at room temperature. To the resultant suspension was added more DMF (10 mL). The reaction mixture was heated at 40° C. (oil bath). After 30 minutes, the reaction was cooled to room temperature, diluted with EtOAc, and washed with brine, aqueous LiCl (5%) and aqueous saturated sodium bicarbonate solution/brine (1/1). The organic layer was dried over sodium sulfate. Filtration and evaporation of solvents afforded crude reaction mixture which was purified via chromatography on silica gel (eluent: EtOAc/hexanes) to afford the product Compound 10d (1.65 g, 3.37 mmol).

$^1$H-NMR (400 MHz, CDCl$_3$): □δ 10.08 (s, 1H), 8.13 (d, J=7.2 Hz, 2H), 8.07 (d, J=7.2 Hz, 2H), 7.57-7.37 (m, 7H), 5.77 (m, 1H), 5.71 (m, 1H), 5.13 (s, 1H), 5.04 (s, 1H), 4.79 (d,d, J=8.4/1.6 Hz, 1H), 4.59 (m, 1H), 1.52 (d, J=6.8 Hz, 3H) ppm. MS=492 (M–H$^+$). LC/MS retention time on a 6 minute LC/MS method (Polar RP column)=3.71 min.

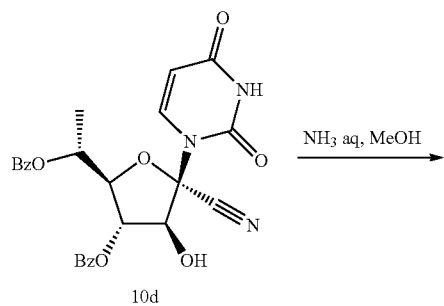

10d

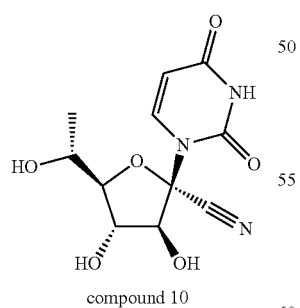

compound 10

To a solution of Compound 10d (65.2 mg, 0.132 mmol) in MeOH (1 mL) at room temperature was added 2 mL conc. aq. ammonia. The reaction mixture was stirred at room temperature for 12 hours. The reaction was concentrated in vacuo. The crude reaction product was dissolved in water, and purified via reverse phase HPLC (eluent: water/MeCN). The product containing fractions were combined, frozen, and lyophilized to afford Compound 10 (10.3 mg, 0.036 mmol). $^1$H-NMR (400 MHz, D$_2$O): □δ 7.74 (d, J=8.4 Hz, 1H), 5.76 (d, J=8.4 Hz, 1H), 4.69 (m, 1H), 4.26 (m, 1H), 4.13 (m, 1H), 3.99 (m, 1H), 1.17 (d, J=6.4 Hz, 3H) ppm. MS=284 (M+H$^+$). LC/MS retention time on a 6 minute LC/MS method (Polar RP column)=1.37 min.

Compound 11

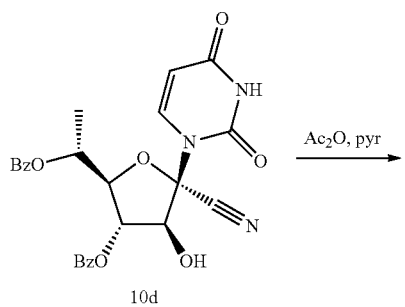

10d

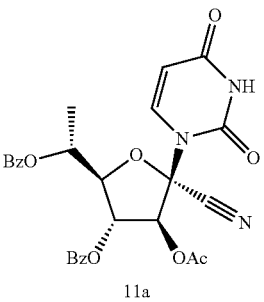

11a

To a solution of Compound 10d (189.2 mg, 0.385 mmol) in pyridine (2 mL) at room temperature was added acetic anhydride (47.5 mg, 0.462 mmol). After 2 hours, the volatiles were removed in vacuo. The crude reaction mixture was diluted with EtOAc and washed with aqueous HCl (1N) and aqueous saturated sodium bicarbonate solution/brine (1/1). The organic layer was dried over sodium sulfate. Filtration and evaporation of solvents afforded crude material which was purified by chromatography on silica gel (eluent: EtOAc/hexanes) to afford Compound 11a (185.5 mg, 0.348 mmol). $^1$H-NMR (400 MHz, CDCl$_3$): □δ 8.15 (m, 3H), 8.04 (d, J=7.6 Hz, 2H), 7.65-7.44 (m, 7H), 5.99 (s, 1H), 5.81-5.73 (m, 3H), 4.69 (m, 1H), 1.57-1.54 (m, 6H) ppm. MS=533 (M+H$^+$). LC/MS retention time on a 6 minute LC/MS method (Polar RP column)=3.89 min.

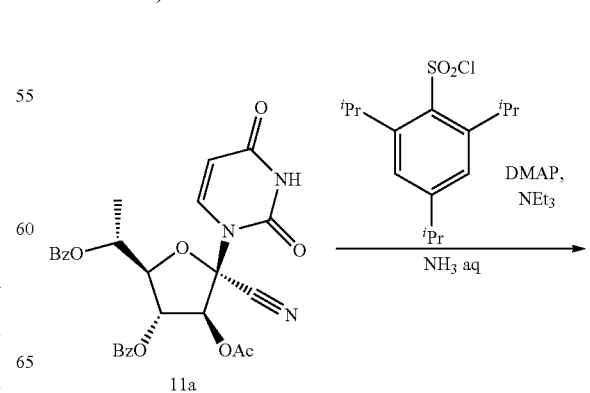

11a

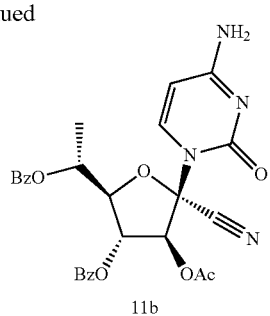

11b

To a solution of Compound 11a (180.0 mg, 0.338 mmol), DMAP (82.4 mg, 0.676 mmol), and triethylamine (68.2 mg, 0.676 mmol) in acetonitrile (8 mL) at room temperature was added triisopropylphenylsulfonylchloride (204 mg, 0.676 mmol). Stirring at room temperature was continued. After 30 minutes, the reaction was cooled to 0° C. Aqueous concentrated NH$_3$ solution (2 mL) was added and the reaction was allowed to warm to room temperature. After additional 30 minutes, the reaction mixture volume was reduced in vacuo. The crude reaction mixture was diluted with EtOAc and washed with aqueous HCl (1N) and aqueous saturated sodium bicarbonate solution/brine (1/1). The organic layer was dried over sodium sulfate. Filtration and evaporation of solvents afforded crude material which was purified by chromatography on silica gel (eluent: EtOAc/hexanes) to afford a mixture of Compound 11b and its 2'0' des-acetyl derivative (128.5 mg, combined). This mixture was used in the next reaction. LC/MS retention time on a 6 minute LC/MS method (Polar RP column)=3.59 min (Compound 11b) and 3.42 min (des-Ac).

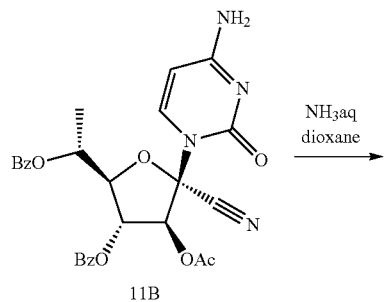

compound 11

To a solution of Compound 11b and its des-acetyl derivative (11.0 mg, ~0.230 mmol) in dioxane (1 mL) at room temperature was added 2 mL conc. aq. ammonia. The reaction mixture was stirred at room temperature for 1.5 hours and at 50° C. for 6 hours. The reaction was cooled to room temperature and concentrated in vacuo. The crude reaction product was dissolved in water, and purified via reverse phase HPLC (eluent: water/MeCN). The product containing fractions were combined, frozen, and lyophilized to afford Compound 11 (22.7 mg, 0.081 mmol). $^1$H-NMR (400 MHz, D$_2$O): δ 7.68 (d, J=7.6 Hz, 1H), 5.91 (d, J=7.6 Hz, 1H), 4.70 (s, 1H), 4.23 (m, 1H), 4.10 (m, 1H), 3.98 (m, 1H), 1.17 (d, J=6.4 Hz, 3H) ppm. MS=283 (M+H$^+$). LC/MS retention time on a 6 minute LC/MS method (Polar RP column)=0.62 min.

Compound 12

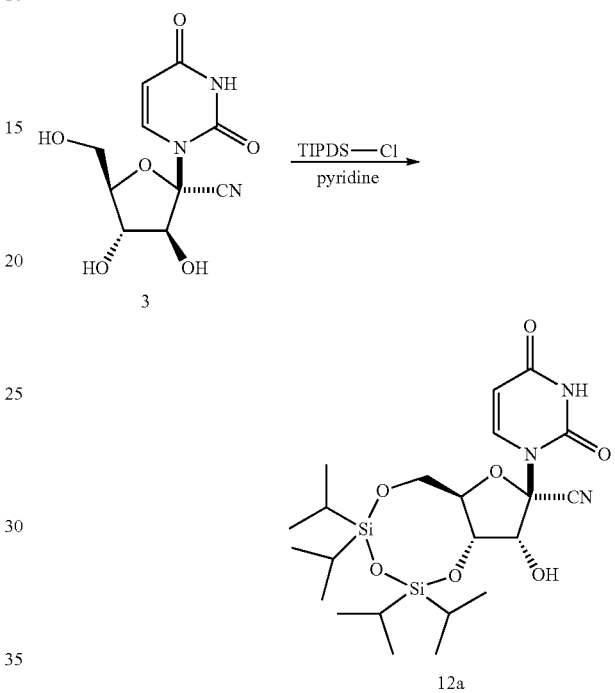

Compound 3 (2.0 g, 7.4 mmol) was dissolved in dry pyridine (24 mL). To this mixture, 1,3-dichloro-1,1,3,3-tetraisopropyl disiloxane (2 mL. 1.3 eq) was added dropwise. The solution was stirred at room temperature for 16 hours. The solvent was then removed under vacuum and the resulting residue was dissolved in EtOAc, washed with H$_2$O and brine. The organic phase was dried over Na$_2$SO$_4$ and evaporated to dryness. The crude product was purified by column chromatography on silica gel using ethyl acetate/hexanes to give Compound 12a (2.1 g, 55% yield). MS=510 (M−H$^+$). LC/MS retention time on a 3.5 minute LC/MS method (Polar RP column)=2.49 min.

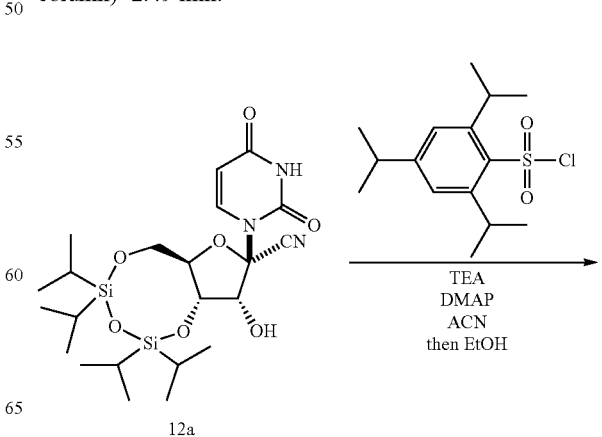

12a

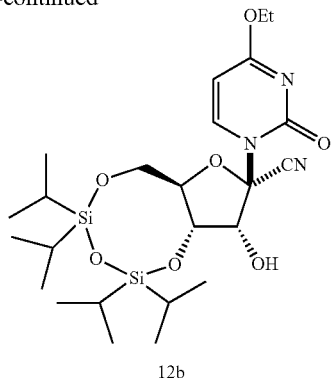

12b

Triethylamine (0.089 mL, 0.64 mmol) was added to a stirring solution of Compound 12a (300 mg, 0.49 mmol) in CH$_3$CN (5 mL). 2,4,6-Triisopropylbenzenesulfonyl chloride (192 mg, 0.64 mmol) and 4-dimethylaminopyridine (78 mg, 0.64 mmol) were added. The reaction mixture was stirred at room temperature for 1 hour. Ethanol (25 mL) was added to the mixture, together with additional triethylamine (0.34 mL). The solution was stirred at room temperature for 5 hours. The solvent was then removed under vacuum and the resulting residue was dissolved in EtOAc, washed with concentrated NH$_4$Cl, H$_2$O and brine. The organic phase was dried over Na$_2$SO$_4$ and evaporated to dryness. The crude product was purified by column chromatography on silica gel using ethyl acetate/hexanes to give Compound 12b (250 g, 95% yield). MS=540 (M+H$^+$). LC/MS retention time on a 3.5 minute LC/MS method (Polar RP column)=2.69 min.

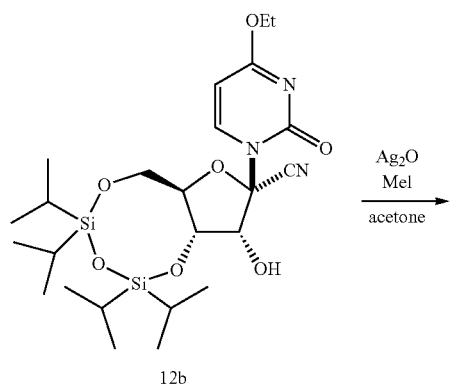

12b

Compound 12b (900 mg, 1.8 mmol) was dissolved in dry acetone (20 mL). Silver (I) oxide (3.3 g, 14 mmol) was added to the solution, followed by the addition of methyl iodide (2.5 g, 18 mmol). The solution was stirred at room temperature for 16 hours. The mixture was filtered to remove the suspended oxide, concentrated under vacuum and purified by column chromatography on silica gel using ethyl acetate/hexanes to give Compound 12c (250 g, 26% yield). MS=554 (M+H$^+$). LC/MS retention time on a 3.5 minute LC/MS method (Polar RP column)=2.75 min.

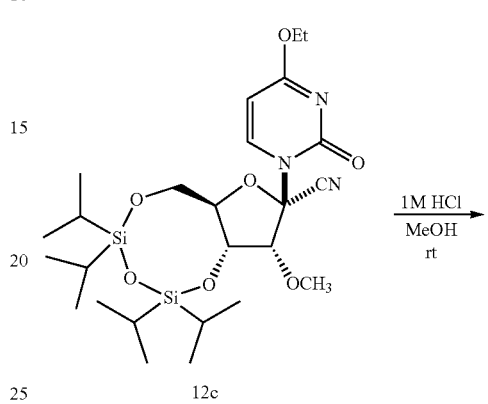

12c

Compound 12c (220 mg, 0.40 mmol) was dissolved in methanol (6 mL) and the resulting solution was cooled to 0° C. in an ice bath. Hydrochloric acid (0.6 mL, 1 M in H$_2$O) was added drop-wise. After the addition was complete, the mixture was allowed to warm up to room temperature and stirred for 12 hours. The solvent was concentrated and the residue was washed twice with DCM to remove silyl impurities. The crude purified by column chromatography on silica gel using MeOH/DCM to give Compound 12 (80 mg, 70% yield). MS=284 (M+WI LC/MS retention time on a 3.5 minute LC/MS method (Polar RP column)=0.90 min.

Compound 13

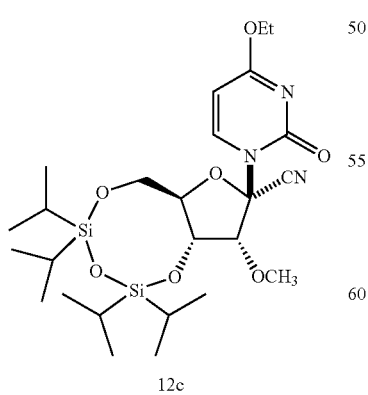

Compound 12

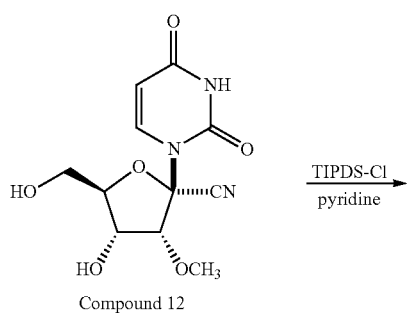

Compound 12

-continued

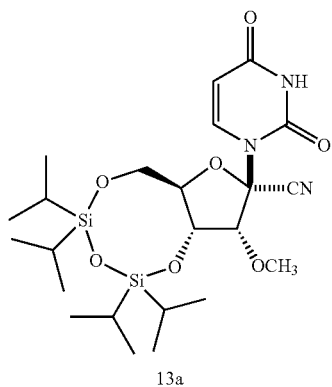

13a

Compound 12 (70 mg, 0.25 mmol) was dissolved in dry pyridine (2 mL). To this mixture, 1,3-dichloro-1,1,3,3-tetraisoporpyl disiloxane (0.10 mL. 1.3 eq) was added dropwise. The solution was stirred at room temperature for 2 hours. The solvent was then removed under vacuum and the resulting residue was dissolved in EtOAc, washed with H$_2$O and brine. The organic phase was dried over Na$_2$SO$_4$ and evaporated to dryness. The crude product was purified by column chromatography on silica gel using ethyl acetate/hexanes to give Compound 13a (120 mg, 55% yield). MS=526 (M+H$^+$). LC/MS retention time on a 3.5 minute LC/MS method (Polar RP column)=2.57 min.

Triethylamine (60 mg, 0.60 mmol) was added to a stirring solution of Compound 13a (155 mg, 0.30 mmol) in CH$_3$CN (1 mL). 2,4,6-Triisopropylbenzenesulfonyl chloride (179 mg, 0.60 mmol) and 4-dimethylaminopyridine (72 mg, 0.0.60 mmol) were added. The reaction mixture was stirred at room temperature for 3 hours. The mixture was evaporated to dryness. The residue was dissolved in CH$_3$CN (3 mL), and NH$_3$ (28% aqueous solution, 6 mL) was added. The reaction mixture was stirred at room temperature for 2 hours. Then the solvent was removed under vacuum and the residue was dissolved in CH$_2$Cl$_2$ and washed with brine. The organic phase was dried over Na$_2$SO$_4$ and evaporated to dryness. The crude product was purified by column chromatography on silica gel using ethyl acetate/methanol 3:1 to give Compound 13b (80 mg, 52% yield). MS=556 (M+H$^+$). LC/MS retention time on a 3.5 minute LC/MS method (Polar RP column)=2.45 min.

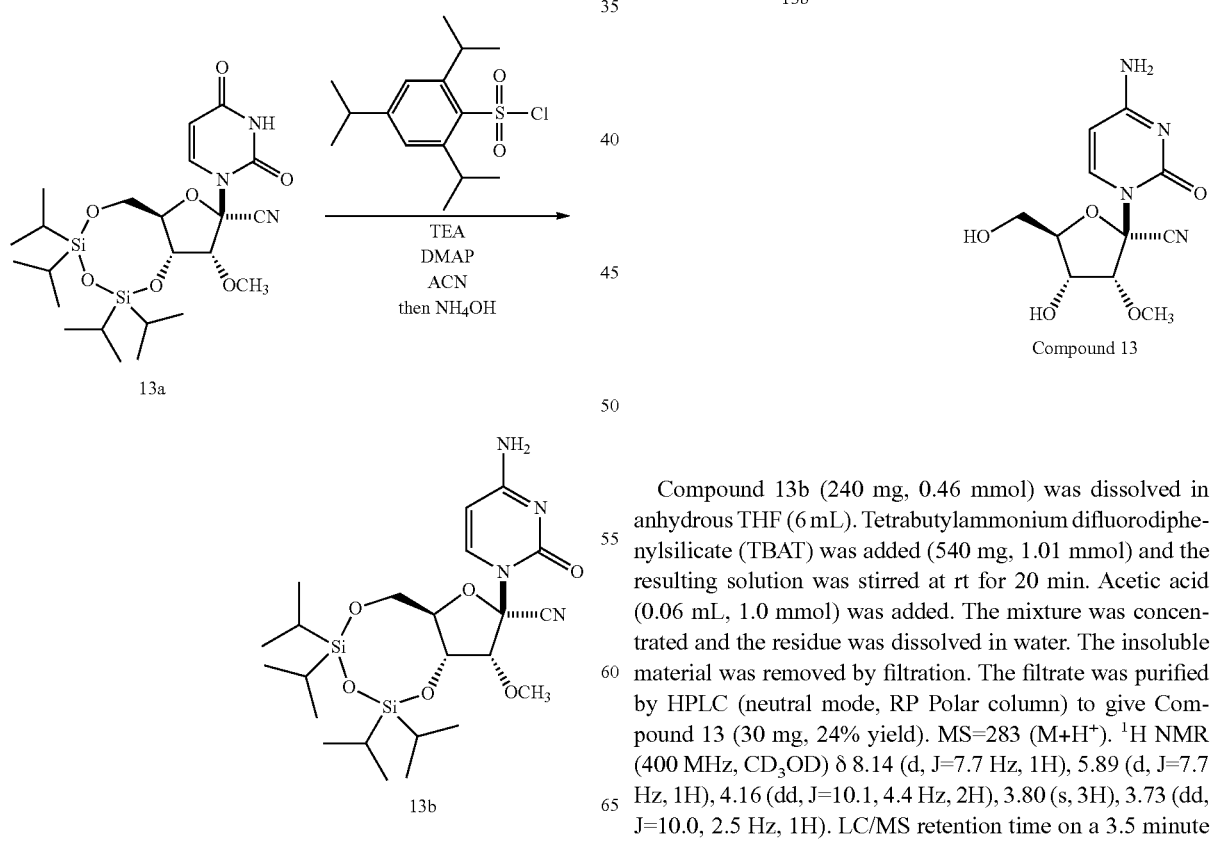

Compound 13b (240 mg, 0.46 mmol) was dissolved in anhydrous THF (6 mL). Tetrabutylammonium difluorodiphenylsilicate (TBAT) was added (540 mg, 1.01 mmol) and the resulting solution was stirred at rt for 20 min. Acetic acid (0.06 mL, 1.0 mmol) was added. The mixture was concentrated and the residue was dissolved in water. The insoluble material was removed by filtration. The filtrate was purified by HPLC (neutral mode, RP Polar column) to give Compound 13 (30 mg, 24% yield). MS=283 (M+H$^+$). $^1$H NMR (400 MHz, CD$_3$OD) δ 8.14 (d, J=7.7 Hz, 1H), 5.89 (d, J=7.7 Hz, 1H), 4.16 (dd, J=10.1, 4.4 Hz, 2H), 3.80 (s, 3H), 3.73 (dd, J=10.0, 2.5 Hz, 1H). LC/MS retention time on a 3.5 minute LC/MS method (Polar RP column)=0.48 min.

Compound 14

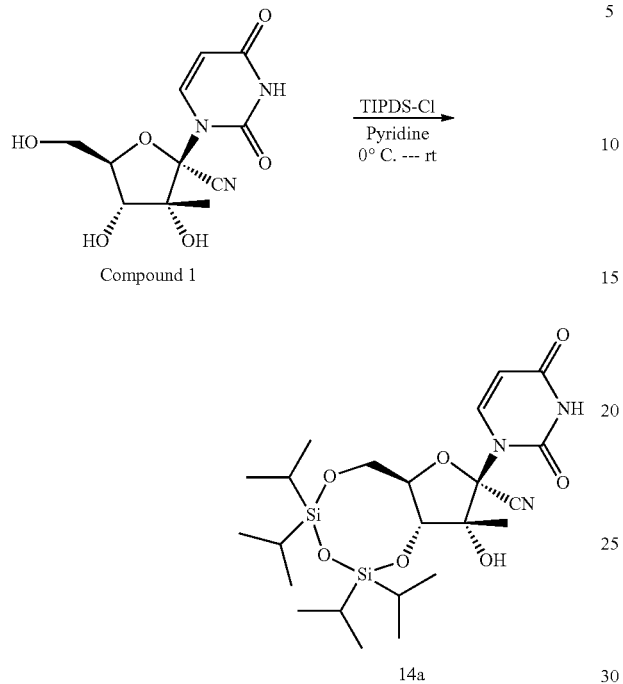

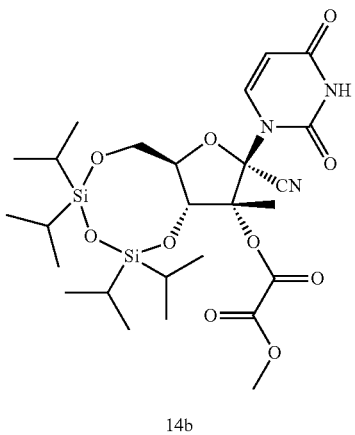

To a dry, argon purged round bottom flask (25 mL) was added Compound 1 and anhydrous pyridine (4 mL). 1,3-Dichloro-1,1,3,3-tetraisoporpyl disiloxane (1.33 mL, 4.16 mmol) was added dropwise and the reaction stirred for 2 h at 0° C. The ice bath was then removed and the mixture warmed to room temperature and continued to stir until complete disappearance of the starting material. After 10 mins of warming, the reaction was diluted with 10 mL of $H_2O$ and the desired material was collected via vacuum filtration. The material was placed under high vacuum overnight for further drying. 1.90 g (96% yield) of the desired material, Compound 14a, was collected. MS=526.4 (M−H$^+$). LC/MS retention time on a 6.0 minute LC/MS method (Polar RP column)=5.09 min.

To a dry, argon purged round bottom flask (50 mL) was added Compound 14a (1.7 g, 3.23 mmol), anhydrous dichloromethane (10 mL) and anhydrous acetonitrile (10 mL). Dimethylamino pyridine (1.19 g, 9.7 mmol) was then added portionwise followed by dropwise addition of methyl chlorooxoacetate (0.89 mL, 9.7 mmol). The reaction was allowed to stir at room temperature until complete disappearance of the starting material. After 1.5 h, the crude reaction mixture was diluted with EtOAc followed by washings with $NaHCO_3$ (sat), water, and brine. The combined organic layers were dried over $NaSO_4$ and the solvent was removed under reduced pressure. The mixture was dried azeotropically using toluene and placed under high vacuum overnight for completeness. 1.72 g (87% yield) of the desired material, Compound 14b, was collected. $^1$H-NMR (400 MHz, CD3OD): δ 7.82 (d, J=8.4 Hz, 1H), 5.78 (d, J=8.4 Hz, 1H), 4.47 (m, 1H), 4.30 (m, 1H), 4.20 (m, 2H), 3.93 (s, 3H), 2.89 (s, 3H), 1.08 (m, 28H). MS=609.8 (M−H$^+$). LC/MS retention time on a 6.0 minute LC/MS method (Polar RP column)=5.35 min.

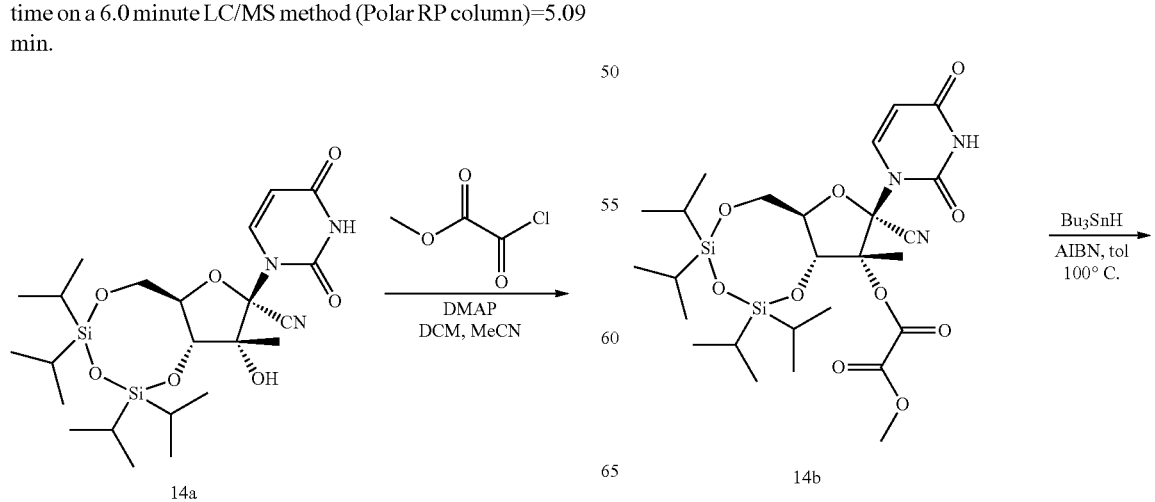

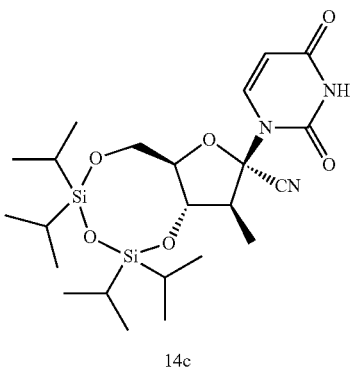

14c

To a dry, argon purged round bottom flask (500 mL) was added Compound 14b (1.75 g, 2.86 mmol) and anhydrous toluene (120 mL). AIBN (118.8 g, 0.49 mmol) and Bu₃SnH (2.3 mL, 8.78 mmol) were then added and the flask was placed into a heating block and set to 100° C. After 3 h, the solvent was removed under reduced pressure and the crude reaction mixture was purified using flash chromatography (Hex/EtOAc). The desired material, Compound 14c, was collected, along with alpha isomer (900 mg; 62%, 78:22 beta/alpha). Beta-isomer after column separation; $^{1}$H-NMR (400 MHz, CD3OD): δ 7.82 (d, J=8.4 Hz, 1H), 5.73 (d, J=8.4 Hz, 1H), 4.22 (m, 2H), 4.09 (m, 2H), 3.15 (m, 1H), 1.01 (m, 31H). MS=507.9 (M−H). LC/MS retention time on a 6.0 minute LC/MS method (Polar RP column)=5.18 min.

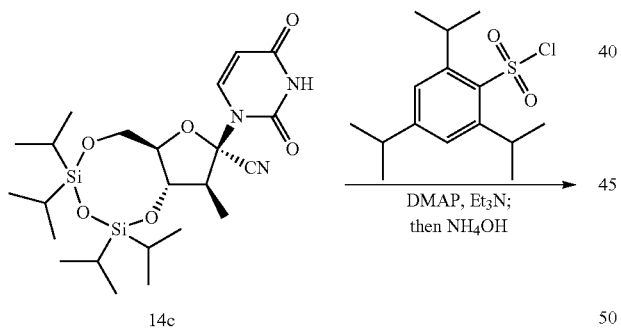

14c

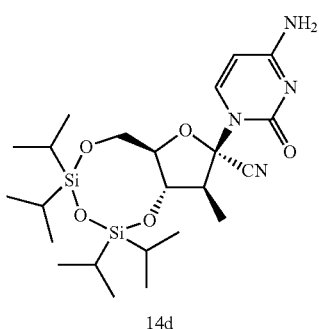

14d

To a dry, argon purged round bottom flask (100 mL) was added Compound 14c (500 mg, 1.00 mmol) and anhydrous acetonitrile (13 mL). Dimethylamino pyridine (244 mg, 2.0 mmol) and triethylamine (0.28 mL, 2.0 mmol) were then added to the flask. Lastly, 2,4,6-triisopropyl benzene sulfonyl chloride (0.28 mL, 2 mmol) was added to the mixture and the solution turned yellow. The reaction continued to stir at room temperature until complete disappearance of the starting material. After 45 min, ammonium hydroxide (2.6 mL, 20% by volume) was added at 0° C. and the reaction was allowed to slowly warm to room temperature. After an additional 20 min, the solvent was removed under reduced pressure. The crude reaction mixture was diluted with EtOAc followed by washings with NaHCO₃ (sat), water, and brine. The combined organic layers were dried over NaSO₄ and the solvent was removed under reduced pressure. The crude reaction mixture was then purified using flash chromatography (DCM/MeOH). 380 mg (75% yield) of the desired material, Compound 14d, was collected. $^{1}$H-NMR (400 MHz, CD3OD): δ 7.77 (d, J=8.4 Hz, 1H), 5.93 (d, J=8.4 Hz, 1H), 4.23 (m, 2H), 4.07 (m, 2H), 3.17 (m, 1H), 1.25 (m, 1H), 1.09 (m, 27H), 0.96 (m, 3H). MS=509.1 (M−H⁺). LC/MS retention time on a 6.0 minute LC/MS method (Polar RP column)=4.83 min.

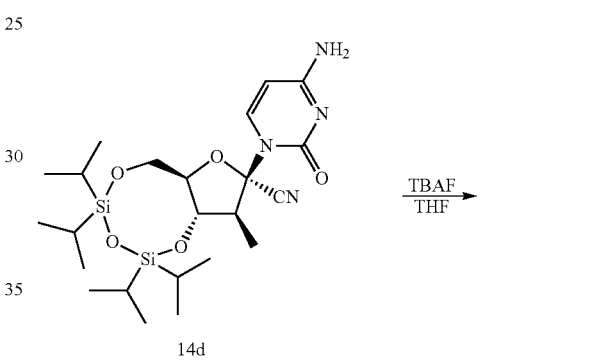

14d / 14

To a dry, argon purged round bottom flask (50 mL) was added Compound 14d (180 mg, 0.35 mmol) and anhydrous tetrahydrofuran (9 mL). TBAF (0.23 mL, 0.778 mmol) was then added and the reaction was allowed to stir at room temperature until complete disappearance of the starting material. After 10 min, acetic acid was added to neutralize the solution and then the solvent was removed under reduced pressure. The crude reaction mixture was dissolved in water, insolubles filtered, and the filtrate purified using prep HPLC. 80 mg (86%) of the desired material, Compound 14, was collected.

$^{1}$H-NMR (400 MHz, CD3OD): δ 7.77 (d, J=8.4 Hz, 1H), 5.94 (d, J=8.4 Hz, 1H), 4.24 (m, 1H), 3.91 (m, 1H), 3.83 (m, 1H), 3.70 (m, 1H), 3.07 (m, 1H), 0.66 (d, J=7.5 Hz, 3H). MS=267.1 (M+H⁺). LC/MS retention time on a 3.0 minute LC/MS method (Polar RP column)=0.40 min.

Compound 15

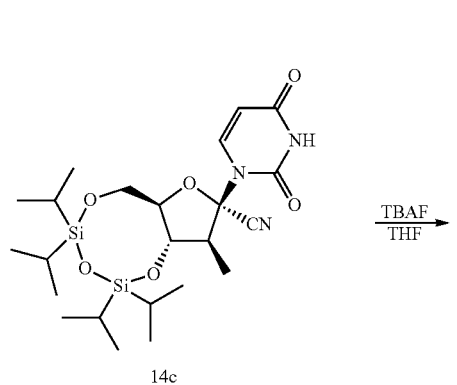
14c

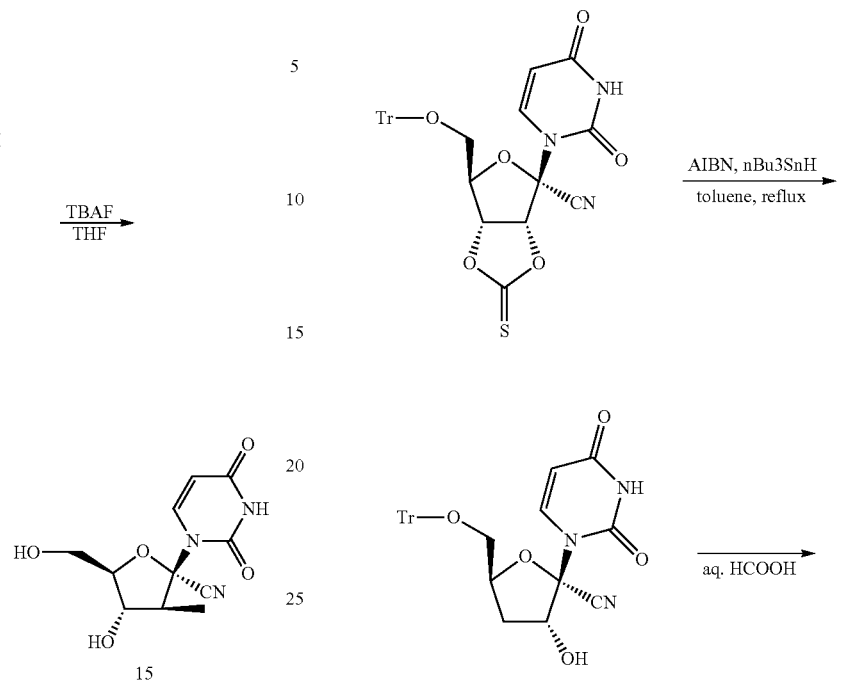

15

Compound 15 was prepared from Compound 14c under conditions similar to those described in conversion of Compound 14d to Compound 14.

$^1$H-NMR (400 MHz, CD3OD): δ 7.83 (d, J=8.4 Hz, 1H), 5.78 (d, J=8.4 Hz, 1H), 4.24 (m, 1H), 3.94 (m, 1H), 3.84 (dd, 1H), 3.71 (dd, 1H), 3.07 (m, 1H), 0.76 (d, J=7.5 Hz, 3H). MS=268.1 (M+H$^+$). LC/MS retention time on a 3.0 minute LC/MS method (Polar RP column)=0.79 min.

Compound 16

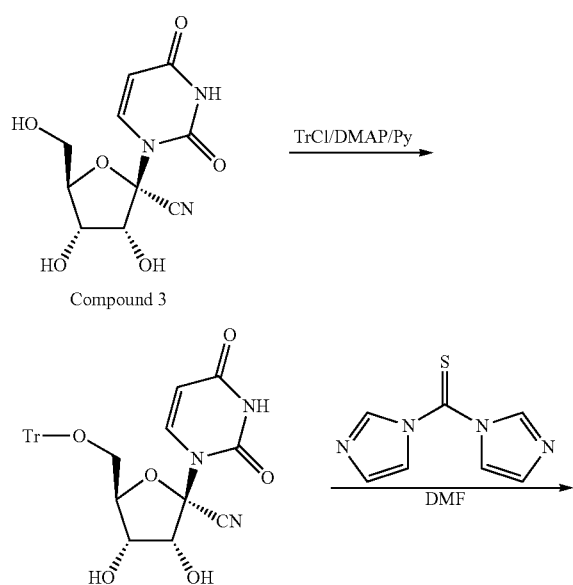

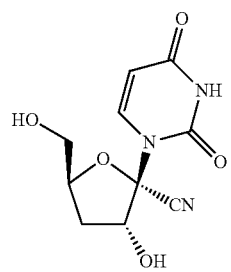
Compound 16

Compound 16 may be obtained from Compound 3 following synthetic sequence shown above, of which procedures are described in *Journal of Organic Chemistry*, 1981, 46, 3603. Briefly, a solution of Compound 3 and trityl chloride (~1.1 eq) in pyridine is stirred at room temperature. If necessary, additional trityl chloride is added at about 24 h and about 48 h. After the reaction is complete, the solvent is removed and the residue is partitioned between dichloromethane and water. The organic layer is concentrated and the residue is purified by silica gel chromatography. The tritylated intermediate is then treated with (thiocarbonyl)diimidazole (~1.4 eq.) in DMF for about 1 h to 24 h to afford, after usual work-up, the 2',3'-O-thiocarbonate. A solution of the thiocarbonate in toluene is treated with a solution of tri-n-butyltin hydride (3-4 eq.) and a catalytic amount of AIBN in toluene at about 80 to about 120° C. for about 30 min. to 5 hr. The usual work-up and purification afford the 3'-deoxy product, along with 2'-deoxy product. The desired 3'-deoxy intermediate is then treated with 80-95% formic acid to afford Compound 16.

Compound 17
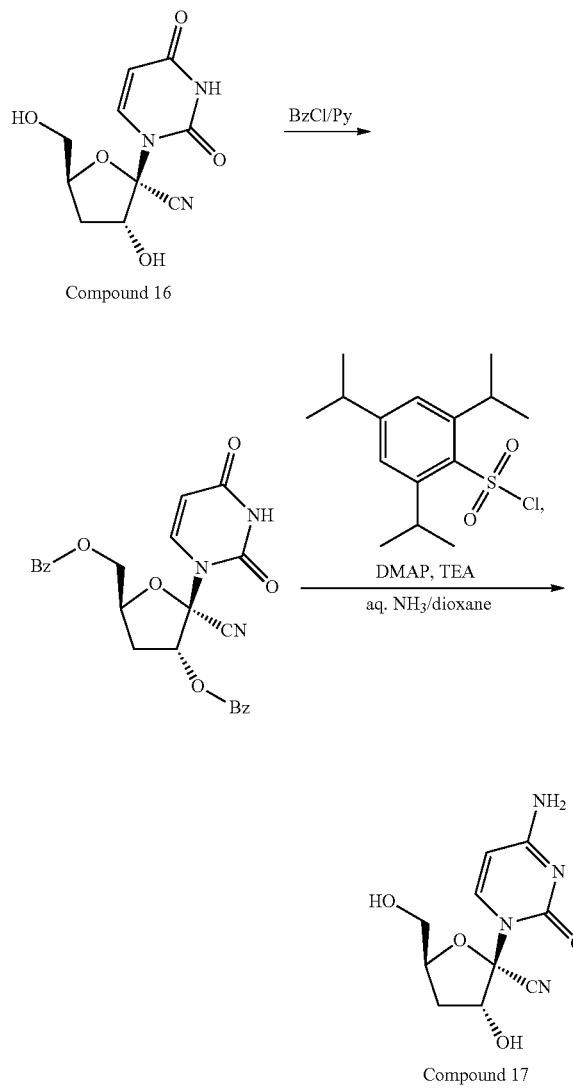
Compound 17 is obtained from Compound 16 by following the procedure similar to that for preparation of Compound 4.
Compound 18
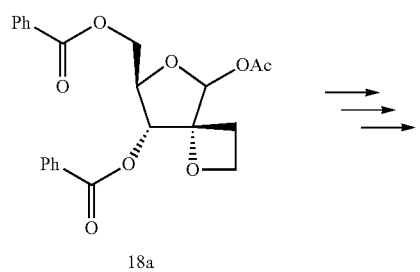
Compound 18 is prepared by following synthetic sequence similar to that for Compound 8 substituting Compound 18a for Compound 8a.
Preparation of 18a
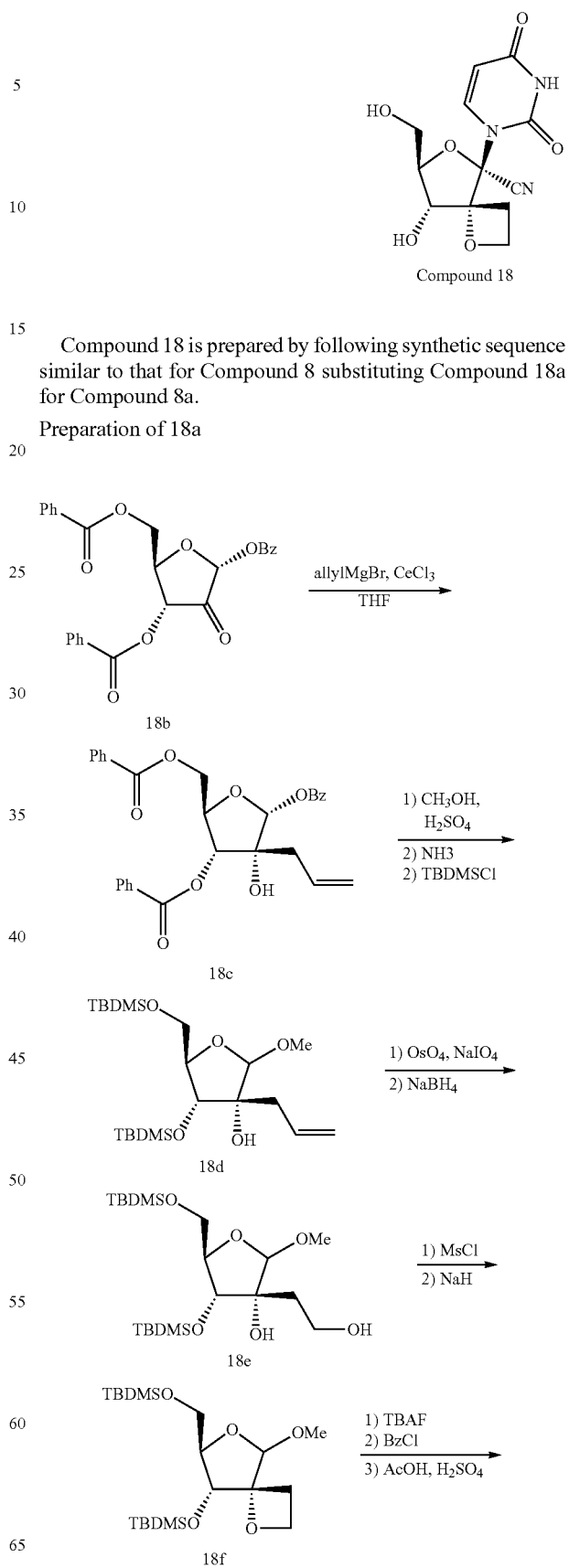

-continued

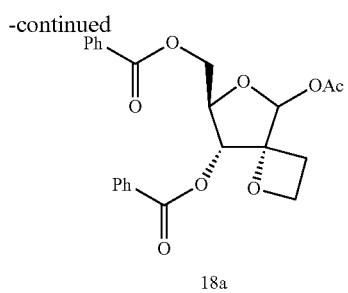

18a

Compound 18a may be obtained by a reaction sequence as shown above. Detailed procedures for construction of the oxetane ring is described in *Organic Biomolecular Chemistry*, 2003, 1, 3513. Protection and de-protection in this preparation are achieved by general methods well-established in the practice of nucleoside chemistry.

Compound 19 compound 19

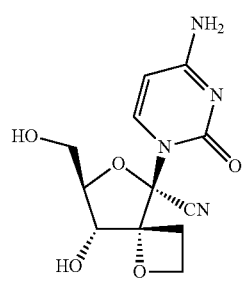

Compound 19 is obtained from Compound 18 by following the procedure similar to that for preparation of Compound 4.

General method for the preparation of 1'-CN-4'-azido substituted nucleosides

Incorporation of the azido group at the 4'-position of 1'-CN substituted nucleoside consists of dehydration to Compounds G-I from Compounds G-H and subsequent azido-hydroxylation to G-J (Scheme 3). Compounds G-J are prepared according to methods well established in the art. Relevant references include *Arch. Pharm. Res.,* 1995, 364; *Antiviral Chemistry and Chemotherapy,* 2009, 99; *Bioorganic and Medicinal Chemistry Letters,* 2007, 2570; *Journal of Medicinal Chemistry,* 1992, 1440; *Journal of Medicinal Chemistry,* 2007, 5463; *Journal of Medicinal Chemistry,* 2009, 2971; Synlett, 2011, 57; *EP371366,* 1990.

Scheme 3

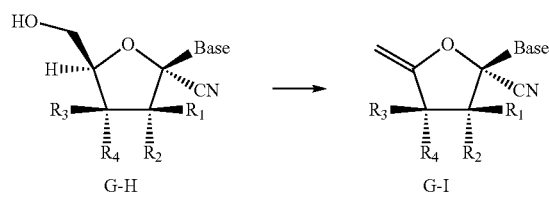

-continued

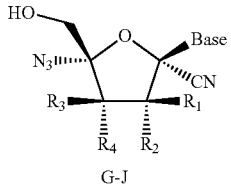

G-J

Compound 20

Compound 20

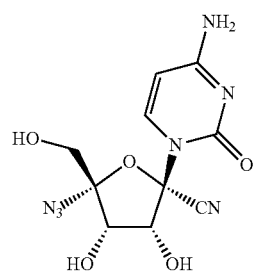

Compound 20 is prepared according to the general method, starting from Compound 3.

Compound 21

Compound 21

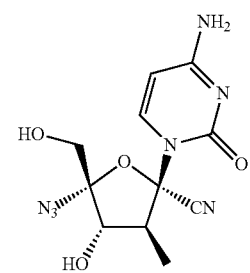

Compound 21 is prepared according to the general method, starting from Compound 15.

Compound 22

Compound 22

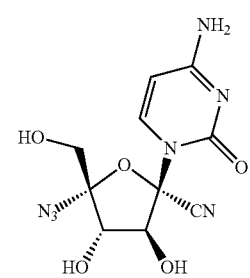

Compound 22 is prepared starting from Compound 20. The stereochemistry of 2'-alpha-OH is switched to 2'-beta-OH in a matter similar to that of Compound 10.

Compound 23

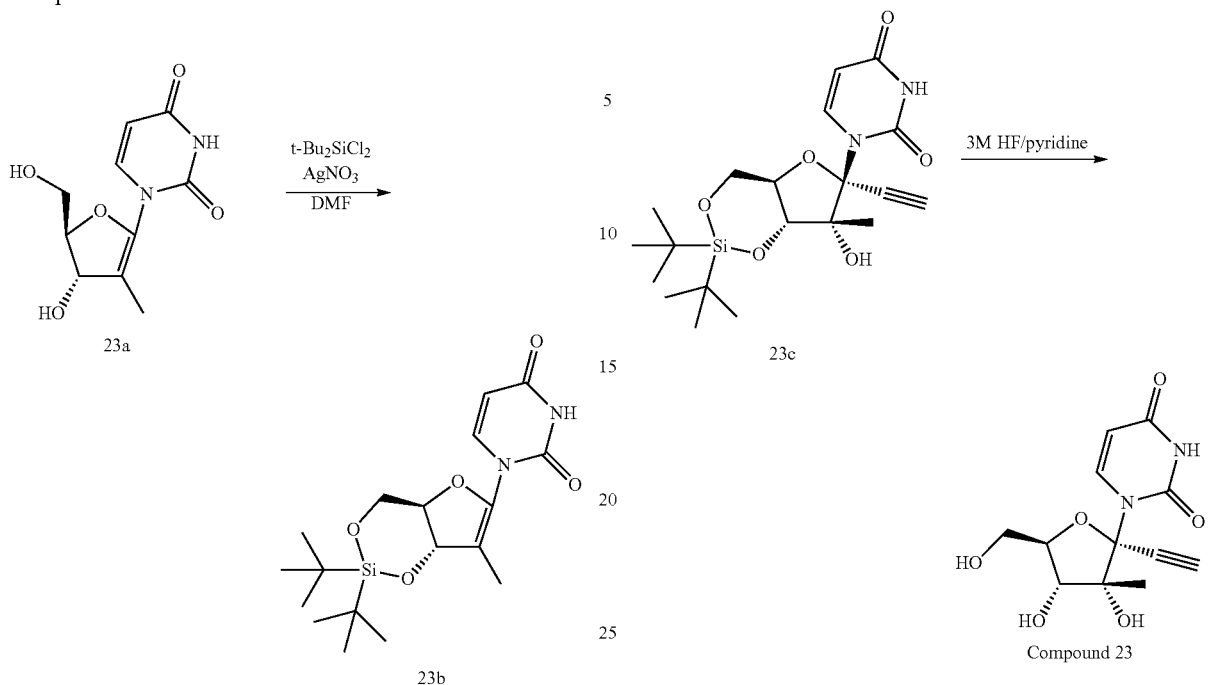

Compound 23b is obtained from Compound 23a (prepared according to *Tetrahedron*, 2000, 5363) by a method similar to that described in *Tetrahedron Letters*, 1995, 1683, using di-t-butyl-dichlorosilane and silver nitrate.

Compound 23c is obtained from Compound 23b by a method similar to that described in *Journal of Organic Chemistry*, 2004, 1831, using dimethyldioxirane and triethynylaluminum.

Compound 23 is obtained from Compound 23c by a method similar to that described in *Tetrahedron Letters*, 1995, 1683, using pyridinium poly(hydrogen fluoride).

Compound 24

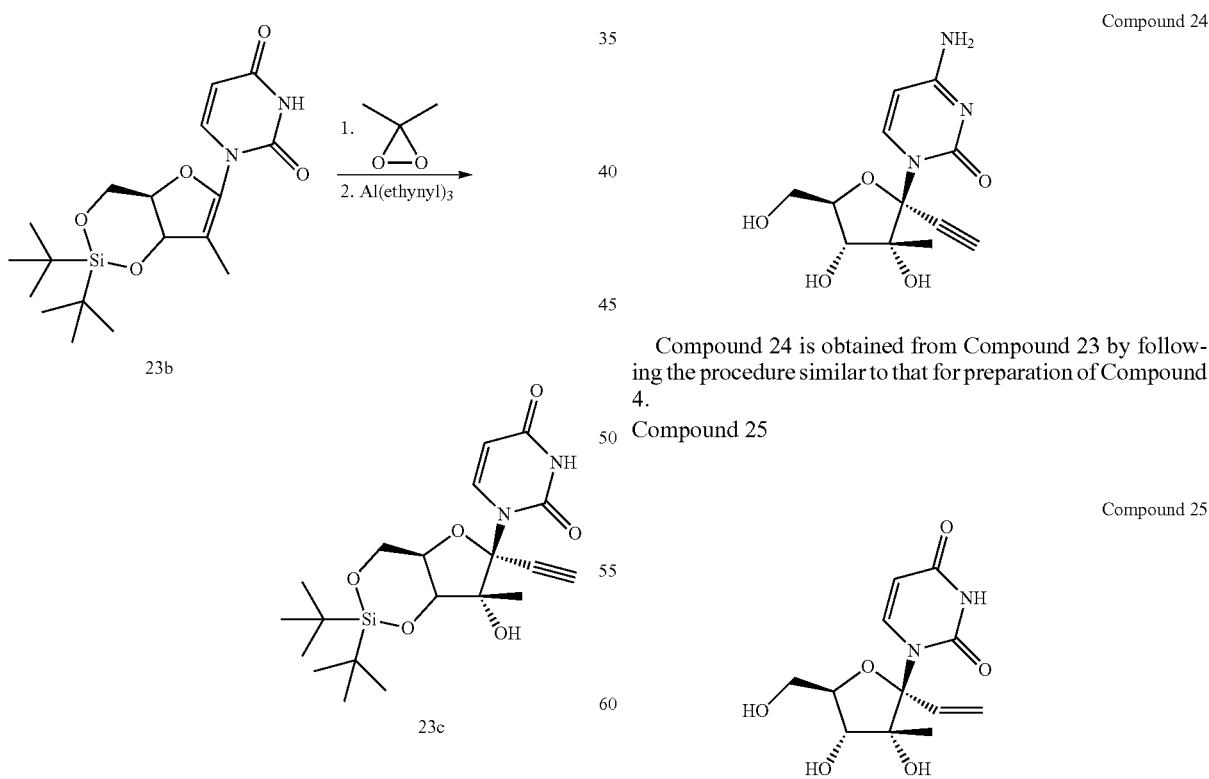

Compound 24 is obtained from Compound 23 by following the procedure similar to that for preparation of Compound 4.

Compound 25

Compound 25 is obtained by a manner similar to preparation of Compound 23, except using trivinylaluminum instead of triethynylaluminum.

Compound 26

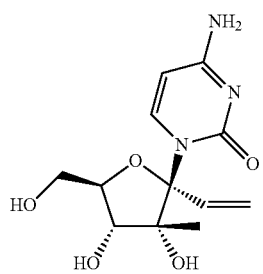

Compound 26

Compound 26 is obtained from Compound 25 by following the procedure similar to that for preparation of Compound 4.

General Procedure for Preparation of Nucleotide Triphosphates:

To a pear-shaped flask (5-15 mL) is charged with a nucleoside (~20 mg). Trimethyl phosphate (0.5-1.0 mL) is added. The solution is cooled with ice-water bath. POCl$_3$ (40-45 mg) is added and stirred at 0° C. until the reaction is complete (1 to 4 h; the reaction progress is monitored by ion-exchange HPLC; analytical samples are prepared by taking about 3 μL of the reaction mixture and diluting it with 1.0 M Et$_3$NH$_2$CO$_3$ (30-50 μL)). A solution of pyrophosphate-Bu$_3$N (250 mg) and Bu$_3$N (90-105 mg) in acetonitrile or DMF (1-1.5 mL) is then added. The mixture is stirred at 0° C. for 0.3 to 2.5 h, and then the reaction is quenched with 1.0 M Et$_3$NH$_2$CO$_3$ (~5 mL). The resulting mixture is stirred for additional 0.5-1 h while warming up to room temperature. The mixture is concentrated to dryness, re-dissolved in water (4 mL), and purified by ion exchange HPLC. The fractions containing the desired product is concentrated to dryness, dissolved in water (~5 mL), concentrated to dryness, and again dissolved in water (~5 mL). NaHCO$_3$ (30-50 mg) is added and concentrated to dryness. The residue is dissolved in water and concentrated to dryness again. This process is repeated 2-5 times. The residue is then subjected to C-18 HPLC purification, affording the desired product as a sodium salt. Alternatively, the crude reaction mixture is subjected to C-18 HPLC first and then ion exchange HPLC purification to afford the desired product as a triethylammonium salt.

Compound 27

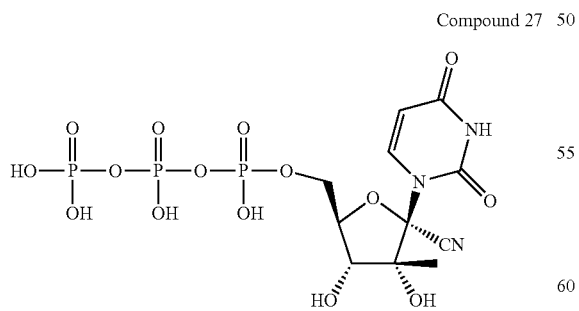

Compound 27

Compound 27 was prepared by the general method using Compound 1 as starting material. $^1$H NMR (400 MHz, D$_2$O): δ 7.82 (d, 1H), 5.75 (d, 1H), 4.1-4.3 (m, 3H), 3.95 (d, 1H), 1.10 (s, 3H). $^{31}$P NMR (162 MHz, D$_2$O): δ −5.5 (d), −10.9(d), −21.3(t). MS=522.0 (M−H$^+$).

Compound 28

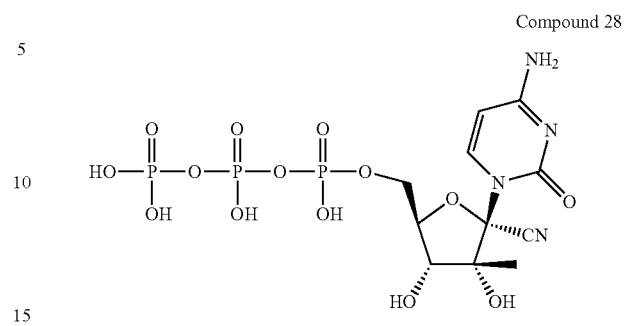

Compound 28

Compound 28 was prepared by the general method using Compound 2 as starting material. $^1$H NMR (400 MHz, D$_2$O): δ 7.95 (d, 1H), 6.04 (d, 1H), 4.1-4.4 (m, 3H), 3.87 (d, 1H), 3.10 (NCH$_2$CH$_3$), 1.10 (s, 3H, overlapped with NCH$_2$CH$_3$). $^{31}$P NMR (162 MHz, D$_2$O): δ −10.7 (d), −11.5(d), −23.2(t). MS=521.0 (M−H$^+$).

General Procedure for Preparation of a Nucleoside Prodrug Type PD-A:

Non-limiting examples of mono-phosphoramidate prodrugs comprising the instant invention may be prepared according to general Scheme 4.

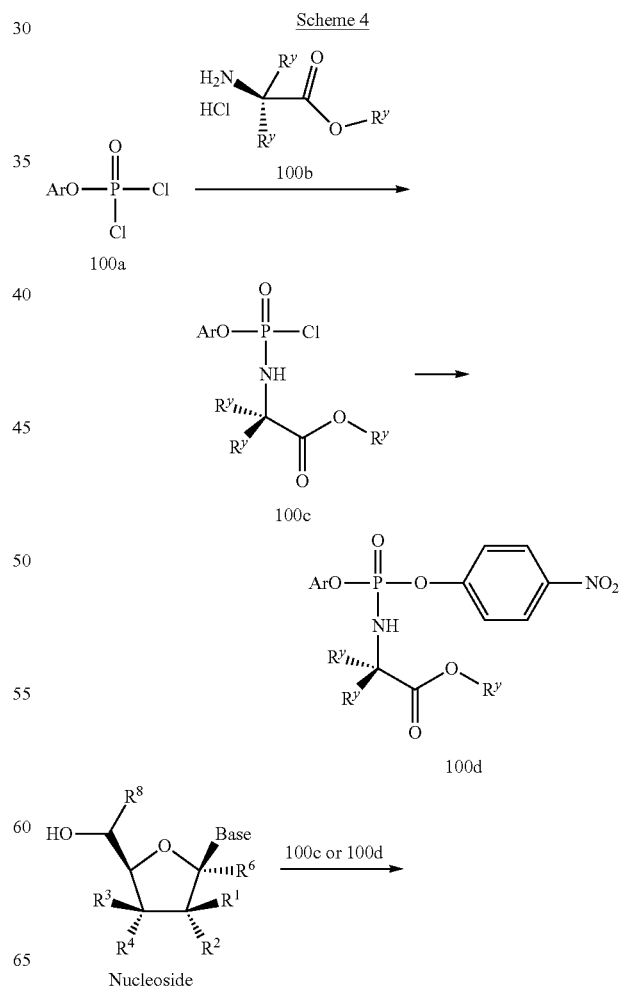

Scheme 4

-continued

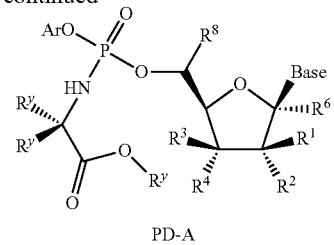

PD-A

The general procedure comprises the reaction of an amino acid ester salt Compound 100b, e.g., HCl salt, with an aryl dichlorophosphate Compound 100a in the presence of about two to ten equivalents of a suitable base to give the phosphoramidate Compound 100c. Suitable bases include, but are not limited to, imidazoles, pyridines such as lutidine and DMAP, tertiary amines such as triethylamine and DABCO, and substituted amidines such as DBN and DBU. Tertiary amines are particularly preferred. Preferably, the product of each step is used directly in the subsequent steps without recrystallization or chromatography. Specific, but non-limiting, examples of Compound 100a, Compound 100b, and Compound 100c can be found in WO 2006/121820 that is hereby incorporated by reference in its entirety. A Nucleoside reacts with the phosphorous chloridate Compound 100c in the presence of a suitable base. Suitable bases include, but are not limited to, imidazoles, pyridines such as lutidine and DMAP, tertiary amines such as triethylamine and DABCO, and substituted amidines such as DBN and DBU. The product Compound PD-A may be isolated by recrystallization and/or chromatography.

Alternative General Procedure for PD-A

The phosphorous chloridate Compound 100c reacts with an activated phenol such as 4-nitrophenol, 2-nitrophenol, and 2,4-dinitrophenol, in the presence of a suitable base to give a phosphorous phenolate Compound 100d that is stable for further purification. Compound 100d is then coupled with a Nucleoside; a solution of a Nucleoside in NMP (~30 mL/mmol) is cooled to 0° C. using an ice bath. To this mixture, a solution of t-BuMgCl in THF (1.0 M, 1.5-2.5 eq. to the nucleoside) is added dropwise. A solution of Compound 100d (~1.5 eq. to the nucleoside) in THF (~15 mL/mmol) is then added dropwise to the reaction mixture. The resulting mixture is allowed to warm up to room temperature and stirred for 16 h. The solution is then quenched with $H_2O$ (~30 mL/mmol) and purified via reverse phase HPLC (30-60% $CH_3CN$ in $H_2O$). The product fractions are combined, concentrated under vacuum, and then further purified using flash silica gel chromatography (1-35% MeOH in $CH_2Cl_2$) to give a monophosphate prodrug Compound PD-A. The diasteromeric mixture of Compound 100d is optionally separated into two single stereoisomers Compound (S)-100d and Compound (R)-100d by crystallization or chromatography prior to coupling with the Nucleoside to afford a single stereoisomer Compound (S)-PD-A or Compound (R)-PD-A.

Compound 29

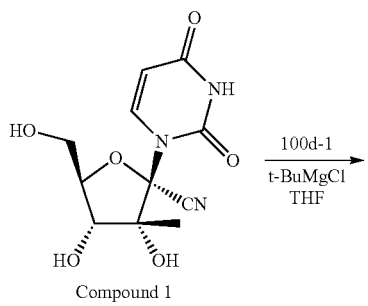

Compound 1

-continued

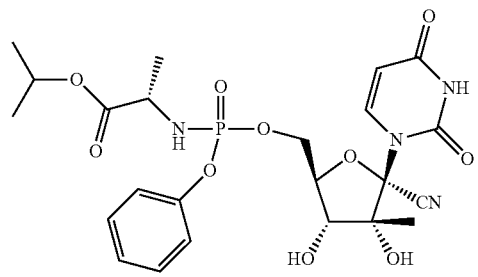

Compound 29

A solution of Compound 1 (37 mg, 0.13 mmol) in NMP (4 mL) was cooled to 0° C. using an ice bath. To this mixture, a solution of t-BuMgCl in THF (0.46 mL, 1.0 M) was added dropwise. A solution of Compound 100d-1 (82 mg, 0.20 mmol) in THF (2 mL) was then added dropwise to the reaction mixture. The resulting mixture was allowed to warm up to room temperature and stirred for 16 h. The solution was then quenched with $H_2O$ (4 mL) and purified via reverse phase HPLC (30-60% $CH_3CN$ in $H_2O$). The product fractions were combined, concentrated under vacuum, and then further purified using flash silica gel chromatography (2-35% MeOH in $CH_2Cl_2$) to give Compound 29 (8 mg, 14%) as a diastereomeric mixture. $^1$H NMR (400 MHz, $CD_3OD$) δ 7.86 (d, J=8.4 Hz, 1H), 7.36 (t, J=7.9 Hz, 2H), 7.31-7.14 (m, 3H), 5.62 (d, J=8.4 Hz, 1H), 4.96 (dt, J=12.5, 6.3 Hz, 1H), 4.55 (ddd, J=12.2, 6.3, 1.9 Hz, 1H), 4.45-4.24 (m, 2H), 4.08 (q, J=7.1 Hz, 1H), 3.98-3.60 (m, 2H), 1.34 (dd, J=7.1, 0.6 Hz, 3H), 1.27-1.17 (m, 9H). $^{31}$P NMR (162 MHz, $CD_3OD$) δ −4.16, −4.02. MS=551 (M−H$^+$). LC/MS retention time on a 3.5 minute LC/MS method (Polar RP column)=1.89 min.

Compound 30

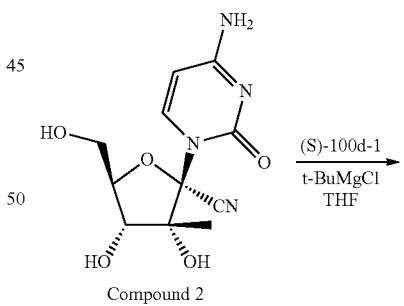

Compound 2

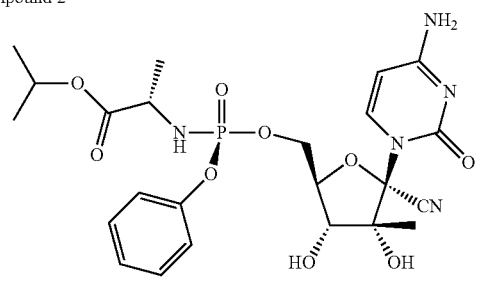

Compound 30

A solution of Compound 2 (40 mg, 0.14 mmol) in NMP (4 mL) was cooled to 0° C. using an ice bath. To this mixture, a solution of t-BuMgCl in THF (0.49 mL, 1.0 M) was added dropwise. A solution of Compound (S)-100d-1 (86 mg, 0.21 mmol) in THF (2 mL) was then added dropwise to the reaction mixture. The resulting reaction mixture was allowed to warm up to room temperature and stirred for 16 h. The solution was then quenched with H$_2$O (4 mL) and purified via reverse phase HPLC (30-60% CH$_3$CN in H$_2$O). The product fractions were combined, concentrated under vacuum, and then further purified using flash silica gel chromatography (2-40% MeOH in CH$_2$Cl$_2$) to give Compound (S)-30 (16 mg, 21%). $^1$H NMR (400 MHz, CD$_3$OD) δ 7.83 (t, J=9.0 Hz, 1H), 7.35 (t, J=7.9 Hz, 2H), 7.28-7.12 (m, 3H), 5.87 (dd, J=12.8, 7.8 Hz, 1H), 4.96 (dt, J=12.6, 6.3 Hz, 1H), 4.64-4.46 (m, 1H), 4.35 (ddd, J=11.7, 6.4, 2.9 Hz, 2H), 3.91 (dq, 14.1, 7.1 Hz, 1H), 3.66 (d, J=7.7 Hz, 1H), 1.33 (t, J=9.3 Hz, 3H), 1.21 (dd, J=6.2, 2.0 Hz, 6H), 1.11 (s, 3H). $^{31}$P NMR (162 MHz, CD$_3$OD) δ −4.00. MS=552 (M+H$^+$). LC/MS retention time on a 3.5 minute LC/MS method (Polar RP column)=1.80 min.

Preparation of Compound (S)-100d-1

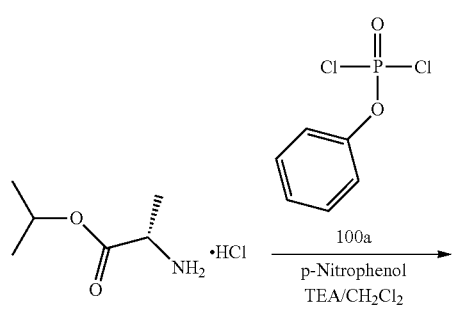

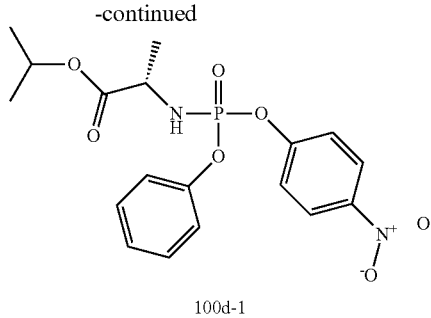

100d-1

Alanine isopropyl ester hydrochloride (7.95 g, 47.4 mmol) was suspended in dichloromethane (100 mL). Compound 100a (10 g, 47.4 mmol) was added. Triethylamine (13.2 mL, 95 mmol) was then dropwise added over a period of 15 min. (internal reaction temperature; −10° C.~−3° C.). When the reaction was almost complete (by phosphorous NMR), p-nitrophenol (6.29 g, 45.0 mmol) was added as a solid in one portion. To the resulting slurry was added triethylamine (6.28 mL, 45 mmol) over a period of 15 min. The mixture was then warmed up to room temperature. When the reaction was complete, MTBE (100 mL) was added. The white precipitate was removed by filtration. The filter cake was washed with MTBE (3×50 mL). The filtrate and washings were combined and concentrated. The residue was purified by silica gel column chromatography (0 to 50% ethyl acetate/hexanes), affording Compound 100d-1 as a 1:1 ratio of diasteromeric mixture (14.1 g, 77%). $^1$H NMR (300 MHz, CDCl$_3$): δ 8.22 (2d, 2H), 7.2-7.4 (m, 7H), 5.0 (m, 1H), 4.09 (m, 1H), 3.96 (m, 1H), 1.39 (2d, 3H), 1.22 (m, 6H). MS=409.0 (M+H$^+$), 407.2 (M−H$^+$).

Separation of Two Diastereomers of Compound 100d-1

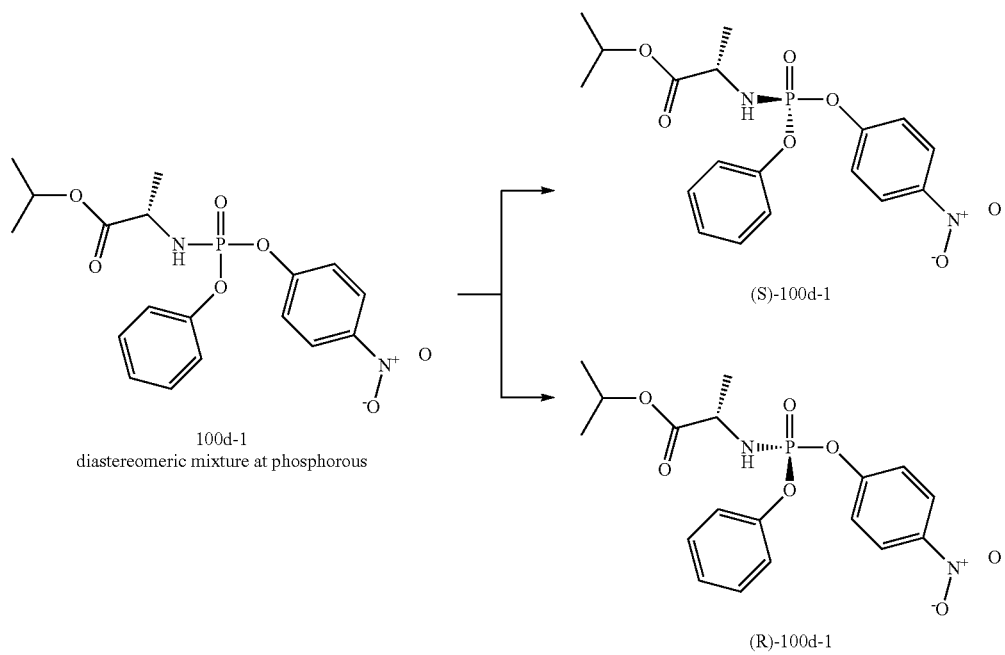

The two diastereomers were separated by chiral column chromatography under the following conditions;

Column: Chiralpak IC, 2×25 cm

Solvent system: 70% heptane and 30% isopropanol (IPA)

Flow rate: 6 mL/min.

Loading volume per run: 1.0 mL

Concentration of loading sample: 150 mg/mL in 70% heptane and 30% IPA

Compound (S)-100d-1: retention time 43 min. $^{31}$P NMR (162.1 MHz, CDCl$_3$): δ-2.99 (s). Compound (R)-100d-1: retention time 62 min. $^{31}$P NMR (162.1 MHz, CDCl$_3$): δ-3.02 (s).

Alternatively, the two diastereomers were separated by crystallization under the following procedure;

Compound 100d-1 was dissolved in diethyl ether (~10 mL/gram). While stirring, hexanes was then added until the solution became turbid. Seed crystals (~10 mg/gram of Compound (S)-100d-1) were added to promote crystallization. The resulting suspension was gently stirred for 16 h, cooled to ~0° C., stirred for an additional 2 h, and filtered to collect the crystalline material (recovery yield of the crystalline material 35%-35%). The crystalline material contains ~95% of Compound (S)-100d-1 and ~5% of Compound (R)-100d-1. Re-crystallization afforded 99% diastereomerically pure (S)-isomer.

Compound 31

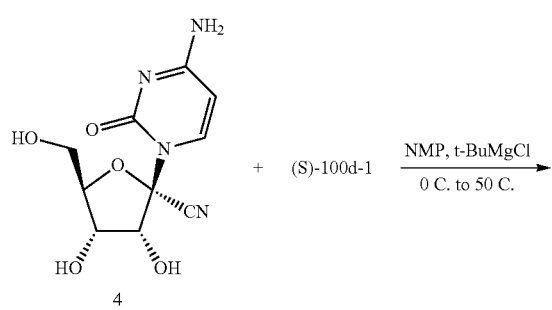

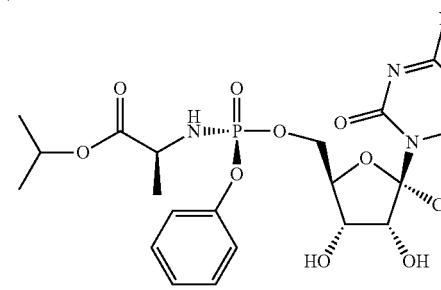

Compound 31

A solution of Compound 4 (50 mg, 0.188 mmol) in NMP (5 mL) was cooled to 0° C. under argon. To this was added 3.5 eq. of t-BuMgCl dropwise. To the resulting suspension was added Compound (S)-100d-1 (218 mg, 0.47 mmol) predissolved in THF (3 mL) dropwise. Reaction was then immediately heated to 50° C. and reaction progress was monitored for completion by LCMS (45-60 minutes). When reaction was determined to be complete reaction was cooled, 0.5 mL of each water and MeOH were added to the reaction, the reaction was filtered, and purified by prep HPLC to afford Compound (S)-31 (43 mg, 43% yield). MS [M+H$^+$]=538.9

Compound 32

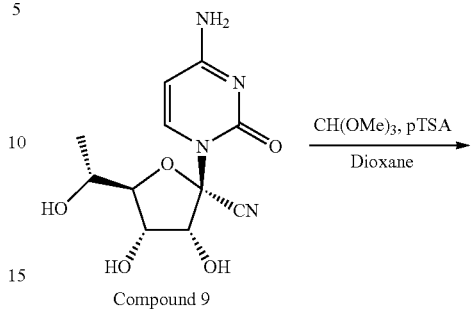

Compound 9

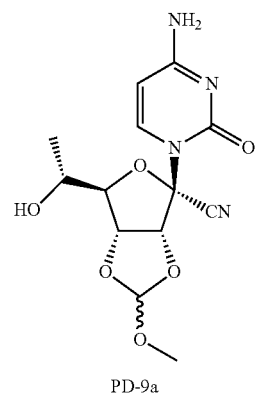

PD-9a

A solution of Compound 9 (148 mg, 0.52 mmol), p-toluenesulfonic acid monohydrate (76 mg, 0.40 mmol) and trimethylortho formate (6 mL) in 1,4-dioxane (6 mL) was stirred at room temperature for 1.5 h. The reaction was neutralized with triethylamine (0.06 mL) and the solvent was removed under reduced pressure. The residue was take up in methanol (8 mL) and stirred at room temperature for 30 minutes. The solvent was removed under reduced pressure. The residue was subjected to silica gel chromatography with an eluent of methanol and 1% triethylamine in dichloromethane. The product containing fractions were combined and the solvent was removed under pressure to provide Compound PD-9a (143 mg, 84%).

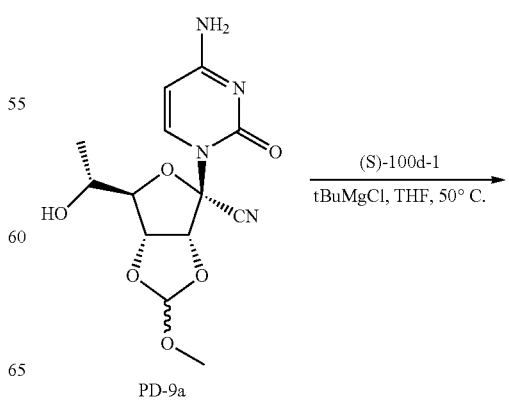

PD-9a

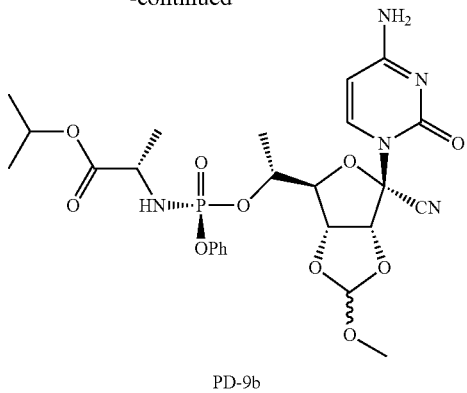

PD-9b

A solution of tert-butylmagnesium chloride (0.23 mL, 0.23 mmol 1.0 M) in tetrahydrofuran was added to a solution of Compound PD-9a (50 mg, 0.15 mmol) in tetrahydrofuran (2 mL) under argon. A white solid formed. After 30 minutes, a solution of Compound (S)-100d-1 (126 mg, 0.31 mmol) in tetrahydrofuran (1 mL) was added and the mixture was heated to 50° C. After 20 minutes the solid had dissolved and the solution was yellow. The reaction was cooled to 0° C. and quenched with methanol (1 mL). The solvent was removed under reduced pressure and the residue was subjected to silica gel chromatography with an eluent of methanol in dichloromethane. The product containing fractions were combined and the solvent was removed under pressure to provide Compound (S)-PD-9b (76.8 mg, 83%).

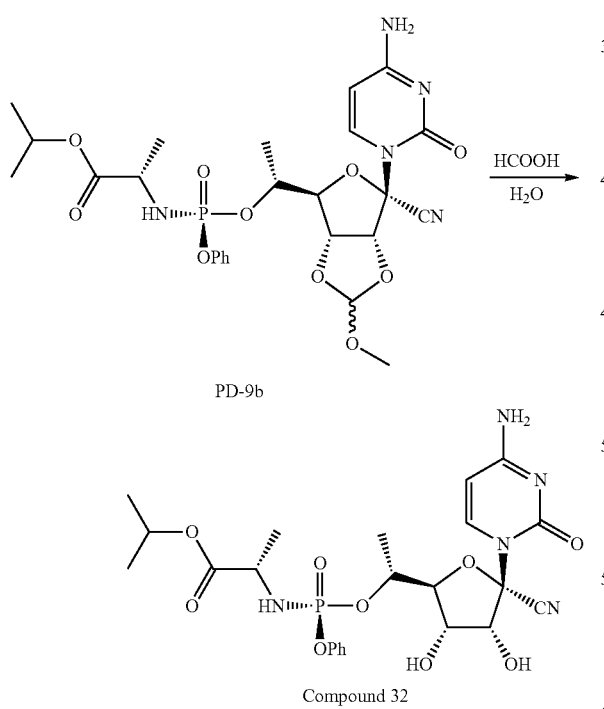

PD-9b

Compound 32

A solution of Compound (S)-PD-9b (76.8 mg, 0.13 mmol) in formic acid (5 mL, 95%) and water (1 mL) was stirred for 20 min. The solvent was removed under reduced pressure and the residue was azeotroped with ethyl acetate. The resulting residue was subjected to reverse phase chromatography with an eluent of acetonitrile and water. The product containing fractions were combined. The solvent was removed by lyophilization to provide Compound (S)-32 (8.3 mg, 31%). $^1$H-NMR (400 MHz, DMSO): δ7.92 (d, J=7.6 Hz, 1H), 7.45 (s, 1H), 7.39 (s, 1H), 7.35 (t, J=8.0 Hz, 2H), 7.16 (m, 3H), 6.72 (d, J=5.2 Hz, 1H), 6.04 (dd, $J_1$=10.0 Hz, $J_2$=13.2 Hz, 1H), 5.68 (d, J=7.6 Hz, 1H), 5.27 (d, J=7.2 HZ, 1H), 4.83 (m, 2H), 4.22 (m, 2H), 3.87 (m, 1H), 3.75 (m, 1H), 1.38 (d, J=6.8 Hz, 3H), 1.18 (d, J=6.8 Hz, 3H), 1.11 (m, 6H). $^{31}$P-NMR (400 MHz, DMSO): δ 3.22 (s). MS=552.0 (M+H$^+$). LC/MS retention time on a 6.0 minute LC/MS method (Polar RP column)=2.52 min.

Compound 33

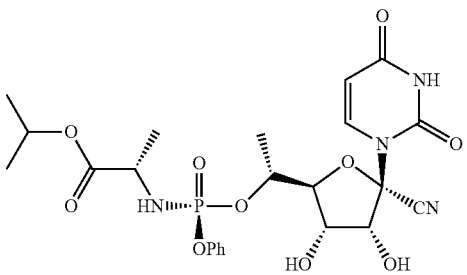

Compound 33

Compound (S)-33 was prepared following the procedure for Compound (S)-32 except using Compound 8 as the starting material. $^1$H-NMR (400 MHz, DMSO): δ 11.53 (d, 18 Hz), 7.91 (m, 1H), 7.30 (m, 2H), 7.12 (m, 3H), 6.74 (d, J=6.0 HZ, 1H), 5.97 (m, 1H), 5.32 (m, 2H), 4.78 (m, 2H), 4.32 (t, J=5.2 Hz, 1H), 3.89 (m, 1H), 3.73 (m, 1H), 1.31 (m, 3H), 1.47 (m, 3H), 1.07 (m, 6H). $^{31}$P-NMR (400 MHz, DMSO): δ3.52 (s). MS=553.3 (M+H$^+$). LC/MS retention time on a 6.0 minute LC/MS method (Polar RP column)=2.76 min.

Compound 34

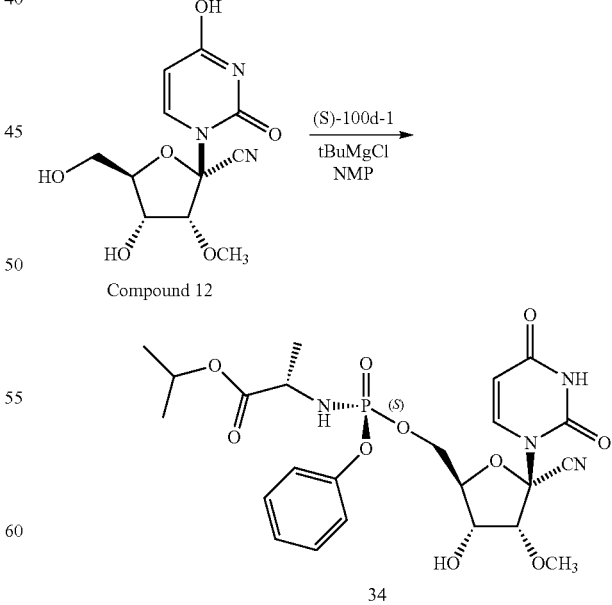

Compound 12

34

A solution of Compound 12 (10 mg, 0.035 mmol) in NMP (1 mL) was cooled to 0° C. using an ice bath. To this mixture, a solution of t-BuMgCl in THF (0.12 mL, 1.0 M) was added dropwise. A solution of Compound (S)-100d-1 (22 mg, 0.053 mmol) in THF (1 mL) was then added dropwise to the reaction mixture. The resulting mixture was allowed to warm up to room temperature and stirred for 16 h. The solution was then quenched with H$_2$O (2 mL) and purified via reverse phase HPLC (30-60% CH$_3$CN in H$_2$O to give Compound (S)-34 (1 mg, 10%). $^1$H NMR (400 MHz, CD$_3$OD) δ 7.86 (d, J=8.3 Hz, 1H), 7.36 (t, J=7.9 Hz, 2H), 7.28-7.11 (m, 3H), 5.59 (d, J=8.3 Hz, 1H), 4.95 (dt, J=12.5, 6.2 Hz, 1H), 4.52 (dd, J=10.8, 5.9 Hz, 1H), 4.42-4.21 (m, 2H), 4.02 (dd, J=9.7, 4.9 Hz, 1H), 3.89 (dt, J=17.4, 7.3 Hz, 1H), 3.78 (s, 3H), 1.41-1.12 (m, 10H). MS=553 (M+H$^+$). $^{31}$P NMR (162.1 MHz, CDOD): δ 4.03 (s). LC/MS retention time on a 3.5 minute LC/MS method (Polar RP column)=2.04 min.

General Procedure for Preparation of a Nucleoside Prodrug Type PD-B:

Non-limiting examples of 3'-O-acylated mono-phosphoramidate prodrugs comprising the instant invention may be prepared according to general Scheme 5.

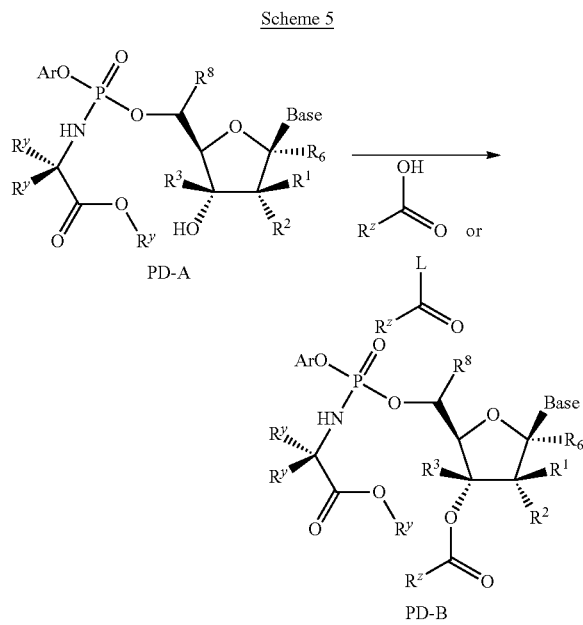

Scheme 5

PD-A

PD-B wherein R$^z$ is (C$_1$-C$_8$)alkyl.

The general procedure comprises the reaction of Compound PD-A (R$^4$=OH) with a carboxylic acid or an activated carboxylate such as an acyl chloride or an acid anhydride, which is generally known to those skilled in the art (*Journal of Medicinal Chemistry*, 2006, 49, 6614 and *Organic Letters*, 2003, 6, 807). When R$^8$=NH$_2$, protection of the amino group may be necessary. Briefly, to a solution of Compound PD-A in acetonitrile (2 mL) is added N,N-dimethylformamide dimethyl acetal (~1.1 eq.) and stirred at room temperature for 1 h. After the protection of 6-amino group is complete, the mixture is then concentrated to dryness. To the residue are added a dehydrating agent such as DCC (~4 eq.), acetonitrile and a carboxylic acid (~2 eq.). The mixture is stirred at room temperature for 24-48 h. Water (0.2 mL) and trifluoroacetic acid (0.1 mL) are added at 0° C. and stirred at room temperature for 64 h. Sodium bicarbonate was added at 0° C. The mixture is stirred at room temperature for 0.5 h and filtered. The filtrate is concentrated and the residue was purified by silica gel column chromatography to afford Compound PD-B. If an acyl chloride or an acid anhydride is used, a suitable base, such as triethylamine, is added instead of a dehydrating agent.

Compound 35

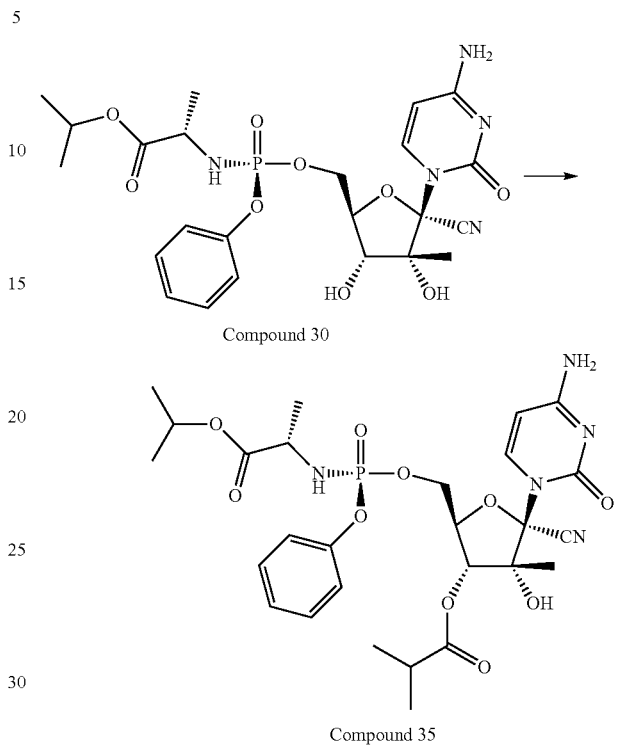

Compound 30

Compound 35

To a solution of Compound (S)-30 (34 mg, 0.062 mmol) in THF (0.8 mL) under an atmosphere of argon at room temperature was added N,N-dimethylformamide-dimethylacetal (8.2 μL, 0.062 mmol). After 8 h, an additional N,N-dimethylformamide-dimethylacetal (10 μL) was added and stirred for 16 h. The reaction mixture was concentrated. The reaction was taken up in DCM and concentrated. This process was repeated twice. The resulting residue was taken up in THF (0.8 mL) and cooled to 0° C. under an atmosphere of argon. To the solution was added triethylamine (11 μL, 0.075 mmol) and DMAP (0.4 mg, 0.003 mmol). After 5 minutes, isobutyryl chloride (7.4 μL, 0.07 mmol) was added. After 30 minutes, the reaction was allowed to warm to room temperature and was stirred for 3 hours. The mixture was cooled to 0° C., quenched with a 5% TFA solution in water, and then allowed to stir at room temperature for 4 hours. The resulting mixture was neutralized with solid sodium bicarbonate, diluted with water, and extracted with ethyl acetate (3×). The combined organic layers were dried with sodium sulfate, filtered and concentrated. The residue was purified by RP HPLC (acetonitrile/water), affording Compound (S)-35 (32 mg, 83%). $^1$H NMR (400 MHz, CDCl$_3$): δ 7.96 (br s, 1H), 7.76 (d, 1H), 7.13-7.32 (m, 5H), 6.29 (br s, 1H) 5.94 (s, 1H), 5.87 (d, 1H), 5.00 (m, 2H), 4.48-4.58 (m, 2H), 4.29 (m, 1H), 3.88-4.05 (m, 2H), 2.67 (m, 1H), 1.39 (d, 3H), 1.22 (12H), 1.02 (s, 3H). $^{31}$P NMR (161 MHz, CDCl$_3$): δ 3.20 (s). LC/MS=622 (M+H$^+$).

General Procedure for Preparation of a Nucleoside Prodrug Type PD-C:

Non-limiting examples of mono-phosphoramidate prodrugs comprising the instant invention may be prepared according to general Scheme 6.

Scheme 6

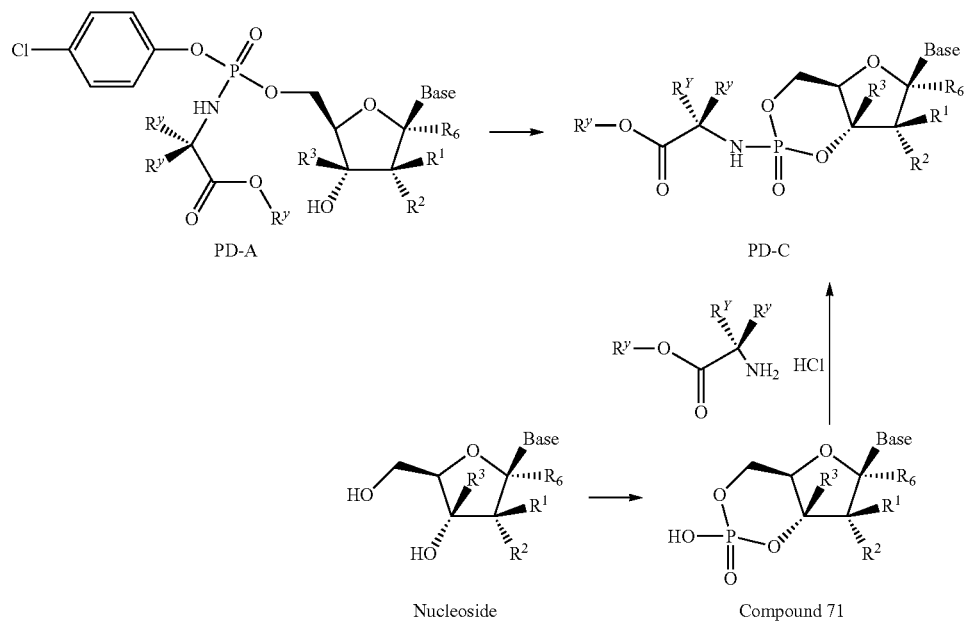

Scheme 6 illustrates chemical processes that may be useful for preparation of Compound PD-C. Accordingly, Compound PD-A is converted to Compound PD-C in the presence of a base when Ar is substituted with an electron-withdrawing p-nitro or p-chloro group (*European Journal of Medicinal Chemistry*, 2009, 44, 3769). Alternatively, a Nucleoside is converted to a cyclic phosphate Compound 71 according to *Bioorganic and Medicinal Chemistry Letters*, 2007, 17, 2452, which is then coupled with an amino acid ester salt to form Compound PD-C.

Compound 36

A solution of Compound 36a in DMSO is treated at room temperature with potassium t-butoxide (~1 eq.) and the resulting mixture is stirred for about 10 min. to about 2 h. The mixture is then cooled to 0° C. and neutralized with 1N HCl to ~pH 6. The mixture is purified by HPLC to afford Compound 36. The intermediate Compound 36a is obtained by the general method for preparation of prodrug type Compound PD-A, starting with Compound 100a (ArO=4-chlorophenol), Compound 100b (2'-ethylbutyl ester of alanine hydrochloride) and Compound 2.

Compound 37

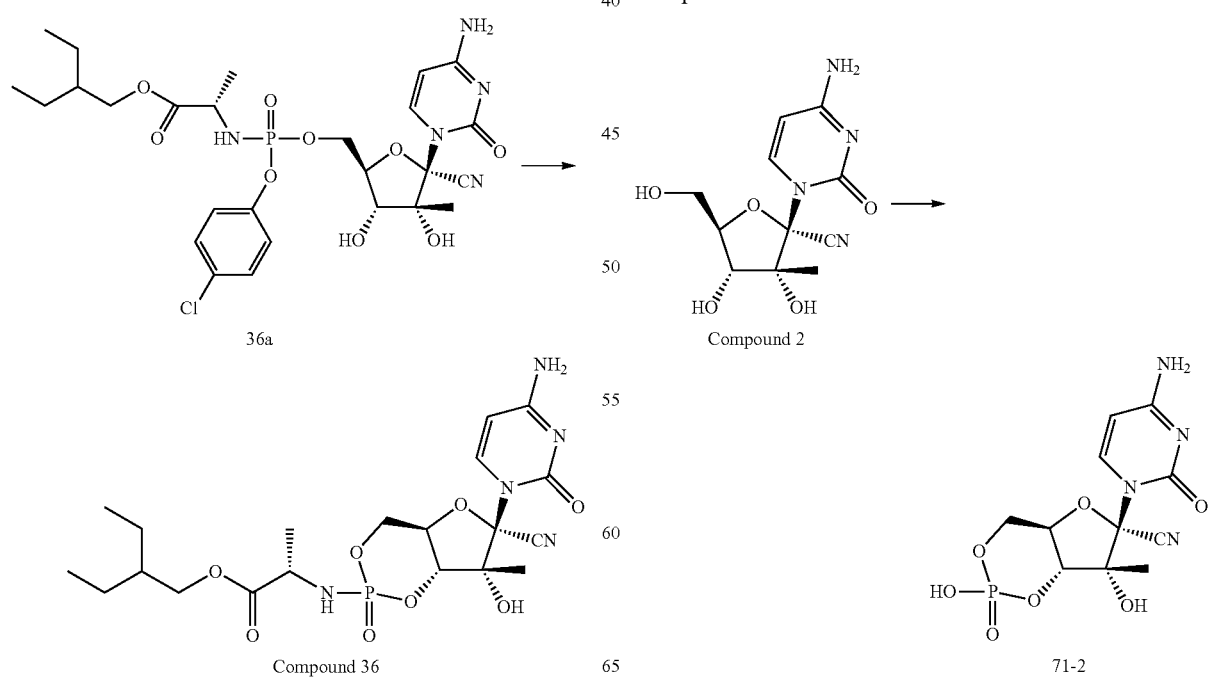

Compound 2 is dissolved in PO(OMe)₃ (0.1-0.5 M solution) and cooled to 0° C. under argon. To this stirring solution is added POCl₃ (1.0-5.0 eq.) dropwise, and the reaction mixture is allowed to warm to room temperature for about 2-16 h. The resulting solution is added dropwise to a rapidly stirring solution of acetonitrile and 0.05-0.5 M aqueous KOH. When addition is complete, the solvents are removed under reduced pressure. The resulting residue is dissolved in water and purified by HPLC to give Compound 71-2.

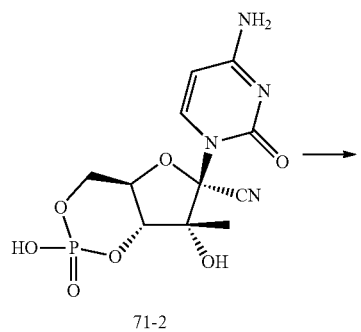

71-2

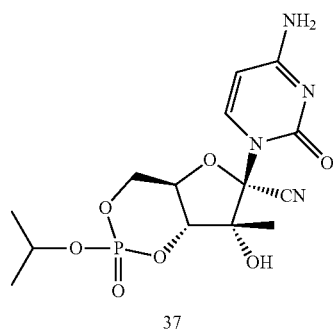

37

A solution of Compound 71-2 in DCM and PO(OMe)₃ is prepared and cooled to 0° C. To this solution is added oxalyl chloride (1.0-5.0 eq.) followed by a catalytic amount of DMF. The mixture is allowed to stir for about 10 min. to about 1 h. When activation is complete, a large volume of 2-propanol is added to the reaction mixture and allowed to stir and warm to room temperature. The solvents are removed under reduced pressure, and the resulting crude material is purified by preparative HPLC to give Compound 37.

Compound 38

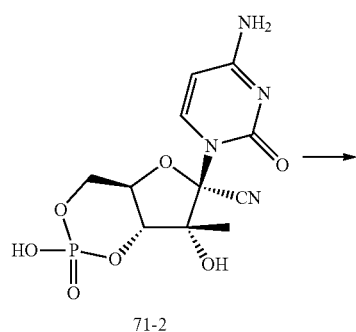

71-2

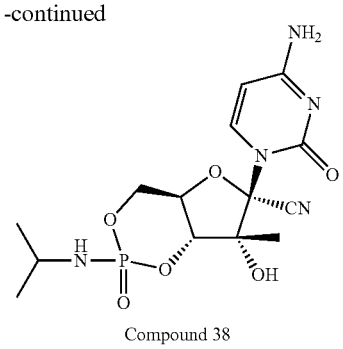

Compound 38

Compound 38 is prepared from Compound 71-2 in a matter similar to that of Compound 37 substituting 2-aminopropane for 2-propanol.

Compound 39

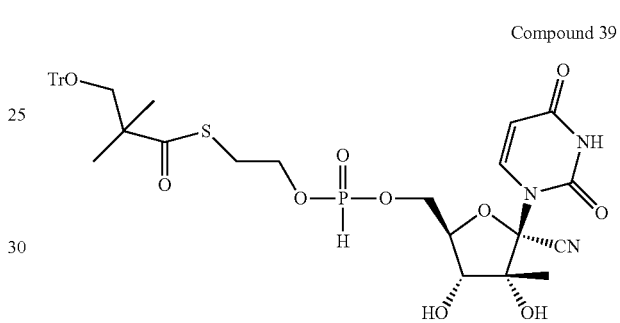

Compound 39

A mixture of about 1.25 mmol of Compound 1 and about 1.9 mmol of triethylammonium 2-(2,2-dimethyl-3-(trityloxy)propanoylthio)ethyl phosphinate (WO2008082601) is dissolved in anhydrous pyridine (about 19 mL). Pivaloyl chloride (about 2.5 mmol) is added dropwise at about −30 to about 0° C. and the solution is stirred at for about 30 min to about 24 hours. The reaction is diluted with methylene chloride and is neutralized with aqueous ammonium chloride (about 0.5 M). The dichloromethane phase is evaporated and the residue is dried and is purified by chromatography to give Compound 39.

Compound 40

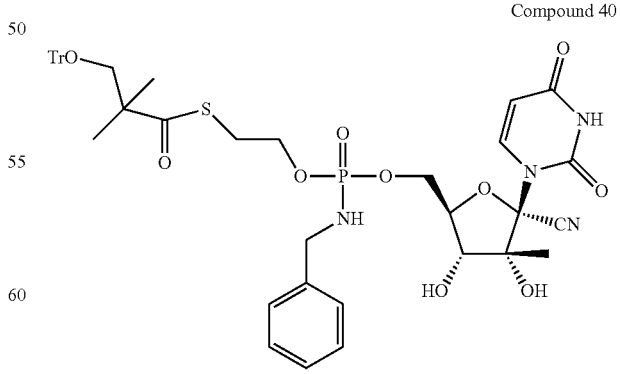

Compound 40

To a solution of about 0.49 mmol of Compound 39 in anhydrous carbon tetrachloride (about 5 mL) is added dropwise benzylamine (about 2.45 mmol). The reaction mixture is stirred for about one to about 24 hours. The solvent is evaporated and the residue is purified by chromatography to give Compound 40.

Compound 41

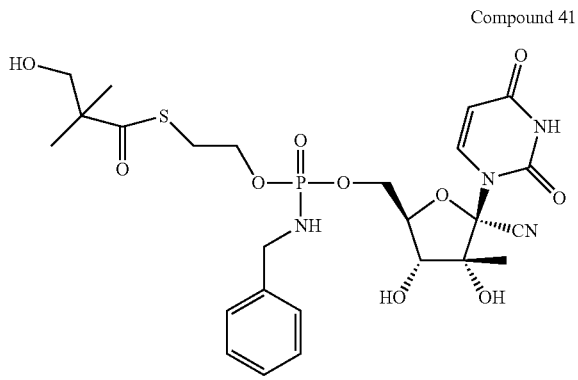 [SMILES: CC(C)(CO)C(=O)SCCOP(=O)(NCc1ccccc1)OC[C@H]1O[C@@](C#N)(n2ccc(=O)[nH]c2=O)[C@](C)(O)[C@@H]1O]

Compound 41

A solution of about 2 mmol of Compound 40 in dichloromethane (about 10 mL) is treated with an aqueous solution of trifluoroacetic acid (90%, about 10 mL). The reaction mixture is stirred at about 25 to about 60° C. for about one to about 24 hours. The reaction mixture is diluted with ethanol, the volatiles are evaporated and the residue is purified by chromatography to give Compound 41.

Compound 42

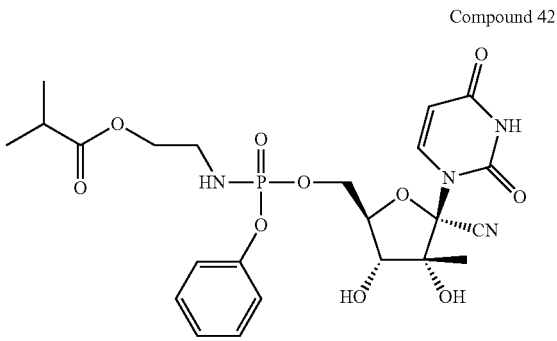 [SMILES: CC(C)C(=O)OCCNP(=O)(OC[C@H]1O[C@@](C#N)(n2ccc(=O)[nH]c2=O)[C@](C)(O)[C@@H]1O)Oc1ccccc1]

Compound 42

About 90 mM Compound 1 in THF is cooled to about −78° C. and about 2.2 to about 5 equivalents of t-butylmagneisum chloride (about 1 M in THF) is added. The mixture is warmed to about 0° C. for about 30 min and is again cooled to about −78° C. A solution of 2-{[chloro(1-phenoxy)phosphoryl]amino}ethyl isobutyrate (WO2008085508) (1 M in THF, about 2 equivalents) is added dropwise. The cooling is removed and the reaction is stirred for about one to about 24 hours. The reaction is quenched with water and the mixture is extracted with ethyl acetate. The extracts are dried and evaporated and the residue purified by chromatography to give Compound 42.

Antiviral Activity

Another aspect of the invention relates to methods of inhibiting viral infections, comprising the step of treating a sample or subject suspected of needing such inhibition with a composition of the invention.

Within the context of the invention samples suspected of containing a virus include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing an organism which induces a viral infection, frequently a pathogenic organism such as a tumor virus. Samples can be contained in any medium including water and organic solvent\water mixtures. Samples include living organisms such as humans, and man made materials such as cell cultures.

If desired, the anti-virus activity of a compound of the invention after application of the composition can be observed by any method including direct and indirect methods of detecting such activity. Quantitative, qualitative, and semiquantitative methods of determining such activity are all contemplated. Typically one of the screening methods described above are applied, however, any other method such as observation of the physiological properties of a living organism are also applicable.

The antiviral activity of a compound of the invention can be measured using standard screening protocols that are known. For example, the antiviral activity of a compound can be measured using the following general protocols.

Cell-Based Flavivirus Immunodetection Assay

BHK21 or A549 cells are trypsinized, counted and diluted to $2 \times 10^5$ cells/mL in Hams F-12 media (A549 cells) or RPMI-1640 media (BHK21 cells) supplemented with 2% fetal bovine serum (FBS) and 1% penicillin/streptomycin. $2 \times 10^4$ cells are dispensed in a clear 96-well tissue culture plates per well and placed at 37° C., 5% $CO_2$ overnight. On the next day, the cells are infected with viruses at multiplicity of infection (MOI) of 0.3 in the presence of varied concentrations of test compounds for 1 hour at 37° C. and 5% $CO_2$ for another 48 hours. The cells are washed once with PBS and fixed with cold methanol for 10 min. After washing twice with PBS, the fixed cells are blocked with PBS containing 1% FBS and 0.05% Tween-20 for 1 hour at room temperature. The primary antibody solution (4G2) is then added at a concentration of 1:20 to 1:100 in PBS containing 1% FBS and 0.05% Tween-20 for 3 hours. The cells are then washed three times with PBS followed by one hour incubation with horseradish peroxidase (HRP)-conjugated anti-mouse IgG (Sigma, 1:2000 dilution). After washing three times with PBS, 50 microliters of 3,3',5, 5'-tetramethylbenzidine (TMB) substrate solution (Sigma) is added to each well for two minutes. The reaction is stopped by addition of 0.5 M sulfuric acid. The plates are read at 450 nm absorbance for viral load quantification. After measurement, the cells are washed three times with PBS followed by incubation with propidium iodide for 5 min. The plate is read in a Tecan Safire™ reader (excitation 537 nm, emission 617 nm) for cell number quantification. Dose response curves are plotted from the mean absorbance versus the log of the concentration of test compounds. The $EC_{50}$ is calculated by non-linear regression analysis. A positive control such as N-nonyl-deoxynojirimycin may be used.

Cell-Based Flavivirus Cytopathic Effect Assay

For testing against West Nile virus or Japanese encephalitis virus, BHK21 cells are trypsinized and diluted to a concentration of $4 \times 10^5$ cells/mL in RPMI-1640 media supplemented with 2% FBS and 1% penicillin/streptomycin. For testing against dengue virus, Huh7 cells are trypsinized and diluted to a concentration of $4 \times 10^5$ cells/mL in DMEM media supplemented with 5% FBS and 1% penicillin/streptomycin. A 50 microliter of cell suspension ($2 \times 10^4$ cells) is dispensed per well in a 96-well optical bottom PIT polymer-based plates (Nunc). Cells are grown overnight in culture medium at 37°

C., 5% CO$_2$, and then infected with West Nile virus (e.g., B956 strain) or Japanese encephalitis virus (e.g., Nakayama strain) at MOI=0.3, or with dengue virus (e.g., DEN-2 NGC strain) at MOI=1, in the presence of different concentrations of test compounds. The plates containing the virus and the compounds are further incubated at 37° C., 5% CO$_2$ for 72 hours. At the end of incubation, 100 microliters of CellTiter-Glo™ reagent is added into each well. Contents are mixed for 2 minutes on an orbital shaker to induce cell lysis. The plates are incubated at room temperature for 10 minutes to stabilize luminescent signal. Luminescence reading is recorded using a plate reader. A positive control such as N-nonyl-deoxynojirimycin may be used.

Antiviral Activity in a Mouse Model of Dengue Infection

Compounds are tested in vivo in a mouse model of dengue virus infection (Schul et al. J. Infectious Dis. 2007; 195:665-74). Six to ten week old AG129 mice (B&K Universal Ltd, HII, UK) are housed in individually ventilated cages. Mice are injected intraperitoneally with 0.4 mL TSV01 dengue virus 2 suspension. Blood samples are taken by retro orbital puncture under isoflurane anesthesia. Blood samples are collected in tubes containing sodium citrate to a final concentration of 0.4%, and immediately centrifuged for 3 minutes at 6000 g to obtain plasma. Plasma (20 microliters) is diluted in 780 microliters RPMI-1640 medium and snap frozen in liquid nitrogen for plaque assay analysis. The remaining plasma is reserved for cytokine and NS1 protein level determination. Mice develop dengue viremia rising over several days, peaking on day 3 post-infection.

For testing of antiviral activity, a compound of the invention is dissolved in vehicle fluid, e.g., 10% ethanol, 30% PEG 300 and 60% D5W (5% dextrose in water; or 6N HCl (1.5 eq):1N NaOH (pH adjusted to 3.5): 100 mM citrate buffer pH 3.5 (0.9% v/v:2.5% v/v: 96.6% v/v). Thirty six 6-10 week old AG129 mice are divided into six groups of six mice each. All mice are infected with dengue virus as described above (day 0). Group 1 is dosed by oral gavage of 200 mL/mouse with 0.2 mg/kg of a compound of the invention twice a day (once early in the morning and once late in the afternoon) for three consecutive days starting on day 0 (first dose just before dengue infection). Groups 2, 3 and 4 are dosed the same way with 1 mg/kg, 5 mg/kg and 25 mg/kg of the compound, respectively. A positive control may be used, such as (2R,3R,4R,5R)-2-(2-amino-6-hydroxy-purin-9-yl)-5-hydroxymethyl-3-methyl-tetrahydro-furan-3,4-diol, dosed by oral gavage of 200 microliters/mouse the same way as the previous groups. A further group is treated with only vehicle fluid.

On day 3 post-infection approximately 100 microliter blood samples (anti-coagulated with sodium citrate) are taken from the mice by retro-orbital puncture under isoflurane anesthesia. Plasma is obtained from each blood sample by centrifugation and snap frozen in liquid nitrogen for plaque assay analysis. The collected plasma samples are analyzed by plague assay as described in Schul et al. Cytokines are also analyzed as described by Schul. NS1 protein levels are analyzed using a Platelia™ kit (BioRad Laboratories). An antiviral effect is indicated by a reduction in cytokine levels and/or NS1 protein levels.

Typically, reductions in viremia of about 5-100 fold, more typically 10-60 fold, most typically 20-30 fold, are obtained with 5-50 mg/kg bid dosages of the compounds of the invention.

HCV IC$_{50}$ Determination

Assay Protocol: Either wild type or S282T (Migliaccio, et al., J. Biol. Chem. 2003, 49164-49170; Klumpp, et al., J. Biol. Chem. 2006, 3793-3799) mutant polymerase enzyme was used in this assay. NS5b polymerase assay (40 µL) was assembled by adding 28 µL polymerase mixture (final concentration: 50 mM Tris-HCl at pH 7.5, 10 mM KCl, 5 mM MgCl$_2$, 1 mM DTT, 10 mM EDTA, 4 ng/µL of RNA template, and 75 nM HCV Δ21 NS5b polymerase) to assay plates followed by 4 µL of compound dilution. The polymerase and compound were pre-incubated at 35° C. for 10 minute before the addition of 8 µL of nucleotide substrate mixture (33P-γ-labeled competing nucleotide at K$_M$ and 0.5 mM of the remaining three nucleotides). The assay plates were covered and incubated at 35° C. for 90 min. Reactions were then filtered through 96-well DEAE-81 filter plates via vacuum. The filter plates were then washed under vacuum with multiple volumes of 0.125 M NaHPO$_4$, water, and ethanol to remove unincorporated label. Plates were then counted on TopCount to assess the level of product synthesis over background controls. The IC$_{50}$ value is determined using Prism fitting program.

Preferably, compounds described herein inhibited NS5b polymerase with IC$_{50}$'s below 1000 µM, more preferably below 100 µM, and most preferably below 10 µM. Data for representative compounds are found in the Table below.

| Compound # | Structure | IC$_{50}$, µM |
|---|---|---|
| 27 | (structure) | 27 |
| 28 | (structure) | 18 |

HCV EC$_{50}$ Determination

Replicon cells were seeded in 96-well plates at a density of 8×10$^3$ cells per well in 100 µL of culture medium, excluding Geneticin. Compound was serially diluted in 100% DMSO and then added to the cells at a 1:200 dilution, achieving a final concentration of 0.5% DMSO and a total volume of 200 µL. Plates were incubated at 37° C. for 3 days, after which culture medium was removed and cells were lysed in lysis buffer provided by Promega's luciferase assay system. Following the manufacturer's instruction, 100 µL of luciferase substrate was added to the lysed cells and luciferase activity was measured in a TopCount luminometer. Preferably, compounds described herein have EC50's below 1000 µM, more preferably below 100 µM, and most preferably below 10 µM.

Data for representative compounds are shown in the table below.

| Compound # | Structure | EC$_{50}$, μM |
|---|---|---|
| 29 | (structure shown) | 8.2 |
| 30 | (structure shown) | 2.6 |

Mitochondrial Biogenesis Assay after 5-Day Treatment in PC-3 Cells

Three-fold serial dilutions of compounds were prepared in duplicate in 96-well plates starting at a concentration close to the CC$_{50}$ value of the compound after 5-day treatment. For compounds with CC$_{50}$≥100 μM, the starting concentration was 100 μM. PC-3 cells were plated at a density of 2.5×10$^3$ cells per well in a final assay volume of 100 μL per well with a constant amount of DMSO equal to 0.5%. After 5-day incubation, the cells were analyzed with the MitoSciences MitoBiogenesis™ In-Cell ELISA Kit (catalog #MS642), which uses quantitative immunocytochemistry to measure protein levels of Complexes II and IV in cultured cells. Cells were fixed in a 96-well plate and target proteins were detected with highly-specific, well-characterized monoclonal antibodies. The protein levels were quantified with IRDyee-labeled Secondary Antibodies. IR imaging and quantitation was performed using a LI-COR® Odyssey instrument. All ratios were expressed as a percentage of the 0.5% DMSO control. In cases where cell viability was severely affected, the data for mitochondrial biogenesis was not included for analysis due to significant errors associated with low signals. Chloramphenicol was used as the positive control for the assay.

The cytotoxicity of a compound of the invention can be determined using the following general protocol.

Cytotoxicity Cell Culture Assay (Determination of CC50)

The assay is based on the evaluation of cytotoxic effect of tested compounds using a metabolic substrate.

Assay Protocol for Determination of CC$_{50}$:
1. Maintain MT-2 cells in RPMI-1640 medium supplemented with 5% fetal bovine serum and antibiotics.
2. Distribute the cells into a 96-well plate (20,000 cell in 100 μL media per well) and add various concentrations of the tested compound in triplicate (100 μL/well). Include untreated control.
3. Incubate the cells for 5 days at 37° C.
4. Prepare XTT solution (6 ml per assay plate) in dark at a concentration of 2 mg/ml in a phosphate-buffered saline pH 7.4. Heat the solution in a water-bath at 55° C. for 5 min. Add 50 μl of N-methylphenazonium methasulfate (5 μg/mL) per 6 ml of XTT solution.
5. Remove 100 μl media from each well on the assay plate and add 100 μl of the XTT substrate solution per well. Incubate at 37° C. for 45 to 60 min in a CO$_2$ incubator.
6. Add 20 μl of 2% Triton X-100 per well to stop the metabolic conversion of XTT.
7. Read the absorbance at 450 nm with subtracting off the background at 650 nm.
8. Plot the percentage absorbance relative to untreated control and estimate the CC$_{50}$ value as drug concentration resulting in a 50% inhibition of the cell growth. Consider the absorbance being directly proportional to the cell growth.

It has been observed that nucleoside analogs with R$^6$ as currently claimed can have enhanced cellular selectivity over their counterparts with R$^6$=H. As shown in the table below, structurally closely related compounds Compound A (R$^6$=H) and Compound 30 (R$^6$=CN) had the same level of antiviral activity, where Compound A displayed EC$_{50}$ of 2.5 μM and Compound 30 did EC$_{50}$ of 2.6 μM. However, mitochondrial toxicity of these two compounds was surprisingly different from each other. Compound A showed 50% inhibition of mitochondrial protein levels at 43 μM, while Compound 30 showed no inhibitory effect even at 100 μM, which was a maximum concentration tested in the Mitochondrial Biogenesis assay.

| Compound# | Structure | HCV EC50 (uM) | CC50 (μM) |
|---|---|---|---|
| Chloramphenicol | — | — | 2.5 |
| A | (structure shown) | 2.5 | 43 |

| Compound# | Structure | HCV EC50 (uM) | CC50 (μM) |
|---|---|---|---|
| 30 | 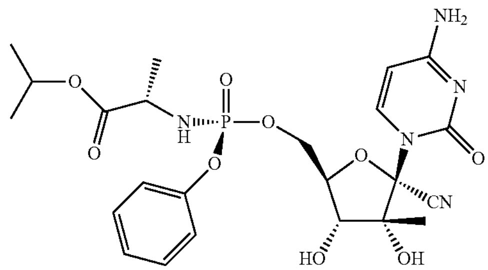 [SMILES: CC(C)OC(=O)[C@H](C)N[P@](=O)(OC[C@H]1O[C@@](C#N)(n2ccc(N)nc2=O)[C@](C)(O)[C@@H]1O)Oc1ccccc1] | 2.6 | Not toxic effect up to 100 μM |

Anti-Influenza Assays

MDCK cells (Friedrich-Loeffler Institute, Riems, Germany) are grown in Eagle minimum essential medium (EMEM) supplemented with 10% fetal bovine serum, 100 U/mL penicillin, and 100 U/mL streptomycin. Medium applied in plaque reduction assays is formulated with about 2 μg/mL trypsin and about 1.2 mM bicarbonate and does not contain serum.

A/Horneburg/IDT7489/08 and Brest/IDT490/08 are isolated in embryonated hens eggs and from nasal swabs obtained from pigs with clinical symptoms.

Stocks of H1N1 influenza virus A/PR/8/34 (Institute of Virology, Philipps University, Marburg), the oseltamivir-resistant human H1N1 isolate N342109 (Robert Koch Institute, Berlin, Germany) and the porcine H1N1 isolates A/Belzig/2/01, A/Potsdam/15/81 (Dr. Schrader, Bundesinstitut for Risikoforschung, Berlin, Germany), A/Horneburg/IDT7489/08, and Brest/IDT490/08 are propagated in MDCK cells, aliquoted, and stored at −80° C. until use.

Immediately before use, compound stocks are prepared in water and stored at 4° C. Stock solutions of compounds are prepared in DMSO.

Cytotoxicity as well as antiviral activity of test compounds is determined on 3-day-old MDCK cell monolayers as described previously by Schmidtke (*Antivir. Res.* 2002, 55, 117-127). Briefly, to determine the $CC_{50}$, confluent cell monolayers grown in 96-well plates are incubated with serial 2-fold dilutions (each in triplicate) of compound, a test compound or standard such as oseltamivir, for 72 h (37° C., 5% $CO_2$). Then the cells are fixed and stained with a crystal violet formalin solution. After dye extraction, the optical density of individual wells are quantified spectrophotometrically at 550/630 nm with a microplate reader. Cell viability of individual compound-treated wells are evaluated as the percentage of the mean value of optical density resulting from six mock-treated cell controls which was set 100%. The $CC_{50}$ is defined as the compound concentration reducing the viability of untreated cell cultures by 50%. It is calculated from the mean dose-response curve of two independent assays.

A plaque reduction assay is used for antiviral testing with influenza virus A/Puerto Rico/8/34 on MDCK cell. Cell monolayers are inoculated with approximately 70 plaque forming units (pfu) of the virus and are overlaid with 0.4% agar supplemented with serial 2-fold compound concentrations; each tested in duplicate. One uninfected, untreated cell control as well as three infected untreated virus controls are included in all assays. After 48 h of incubation at 37° C., plates are fixed and stained with a crystal violet formalin solution, the number of virus-induced plaques are counted, and the compound-induced plaque reduction is calculated. The concentration required to reduce the plaque number by 50% is calculated from the mean dose-response curves of at least 2 independent assays.

Anti-Enterovirus Assays

Clinical virus isolates are passaged once in the cell line used for their original isolation to establish working virus stocks and are then stored as aliquots in glass ampoules at −80° C. Enteroviruses (EVs) are propagated in human embryonal rhabdomyosarcoma (RD) cells grown in minimal essential medium (MEM) supplemented with 10% heat-inactivated fetal bovine serum (FBS). CVA9 and CVB isolates are passaged in LLC-$MK_{2D}$ cells grown in MEM plus 5% FBS. Viruses are assayed for drug sensitivity in the cell line used for their original isolation with the exception of the CVA9 isolates, which are assayed in HeLa cells.

Virus Cytopathic Effect Assay

The sensitivities of enteroviruses to compounds of Formula I may be determined in a cell culture assay that measures the protection by the drug of an infected cell monolayer from the cytopathic effects of the viruses. Examples of prototypical strains of the 15 most commonly isolated enteroviruses (Strikas, et al., *J. Infect. Dis.* 1986, 153, 346-351) are shown in Table II Ninety-six-well tissue culture plates (Costar 3598) are seeded at a density of $2.8 \times 10^4$ cells/well for HeLa cells (in MEM plus 5% FBS), $3.6 \times 10^4$ cells/well for LLC-$MK_{2D}$ cells (in MEM plus 5% FBS), or $6 \times 10^4$ cells/well for RD cells (in MEM plus 10% FBS). The cells are incubated for 24 h at 37° C. in a humidified, 5% $CO_2$ atmosphere prior to their use in the assay.

To determine the virus inoculum in the assay, serial 0.5 $log_{10}$ dilutions of individual viruses are plated in octuplicate onto their respective cell lines in medium 199 (M199) plus 5% FBS supplemented with 30 mM $MgCl_2$ and 15 μg of DEAE dextran per ml (complete M199 medium). The plates are incubated for 3 days and are then fixed with 5% glutaraldehyde and stained with 0.1% crystal violet. After rinsing and drying, the optical density of the wells at a wavelength of 570 nm ($OD_{570}$) are read on a Bio-Tek 300 plate reader. The highest dilution of virus that produces an $OD_{570}$ reading of ≤15% of the cell culture control value is used for drug sensitivity testing.

To test for drug sensitivity, cells in 96-well plates are infected with the appropriate virus dilution at 37° C. in 150 μl of complete M199 medium. During the 1-h virus attachment period, compounds of Formula I are solubilized in dimethyl sulfoxide (DMSO) to 400 times the highest concentration to be tested in the assay and are then serially diluted twofold in DMSO in U-bottom, 96-well polypropylene plates (Costar 3790) to yield 10 compound dilutions. Two microliters of the DMSO compound dilutions are then diluted into 198 μl of complete M199 medium to effect a 100-fold dilution of compound. After virus attachment, 50 µl of this drug dilution is added to the 150 µl virus inoculum, resulting in a final 400-fold dilution of compound in 0.25% DMSO. Each compound concentration is run in quadruplicate. Uninfected cells and cells that receive virus in the absence of compound are included on each plate. The plates are then incubated for 3 days at 37° C. in a humidified, 2.5% $CO_2$ atmosphere prior to fixation and staining. The 50% inhibitory concentration ($IC_{50}$) is defined as the concentration of compound that protects 50% of the cell monolayer from virus-induced cytopathic effect.

TABLE 4

Commonly isolated enteroviruses.

EV3 Morrisey
EV4 Pesacek
EV5 Noyce
EV6 D'Amori
EV7 Wallace
EV9 Hill
EV11 (Gregory)
EV24 (DeCamp)
EV30 (Bastianni)
CVA9 Bozek
CVB1 Conn-5
CVB2 Ohio-1
CVB3 Nancy
CVB3 M
CVB4 JVB
CVB5 Faulkner Respiratory Syncytial Virus (RSV) Antiviral Activity and Cytotoxicity Assays Anti-RSV Activity Antiviral activity against RSV is determined using an in vitro cytoprotection assay in Hep2 cells. In this assay, compounds inhibiting the virus replication exhibit cytoprotective effect against the virus-induced cell killing that can be quantified using a cell viability reagent. The method used is similar to methods previously described in published literature (Chapman et al., *Antimicrob Agents Chemother.* 2007, 51(9): 3346-53.)

Hep2 cells are obtained from ATCC (Manassas, VI) and maintained in MEM media supplemented with 10% fetal bovine serum and penicillin/streptomycin. Cells are passaged twice a week and kept at subconfluent stage. Commercial stock of RSV strain A2 (Advanced Biotechnologies, Columbia, Md.) is titered before compound testing to determine the appropriate dilution of the virus stock that generates desirable cytopathic effect in Hep2 cells.

For antiviral tests, Hep2 cells are seeded into 96-well plates 24 hours before the assay at a density of 3,000 cells/well. On a separate 96well plate, compounds to be tested are serially diluted in cell culture media. Eight concentrations in 3-fold serial dilution increments are prepared for each tested compound and 100 µL/well of each dilution is transferred in duplicate onto plates with seeded Hep2 cells. Subsequently, appropriate dilution of virus stock previously determined by titration is prepared in cell culture media and 100 µL/well is added to test plates containing cells and serially diluted compounds. Each plate includes three wells of infected untreated cells and three wells of uninfected cells that served as 0% and 100% virus inhibition control, respectively. Following the infection with RSV, testing plates are incubated for 4 days in a tissue culture incubator. After the incubation, RSV-induced cytopathic effect is determined using a Cell TiterGlo reagent (Promega, Madison, Wis.) followed by a luminescence read-out. The percentage inhibition is calculated for each tested concentration relative to the 0% and 100% inhibition controls and the EC50 value for each compound is determined by non-linear regression as a concentration inhibiting the RSV-induced cytopathic effect by 50%. Ribavirin (purchased from Sigma, St. Louis, Mo.) is used as a positive control for antiviral activity.

Compounds were also tested for antiviral activity against RSV in Hep2 cells using a 384 well format. Compounds were diluted in DMSO using a 10-step serial dilution in 3-fold increments via automation in 4 adjacent replicates each. Eight compounds were tested per dilution plate. 0.4 uL of diluted compounds were then stamped via Biomek into 384-well plates (Nunc 142761 or 164730 w/lid 264616) containing 20 µL of media (Mediatech Inc. MEM supplemented with Glutamine, 10% FBS and Pen/Strep). DMSO and a suitable positive control compound, such as 80 µM GS-329467 or 10 µM 427346 was used for the 100% and 0% cell killing controls, respectively.

Hep2 cells (1.0×105 cells/mil) were prepared as above in batch to at least 40 mls excess of the number of sample plates (8 mls cell mix per plate) and infected with vendor supplied (ABI) RSV strain A2 to arrive at an MOI of 1:1000 (virus:cell #) or 1:3000 (vol virus: cell vol). Immediately after addition of virus, the RSV infected Hep2 cell suspension was added to each stamped 384-well plate at 20 µl per well using a uFlow dispenser, giving a final volume of 40 µL/well, each with 2000 infected cells. The plates were then incubated for 5 days at 37° C. and 5% $CO_2$. Following incubation, the plates were equilibrated to room temperature in a biosafety cabinet hood for 1.5 hrs and 40 µL of Cell-Titer Glo viability reagent (Promega) was added to each well via uFlow. Following a10-20 minute incubation, the plates were read using an EnVision or Victor Luminescence plate reader (Perkin-Elmer). The data was then uploaded and analyzed on the Bioinformatics portal under the RSV Cell Infectivity and 8-plate EC50-Hep2-384 or 8-plate EC50-Hep2-Envision protocols.

Representative activity for the compounds of the invention against RSV-induced cytopathic effects using 384 well method are shown in the Table below.

| Compound # | Structure | $EC_{50}$ (µM) |
|---|---|---|
| 3 | 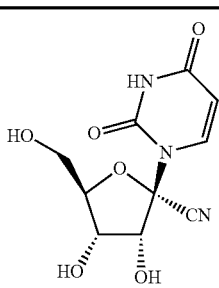 | 10.865 |

-continued

| Compound # | Structure | EC$_{50}$ (µM) |
|---|---|---|
| 4 | (cytidine with 2'-CN, ribose) | 11.302 |
| 10 | (uridine analog with 5'-methyl, 2'-CN) | 200 |
| 11 | (cytidine analog with 5'-methyl, 2'-CN) | 200 |
| 12 | (uridine with 2'-CN, 3'-OCH$_3$) | 200 |
| 13 | (cytidine with 2'-CN, 3'-OCH$_3$) | 200 |
| 15 | (uridine with 2'-CN, 2'-methyl) | 200 |
| 30 | (phosphoramidate prodrug of cytidine-2'-CN-2'-methyl) | 200 |
| 35 | (phosphoramidate prodrug with 3'-isobutyryl ester) | 200 |

Cytotoxicity

Cytotoxicity of tested compounds is determined in uninfected Hep2 cells in parallel with the antiviral activity using the cell viability reagent in a similar fashion as described before for other cell types (Cihlar et al., *Antimicrob Agents Chemother.* 2008, 52(2):655-65.). The same protocol as for the determination of antiviral activity is used for the measurement of compound cytotoxicity except that the cells are not infected with RSV. Instead, fresh cell culture media (100 µL/well) without the virus is added to tested plates with cells and prediluted compounds. Cells are then incubated for 4 days followed by a cell viability test using CellTiter Glo reagent and a luminescence read-out. Untreated cell and cells treated with 50 ug/mL puromycin (Sigma, St. Louis, Mo.) are used as 100% and 0% cell viability control, respectively. The percent of cell viability is calculated for each tested compound concentration relative to the 0% and 100% controls and the CC$_{50}$ value is determined by non-linear regression as a compound concentration reducing the cell viability by 50%.

All publications, patents, and patent documents cited herein above are incorporated by reference herein, as though individually incorporated by reference. The invention has been described with reference to various specific and preferred embodiments and techniques. However, one skilled in the art will understand that many variations and modifications may be made while remaining within the spirit and scope of the invention.

The invention claimed is:

1. A compound of Formula I:

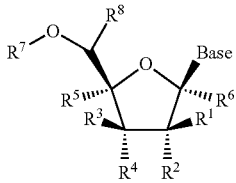

Formula I or a pharmaceutically acceptable salt thereof;
wherein:
Base is a naturally occurring or modified pyrimidine base;
$R^1$ is H, CN, $OR^a$, $(C_1-C_4)$alkyl, $(C_1-C_4)$substituted alkyl, $(C_2-C_4)$alkenyl, $(C_2-C_4)$substituted alkenyl, $(C_2-C_4)$alkynyl, $(C_2-C_4)$substituted alkynyl or $S(O)_nR^a$;
$R^2$ is H, $OR^a$, $N(R^a)_2$, $N_3$, CN, $NO_2$, $S(O)_nR^a$, $(C_1-C_4)$alkyl, $(C_4-C_6)$cycloalkylalkyl, $(C_1-C_4)$substituted alkyl, $(C_2-C_4)$alkenyl, $(C_2-C_4)$substituted alkenyl, $(C_2-C_4)$alkynyl, or $(C_2-C_4)$substituted alkynyl;
or $R^1$ and $R^2$ taken together with the carbon to which they are attached form a 3- to 6-membered cycloalkyl ring wherein 1 to 3 carbon atoms of said cycloalkyl ring is optionally replaced by O or $S(O)_n$;
$R^3$, $R^4$, and $R^5$ are each independently H, $OR^a$, $N(R^a)_2$, $N_3$, CN, $NO_2$, $S(O)_nR^a$, halogen, $(C_1-C_4)$alkyl, $(C_4-C_8)$cycloalkylalkyl, $(C_1-C_4)$substituted alkyl, $(C_2-C_4)$alkenyl, $(C_2-C_4)$substituted alkenyl, $(C_2-C_4)$alkynyl, or $(C_2-C_4)$substituted alkynyl;
or any two of $R^3$, $R^4$ or $R^5$ on adjacent carbon atoms when taken together are —O(CO)O— or when taken together with the ring carbon atoms to which they are attached to form a double bond;
$R^6$ is CN, 2-haloethen-1-yl, or $(C_2-C_8)$alkyn-1-yl,
each n is independently 0, 1, or 2;
each $R^a$ is independently H, $(C_1-C_8)$alkyl, $(C_2-C_8)$alkenyl, $(C_2-C_8)$alkynyl, aryl$(C_1-C_8)$alkyl, $(C_4-C_8)$cycloalkylalkyl, —C(=O)$R^{11}$, —C(=O)$OR^{11}$, —C(=O)$NR^{11}R^{12}$, —C(=O)$SR^{11}$, —S(O)$R^{11}$, —S(O)($OR^{11}$), —S(O)$_2$($OR^{11}$), or —SO$_2$$NR^{11}R^{12}$;
$R^7$ is H, —C(=O)$OR^{11}$, —C(=O)$NR^{11}R^{12}$, —C(=O)$SR^{11}$, —S(O)$R^{11}$, —S(O)$_2R^{11}$, —S(O)($OR^{11}$), —S(O)$_2$($OR^{11}$), —SO$_2$$NR^{11}R^{12}$, or the group of Formula Ia

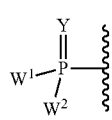

Formula Ia wherein
Y is O, S, NR, $^+$N(O)(R), N(OR), $^+$N(O)(OR), or N—NR$_2$;
$W^1$ and $W^2$, when taken together, are —$Y^3$(C($R^y$)$_2$)$_3Y^3$—;
or one of $W^1$ or $W^2$ together with either $R^3$ or $R^4$ is —$Y^3$— and the other of $W^1$ or $W^2$ is Formula Ib;
or $W^1$ and $W^2$ are each, independently, a group of Formula Ib:

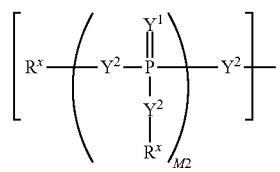

Formula Ib wherein:
each $Y^1$ is independently 0, S, NR, $^+$N(O)(R), N(OR), $^+$N(O)(OR), or N—NR$_2$;
each $Y^2$ is independently a bond, 0, CR$_2$, NR, $^+$N(O)(R), N(OR), $^+$N(O)(OR), N—NR$_2$, S, S—S, S(O), or S(O)$_2$;
each $Y^3$ is independently 0, S, or NR;
M2 is 0, 1, or 2;
each $R^x$ is a group of Formula Ic

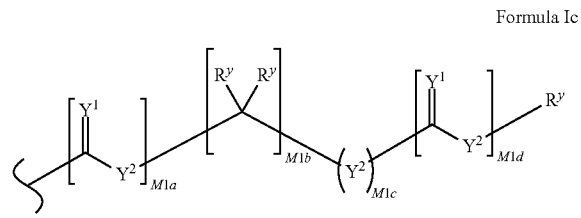

Formula Ic wherein:
each M1a, M1c, and M1d is independently 0 or 1;
M1b is 0, 1, 2, 3, 4, 5, 6, 7, 8, 9, 10, 11 or 12;
each $R^y$ is independently H, F, Cl, Br, I, —CN, —N$_3$, —NO$_2$, —OR, —C(R)$_2$—O—C(R)$_3$, —C(=$Y^1$)R, —C(=$Y^1$)$R^{13}$, —C(=$Y^1$)OR, —C(=$Y^1$)N(R)$_2$, —N(R)$_2$, —N(R)$_3$, —SR, —S(O)R, —S(O)$_2$R, —S(O)$_2R^{13}$, —S(O)(OR), —S(O)$_2$(OR), —OC(=$Y^1$)R, —OC(=$Y^1$)OR, —OC(=$Y^1$)(N(R)$_2$), —SC(=$Y^1$)R, —SC(=$Y^1$)OR, —SC(=$Y^1$)(N(R)$_2$), —N(R)C(=$Y^1$)R, —N(R)C(=$Y^1$)OR, —N(R)C(=$Y^1$)N(R)$_2$, —SO$_2NR^2$, $(C_1-C_8)$ alkyl, $(C_2-C_8)$alkenyl, $(C_2-C_8)$alkynyl, $C_6-C_{20}$ aryl, $C_3-C_{20}$ cycloalkyl, $(C_2-C_{20})$ heterocyclyl, arylalkyl, or heteroarylalkyl,
wherein each $(C_1-C_8)$ alkyl, $(C_2-C_8)$alkenyl, $(C_2-C_8)$ alkynyl, $(C_6-C_{20})$ aryl, $(C_3-C_{20})$ cycloalkyl, $(C_2-C_{20})$ heterocyclyl, arylalkyl, or heteroarylalkyl is optionally substituted with 1-3 $R^{20}$ groups;
or when taken together, two $R^y$ groups on the same carbon atom form a cycloalkyl ring of 3 to 7 carbon atoms;
each R is independently H, $(C_1-C_8)$ alkyl, $(C_2-C_8)$alkenyl, $(C_2-C_8)$ alkynyl, $(C_6-C_{20})$ aryl, $(C_3-C_{20})$ cycloalkyl, $(C_2-C_{20})$ heterocyclyl, or arylalkyl;
$R^8$ is H, $(C_1-C_4)$ alkyl, or $(C_1-C_4)$ substituted alkyl;
each $R^{11}$ or $R^{12}$ is independently H, $(C_1-C_8)$alkyl, $(C_2-C_8)$ alkenyl, $(C_2-C_8)$alkynyl, $(C_4-C_8)$cycloalkylalkyl, $(C_3-C_{20})$cycloalkyl, $(C_2-C_{20})$heterocyclyl, optionally substituted aryl, optionally substituted heteroaryl, —C(=O)$(C_1-C_8)$alkyl, —S(O)$_n(C_1-C_8)$alkyl or aryl $(C_1-C_8)$alkyl; or $R^{11}$ and $R^{12}$ taken together with a nitrogen to which they are both attached form a 3- to 7-membered heterocyclic ring wherein any one carbon atom of said heterocyclic ring can optionally be replaced with —O—, —S— or —NH—;
each $R^{13}$ is independently a cycloalkyl or heterocyclyl optionally substituted with 1-3 R or $R^{20}$ groups;

each $R^{20}$ is independently, halogen, CN, $N_3$, $N(R)_2$, OR, —SR, —S(O)R, —S(O)$_2$R, —S(O)(OR), —S(O)$_2$(OR), —C(=$Y^1$)R, —C(=$Y^1$)OR, or C(=$Y^1$)N(R)$_2$;

wherein each alkyl, alkenyl, alkynyl, aryl or heteroaryl of each of $R^1$, $R^2$, $R^3$, $R^4$, $R^5$, or $R^8$ is, independently, optionally substituted with 1 to 3 halo, hydroxy, CN, $N_3$, $N(R^a)_2$ or $OR^a$; and wherein 1 to 3 of the non-terminal carbon atoms of each said ($C_1$-$C_8$)alkyl may be optionally replaced with —O—, —S— or —$NR^a$—;

wherein each $R^{11}$ or $R^{12}$ is, independently, optionally substituted with 1 to 3 halo, hydroxy, CN, $N_3$, $NH_2$ or OH; and wherein 1 to 3 of the non-terminal carbon atoms of each said ($C_1$-$C_8$)alkyl may be optionally replaced with —O—, —S— or —NH—;

with the following provisos:
a) when $R^1$, $R^3$, and $R^5$ are H, $R^2$ and $R^4$ are hydroxy, $R^6$ is cyano and $R^7$ and $R^8$ are H, then Base is not uracil or thymine;
b) when $R^1$ and $R^4$ are hydroxy, $R^2$, $R^3$, and $R^5$ are H, $R^6$ is cyano and $R^7$ and $R^8$ are H, then Base is not uracil or cytosine;
c) when $R^1$, $R^2$, $R^3$, and $R^5$ are H, $R^4$ is hydroxy, $R^6$ is cyano and $R^7$ and $R^8$ are H, then Base is not uracil, cytosine, thymine or 5-iodo-uracil;
d) when $R^5$ is other than H, then $R^8$ is H;
e) when $R^1$ is hydroxy, $R^2$, $R^3$, $R^5$, and $R^8$ are H, $R^6$ is cyano, $R^4$ is H or benzoyl, and $R^7$ is H or benzoyl, then Base is not cytosine;
f) when $R^1$ is acetyl or hydroxy, $R^2$, $R^3$, $R^5$, $R^7$, and $R^8$ are H, $R^4$ is hydroxy or —OC(O)phenyl, then Base is not 2-oxo-4-hydroxypyrimidinyl;
g) when $R^1$ is acetoxy, $R^4$ is benzoyloxy, $R^6$ is cyano, $R^7$ is benzoyl, and $R^2$, $R^3$, $R^5$, and $R^8$ are H, then base is not uracil; and
h) at least one of $R^1$, $R^2$, $R^3$, $R^4$ and $R^5$ is not H.

2. The compound according to claim 1 represented by Formula II:

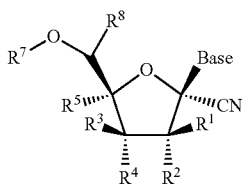

Formula II wherein each Y and $Y^1$ is O.

3. The compound according to claim 1 represented by Formula IV:

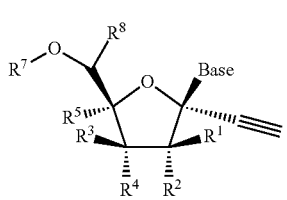

Formula IV wherein each Y and $Y^1$ is O.

4. The compound according to claim 1 represented by Formula V:

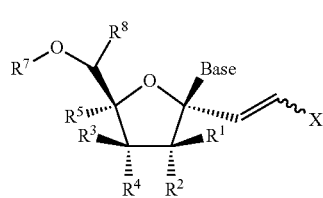

Formula V wherein each Y and $Y^1$ is O and X is halogen.

5. The compound according to claim 4, wherein halogen is fluoro, chloro, or iodo.

6. The compound according to claim 1, wherein $R^1$ is H, CN, $OR^a$, ($C_1$-$C_4$)alkyl, ($C_2$-$C_4$)alkenyl, or ($C_2$-$C_4$)alkynyl.

7. The compound according to claim 6, wherein $R^1$ is H, methyl, or hydroxy.

8. The compound according to claim 1, wherein $R^2$ is H or $OR^a$.

9. The compound according to claim 8, wherein $R^2$ is H, methoxy, or hydroxy.

10. The compound according to claim 1, wherein $R^1$ and $R^2$ taken together with the carbon to which they are attached form a 4-membered cycloalkyl ring wherein one carbon atom of said cycloalkyl ring is optionally replaced by O.

11. The compound according to claim 1, wherein $R^3$, $R^4$, and $R^5$ are each independently H, $OR^a$, $N_3$, CN, ($C_1$-$C_4$) alkyl, or ($C_2$-$C_4$) alkynyl.

12. The compound according to claim 11, wherein $R^3$, $R^4$, and $R^5$ are each independently H, hydroxy, $N_3$, or —OC(O)-isopropyl.

13. The compound according to claim 1, wherein Base is uracil optionally substituted with halogen.

14. The compound according to claim 1, wherein Base is cytosine optionally substituted with halogen.

15. The compound according to claim 1, wherein Base is a pyrimidine represented by Formula VI or VII:

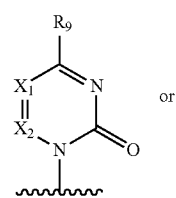

Formula VI

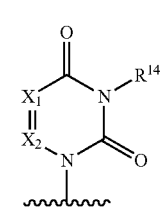

Formula VII or tautomer thereof,
wherein:
each $X^1$ or $X^2$ is independently C—$R^{10}$ or N provided that at least one of $X^1$ or $X^2$ is C—$R^{10}$;
each $R^9$ is H, halogen, $NR^{11}R^{12}$, $N(R^{11})OR^{11}$, $NR^{11}NR^{11}R^{12}$, $N_3$, NO, $NO_2$, $OR^{11}$ or $SR^{11}$; and
each $R^{10}$ is independently H, halogen, $NR^{11}R^{12}$, $N(R^{11})OR^{11}$, $NR^{11}NR^{11}R^{12}$, $N_3$, NO, $NO_2$, CHO, CN, —CH(=$NR^{11}$), —CH=$NHNR^{11}$, —CH=N($OR^{11}$), —CH (OR¹¹)₂, —C(=O)NR¹¹R¹², —C(=S)NR¹¹R¹², —C(=O)OR¹¹, R¹¹, OR¹¹ or SR¹¹;

each $R^{11}$ or $R^{12}$ is independently H, $(C_1-C_8)$alkyl, $(C_2-C_8)$alkenyl, $(C_2-C_8)$alkynyl, $(C_4-C_8)$cycloalkylalkyl, $(C_3-C_{20})$cycloalkyl, $(C_2-C_{20})$heterocyclyl, optionally substituted aryl, optionally substituted heteroaryl, —C(=O)(C₁-C₈)alkyl, —S(O)ₙ(C₁-C₈)alkyl or aryl (C₁-C₈)alkyl; or $R^{11}$ and $R^{12}$ taken together with a nitrogen to which they are both attached form a 3- to 7-membered heterocyclic ring wherein any one carbon atom of said heterocyclic ring can optionally be replaced with —O—, —S— or NH; and $R^{14}$ is H, $(C_1-C_8)$alkyl, or $(C_4-C_8)$cycloalkylalkyl.

16. The compound according to claim 1, wherein $R^6$ is CN or ethynyl.

17. The compound according to claim 1, wherein $R^7$ is H or

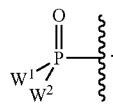

18. The compound according to claim 1, wherein $R^7$ is H or

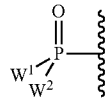

wherein $W^1$ and $W^2$ are each, independently, a group of the Formula Ib.

19. The compound according to claim 1, wherein $R^1$ is H, OH, CN, $(C_1-C_4)$alkyl, $(C_2-C_4)$alkenyl, or $(C_2-C_4)$alkynyl;

$R^2$ is H, OH or $O(C_1-C_4)$alkyl;

or $R^1$ and $R^2$ taken together with the carbon to which they are attached form a 3- to 6-membered cycloalkyl ring wherein one carbon atom of said cycloalkyl ring is optionally replaced by O;

$R^3$ is H or $(C_1-C_4)$alkyl;

$R^4$ is H, OH, $O(C_1-C_4)$alkyl, or $OC(O)$—$(C_1-C_4)$alkyl;

$R^5$ is H, CN, N₃, $(C_1-C_4)$alkyl, $(C_2-C_4)$alkenyl, or $(C_2-C_4)$alkynyl;

$R^6$ is CN, 2-haloethen-1-yl, or $(C_2-C_8)$alkyn-1-yl; and $R^8$ is H or $(C_1-C_4)$alkyl.

20. The compound of claim 1, wherein:

$R^1$ is H, OH, or $(C_1-C_4)$alkyl;

$R^2$ is H, OH or $O(C_1-C_4)$alkyl;

or $R^1$ and $R^2$ taken together with the carbon to which they are attached form a 4-membered cycloalkyl ring wherein one carbon atom of said cycloalkyl ring is optionally replaced by O;

$R^3$ is H or $(C_1-C_4)$alkyl;

$R^4$ is H, OH, $O(C_1-C_4)$alkyl, or —OC(O)—$(C_1-C_4)$alkyl;

$R^5$ is H, N₃, or $(C_1-C_4)$alkyl;

$R^6$ is CN or ethynyl; and $R^8$ is H or $(C_1-C_4)$ alkyl.

21. The compound according to claim 1, wherein $R^7$ is H or

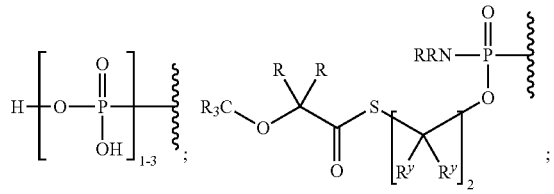

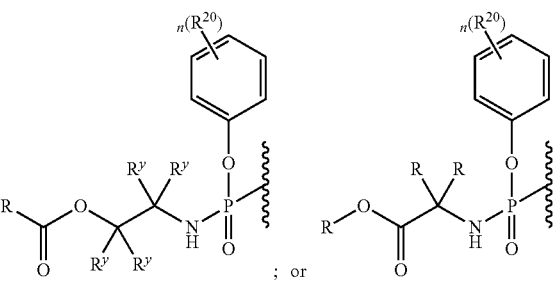

22. The compound according to claim 1, wherein the group —R⁷—O—C(R⁸)—C(R⁵)—C(R³)(R⁴)— is of the following formula:

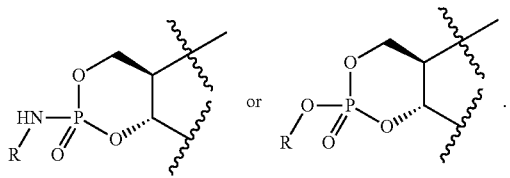

23. The compound according to claim 1, wherein at least one of $R^1$, $R^2$, $R^3$, and $R^4$ are hydroxy.

24. The compound according to claim 23, wherein at least two of $R^1$, $R^2$, $R^3$, and $R^4$ are hydroxy.

25. A compound selected from

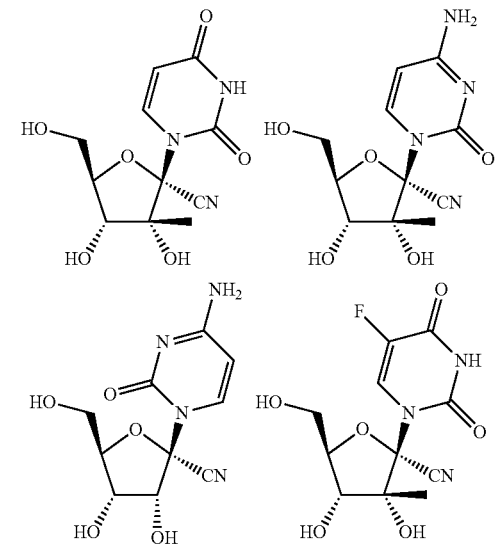

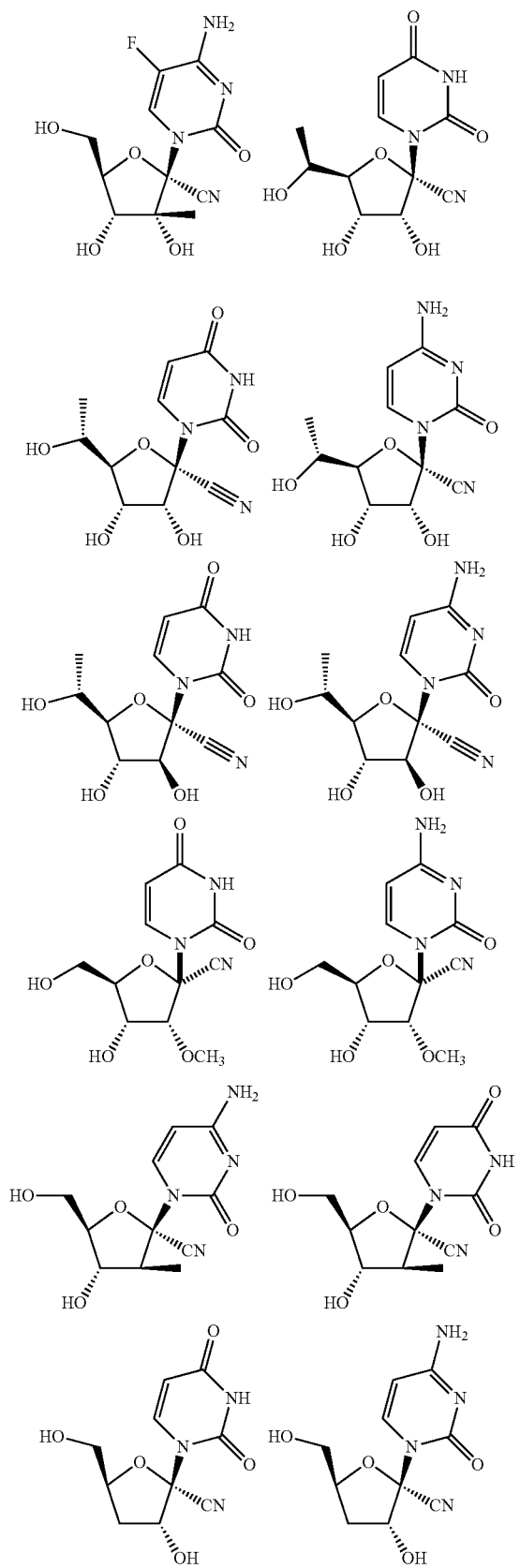
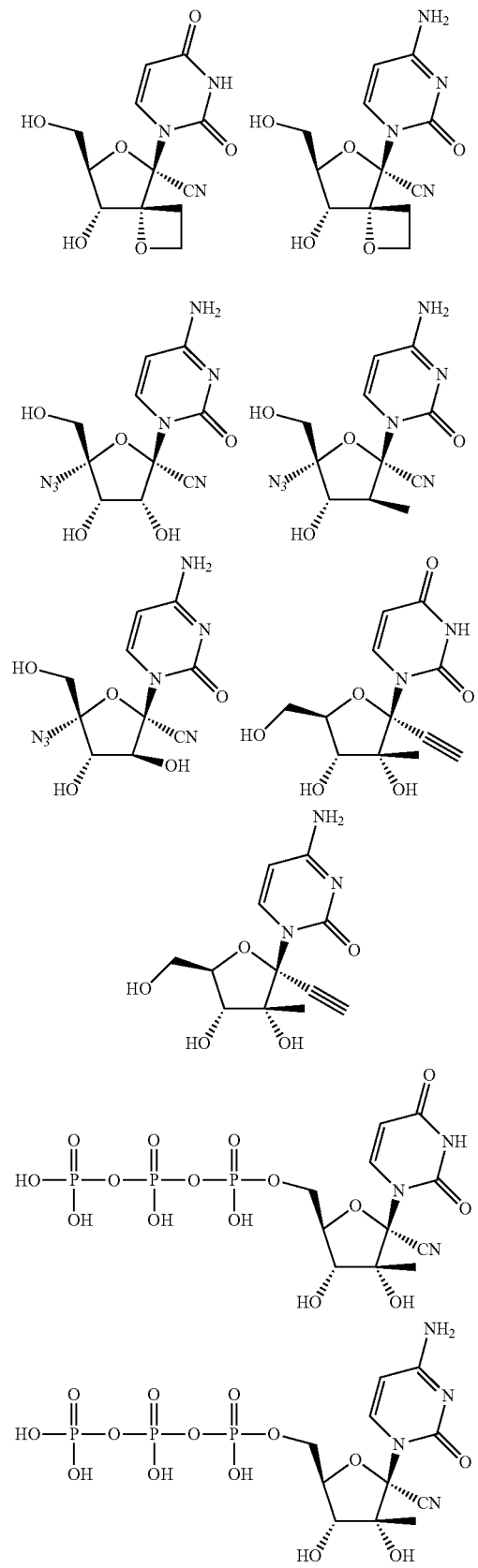

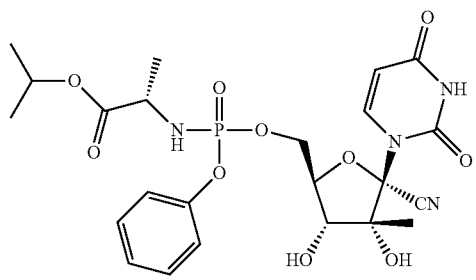
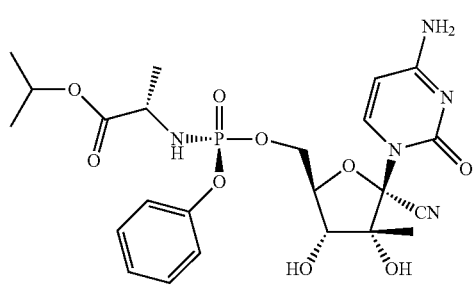
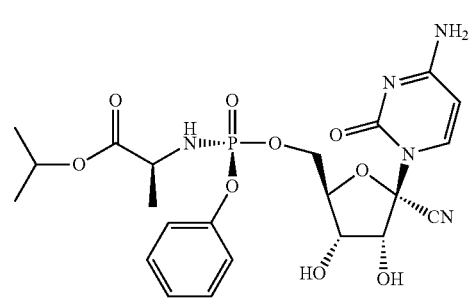
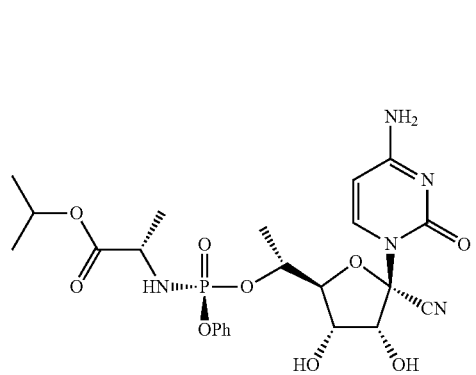
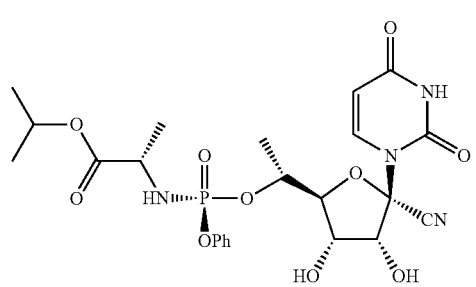
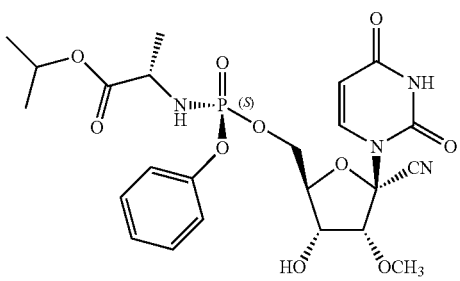
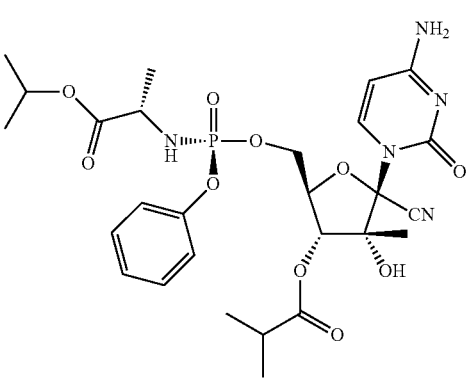
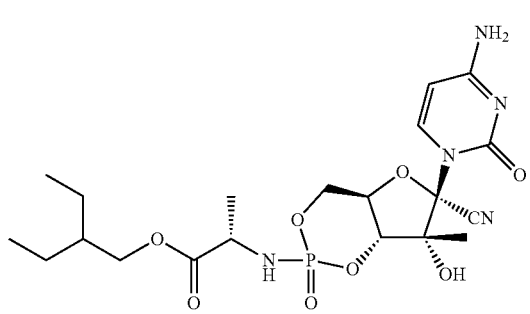
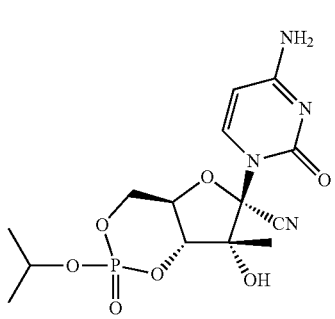
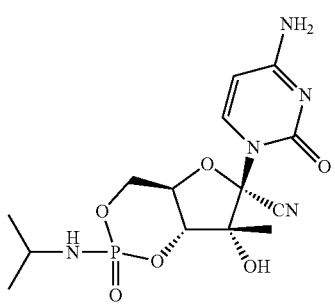

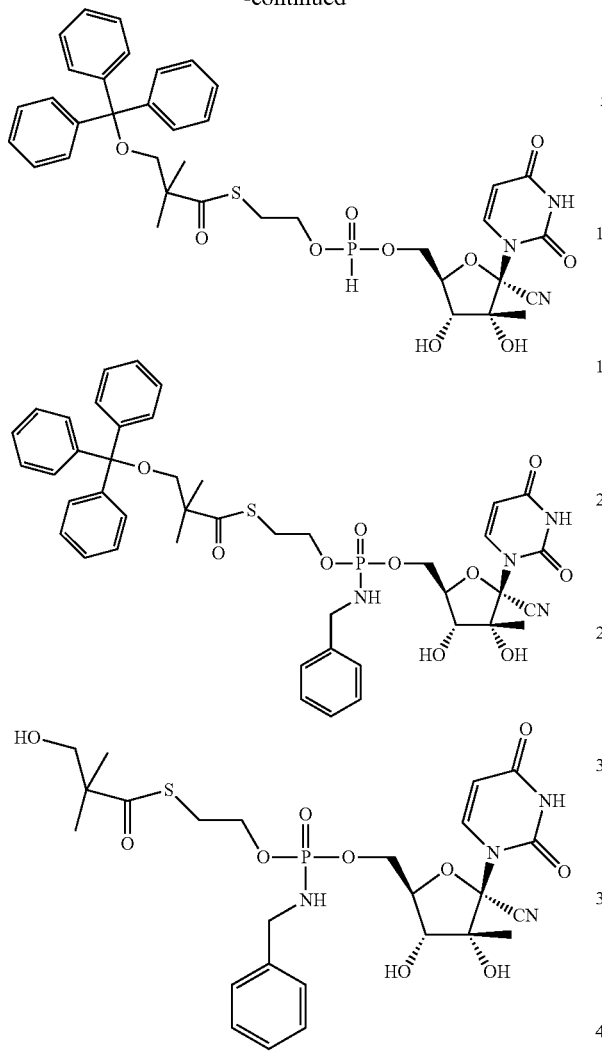

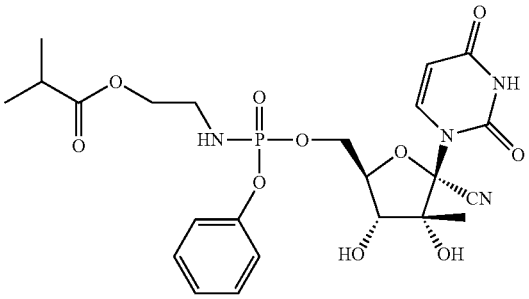 [SMILES: CC(C)C(=O)OCCNP(=O)(OC[C@H]1O[C@@](C#N)(n2ccc(=O)[nH]c2=O)[C@](C)(O)[C@@H]1O)Oc1ccccc1]

or a pharmaceutically acceptable salt thereof.

26. A pharmaceutical composition comprising a therapeutically effective amount of a compound of claim 1 and a pharmaceutically acceptable carrier.

27. A method of inhibiting HCV polymerase comprising administering to a mammal in need thereof a therapeutically effective amount of a compound of claim 1.

28. A method of treating a viral infection caused by a Flaviviridae virus comprising administering to a mammal in need thereof a therapeutically effective amount of a compound of claim 1.

29. The method of claim 28, wherein the virus is selected from the group consisting of dengue virus, yellow fever virus, West Nile virus, Japanese encephalitis virus, tick-borne encephalitis virus, Kunjin virus, Murray Valley encephalitis virus, St. Louis encephalitis virus, Omsk hemorrhagic fever virus, bovine viral diarrhea virus, Zika virus and Hepatitis C virus.

30. The method of claim 29, wherein the viral infection is caused by Hepatitis C virus.

* * * * *